(12) United States Patent
Seitz et al.

(10) Patent No.: US 10,559,409 B2
(45) Date of Patent: *Feb. 11, 2020

(54) PROCESS FOR MANUFACTURING A LEADLESS FEEDTHROUGH FOR AN ACTIVE IMPLANTABLE MEDICAL DEVICE

(71) Applicant: Greatbatch Ltd., Clarence, NY (US)

(72) Inventors: Keith W. Seitz, Clarence Center, NY (US); Dallas J. Rensel, Sanborn, NY (US); Brian P. Hohl, Clarence, NY (US); Jonathan Calamel, Williamsville, NY (US); Xiaohong Tang, Williamsville, NY (US); Robert A. Stevenson, Canyon County, CA (US); Christine A. Frysz, Orchard Park, NY (US); Thomas Marzano, East Amherst, NY (US); Jason Woods, Carson City, NV (US); Richard L. Brendel, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,862

(22) Filed: Mar. 25, 2019

(65) Prior Publication Data

US 2019/0244729 A1    Aug. 8, 2019

Related U.S. Application Data

(63) Continuation of application No. 15/863,194, filed on Jan. 5, 2018, now Pat. No. 10,249,415, which is a
(Continued)

(51) Int. Cl.
*A61N 1/375* (2006.01)
*B23K 1/19* (2006.01)
(Continued)

(52) U.S. Cl.
CPC ........... *H01B 17/30* (2013.01); *A61N 1/3754* (2013.01); *B23K 1/008* (2013.01); *B23K 1/0016* (2013.01);
(Continued)

(58) Field of Classification Search
None
See application file for complete search history.

(56) References Cited

U.S. PATENT DOCUMENTS

| 3,137,808 A | 6/1964 | Coda et al. |
| 3,189,978 A | 6/1965 | Stetson |

(Continued)

FOREIGN PATENT DOCUMENTS

| EP | 0243573 | 11/1987 |
| EP | 0145430 | 5/1991 |

(Continued)

OTHER PUBLICATIONS

European Search Report, Application No. 13151535.5, dated Jul. 22, 2013.
(Continued)

*Primary Examiner* — Devang R Patel
(74) *Attorney, Agent, or Firm* — Michael F. Scalise

(57) ABSTRACT

A method for manufacturing a feedthrough dielectric body for an active implantable medical device includes the steps of first forming a ceramic reinforced metal composite (CRMC) paste by mixing platinum with a ceramic material to form a CRMC material, subjecting the CRMC material to a first sintering step to thereby form a sintered CRMC material, ball-milling or grinding the sintered CRMC material to form a powdered CRMC material; and then mixing the powdered CRMC material with a solvent to form the CRMC paste. The method further includes forming an alumina ceramic body in a green state, forming at least one
(Continued)

via hole through the alumina ceramic body, filling the via hole with the CRMC paste, drying the ceramic body including the CRMC paste to form a first CRMC material filling the via hole, forming a second via hole through the first CRMC material, providing a metal core in the second via hole, and subjecting the ceramic body including the first CRMC material and the metal core to a second sintering step to thereby form the dielectric body. The dielectric body is then sealed in a ferrule opening to form a feedthrough.

35 Claims, 110 Drawing Sheets

Related U.S. Application Data continuation-in-part of application No. 15/797,278, filed on Oct. 30, 2017, now Pat. No. 10,272,253.

(60) Provisional application No. 62/443,011, filed on Jan. 6, 2017, provisional application No. 62/450,187, filed on Jan. 25, 2017, provisional application No. 62/461,872, filed on Feb. 22, 2017, provisional application No. 62/552,363, filed on Aug. 30, 2017, provisional application No. 62/613,500, filed on Jan. 4, 2018.

(51) Int. Cl.
| | |
|---|---|
| *C04B 41/51* | (2006.01) |
| *H01B 17/30* | (2006.01) |
| *C04B 41/45* | (2006.01) |
| *C04B 41/88* | (2006.01) |
| *H01B 19/02* | (2006.01) |
| *B23K 1/00* | (2006.01) |
| *C04B 41/00* | (2006.01) |
| *B23K 1/008* | (2006.01) |
| *B23K 26/32* | (2014.01) |
| *B23K 26/21* | (2014.01) |
| *B22F 7/04* | (2006.01) |
| *B23K 101/36* | (2006.01) |
| *B23K 103/14* | (2006.01) |
| *B22F 7/08* | (2006.01) |

(52) U.S. Cl.
CPC ............ *B23K 1/19* (2013.01); *B23K 26/21* (2015.10); *B23K 26/32* (2013.01); *C04B 41/0072* (2013.01); *C04B 41/4578* (2013.01); *C04B 41/5122* (2013.01); *C04B 41/5177* (2013.01); *C04B 41/5194* (2013.01); *C04B 41/88* (2013.01); *H01B 19/02* (2013.01); *B22F 7/04* (2013.01); *B22F 7/08* (2013.01); *B23K 2101/36* (2018.08); *B23K 2103/14* (2018.08)

(56) References Cited

U.S. PATENT DOCUMENTS

| | | | |
|---|---|---|---|
| 3,617,830 | A | 11/1971 | Perna |
| 3,681,612 | A | 8/1972 | Kinzler et al. |
| 3,745,430 | A | 7/1973 | Kerr et al. |
| 3,871,382 | A | 3/1975 | Mann |
| 3,961,294 | A | 6/1976 | Hollyday |
| 3,968,802 | A | 7/1976 | Ballis |
| 3,980,975 | A | 9/1976 | Maxon et al. |
| 4,188,598 | A | 2/1980 | Hunt |
| 4,236,127 | A | 11/1980 | Scherba |
| 4,295,467 | A | 10/1981 | Mann et al. |
| 4,320,763 | A | 3/1982 | Money |
| 4,424,551 | A | 1/1984 | Stevenson et al. |
| 4,431,005 | A | 2/1984 | McCormick |
| 4,437,474 | A | 3/1984 | Peers-Trevarton et al. |
| 4,445,501 | A | 5/1984 | Bresler |
| 4,572,198 | A | 2/1986 | Codrington |
| 4,585,001 | A | 4/1986 | Belt |
| 4,633,181 | A | 12/1986 | Murphy-Boesch et al. |
| 4,643,186 | A | 2/1987 | Rosen et al. |
| 4,654,880 | A | 3/1987 | Sontag |
| 4,672,972 | A | 6/1987 | Berke |
| 4,689,621 | A | 8/1987 | Kleinberg |
| 4,712,555 | A | 12/1987 | Thornander et al. |
| 4,746,864 | A | 5/1988 | Satoh et al. |
| 4,754,752 | A | 7/1988 | Ginsburg et al. |
| 4,757,820 | A | 7/1988 | Itoh |
| 4,766,381 | A | 8/1988 | Conturo et al. |
| 4,799,499 | A | 1/1989 | Bisping |
| 4,813,429 | A | 3/1989 | Eshel et al. |
| 4,823,812 | A | 4/1989 | Eshel et al. |
| 4,832,023 | A | 5/1989 | Murphy-Chutorian et al. |
| 4,858,064 | A | 8/1989 | Segawa et al. |
| 4,858,623 | A | 8/1989 | Bradshaw et al. |
| 4,859,950 | A | 8/1989 | Keren |
| 4,932,411 | A | 6/1990 | Fritschy et al. |
| 4,940,052 | A | 7/1990 | Mann et al. |
| 4,960,106 | A | 10/1990 | Kubokawa et al. |
| 4,989,608 | A | 2/1991 | Ratner |
| 4,991,580 | A | 2/1991 | Moore |
| 5,019,075 | A | 5/1991 | Spears et al. |
| 5,039,965 | A | 8/1991 | Higgins |
| 5,044,375 | A | 9/1991 | Bach et al. |
| 5,052,404 | A | 10/1991 | Hodgson et al. |
| 5,063,348 | A | 11/1991 | Kuhara et al. |
| 5,095,911 | A | 3/1992 | Pomeranz |
| 5,099,208 | A | 3/1992 | Fitzpatrick et al. |
| 5,167,233 | A | 12/1992 | Eberle et al. |
| 5,178,618 | A | 1/1993 | Kandarpa |
| 5,190,046 | A | 3/1993 | Shturman |
| 5,197,468 | A | 3/1993 | Proctor et al. |
| 5,209,233 | A | 5/1993 | Holland et al. |
| 5,211,165 | A | 5/1993 | Dumoulin et al. |
| 5,217,010 | A | 6/1993 | Tsitlik et al. |
| 5,222,506 | A | 6/1993 | Patrick et al. |
| 5,246,438 | A | 9/1993 | Langberg |
| 5,251,120 | A | 10/1993 | Smith |
| 5,268,810 | A | 12/1993 | Dimarco et al. |
| 5,271,400 | A | 12/1993 | Dumoulin et al. |
| 5,272,283 | A | 12/1993 | Kuzma |
| 5,300,108 | A | 4/1994 | Rebell et al. |
| 5,306,291 | A | 4/1994 | Kroll et al. |
| 5,307,808 | A | 5/1994 | Dumoulin et al. |
| 5,307,814 | A | 5/1994 | Kressel et al. |
| 5,318,025 | A | 6/1994 | Dumoulin et al. |
| 5,323,776 | A | 6/1994 | Blakeley et al. |
| 5,323,778 | A | 6/1994 | Kandarpa et al. |
| 5,331,505 | A | 7/1994 | Wilheim |
| 5,333,095 | A | 7/1994 | Stevenson et al. |
| 5,334,045 | A | 8/1994 | Cappa et al. |
| 5,334,193 | A | 8/1994 | Nardella |
| 5,348,010 | A | 9/1994 | Schnall et al. |
| 5,352,979 | A | 10/1994 | Conturo |
| 5,358,515 | A | 10/1994 | Hurter et al. |
| 5,363,845 | A | 11/1994 | Chowdhury et al. |
| 5,365,928 | A | 11/1994 | Rhinehart et al. |
| 5,370,644 | A | 12/1994 | Langberg |
| 5,398,683 | A | 3/1995 | Edwards et al. |
| 5,400,787 | A | 3/1995 | Marandos |
| 5,404,880 | A | 4/1995 | Throne |
| 5,413,104 | A | 5/1995 | Buijs et al. |
| 5,419,325 | A | 5/1995 | Dumoulin et al. |
| 5,428,337 | A | 6/1995 | Vinclarelli et al. |
| 5,433,717 | A | 7/1995 | Rubinsky et al. |
| 5,434,358 | A | 7/1995 | Glahn et al. |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,447,156 | A | 9/1995 | Dumoulin et al. |
| 5,450,090 | A | 9/1995 | Gels et al. |
| 5,451,232 | A | 9/1995 | Rhinehart et al. |
| 5,462,055 | A | 10/1995 | Casey et al. |
| 5,466,254 | A | 11/1995 | Helland |

(56) References Cited

U.S. PATENT DOCUMENTS

| | | |
|---|---|---|
| 5,470,345 A | 11/1995 | Hassler et al. |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A * | 1/1999 | Haq .................. A61N 1/02 174/256 |
| 5,864,234 A | 1/1999 | Luedeke |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A * | 11/2000 | Haq .................. A61N 1/02 174/257 |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,275,379 B1 | 8/2001 | Sleboda et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |

(56) References Cited

U.S. PATENT DOCUMENTS

| | | |
|---|---|---|
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,680 B2 | 7/2004 | Carr et al. |
| 6,765,779 B2 | 7/2004 | Stevenson et al. |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,035,076 B1 | 4/2006 | Stevenson |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,136,273 B2 | 11/2006 | Stevenson et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,174,223 B2 | 2/2007 | Money et al. |
| 7,199,995 B2 | 4/2007 | Stevenson |
| 7,211,103 B2 | 5/2007 | Greenberg et al. |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,489,495 B2 | 2/2009 | Stevenson |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,535,693 B2 | 5/2009 | Stevenson et al. |
| 7,551,963 B2 | 6/2009 | Rusin et al. |
| 7,561,906 B2 | 7/2009 | Atalar et al. |
| 7,586,728 B2 | 9/2009 | Anthony |
| 7,593,208 B2 | 9/2009 | Anthony et al. |
| 7,623,335 B2 | 11/2009 | Stevenson et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,797,048 B2 | 9/2010 | Stevenson et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,131,376 B1 | 3/2012 | Greenberg et al. |
| 8,163,397 B2 | 4/2012 | Ok et al. |
| 8,179,658 B2 | 5/2012 | Stevenson et al. |
| 8,219,208 B2 | 7/2012 | Stevenson et al. |
| 8,301,249 B2 | 10/2012 | Min |
| 8,494,635 B2 | 7/2013 | Guebler et al. |
| 8,528,201 B2 | 9/2013 | Guebler et al. |
| 8,588,916 B2 | 11/2013 | Satou et al. |
| 8,653,384 B2 | 2/2014 | Tang et al. |
| 8,659,870 B2 | 2/2014 | Brendel et al. |
| 8,670,829 B2 | 3/2014 | Satou et al. |
| 8,755,887 B2 | 6/2014 | Troetzschel et al. |
| 8,763,245 B1 * | 7/2014 | Lucisano ............... H01L 23/10 29/842 |
| 8,841,558 B2 | 9/2014 | Satou et al. |
| 8,855,768 B1 | 10/2014 | Dabney et al. |
| 8,872,035 B2 | 10/2014 | Satou et al. |
| 8,874,206 B2 | 10/2014 | Malinowski et al. |
| 8,886,320 B2 | 11/2014 | Wollenberg et al. |
| 8,929,987 B2 | 1/2015 | Troetzschel et al. |
| 9,008,779 B2 | 4/2015 | Satou et al. |
| 9,014,808 B2 | 4/2015 | Dabney et al. |
| 9,032,614 B2 | 5/2015 | Specht |
| 9,233,253 B2 | 1/2016 | Stevenson et al. |
| 9,407,076 B2 | 8/2016 | Troetzschel et al. |
| 9,418,778 B2 | 8/2016 | Makino et al. |
| 9,480,168 B2 | 10/2016 | Troetzschel et al. |
| 9,492,659 B2 | 11/2016 | Brendel et al. |
| 9,552,899 B2 | 1/2017 | Glynn et al. |
| 2002/0027282 A1 | 3/2002 | Kawakami et al. |
| 2002/0055678 A1 | 5/2002 | Scott et al. |
| 2002/0095197 A1 | 7/2002 | Lardo et al. |
| 2002/0139556 A1 | 10/2002 | Ok et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |

(56) References Cited

U.S. PATENT DOCUMENTS

| | | |
|---|---|---|
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0190527 A1 | 9/2005 | Stevenson et al. |
| 2005/0195556 A1 | 9/2005 | Shah |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0028784 A1 | 2/2006 | Brendel |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0060969 A1 | 3/2007 | Burdon et al. |
| 2007/0060970 A1 | 3/2007 | Burdon et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Iyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0236861 A1 | 10/2007 | Burdon et al. |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2008/0314502 A1 | 12/2008 | Ok et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0259265 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023086 A1 | 1/2010 | Lim |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114246 A1 | 5/2010 | Hill et al. |
| 2010/0114276 A1 | 5/2010 | Min et al. |
| 2010/0114277 A1 | 5/2010 | Zhao et al. |
| 2010/0138192 A1 | 6/2010 | Min |

(56) References Cited

U.S. PATENT DOCUMENTS

| | | |
|---|---|---|
| 2010/0149042 A1 | 6/2010 | Utsi et al. |
| 2010/0151113 A1 | 6/2010 | Shelton |
| 2010/0160989 A1 | 6/2010 | Legay |
| 2010/0160991 A1 | 6/2010 | Lim |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2010/0241206 A1 | 9/2010 | Truex et al. |
| 2011/0000699 A1 | 1/2011 | Bealka et al. |
| 2011/0034965 A1 | 2/2011 | Troetzschel et al. |
| 2011/0043297 A1 | 2/2011 | Stevenson et al. |
| 2011/0048770 A1 | 3/2011 | Reiterer et al. |
| 2011/0048990 A1 | 3/2011 | Goda |
| 2011/0106205 A1 | 5/2011 | Reiterer et al. |
| 2011/0248184 A1 | 10/2011 | Shah |
| 2012/0006576 A1 | 1/2012 | Barry et al. |
| 2012/0193117 A1 | 8/2012 | Specht et al. |
| 2012/0197327 A1 | 8/2012 | Specht |
| 2012/0197335 A1 | 8/2012 | Reisinger |
| 2013/0032378 A1 | 2/2013 | Morioka et al. |
| 2013/0058003 A1 | 3/2013 | Iyer et al. |
| 2013/0138186 A1 | 5/2013 | Iyer et al. |
| 2013/0184796 A1 | 7/2013 | Marzano et al. |
| 2014/0151114 A1 | 6/2014 | Morioka et al. |
| 2014/0168850 A1 | 6/2014 | Stevenson et al. |
| 2015/0004359 A1 | 1/2015 | Shahbazi et al. |
| 2015/0283374 A1 | 10/2015 | Kronmueller et al. |
| 2015/0314131 A1 | 11/2015 | Marzano et al. |
| 2015/0343224 A1 | 12/2015 | Woods et al. |
| 2016/0151635 A1 | 6/2016 | Frysz et al. |
| 2018/0126175 A1 | 5/2018 | Seitz et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0697725 | 2/1996 |
| EP | 0498996 | 3/1997 |
| EP | 1021730 | 4/2003 |
| EP | 0930509 | 3/2004 |
| EP | 1469910 | 12/2006 |
| EP | 1883449 | 1/2009 |
| EP | 2025361 | 2/2009 |
| EP | 2392382 | 12/2011 |
| FR | 2811900 B1 | 2/2003 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2001068958 | 3/2001 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

European Search Report, Application No. 13151536.3, dated Jun. 13, 2013.
European Search Report, Application No. 13151537.1, dated Jun. 24, 2013.
European Search Report, Application No. 13151537.1, dated Jul. 11, 2013.
European Search Report, Application No. 15165863.0, dated Sep. 12, 2016.
European Search Repor, Application No. 18150642.9, dated Jun. 6, 2018.
European Search Report, Application No. 12157697.9, dated Jul. 5, 2012.
Extended European Search Report, Application 17201160.3 dated Apr. 16, 2018.
Extended European Search Report, Application No. 16175505.3, dated Nov. 15, 2016.
Extended European Search Report, Application No. 18177098.3, dated Aug. 8, 2018.
"Holy Stone Enterprise", Ceramic Capacitor Catalog 2008-2009, May 2008.
"Wikipedia article", EIA Class 1 dielectric., Sep. 13, 2006.
Balanis, "Advanced Engineering Electromagnetics", 1989.
Lamouri, et al., "Control of the y-alumina to a-alumina phase transformation for an optimized alumina densification", Boletin de la Sociedad Espanola De Ceramica Y Vidrio 56 (2017) pp. 47-54.
Lu, et al., "Pt—Al2O3 interfacial bonding in implantable hermetic feedthroughs: Morphology and orientation", Society for Biomaterial—2011 Wiley Periodicals, Inc., Dec. 24, 2011, 817-824.
Luchinger, "Safety Aspects of Cardiac Pacemakers in Magnetic Resonance Imaging", A dissertation submitted to the Swiss Federal Institute of Technology Zurich, Switzerland, 2002.
Olenick, "Ultrathin Flexible Ceramics for Electronics Applications", www.ceramicindustry.com—Product Profile, Oct. 2016, pp. 30 and 31.
Roguin, et al., "Modern Pacemaker and Implantable Cardioverter/Defibrillator systems Can Be Magnetic Resonance Imaging Safe", Journal of the American Heart Association, Aug. 4, 2004, 475-482.
Sakabe, et al., "High Frequency Performance of Multilayer Ceramic Capacitors", Electronic Components and Technology Confrence, 1995, Proceedings 45th, May 21, 1995, 234-240.
Sarda, et al., "Ceramic EMI Filters—A Review", American Ceramic Society Bulletin; vol. 67, No. 4, 1988, 737-746.
Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.
Shellock, "MRI Issues for Neuromodulation Devices", Institute for Magnetic Resonance Safety Education, and Research (IMRSER).
Susil, et al., "Multifunctional Interventional Devices for MRI: A Combined Electrophysiology/MRI Catheter", 2002, 594-600.

(56) References Cited

OTHER PUBLICATIONS

Susil, et al., "U.S. Appl. No. 60/283,725", Multifunctional Interventional Devices for Use in MRI, filed Apr. 13, 2001.
Weiner, et al., "U.S. Appl. No. 60/269,817", Electromagnetic Interference immune Cardiac Assist System, Feb. 20, 2001.
Wilk, et al., "High-K Gate Dielectrics: Current Status and Materials Properties Considerations", Journal of Applied Physi s, vol. 89, No. 10, May 15, 2001, 5243-5275.
Becker, "Die Keimbildung Bei Der Ausscheidung in Metallischen Mischkristallen", Published in Annalen der Physik, Issue 5, vol. 32, 1938, pp. 128-140.
Boser, et al., "High Frequency Behavior of Ceramic Multilayer Capacitors", IEEE Transactions on Components, Hybrids, and Manufacturing Technology, vol. CHMT-10, No. 3, Sep. 1987, 437-439.
Clement, et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.
Ennis, et al., "Cautions About the Use of Equivalent Series Resistance (ESR) in Specifying Capacitors", Mar. 8, 1993, 58-64.
European Search Report, Application No. 10167031.3, dated Sep. 19, 2012.
European Search Report, Application No. 10167045.3, dated Oct. 10, 2012.
Gabriel, et al., "The Dielectric Properties of Biological Tissues: II.", Measurements in the Frequency Range 10 Hz to 20 GHz, Apr. 2, 1996, 2251-2269.
Gabriel, et al., "The Dielectric Properties of Biological Tissues: Parametric Models for the Dielectric Spectrum of Tissues", Parametric Models for the Dielectric Spectrum of Tissues, Phys. Med. Bio. 41, 1996, 2271-2291.
Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.
Karbasi, "Developing a High Density PT/Alumina Hermetic Feedthrough", Florida International University, FIU Digital Commons, FIU Electronic Theses and Dissertations, University Graduate School, Published Jun. 15, 2012.
Kingery, et al., "Atom Mobility in Introduction to Ceramics, 2nd Edition", Published in New York, Wiley, copyright 1976, pp. 217-263.
Kingery, et al., "Surfaces, Interfaces, and Grain Boundaries in Introduction to Ceramics", 2nd Edition, Published in New York, Wiley, copyright 1976, pp. 177-215.
Konings, et al., "Heating Around Intravascular Guidewires by Resonating RF Waves", Journal of Magnetic Resonance Imaging, 2000, 79-85.
Extended European Search Report, Application No. 19179547.5, dated Jul. 11, 2019.

* cited by examiner

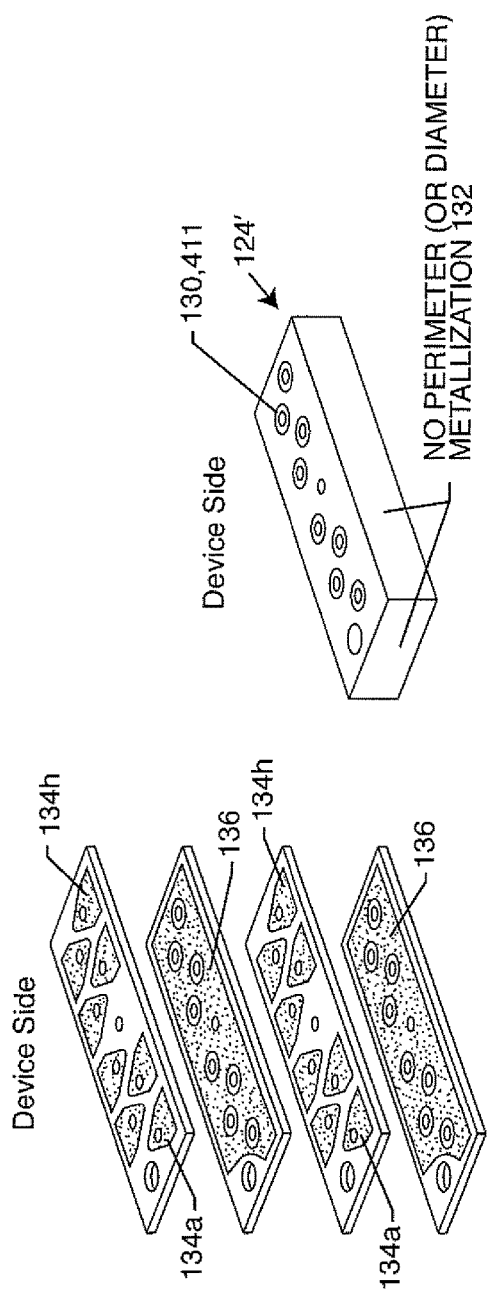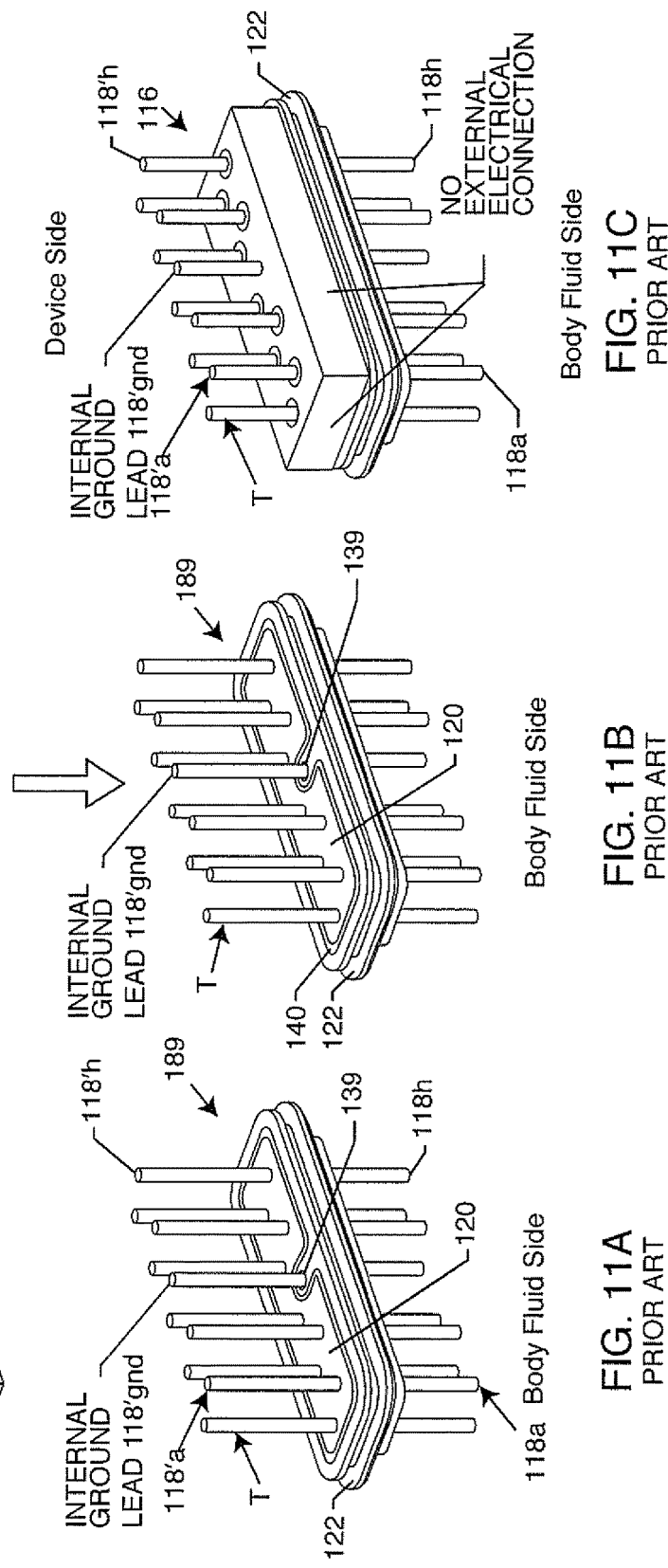
FIG. 11A PRIOR ART
FIG. 11B PRIOR ART
FIG. 11C PRIOR ART

OPTION 1

OPTION 1A

OPTION 2

OPTION 2A

OPTION 2B

OPTION 2B

OPTION 2C

OPTION 2C

OPTION 2D

OPTION 2D

OPTION 2E

OPTION 2F

OPTION 2G

OPTION 2H

OPTION 2I

OPTION 2J

OPTION 3

OPTION 3A

OPTION 3B

OPTION 3C

OPTION 3D

OPTION 3E

OPTION 3D

OPTION 3E

OPTION 3D

OPTION 3E

OPTION 4

OPTION 4A

OPTION 4

OPTION 4A

OPTION 5

OPTION 5A

OPTION 5B

OPTION 5C

OPTION 6

OPTION 6A

STEP 1

STEP 2

STEP 3A

STEP 3B

STEP 4

STEP 5

STEP 6
& STEP 7

DEVICE SIDE

BODY FLUID SIDE

DEVICE SIDE

BODY FLUID SIDE

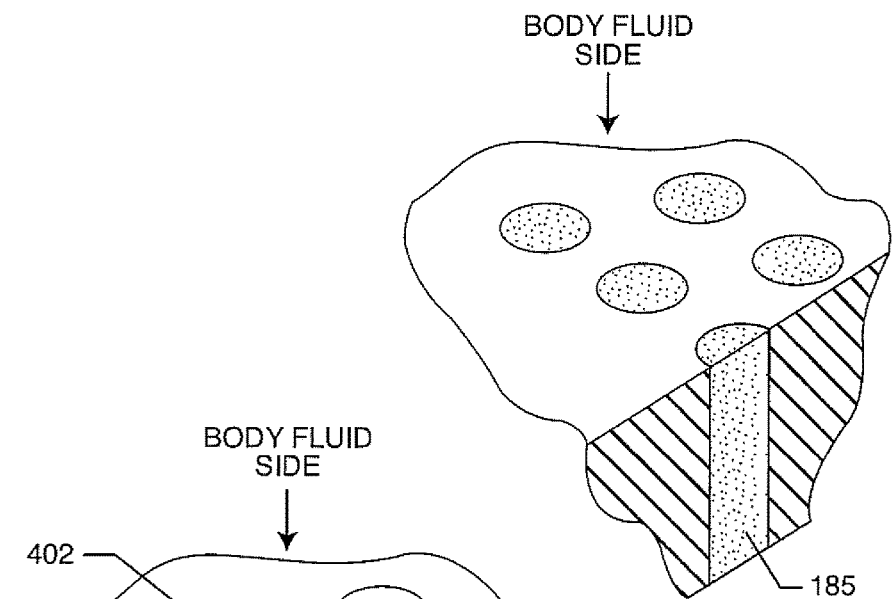
FIG. 104
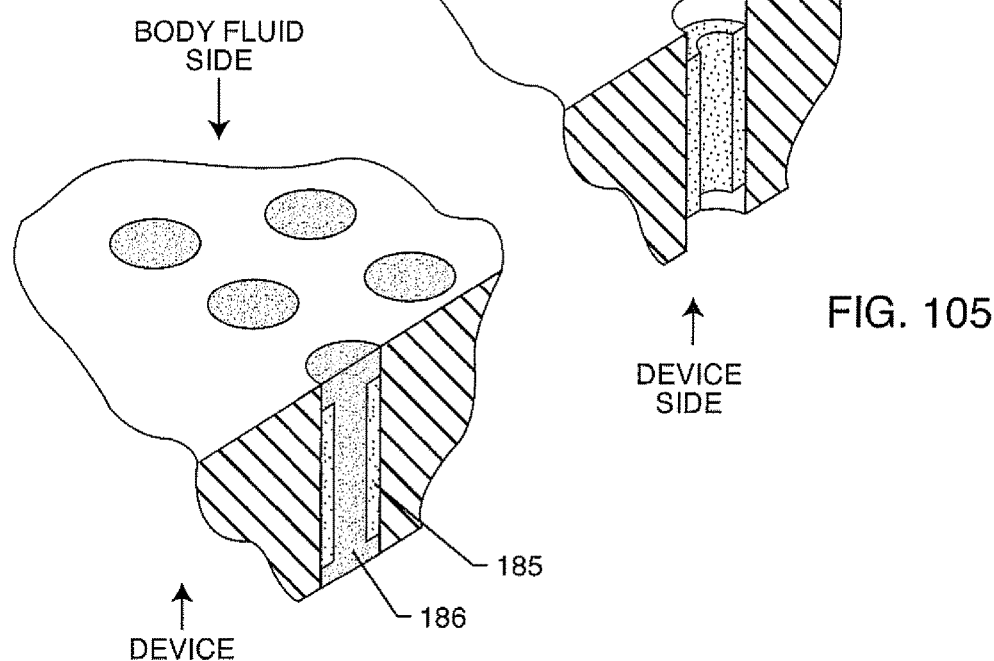
FIG. 105
FIG. 106

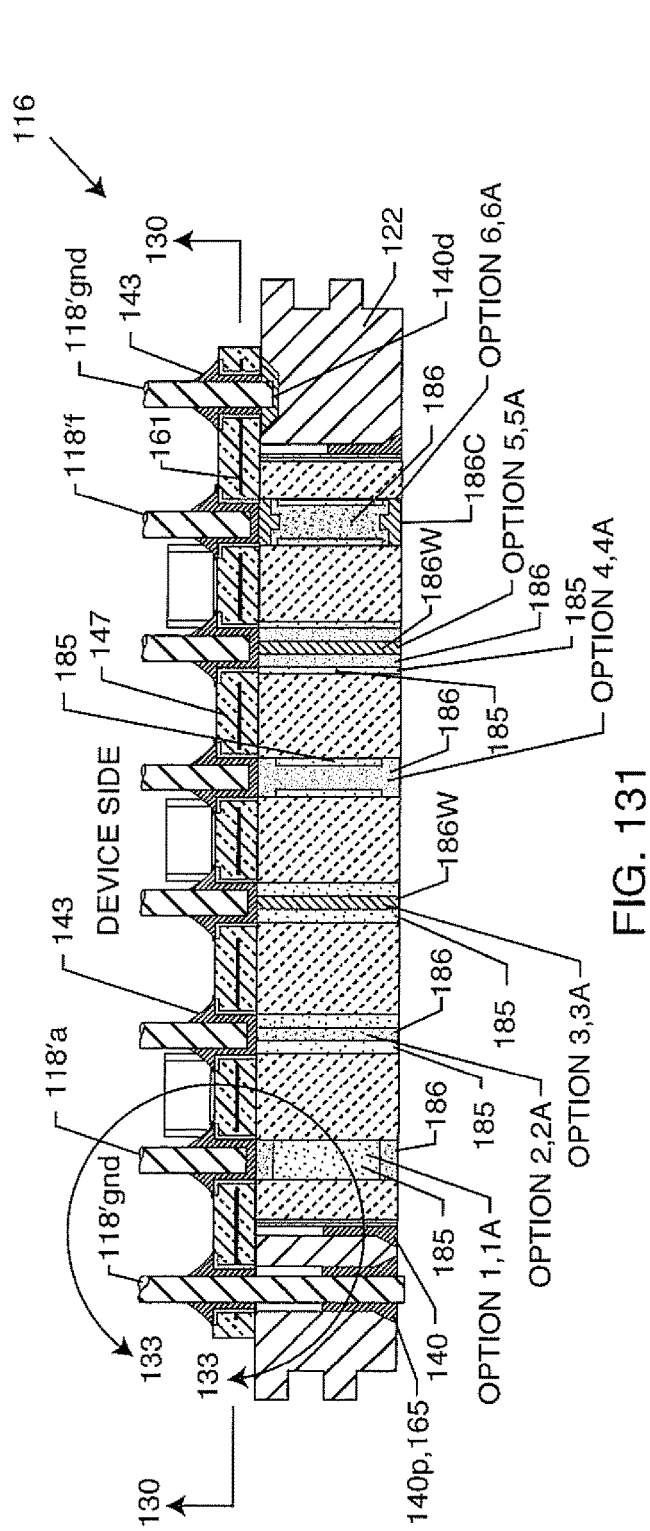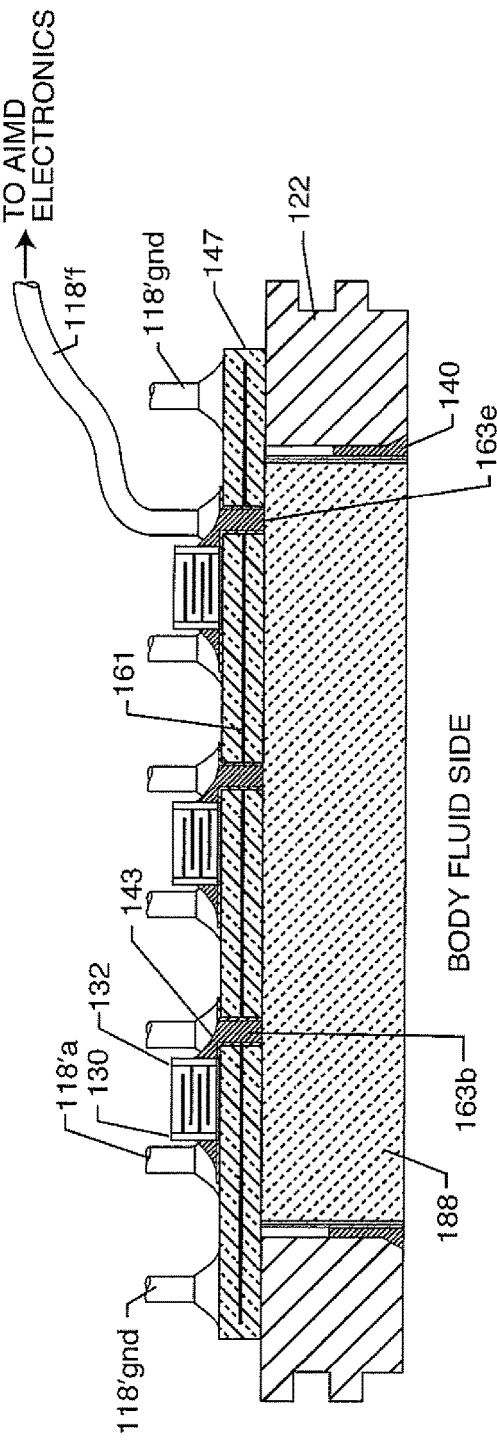

OPTION 1

OPTION 1A

OPTION 2

OPTION 2A

OPTION 2B

OPTION 2B

OPTION 2C

OPTION 2C

OPTION 2G

OPTION 2H

OPTION 3

OPTION 3A

OPTION 3B

OPTION 3C

OPTION 4

OPTION 4A

OPTION 5

OPTION 5A

OPTION 5B

OPTION 5C

OPTION 6

OPTION 6A

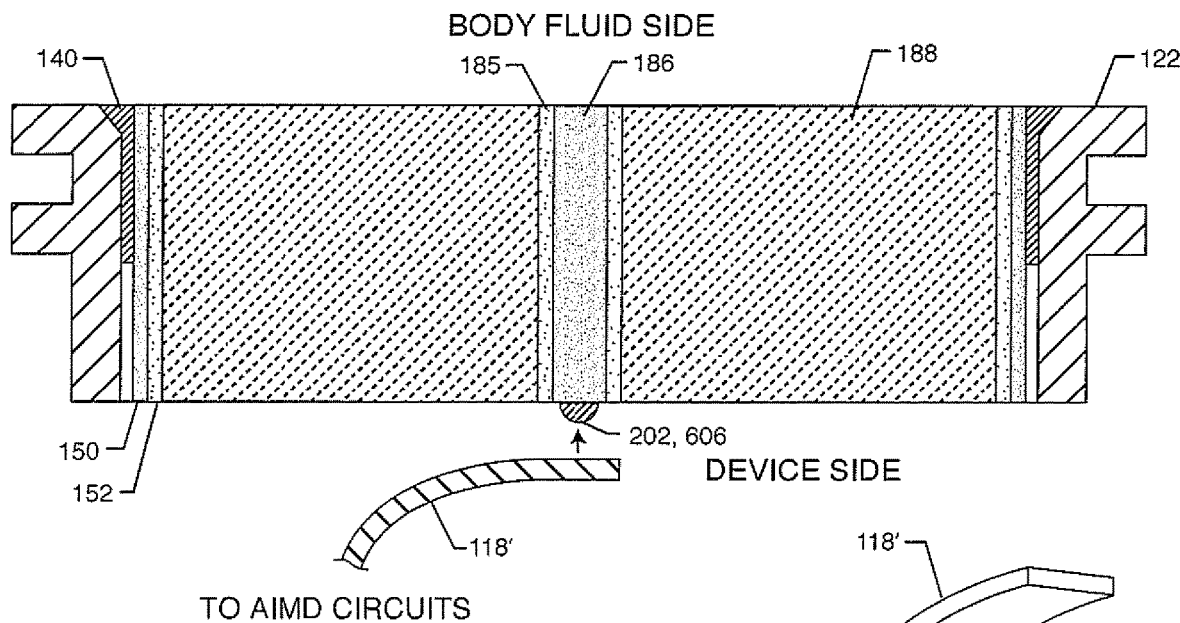
FIG. 172
FIG. 172A
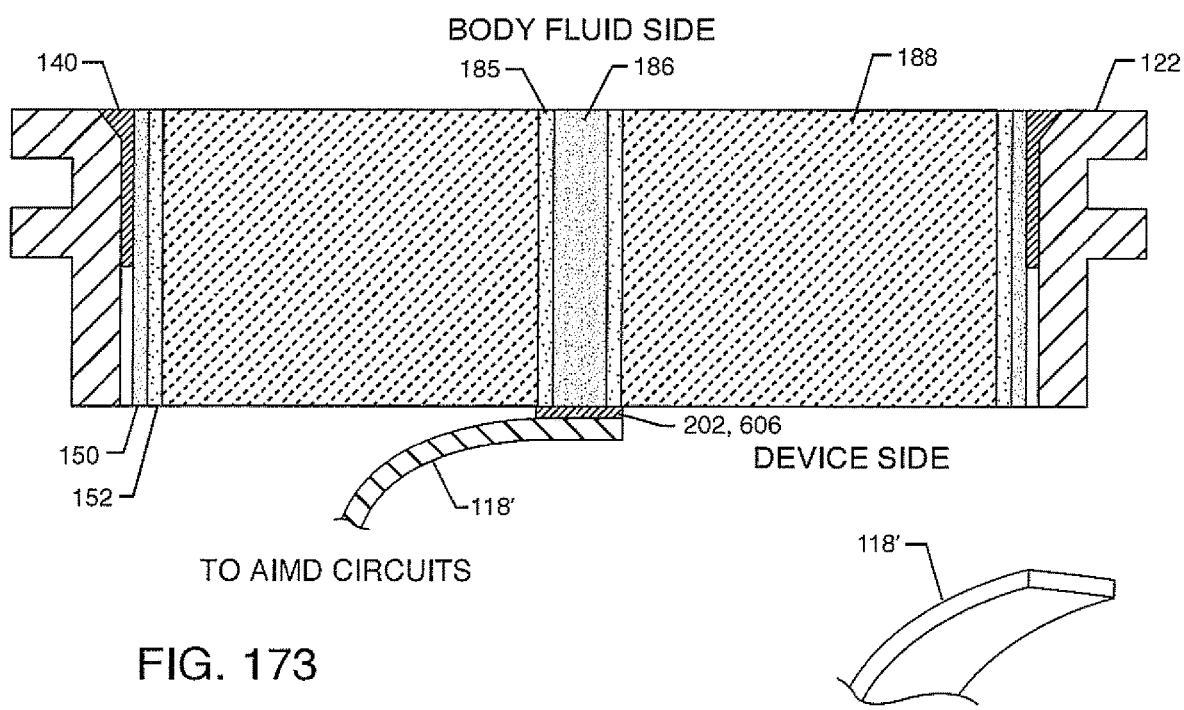
FIG. 173
FIG. 173A

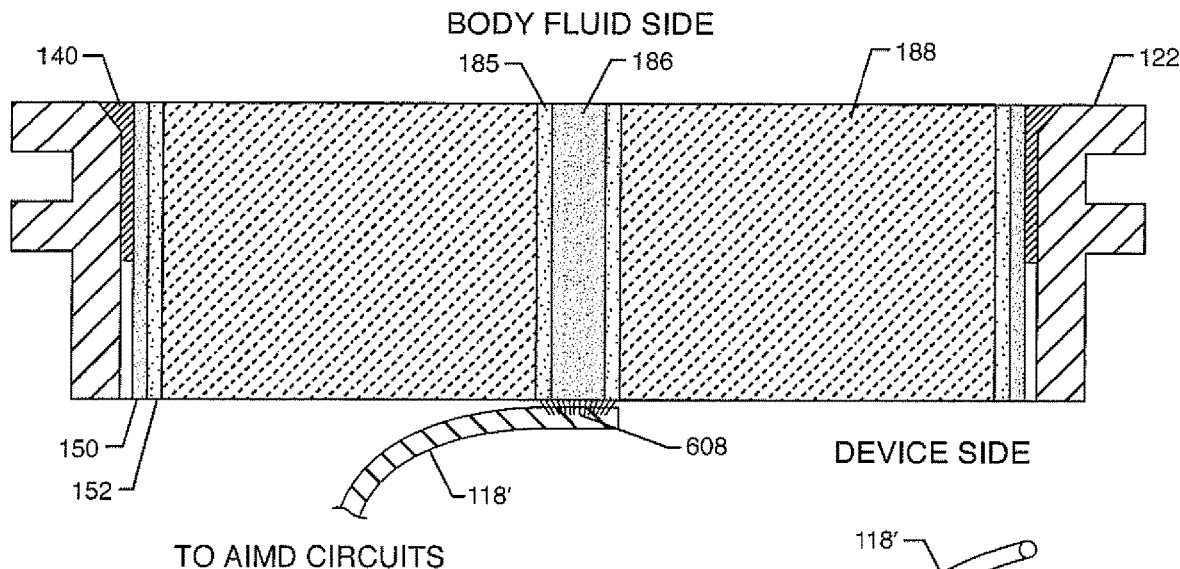
FIG. 174
FIG. 174A
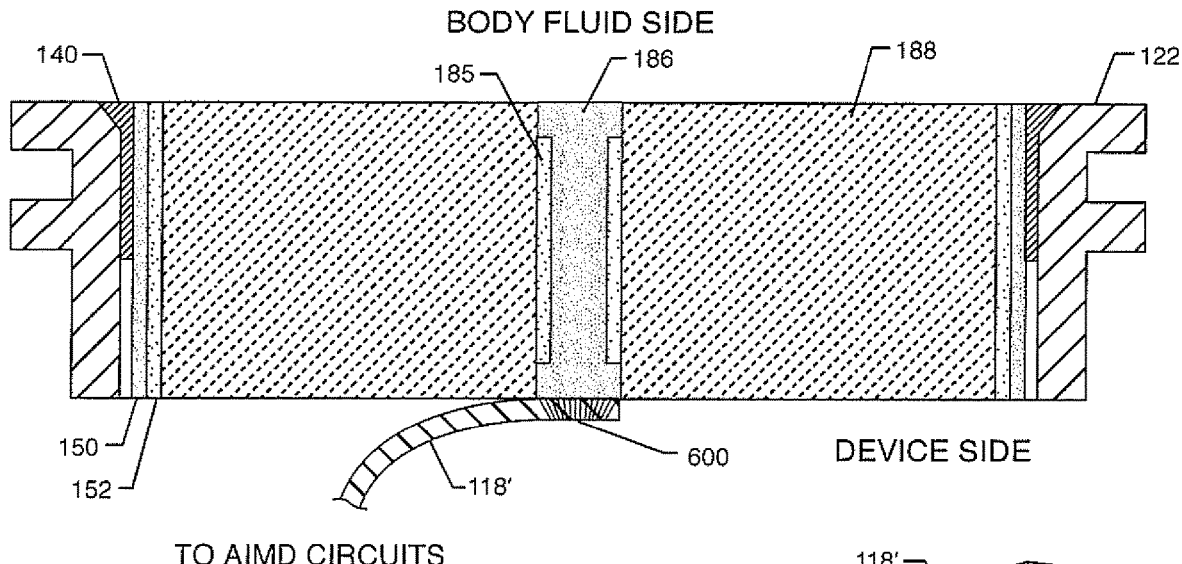
FIG. 175
FIG. 175A

PROCESS FOR MANUFACTURING A LEADLESS FEEDTHROUGH FOR AN ACTIVE IMPLANTABLE MEDICAL DEVICE

CROSS-REFERENCE TO RELATED APPLICATIONS

The present application is a continuation of U.S. application Ser. No. 15/863,194, filed on Jan. 5, 2018, now U.S. Pat. No. 10,249,415, which is a continuation-in-part application of U.S. application Ser. No. 15/797,278, filed on Oct. 30, 2017, now U.S. Pat. No. 10,272,253, which claims priority to U.S. provisional application Ser. No. 62/443,011, filed on Jan. 6, 2017; 62/450,187, filed on Jan. 25, 2017; 62/461,872, filed on Feb. 22, 2017; 62/552,363, filed on Aug. 30, 2017, and 62/613,500, filed on Jan. 4, 2018, the contents of which are fully incorporated herein by reference.

FIELD OF THE INVENTION

The present invention generally relates to implantable medical devices and hermetic terminal subassemblies. More particularly, the present invention relates a hermetic terminal for an active implantable medical device having a composite co-fired filled via with a brazed body fluid side leadwire.

BACKGROUND OF THE INVENTION

A wide assortment of active implantable medical devices (AIMDs) are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue.

The hermetic terminal or feedthrough of these implantable devices is considered critical. Hermetic terminals or feedthroughs are generally well-known in the art for connecting electrical signals through the housing or case of an AIMD. For example, in implantable medical devices such as cardiac pacemakers, implantable cardioverter defibrillators, and the like, a hermetic terminal comprises one or more conductive pathways which may include conductive terminal pins, conductive filled vias, leadwires and the like supported by an insulative structure for feedthrough passage from the exterior to the interior of an AIMD electromagnetic shield housing. Hermetic terminals or feedthroughs for AIMDs must be biocompatible as well as resistant to degradation under applied bias current or voltage (biostable). Hermeticity of the feedthrough is imparted by judicious material selection and carefully prescribed manufacturing processing. Sustainable hermeticity of the feedthrough over the lifetime of these implantable devices is critical because the hermetic terminal intentionally isolates the internal circuitry and components of the device (AIMD) from the external body fluid environment to which the component is exposed. In particular, the hermetic terminal isolates the internal circuitry, connections, power sources and other components in the device from ingress of body fluids. Ingress of body fluids into an implantable medical device is known to be a contributing factor to device malfunction and may contribute to the compromise or failure of electrical circuitry, connections, power sources and other components within an implantable medical device that are necessary for consistent and reliable device therapy delivery to a patient. Furthermore, ingress of body fluids may compromise an implantable medical device's functionality which may constitute electrical shorting, element or joint corrosion, metal migration or other such harmful consequences affecting consistent and reliable device therapy delivery.

In addition to concerns relative to sustained terminal or feedthrough hermeticity, other potentially compromising conditions must be addressed, particularly when a hermetic terminal or feedthrough is incorporated within an implantable medical device. For example, the hermetic terminal or feedthrough pins are typically connected to one or more lead conductors of implantable therapy delivery leads. These implantable therapy delivery leads can effectively act as antennas that receive electromagnetic interference (EMI) signals. Therefore, when these electromagnetic signals enter within the interior space of a hermetic implantable medical device, facilitated by the therapy delivery leads, they can negatively impact the intended function of the medical device and as a result, negatively impact therapy delivery intended for a patient by that device. EMI engineers commonly refer to this as the "genie in the bottle" effect. In other words, once the genie (i.e., EMI) is inside the hermetic housing of the device, it can wreak havoc with electronic circuit functions by cross-coupling and re-radiating within the device.

Another particularly problematic condition associated with implanted therapy delivery leads occurs when a patient is in an MRI environment. In this case, the MRI RF electrical currents imposed on the implanted therapy delivery leads can cause the leads to heat to the point where tissue damage is likely. Moreover, MRI induced RF currents (electromagnetic interference—EMI) may be coupled to implanted therapy delivery leads resulting in undesirable electrical currents which can enter the AIMD and can disrupt or damage the sensitive electronics within the implantable medical device.

Therefore, materials selection and fabrication processing parameters are of utmost importance in creating a hermetic terminal (or feedthrough) or a structure embodying a hermetic terminal (or feedthrough), that can survive anticipated and possibly catastrophically damaging environmental conditions and that can be practically and cost effectively manufactured.

In general, hermetic terminal subassemblies for AIMDs comprise a titanium ferrule and a gold brazed alumina insulator. Alternatively, hermetic terminals may comprise a ferrule and a compression or fusion glass seal. Hermetic terminals or feedthrough assemblies utilizing ceramic dielectric materials may fail in a brittle manner. A brittle failure typically occurs when the ceramic structure is deformed elastically up to an intolerable stress, at which point the ceramic fails catastrophically. Most brittle failures occur by crack propagation in a tensile stress field. Even microcracking caused by sufficiently high tensile stress concentrations may result in a catastrophic failure including loss of hermeticity identified as critical in hermetic terminals for implantable medical devices. Loss of hermeticity may be a result of design aspects such as a sharp corner which creates a stress riser, mating materials with different coefficient of thermal expansion (CTE) that generate tensile stresses that ultimately result in loss of hermeticity of the feedthrough or interconnect structure.

In the specific case of hermetic terminal or feedthrough designs, a tensile stress limit for a given ceramic based hermetic design structure cannot be specified because failure stress in these structures is not a constant. As indicated above, variables affecting stress levels include the design itself, the materials selection, symmetry of the feedthrough, and the bonding characteristics of mating surfaces within the feedthrough. Hence, length, width and height of the overall ceramic structure matters as do the number, spacing, length and diameter of the conductive pathways (vias, terminal pins, leadwires, etc.) in that structure. The selection of the mating materials, that is, the material that fills the vias (or leadwire) and the material that forms the base ceramic, are important. Finally, the fabrication processing parameters, particularly at binder burnout, sintering and cool down, make a difference. When high reliability is required in an application such as indicated with hermetic terminals or feedthroughs for AIMDs, to provide insurance for a very low probability of failure it is necessary to design a hermetic terminal assembly or feedthrough structure so that stresses imparted by design, materials and/or processing are limited to a smaller level of an average possible failure stress. Further, to provide insurance for a very low probability of failure in a critical ceramic based assembly or subassembly having sustainable hermetic requirements, it is also necessary to design structures embodying a hermetic terminal or feedthrough such that stresses in the final assembly or subassembly are limited to a smaller level of an average possible failure stress for the entire assembly or subassembly. In hermetic terminals and structures comprising hermetic terminals for AIMDs wherein the demand for biocompatibility exists, this task becomes even more difficult.

The most critical feature of a feedthrough design or any terminal subassembly is the metal/ceramic interface within the feedthrough that establishes the hermetic seal. One embodiment of the present invention therefore provides where a hermetic feedthrough comprising a monolithic alumina insulator substrate within which a platinum, palladium or the like conductive pathway or via resides or wherein a metallic leadwire (terminal pin) resides. More specifically in the case of a filled via, the present invention provides a hermetic feedthrough in which the hermetic seal is created through the intimate bonding of a CERMET (ceramic metal) or a platinum metal residing within the alumina substrate. As used herein, the hermetic seal insulator is synonymous with a hermetic seal base body and a hermetic seal ceramic body.

A traditional ceramic-to-metal hermetic terminal is an assembly of three components: electrical conductors (leadwires, pins, terminal pins, filled vias) that conduct electrical current, a ceramic insulator, and a metal housing, which is referred to as the flange or the ferrule (or even the AIMD housing itself). Brazed joints typically hermetically seal the metal leadwires and the flange or ferrule to the ceramic insulator. For a braze-bonded joint, the braze material is generally intended to deform in a ductile manner in order to compensate for perturbations that stress the bond between the mating materials as the braze material may provide ductile strain relief when the thermal expansion mismatch between the ceramic and metal is large. Thus, mating materials with large mismatches in CTE can be coupled through braze materials whose high creep rate and low yield strength reduce the stresses generated by the differential contraction existing between these mating materials. Glass seals are also known in the art, which form a hermetic seal to the ferrule and one or more leadwires passing through the glass seal.

Regarding EMI, a terminal or feedthrough capacitor EMI filter may be disposed at, near or within a hermetic terminal or feedthrough resulting in a feedthrough filter capacitor which diverts high frequency electrical signals from lead conductors to the housing or case of an AIMD. Many different insulator structures and related mounting methods are known in the art for use of feedthrough capacitor EMI filters in AIMDs, wherein the insulative structure also provides a hermetic terminal or feedthrough to prevent entry of body fluids into the housing of an AIMD. In the prior art devices, the hermetic terminal subassembly has been combined in various ways with a ceramic feedthrough filter EMI capacitor to decouple interference signals to the housing of the medical device.

In a typical prior art unipolar construction (as described in U.S. Pat. No. 5,333,095 and herein incorporated by reference), a round/discoidal (or rectangular) ceramic feedthrough EMI filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates are electrically connected at an inner diameter cylindrical surface of the coaxial capacitor structure to the conductive terminal pin utilized to pass the desired electrical signal or signals. The other or second set of electrode plates are coupled at an outer diameter surface of the round/discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metalized layer which is fired, sputtered or plated onto the ceramic capacitor. This metalized band, in turn, is coupled to the ferrule by conductive adhesive, soldering, brazing, welding, or the like. The inner feedthrough capacitor electrode plate sets (or "active" plates) are coupled in parallel together by a metalized layer which is either glass frit fired or plated onto the ceramic capacitor. This metalized band, in turn, is mechanically and electrically coupled to the lead wire(s) by conductive adhesive, soldering, or the like. In operation, the coaxial capacitor permits passage of relatively low frequency biologic signals along the terminal pin, while shielding and decoupling/attenuating undesired interference signals of typically high frequency to the AIMD conductive housing. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the ferrule of the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

Therefore, it is very common in the prior art to construct a hermetic terminal subassembly with a feedthrough capacitor attached near the inside of the AIMD housing on the device side. The feedthrough capacitor does not have to be made from biocompatible materials because it is located on the device side inside the AIMD housing. The hermetic terminal subassembly includes conductive pathways (leadwires, pins, terminal pins, filled vias, etc.) to hermetically pass through the insulator in non-conductive relation with the ferrule or the AIMD housing. As used herein, a "pathway" is synonymous with a via and a via hole. As used herein, a conductive pathway is defined as comprising a via or a via hole that is filled and then co-sintered to form the conductive pathway. The conductive pathways also pass through the feedthrough hole of the capacitor to electronic circuits disposed inside of the AIMD housing. These leadwires are typically electrically continuous and, on the body fluid side, must be biocompatible and non-toxic. Generally, these conductive pathways are constructed of platinum or platinum-iridium, palladium or palladium-iridium, niobium pins or filled vias with conductive powders, ceramics, gradient materials or the like. Platinum-iridium is an ideal choice because it is biocompatible, non-toxic and is also mechanically very strong. The iridium is added to enhance material stiffness and to enable the hermetic terminal subassembly leadwire to sustain bending stresses. An issue with the use of platinum for leadwires is that platinum has become extremely expensive and may be subject to premature fracture under rigorous processing such as ultrasonic cleaning or application use/misuse, possibly unintentional damaging forces resulting from Twiddler's Syndrome. Twiddler's Syndrome is a situation documented in the literature where a patient will unconsciously or knowingly twist the implantable device to the point where attached leads may even fracture.

For high density feedthroughs, leadwires are an expensive solution and paste-filled vias have sustainable hermeticity issues related to coefficient of thermal expansion (CTE) mismatching between the ceramic insulator and the metal fill materials caused by post-sinter cracking. Cracking can be imminent, produced during device assembly, or latently, the latter of which is most dangerous as latent hermetic failures are unpredictable.

Manufacturers of implantable medical devices are looking to reduce overall device volume with increased functionality. This will require implantable feedthroughs to possess significantly increased conductive pathway counts with less overall volume while maintaining/improving existing product reliability. Reducing the volumes of the existing feedthrough technology has been limited by the prior art processes for ceramic insulator manufacturing. Solid pellet ceramic insulators for implantable feedthroughs have been historically manufactured using dry pressing technologies. Dry pressing requires significant thickness and webbing between vias to withstand ejection from pressing die and core rods. Multi-layer laminate ceramic insulators are produced follow a process that punches vias into each layer, fills metal into each layer, collates the layers and then undergoes lamination of the collated layers, which typically involves registration and alignment issues that result in reduced volumetric efficiency and potentially higher via resistivities. The prior technology also requires catch pads to address misalignment (see FIG. 168).

Accordingly, what is needed is an improved structure and method of a hermetic seal assembly to provide a lower cost solution while satisfying all the normal standards and regulations on hermetic feedthroughs. The present invention provides these benefits and other benefits as discussed hereinafter.

SUMMARY OF THE INVENTION

The present invention offers a novel hermetic ceramic feedthrough structure and new double drilled (or multi-drilled) forming process for an Active Implantable Medical Device (AIMD) that offers design options in addition to brazed wires and uses platinum and platinum/alumina co-fire materials as the active conductive pathways through the alumina ceramic insulator. As will be shown, there may be multiple conductive pathway structural options through the insulator from one (unipolar), two (bipolar) . . . to n-polar. For neurostimulator applications, hundreds of pathways may be required. As described herein, double drilling means that the insulator is first drilled in the green (pre-sintered) state to form a pathway from a first side to a second side that is then filled with a Ceramic Reinforced Metal Composite (CRMC). The first or second side may be disposed to a hermetic feedthrough body fluid side or device side. Next is a second drilling step that forms a hole in the center of the CRMC that is then filled with a substantially pure metal core. In an embodiment, the insulator may be substantially pure alumina, the CRMC may comprise alumina and platinum and the substantially pure metal core may comprise substantially pure platinum. As will be described, the substantially pure metal core may include enlarged platinum contact areas (counterbores/countersinks) and the like. The novel CRMC forming process includes heat treating or pre-sintering the platinum and alumina to create a composite construct. This CRMC construct is then ball milled (or ground down) to a fine powder blend to which solvents and binders are added to form a flowable paste or ink for filling the pathway. The CRMC pre-sintering and ball milling steps are essential for the alumina-platinum material to reach a thermally stable phase. As used herein, the "thermally stable phase" is defined as a physical state, when under the action of temperature, a phase transformation of structural origin between two solid phases does not occur. Examples of factors that induce a thermally stable phase include temperature, stress (such as ball-milling or grinding), and combinations thereof. During pre-sintering, the CRMC displays various phases that manifest themselves as contractions and expansions until the CRMC reaches a thermally stable phase at >1000° C. Pre-sintering may be conducted on CRMC powders, pastes, inks and the like. Once a thermally stable phase is achieved, the CRMC is ball milled into a particle size and distribution that, when the paste/ink is prepared, the rheology facilitates via filling. The milling mode is fundamentally important for the final sintering process in that milling generates significant amounts of microstructural defects that lower activation energies of transformation by promoting nucleation and diffusion in the composite.

Thermal stability is critical for sustained feedthrough hermeticity. Through one experiment and dilatometry study, the inventors have determined that during pre-sintering temperature rise, the CRMC exhibits an initial shrinkage exhibited by a first phase transformation followed by a rapid expansion due to a second phase transformation and another shrinkage exhibited by a third phase transformation which is its thermally stable phase. It will be understood that although three main phase transformations were identified in this testing, under differing test conditions, either additional secondary or tertiary transformations or transformations less than three as observed in said testing may occur. In any event, pre-sintering the CRMC is essential in that dramatic expansion/contraction volume changes associated with phase transformations are avoided during final co-firing thereby mitigating development of undesirable residual stresses that preclude sustained hermeticity after final co-firing. As used herein, co-firing is synonymous with sintering. It will be appreciated that pre-sintering and ball milling (grinding down) a substantially pure ceramic construct can also be done to further enhance structural stability of a pressed powder or laminated multi-layer insulator (base body) structures during final binder burn-out and sintering.

The present invention advantageously affords significantly smaller conductive pathways/vias, smaller overall ceramic volume, tighter pitch between vias, increased via pitch count, robust hermetic via configurations, thinner and overall smaller hermetic feedthrough structural volumes, less costly hermetic feedthrough options and BGA attachment of both three terminal and two terminal capacitors Additionally the new ceramic forming process enables direct injection of precious metal (platinum) into the ceramic vias in the green state preventing the need for metallizing vias, and providing an alternative to leadwire assembly and brazing following ceramic sintering. The purpose of this invention is to create a next generation hermetic feedthrough for Cardiac Rhythm Management (CRM) and Neuromodulation devices with significantly higher conductive pathway counts, smaller volumes and increased product reliability. Additionally, the present invention offers an alternative to brazed wires, expanding active implantable medical device feedthrough design options. Among these options are platinum and platinum/alumina co-fire materials as the active pathways in the alumina ceramic insulator and combinations of co-fired wires, plugs, pins, nailheads, clips or other solid metal components co-fired within platinum and platinum/alumina co-fire materials as alternative active pathways in the alumina ceramic insulator. The change in ceramic forming technology enables all of the advantages discussed above.

The prior art fails to explain a hermetic feedthrough insulator manufacturing process that laminates all the layers first and then machines vias, counterbores, cavities and the ceramic outer diameter of the insulator after lamination. All prior art multi-layer ceramic insulators involve processes that punch vias into each layer, fills metal into each layer, collates the layers and then laminates the layers. By first laminating and then machinging the vias, the present invention creates very uniform vias that resolve prior art registration issues and eliminates the prior art need for traces on layers or catch pads between vias to ensure connection. These prior art necessities significantly reduce current carrying capacity and demonstrate significant variation via to via and part to part all of which stress optimal performance of implantable devices and sometimes precludes use of these prior art feedthroughs in demanding applications such as cardioverters/defibrillators that deliver high voltage and high current shock. The double or multi-drilling aspect of the present invention provides for vias that have similar current carrying capacity compared to wire and provides for very little variation between via to via and part to part.

Prior art uses cermet as the only conductor through the insulator. Using cermets as the sole conducting material is overly resistive in comparison to traditional high purity Pt/Ir pins. Additionally cermet filled vias are very difficult to weld or solder to because of oxide (alumina) content. The present invention utilizes a CRMC as a CTE transition layer between a substantially pure platinum core and a substantially pure alumina, thereby preserving attachment while preventing cracks and loss of hermeticity from thermal shocks, such as customer laser welding of the hermetic seal subassembly in the opening of the AIMD housing. Moreover, the use of the pure platinum core maintains the same conductivity as existing pure pin technology and enables soldering and welding making this novel structure available for demanding applications like cardioversion/defibrillation and neuromodulation devices having extremely high conductive pathway counts. Lastly, the prior art includes feedthroughs with wires/conductive pathways that range in size from 0.008" to 0.020" in size. The present invention enables conductive pathways/vias of any size including pure metal vias in hermetic medical feedthroughs that are less than 0.008" in size and greater than or equal to 0.001" in size.

As best shown in FIGS. 165, 31 and 32 an exemplary embodiment of the present invention for a method of manufacturing a feedthrough dielectric body for an active implantable medical device comprises the steps of: a) forming an alumina insulator otherwise known as a ceramic body 188 in a green state FIG. 32, or, stacking discrete layers of alumina ceramic in a green state upon one another and pressing to form the alumina ceramic body in the green state FIG. 31, the alumina ceramic body having a first side opposite a second side; b) forming at least one via hole straight through the alumina ceramic body extending between the first and second sides; c) filling the at least one via hole with a ceramic reinforced metal composite paste 185; d) drying the alumina ceramic body and the ceramic reinforced metal composite paste; e) forming a second hole straight through the ceramic reinforced metal composite paste extending between the first and second sides, the second hole smaller in diameter in comparison to the at least one via hole, wherein a portion of the ceramic reinforced metal composite paste remains in the at least one via hole; f) filling the second hole with a metal paste which is substantially free of ceramic 186; g) sintering the alumina ceramic body, the ceramic reinforced metal composite paste and the metal paste together to form the feedthrough dielectric body; and h) hermetically sealing 140 in FIG. 33A the feedthrough dielectric body to a ferrule 140, the ferrule configured to be installed in an opening of a housing of the active implantable medical device.

In other exemplary embodiments, wherein before step f) now including the step of forming a counterbore 195 or countersink in the green state through at least a portion of the ceramic reinforced metal composite paste from either the first or second side. See FIGS. 53-54A, 131 Options 4, 4A.

In other exemplary embodiments, the ceramic reinforced metal composite paste may contain at least 15% or 20% to 80% ceramic by weight or by volume.

In other exemplary embodiments, the substantially pure metal paste contains at least 90%, 95%, 98% metal by weight or by volume.

In other exemplary embodiments, after step g) may now include a step i) of inserting a solid leadwire 186W,118 at least partially into a counterbore or countersink and then in a step j) brazing 138 the solid leadwire to the counterbore or countersink, the braze attaching at one end to the solid leadwire and attaching at another end to either the metal paste and/or the ceramic reinforced metal composite paste, wherein the solid leadwire is electrically connected to the sintered metal paste. See FIG. 33A.

In other exemplary embodiments, between steps f) and g) may now include a step of forming a counterbore or countersink in the green state through the at least one via hole from either the first or second side, the counterbore or countersink exposing an inside portion of the alumina ceramic body. See FIGS. 39, 40. The invention may include the step i) of applying an adhesion layer 152 to the inside portion of the counterbore or countersink and to the metal paste. See FIGS. 39, 40. The invention may include the step j) of applying a wetting layer 150 to the adhesion layer. See FIGS. 39, 40. The invention may include a step l) of inserting a solid leadwire 186W,118 at least partially into the counterbore or countersink and then in a step m) brazing the solid leadwire to the counterbore or countersink, the braze attaching at one end to the solid leadwire and attaching at another end to the wetting layer, wherein the solid leadwire is electrically connected to the sintered metal paste. See FIGS. 39, 40.

In step b) the forming may be a drilling, a punching, a machining or a waterjet cutting. Likewise, in step e) the forming may be a drilling, a punching, a machining or a waterjet cutting.

In step b) the pressing may be by hydro-static pressing, by hot pressing, by cold pressing, by die pressing or by mechanical pressing.

In various embodiments, the ceramic reinforced metal composite paste surrounds the metal paste. See FIGS. 31,32. The metal paste may be a substantially pure platinum paste.

A backing plate may be placed adjacent the alumina ceramic body during the forming steps b) and e). The backing plate may include a backing plate hole aligned to the at least one via hole and wherein the backing plate hole is larger in diameter in comparison to the at least one via hole. The backing plate may be a sacrificial alumina body in a green state.

In various embodiments, before step g) may now include a step of filling the second hole with a second ceramic reinforced metal composite paste 185*b*, wherein the second ceramic reinforced metal composite paste has a higher percentage of metal based on weight in comparison to the ceramic reinforced metal composite paste, and including a next of forming a third hole straight through the second ceramic reinforced metal composite paste, wherein in step f) the metal paste 186 is now filled into the third hole. See FIG. 164. Before step g) may now further include a step of filling the third hole with a third ceramic reinforced metal composite paste 185*c*, wherein the third ceramic reinforced metal composite paste has a higher percentage of metal based on weight in comparison to the second ceramic reinforced metal composite paste, and including a next step of forming a fourth hole straight through the third ceramic reinforced metal composite paste, wherein in step f) the metal paste 186 is now filled into the fourth hole. See FIG. 164.

A gold braze 140 may be used in step h) for hermetically sealing the feedthrough dielectric body to the ferrule. See FIG. 170.

In various embodiments before step h) may now include the step of removing a thin layer of material from either the first side and/or the second side.

In step d) the drying the alumina ceramic body and the ceramic reinforced metal composite paste may be by waiting a period of time, heating at an elevated temperature and/or placing within a vacuum.

In various embodiments it may now include the step i) of attaching a conductive leadwire 186W,118 to the sintered metal paste 186 at either the first or second side. See FIGS. 41, 42. The attaching method may be selected from the group consisting of ultrasonic welding, thermal sonic bonding, laser welding, arc welding, gas welding, resistance welding, projection welding, butt welding, slash welding, upset welding, solid state welding, friction welding, fusion welding, inductive welding, percussion welding or electron beam welding. See FIGS. 41, 42.

The ferrule may be a separately manufactured component attached to the opening of the housing of the active implantable medical device. See FIGS. 161C, 161D, 161E. Or, the ferrule may be formed as a part of the housing of the active implantable medical device. See FIGS. 161A, 161B.

As shown in FIGS. 29 and 30 an exemplary embodiment of a method of manufacturing a feedthrough dielectric body for an active implantable medical device comprises the steps of: a) forming an alumina ceramic body 188 in a green state FIG. 32, or, stacking discrete layers of alumina ceramic in a green state upon one another and pressing to form the alumina ceramic body in the green state FIG. 31, the alumina ceramic body having a first side 500 opposite a second side 502; b) forming at least one via hole straight through the alumina ceramic body extending between the first and second sides; c) filling the at least one via hole with a ceramic reinforced metal composite paste 185; d) drying the alumina ceramic body and the ceramic reinforced metal composite paste; e) forming a counterbore 195 or countersink in the green state through at least a portion of the ceramic reinforced metal composite paste from either the first or second side; f) filling the counterbore or countersink with a metal paste which is substantially free of ceramic 186; g) sintering the alumina ceramic body, the ceramic reinforced metal composite paste and the metal paste together to form the feedthrough dielectric body; and h) hermetically sealing 140 in FIG. 33A the feedthrough dielectric body to a ferrule 140, the ferrule configured to be installed in an opening of a housing of the active implantable medical device.

As shown in FIGS. 53 and 54 an exemplary embodiment of a method of manufacturing a feedthrough dielectric body for an active implantable medical device comprises the steps of: a) forming an alumina ceramic body 188 in a green state FIG. 32, or, stacking discrete layers of alumina ceramic in a green state upon one another and pressing to form the alumina ceramic body in the green state FIG. 31, the alumina ceramic body having a first side opposite a second side; b) forming at least one via hole straight through the alumina ceramic body extending between the first and second sides; c) filling the at least one via hole with a ceramic reinforced metal composite paste 185; d) drying the alumina ceramic body and the ceramic reinforced metal composite paste; e) forming a second hole straight through the ceramic reinforced metal composite paste extending between the first and second sides, the second hole smaller in diameter in comparison to the at least one via hole, wherein a portion of the ceramic reinforced metal composite paste remains in the at least one via hole; f) forming a counterbore 195 or countersink in the green state through at least a portion of the ceramic reinforced metal composite paste from either the first or second side; g) filling the second hole and counterbore or countersink with a metal paste which is substantially free of ceramic 186; h) sintering the alumina ceramic body, the ceramic reinforced metal composite paste and the metal paste together to form the feedthrough dielectric body; and i) hermetically sealing 140 in FIG. 33A the feedthrough dielectric body to a ferrule 140, the ferrule configured to be installed in an opening of a housing of the active implantable medical device.

A previous exemplary embodiment of the present invention was of a feedthrough subassembly (189 shown best in FIGS. 160, 131, 17, 61, 69) attachable to an active implantable medical device, including: (a) a co-fired insulator substrate assembly (183 shown best in FIGS. 29-60) for the active implantable medical device, the co-fired insulator substrate assembly comprising: i) an alumina insulator body (188 shown best in FIG. 29) having a body fluid side (500 shown best in FIG. 29) opposite a device side (502 shown best in FIG. 29), the body fluid side and device side separated and connected by at least one outer perimeter surface (504 shown best in FIG. 29); ii) at least one via hole (402 shown best in FIGS. 77, 97) disposed through the alumina insulator body (188) extending from the body fluid side to the device side; iii) a composite fill (185,186 shown best in FIGS. 131, 160) at least partially disposed within the at least one via hole extending from a first composite fill end (526 shown best in FIGS. 139-158) to a second composite fill end (528 shown best in FIGS. 139-158), wherein the first composite fill end (526) is disposed at or near the device side (502) of the alumina insulator body (188), and wherein the second composite fill end (528) is disposed within the at least one via hole (402) recessed from the body fluid side (500); iv) wherein the alumina insulator body (188) and the composite fill (185,186) are co-fired; (b) a metallic leadwire (118 shown best in FIGS. 139-162) at least partially disposed within the at least one via hole (402) on the body fluid side (500); i) wherein the metallic leadwire is gold brazed (138 shown best in FIGS. 139-162) to a via hole metallization (150, 152 shown best in FIGS. 139-162); ii) wherein the via hole metallization (150,152) is disposed at least partially within the at least one via hole (402) of the alumina insulator body (188) on the body fluid side (500); iii) wherein the via hole metallization (150,152) contacts the second composite fill end (528) of the composite fill (185,186); iv) wherein the gold braze (138) forms a first hermetic seal separating the body fluid side (500) and device side (502); v) wherein the metallic leadwire (118) is in electrical communication through the gold braze (138), the via hole metallization (150,152) and the composite fill (185, 186) to the first composite fill end (526) forming an electrically conductive pathway between the metallic leadwire (118) and the first composite fill end (526); (c) a perimeter metallization (150, 152 shown best in FIG. 33A) disposed at least partially on the at least one outer perimeter surface (504) of the alumina insulator body (188) or a perimeter ceramic reinforced metal composite (185 shown best in FIGS. 37-42) disposed at least partially on the at least one outer perimeter surface (504) of the alumina insulator body (188); and (d) a ferrule (122 shown best in FIG. 33A), comprising a conductive ferrule body (122) having a first ferrule side (520) opposite a second ferrule side (522) and a ferrule opening (524) between and through the first and second ferrule sides, wherein the alumina insulator body (188) is at least partially disposed within the ferrule opening (524); (e) a perimeter braze (140) between either the perimeter metallization (150,152 shown best in FIG. 35) or the perimeter ceramic reinforced metal composite (185 shown best in FIGS. 37-42) of the alumina insulator body (188) and the conductive ferrule body (122), the perimeter braze (140) forming a second hermetic seal hermetically sealing the alumina insulator body (188) to the ferrule opening (524); and (f) wherein the ferrule (122) is configured to be installed in an opening of a housing of the active implantable medical device.

In other exemplary embodiments the composite fill may include: (shown best in FIGS. 131,160) i) a ceramic reinforced metal composite (185) comprising alumina and platinum; and ii) a substantially pure platinum fill (186).

At least a portion of the substantially pure platinum fill (186) may be exposed at the device side. (Options 1, 2, 4, 5 shown best in FIG. 131, 160)

At least a portion of the substantially pure platinum fill (186) at the device side may not be covered by either the alumina insulator body (188) or the ceramic reinforced metal composite (185). (Options 1, 2, 4, 5 shown best in FIG. 131, 160)

At least a portion of the substantially pure platinum fill (186) extending between the body fluid and device side may be surrounded by the ceramic reinforced metal composite (185). (Options 2, 4, 5, 6 best seen in FIG. 131, 160)

At least a portion of the substantially pure platinum fill (186) may form a portion of the electrically conductive pathway that is exposed at the device side. (Options 2, 4, 5 best seen in FIG. 131, 160)

At the device side the ceramic reinforced metal composite (185) may not be exposed. (Options 1, 4, 6 best seen in FIG. 131, 160)

The device side of the at least one via hole may be fully filled by the substantially pure platinum fill (186). (Options 1, 4 best seen in FIG. 131, 160)

A metallic end cap (186C) may be at least partially disposed within the at least one via hole (402) at device side. (Option 6 best seen in FIG. 131, 160) The metallic end cap (186C) may comprise platinum. (Option 6 best seen in FIG. 131, 160)

A platinum wire (186W) may be disposed within the substantially pure platinum fill. (Option 5 best seen in FIG. 131, 160)

The platinum wire (186W) may be at least partially exposed at the device side of the at least one via hole. (Option 5 best seen in FIG. 131, 160)

The platinum wire (186W) may not directly touch the ceramic reinforced metal composite (185). (Option 5 best seen in FIG. 131, 160)

The substantially pure platinum fill (186) may be between the platinum wire (186W) and the ceramic reinforced metal composite (185). (Option 5 best seen in FIG. 131, 160)

The at least one via hole at either of the body fluid side or the device side may comprise a counterbore (195) or a countersink (195'). (Shown best in FIGS. 47-54)

The composite fill may comprise: (shown best in FIGS. 147-150, Option 3 of FIGS. 131 and 160) i) a ceramic reinforced metal composite (185) comprising alumina and platinum; and ii) a metallic wire (186W).

The via hole metallization and/or the perimeter metallization may comprise an adhesion layer (152) and a wetting layer (150), wherein the adhesion layer (152) is attached to the alumina insulator body (188) and wherein the wetting layer (150) is attached to the adhesion layer (152).

Another previous exemplary embodiment of the present invention was of a feedthrough subassembly attachable to an active implantable medical device, including: (a) a feedthrough body comprising a material which is both electrically insulative and biocompatible, wherein the feedthrough body is configured to be hermetically installed within the active implantable medical device separating a body fluid side from a device side; (b) a via hole disposed through the feedthrough body extending from the body fluid side to the device side; (c) a composite fill partially disposed within the via hole extending from a first composite fill end to a second composite fill end, wherein the first composite fill end is disposed at or near the device side of the feedthrough body, and wherein the second composite fill end is disposed within the via hole and recessed from the body fluid side of the feedthrough body, the composite fill comprising: i) a first portion of a ceramic reinforced metal composite comprising alumina and platinum; and ii) a second portion of a substantially pure platinum fill and/or a platinum wire; (d) a via hole metallization disposed at least partially within the at least one via hole of the feedthrough body on the body fluid side and covering at least a portion of the second composite fill end; (e) a metallic leadwire at least partially disposed within the via hole on the body fluid side; and (f) a gold braze on the body fluid side physically and electrically connecting the metallic leadwire and the via hole metallization.

In other exemplary embodiments the gold braze may form a first hermetic seal separating the body fluid side and device side.

The metallic leadwire may be in electrical communication through the gold braze, the via hole metallization and the composite fill to the first composite fill end forming an electrically conductive pathway between the metallic leadwire and the first composite fill end.

A conductive ferrule may comprise a ferrule opening, the ferrule configured to be disposed into an opening of an electromagnetically shielded and hermetic conductive housing of the active implantable medical device, wherein the feedthrough body hermetically seals the ferrule opening.

The composite fill and feedthrough body may be co-fired before the via hole metallization is applied and the metallic leadwire is gold brazed to the via hole metallization.

Another previous exemplary embodiment of the present invention was of a feedthrough subassembly attachable to an active implantable medical device, including: (a) a co-fired insulator substrate assembly for the active implantable medical device, the co-fired insulator substrate assembly comprising: i) an alumina insulator body having a body fluid side opposite a device side, the body fluid side and device side separated and connected by at least one outer perimeter surface; ii) at least one via hole disposed through the alumina insulator body extending from the body fluid side to the device side; iii) a composite fill at least partially disposed within the at least one via hole extending from a first composite fill end to a second composite fill end, wherein the first composite fill end is disposed at or near the device side of the alumina insulator body, and wherein the second composite fill end is disposed within the at least one via hole recessed from the body fluid side; iv) wherein the alumina insulator body and the composite fill are co-fired; and (b) a metallic leadwire at least partially disposed within the at least one via hole on the body fluid side; i) wherein the metallic leadwire is gold brazed to a via hole metallization; ii) wherein the via hole metallization is disposed at least partially within the at least one via hole of the alumina insulator body closer to the body fluid side; iii) wherein the via hole metallization contacts the second composite fill end of the composite fill; iv) wherein the gold braze forms a first hermetic seal separating the body fluid side and device side; v) wherein the metallic leadwire is in electrical communication through the gold braze, the via hole metallization and the composite fill to the first composite fill end forming an electrically conductive pathway between the metallic leadwire and the first composite fill end.

In other exemplary embodiments a perimeter metallization may be disposed at least partially on the at least one outer perimeter surface of the alumina insulator body or a perimeter ceramic reinforced metal composite disposed at least partially on the at least one outer perimeter surface of the alumina insulator body.

A ferrule may comprise a conductive ferrule body having a first ferrule side opposite a second ferrule side and a ferrule opening between and through the first and second ferrule sides, wherein the alumina insulator body is at least partially disposed within the ferrule opening.

A perimeter braze may be between either the perimeter metallization or the perimeter ceramic reinforced metal composite and the conductive ferrule body, the perimeter braze forming a second hermetic seal hermetically sealing the alumina insulator body to the ferrule opening.

The ferrule may be configured to be installed in an opening of a housing of the active implantable medical device.

BRIEF DESCRIPTION OF THE DRAWINGS

The accompanying drawings illustrate the invention. In such drawings:

FIG. 11A illustrates an exploded perspective view of an internally grounded prior art feedthrough capacitor;

FIG. 11B illustrates the structure of FIG. 11A where now the capacitor is formed as a monolithic structure;

FIG. 11C illustrates the structure of FIG. 11B fully assembled into a feedthrough filtered hermetic terminal;

FIG. 104 is a sectional perspective view of one step in the process of forming the hermetically sealed via hole where the via hole is first filled with the CRMC;

FIG. 105 is similar to FIG. 104 but is now the next step where the filled via is drilled out;

FIG. 106 is similar to FIG. 105 but is now the next step where the via hole is filled with a platinum paste similar to Option 4;

FIG. 107 shows that prior to sintering, the individual insulators are removed from the bar;

FIG. 108 illustrates the body fluid side of the device side image of FIG. 107;

FIG. 109 is a sectional view similar to FIGS. 104-106 now showing the capacitors partially cut out from the bar;

Figure 29:
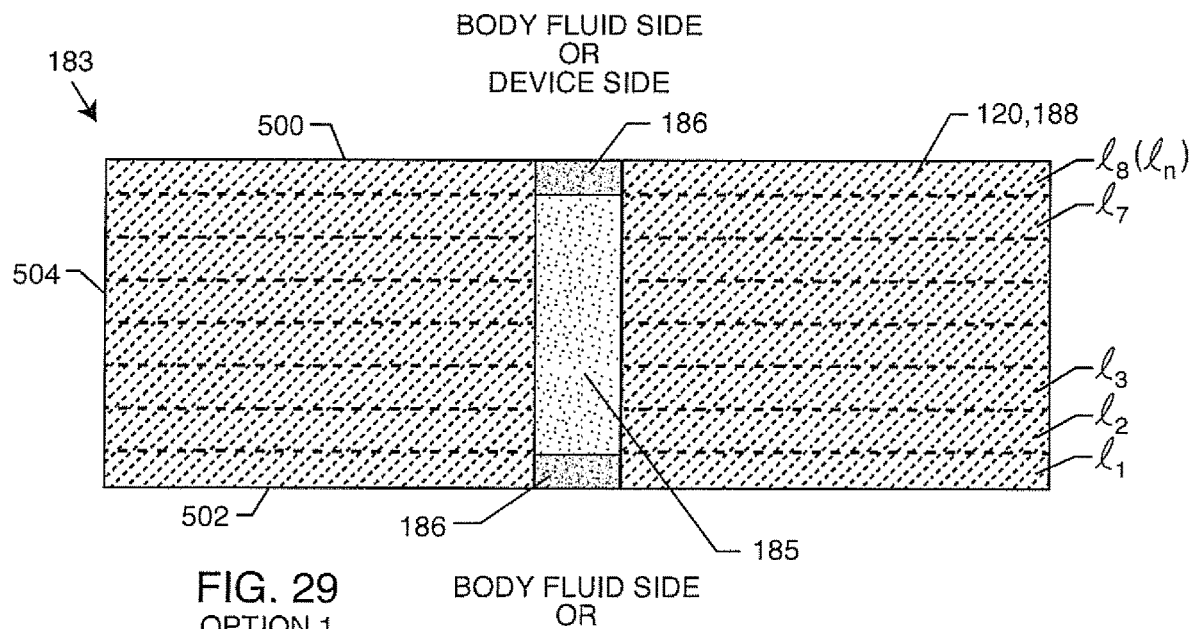
FIG. 29 is generally taken from prior art FIG. 14 of the '659 patent and has been modified to illustrate Option 1 of the present invention.
Figure 31:
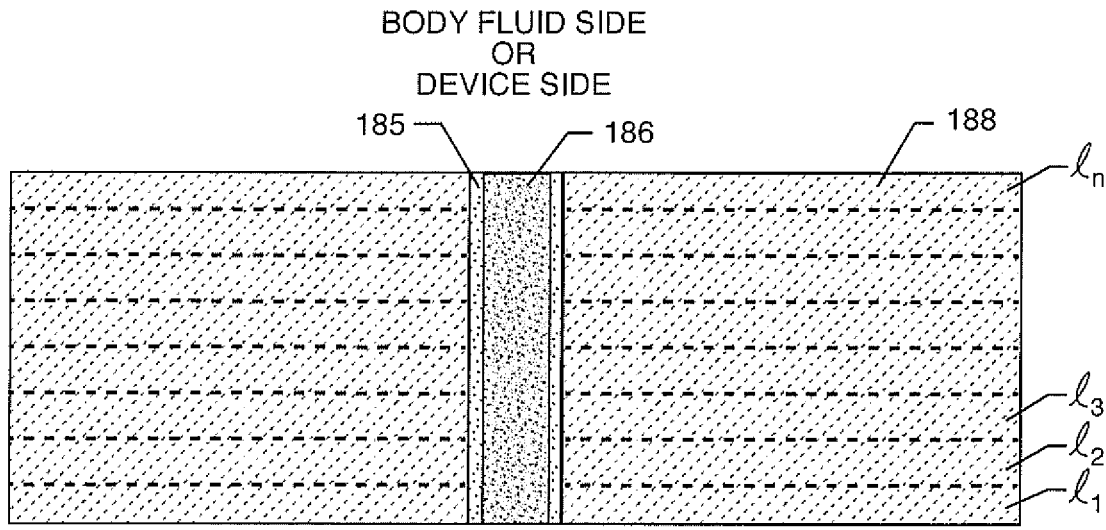
FIG. 31 is generally taken from prior art FIG. 14 of the '659 patent, but has been modified to show Option 2 of the present invention.
Figure 33:
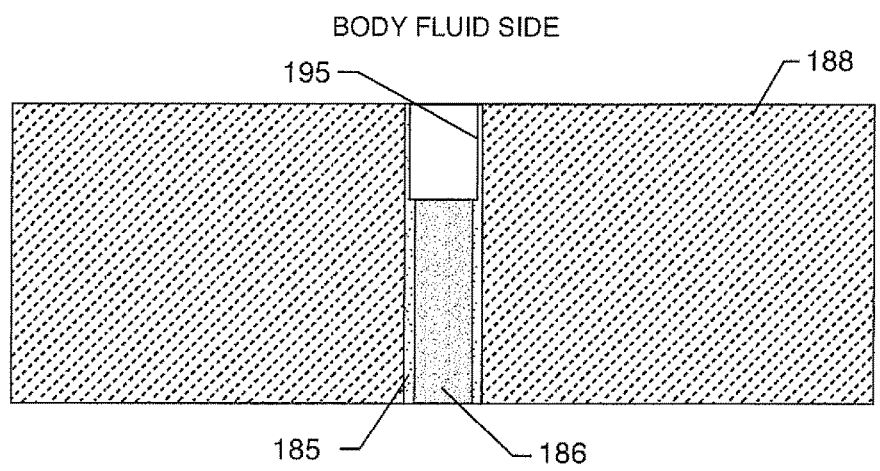
FIG. 33 illustrates Option 2B of the present invention which is very similar to FIGS. 31 and 32, except that a body fluid side counterbore has been added into the CRMC and the material.
Figure 34:
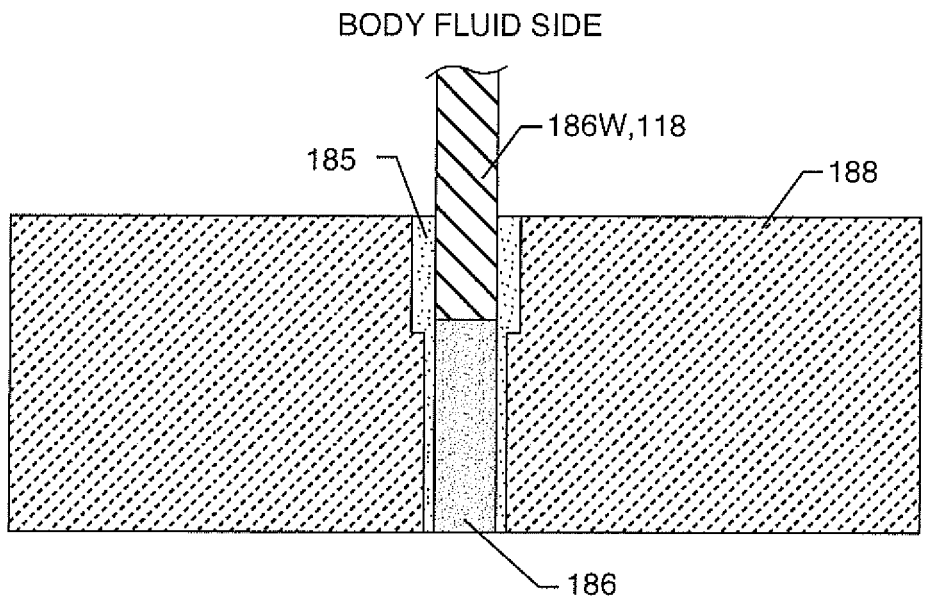
FIG. 34 illustrates Option 2C of the present invention where a body fluid side leadwire will be routed to an implanted lead or an AIMD header block.
Figure 43:
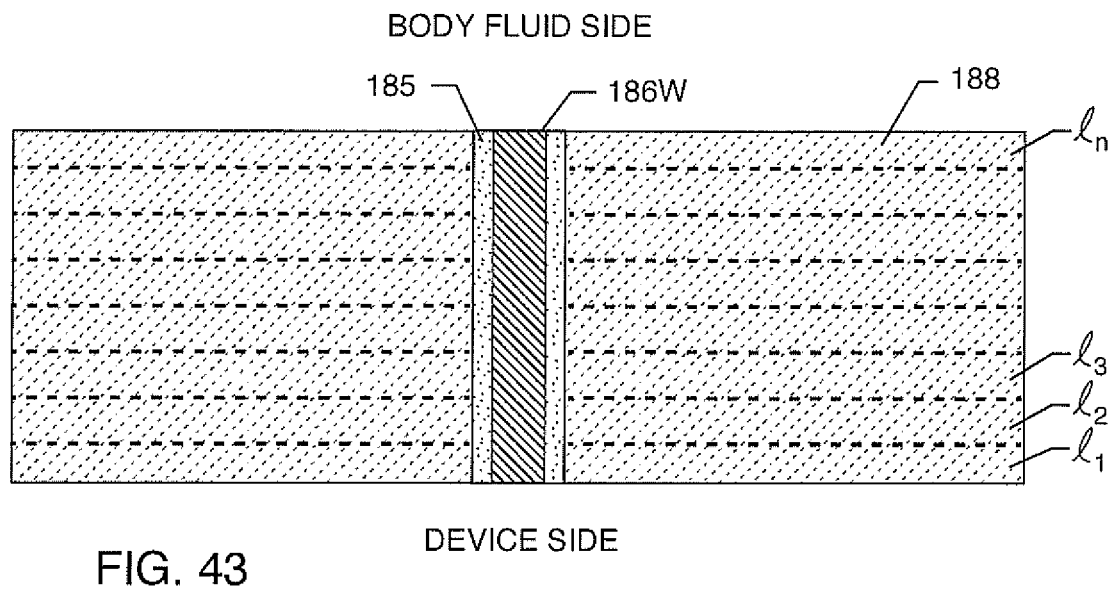
FIG. 43 illustrates Option 3 which is generally taken from prior art FIG. 14 of the '659 patent and has been modified to illustrate Option 3 of the present invention.
Figure 45:
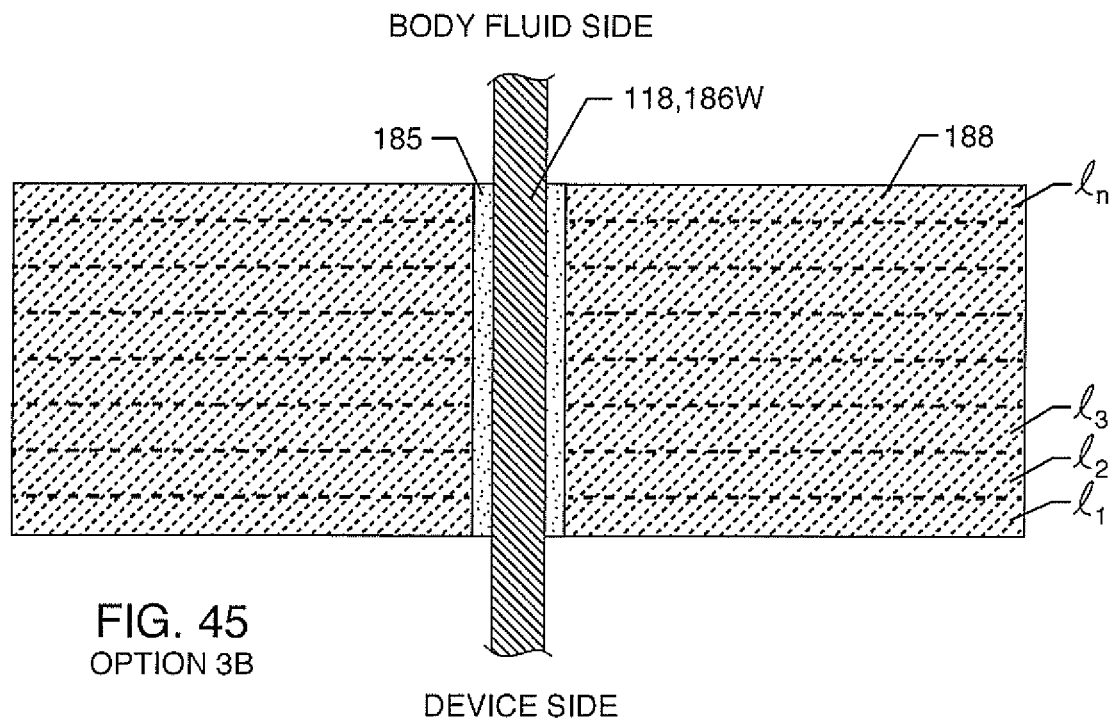
FIG. 45 illustrates Option 3B wherein, the leadwire, previously described in FIGS. 43 and 44, can be extended or lengthened into the body fluid side or into the device side or both.
Figure 53:
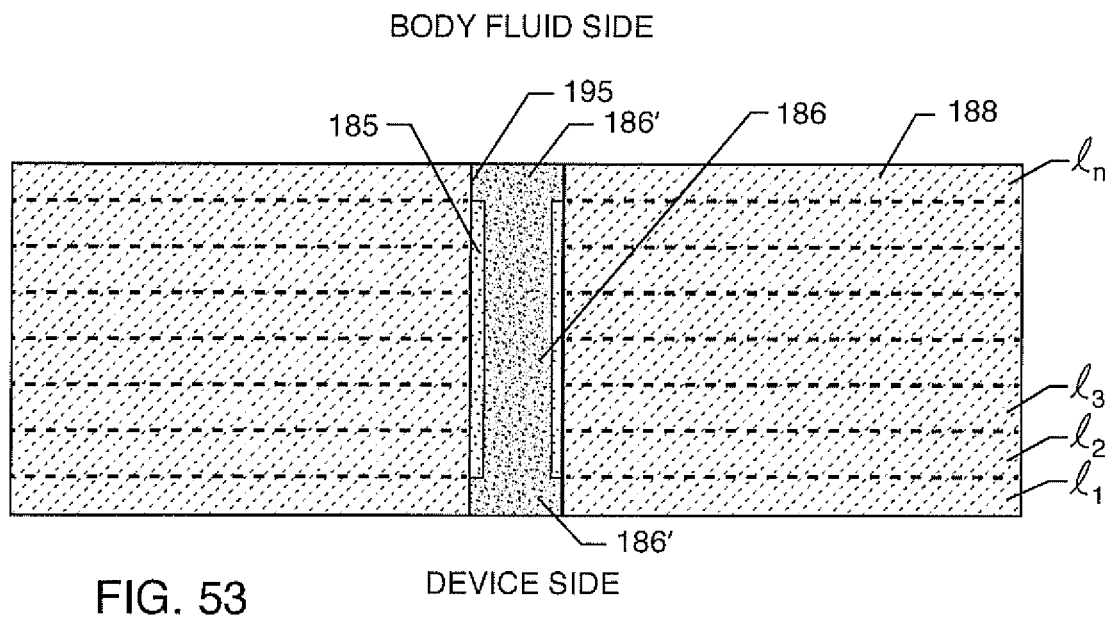
FIG. 53 illustrates Option 4 which is taken from prior art FIG. 17B of the '659 patent and illustrates Option 4 of the present invention.
Figure 55:
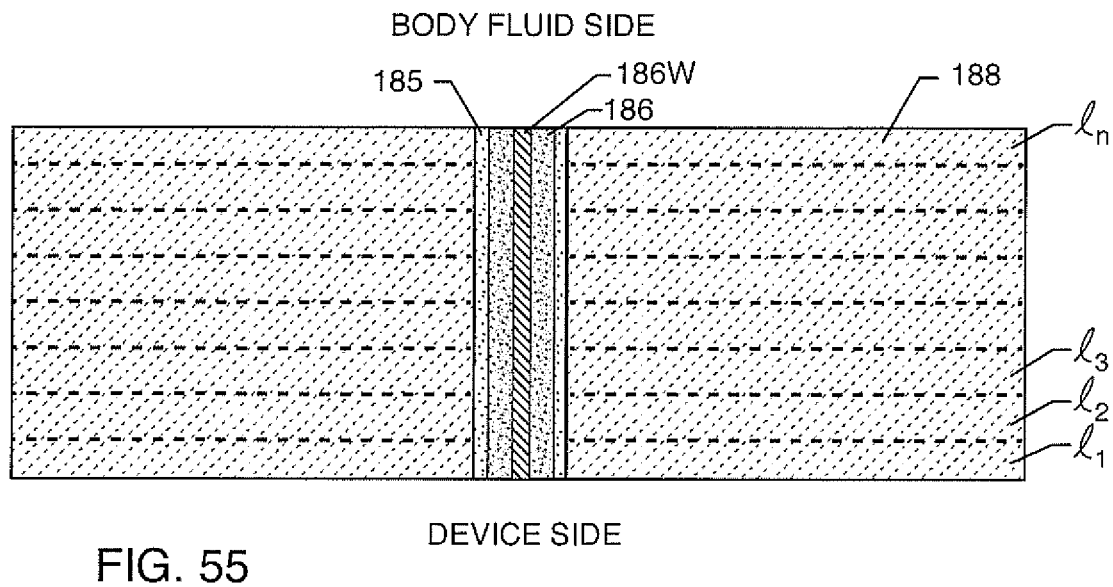
FIG. 55 illustrates Option 5 which is taken from prior art FIG. 14 of the '659 patent and is very similar to FIG. 43 herein, except that the pure platinum wire is surrounded by two different layers.
Figure 57:
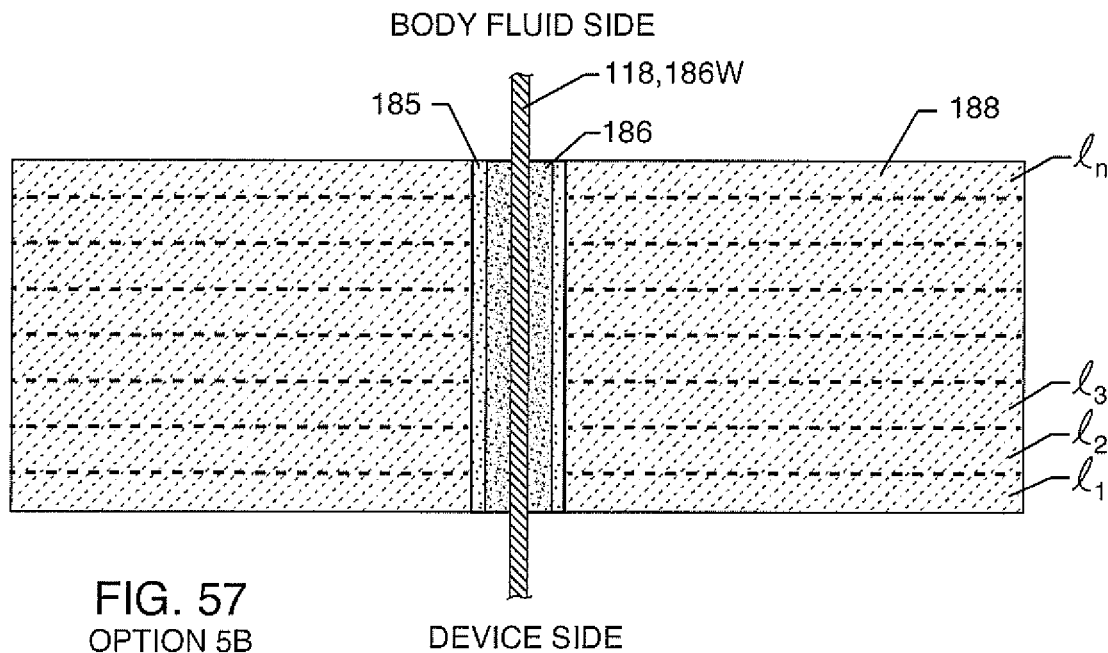
FIG. 57 illustrates Option 5B which is very similar to FIG. 55, except that it shows that the solid leadwire can be extended into the body fluid side or into the device side or both.
Figure 59:
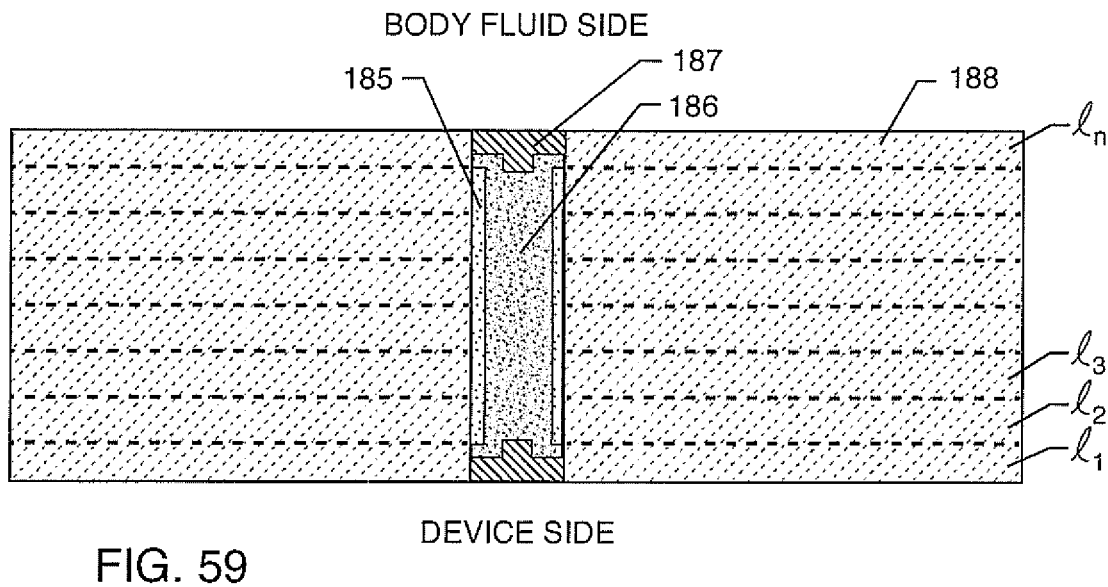
FIG. 59 illustrates Option 6 which is taken from prior art FIG. 14 of the '659 patent.
Figure 74:
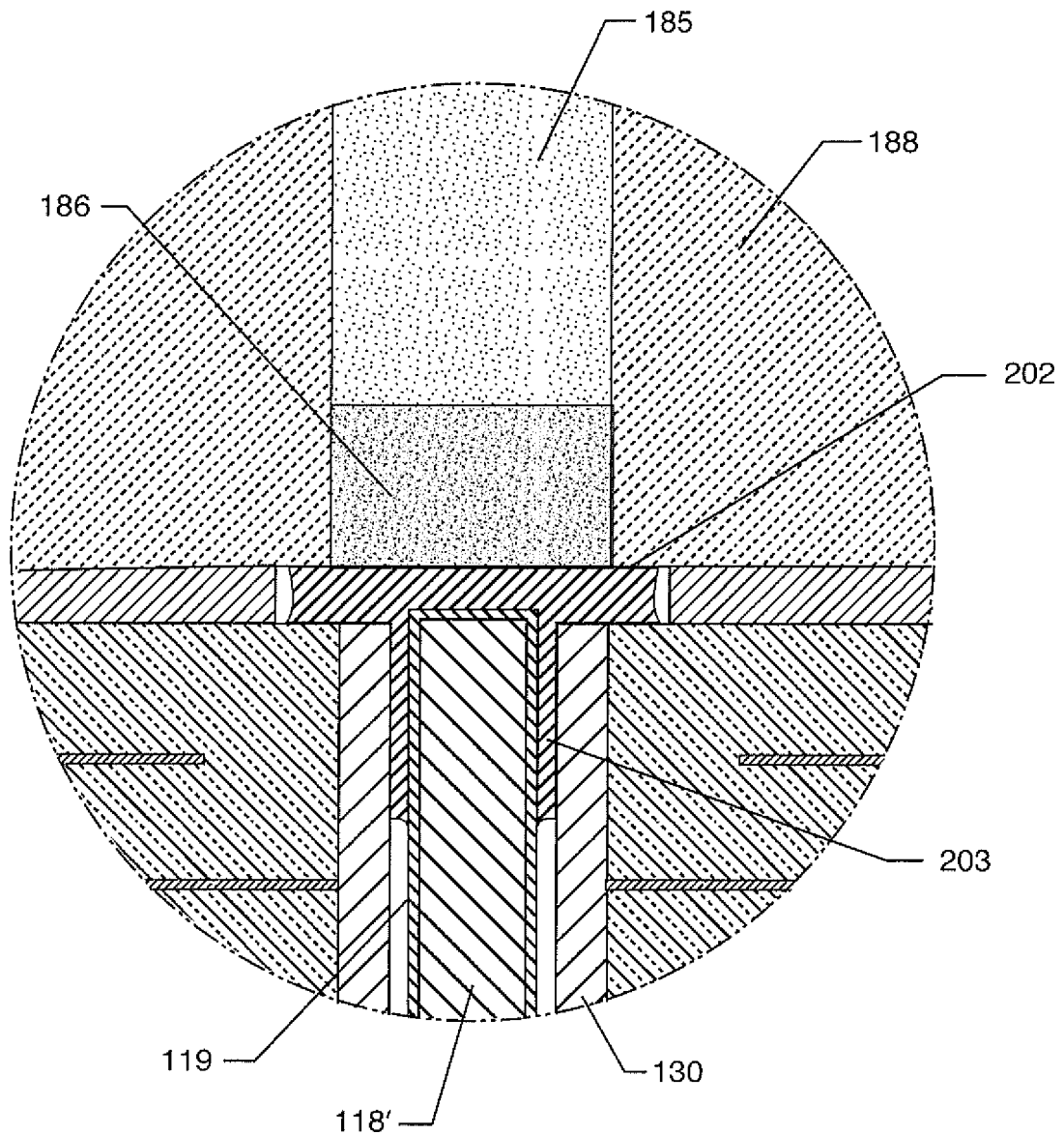
FIG. 74 illustrates section 74-74 from FIG. 73 showing how the ball grid array solder wets directly to the pure platinum fill.
Figure 110:
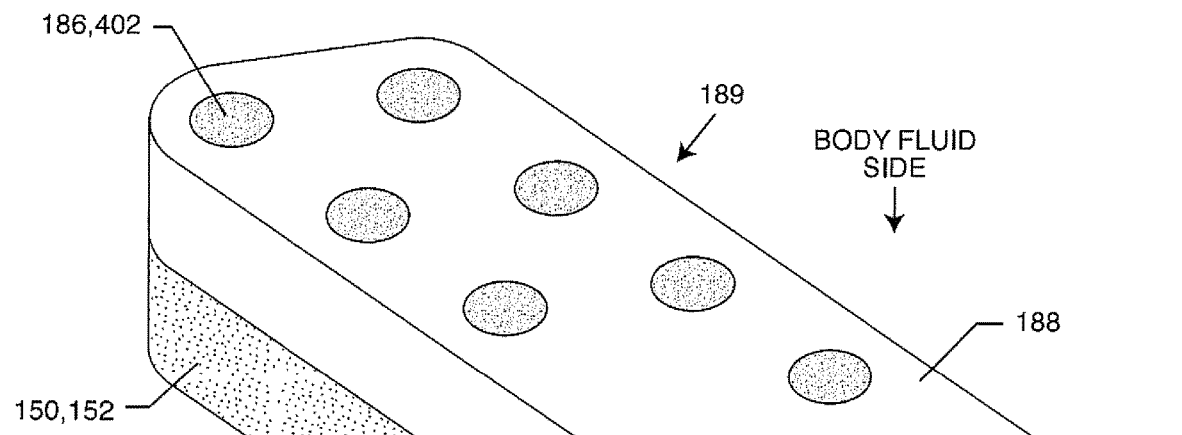
Figure 111:
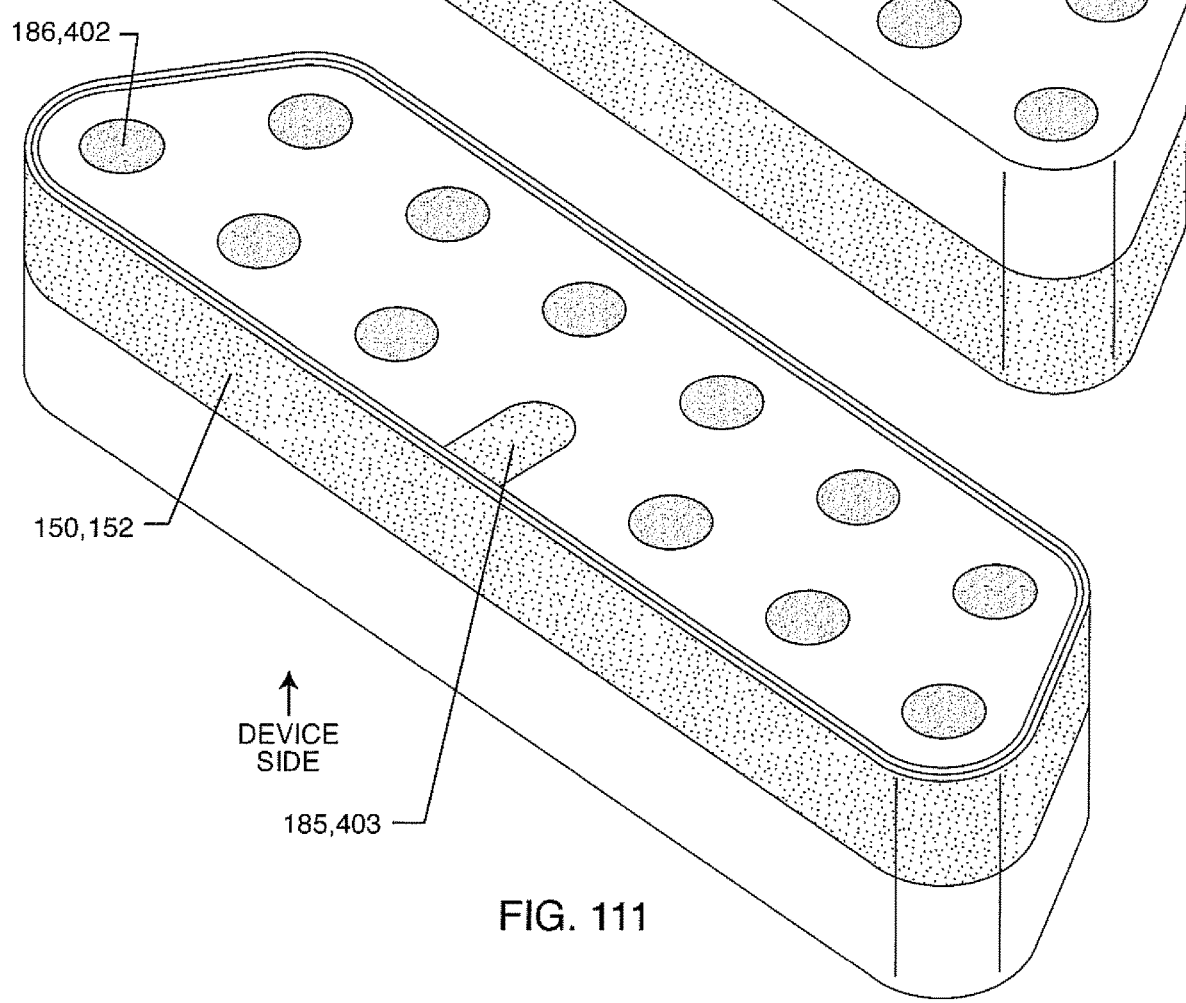
Figure 112:
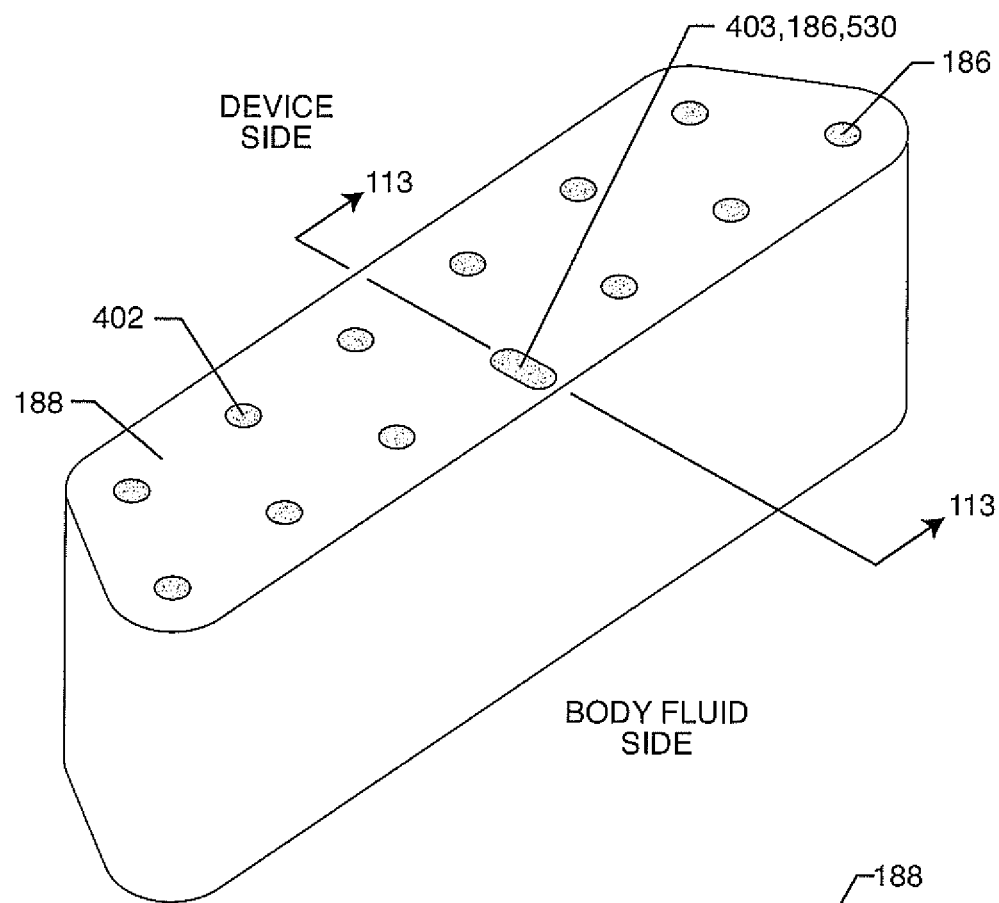
Figure 113:
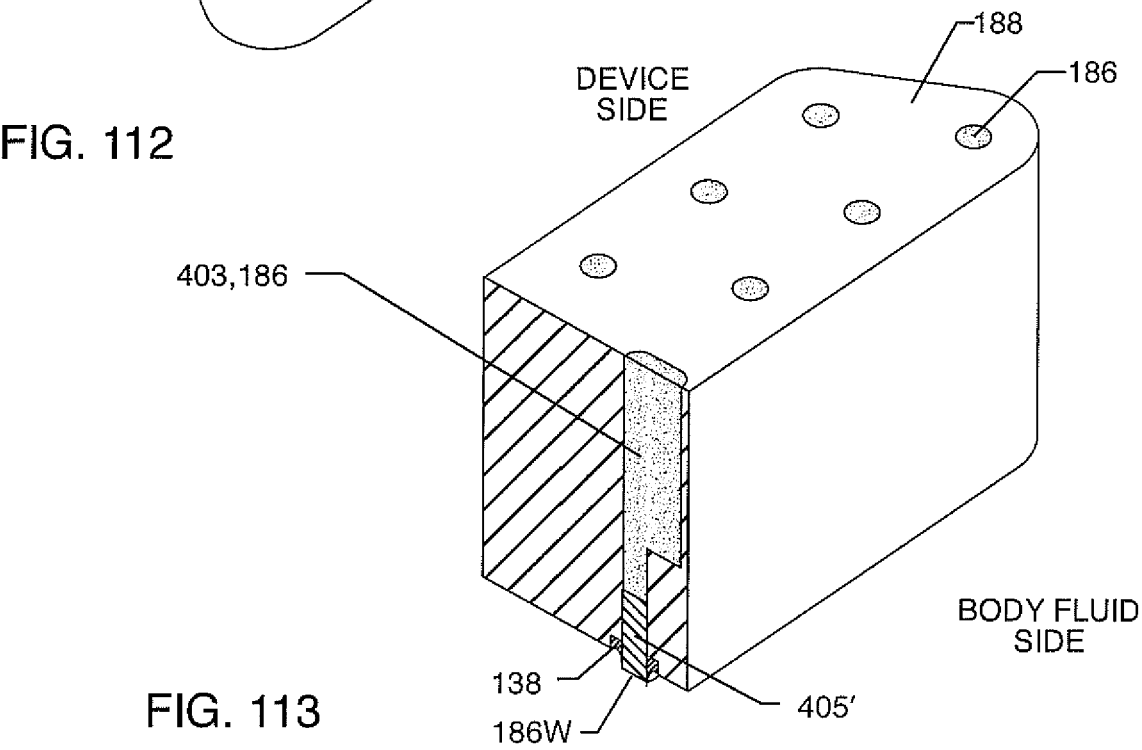
Figure 114:
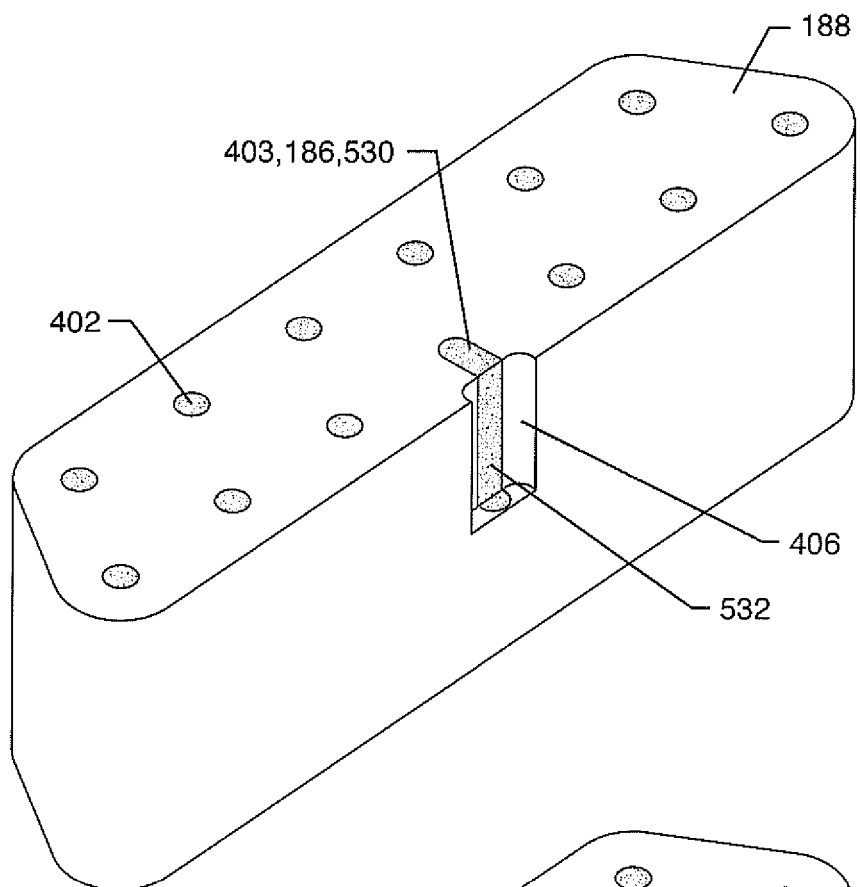
Figure 115:
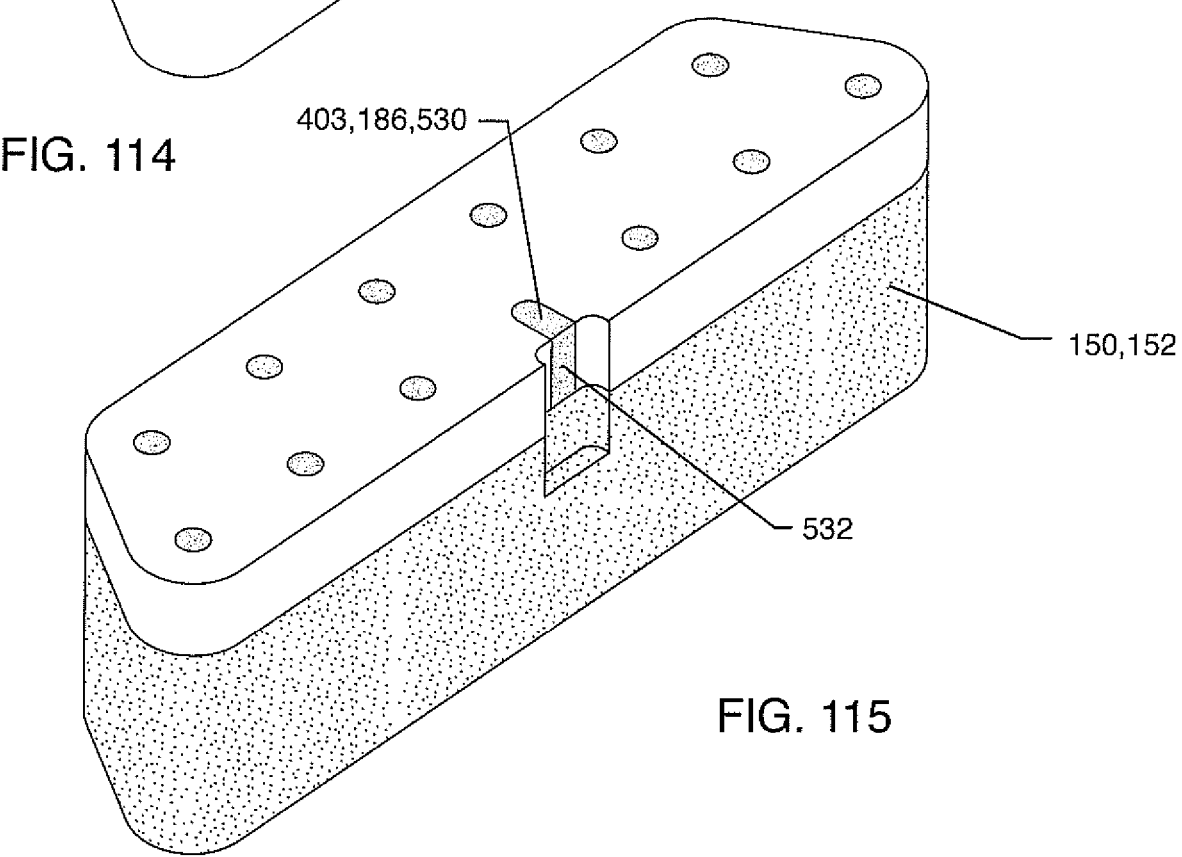
Figure 116:
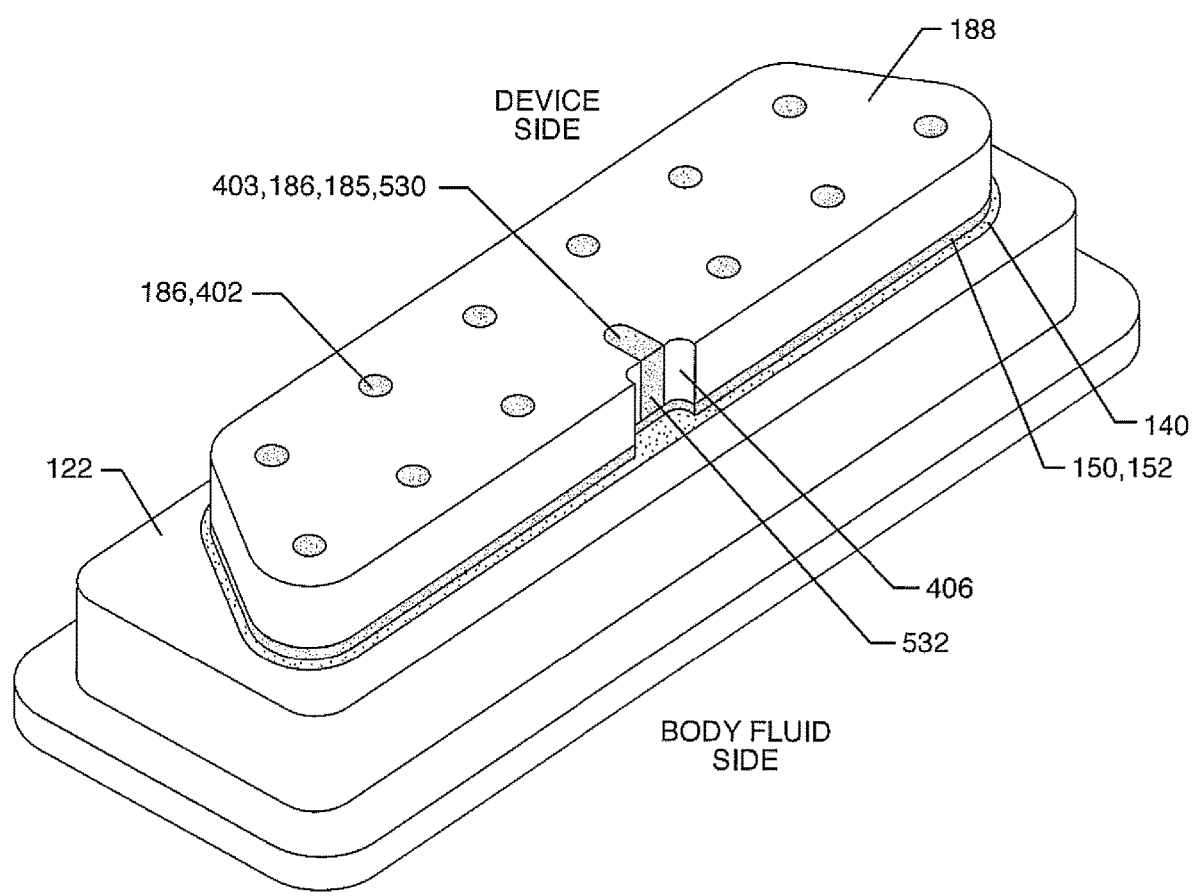
Figure 117:
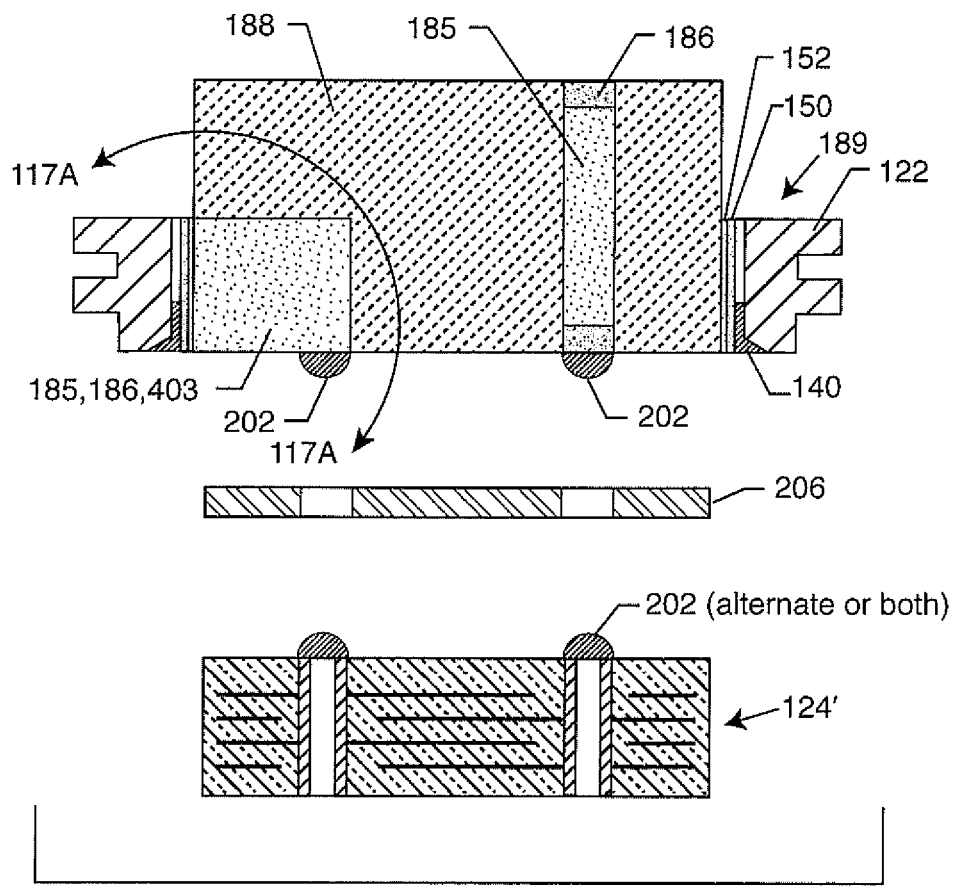
Figure 117A:
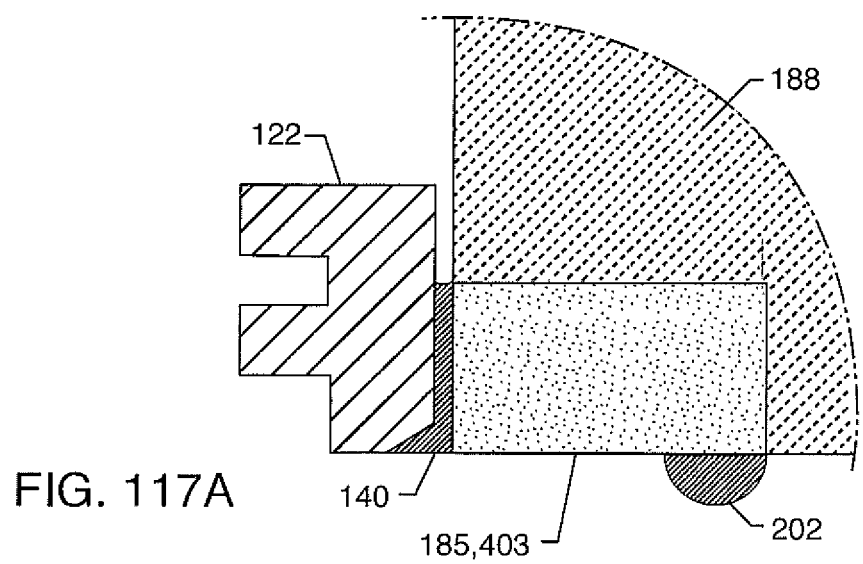
Figure 118:
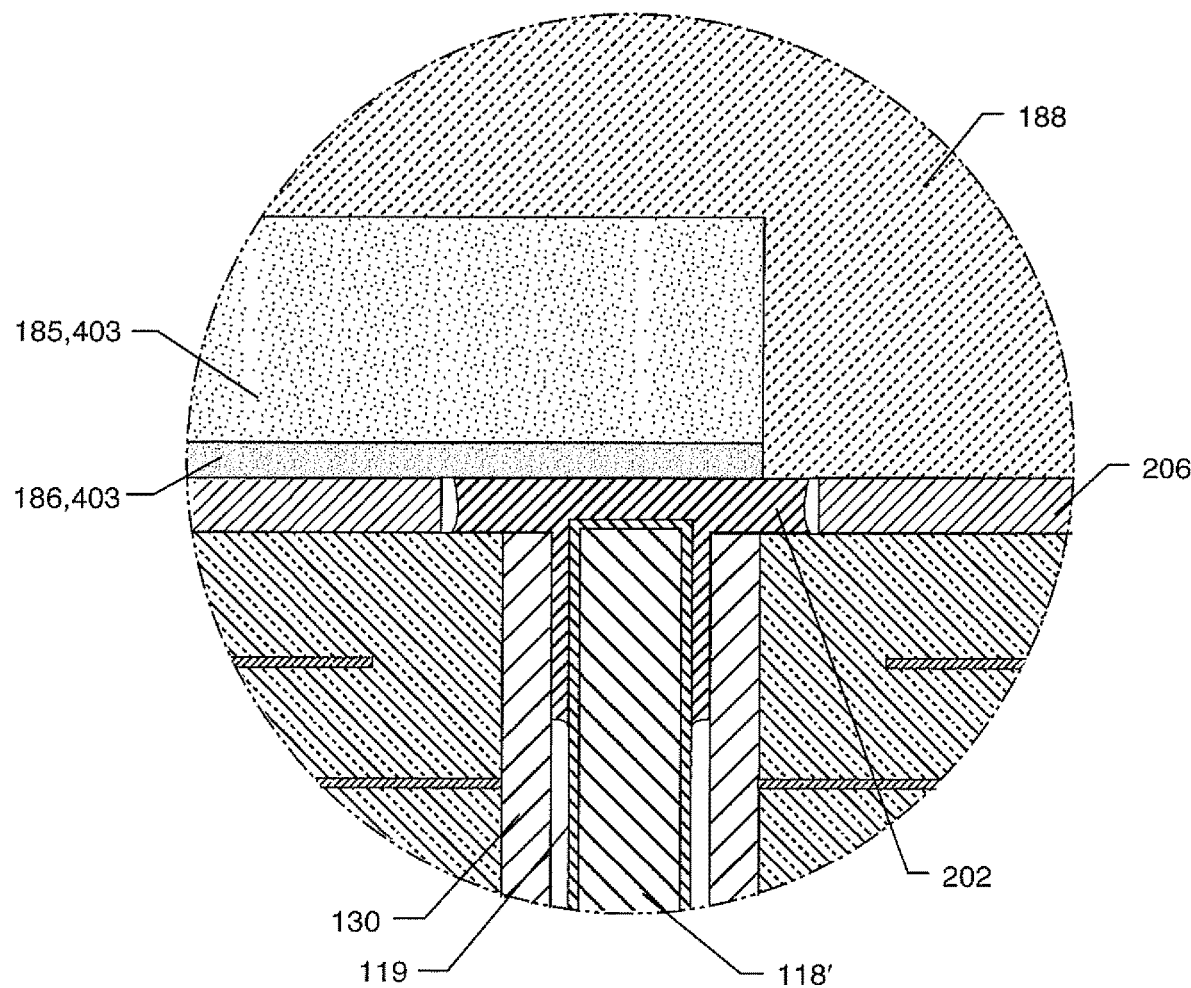
Figure 119:
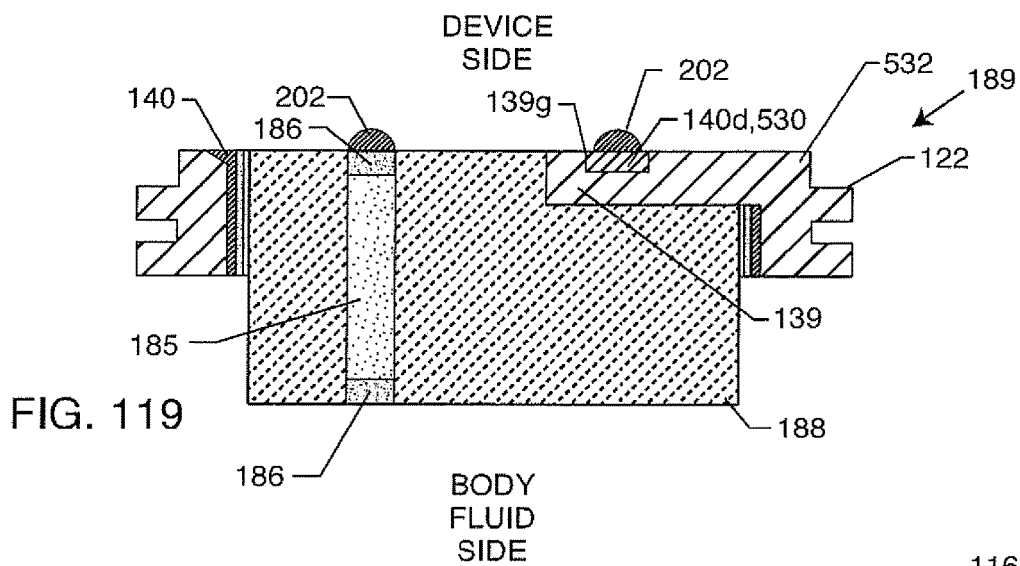
Figure 120:
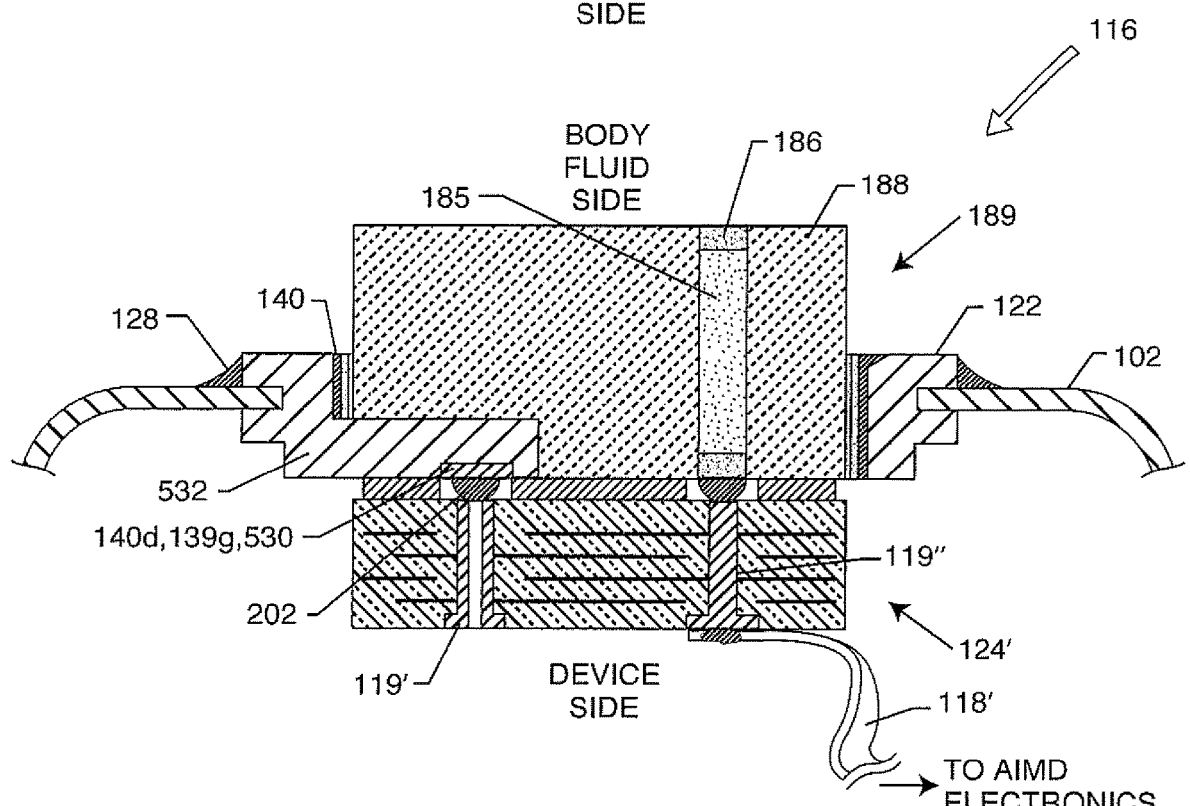
Figure 121:
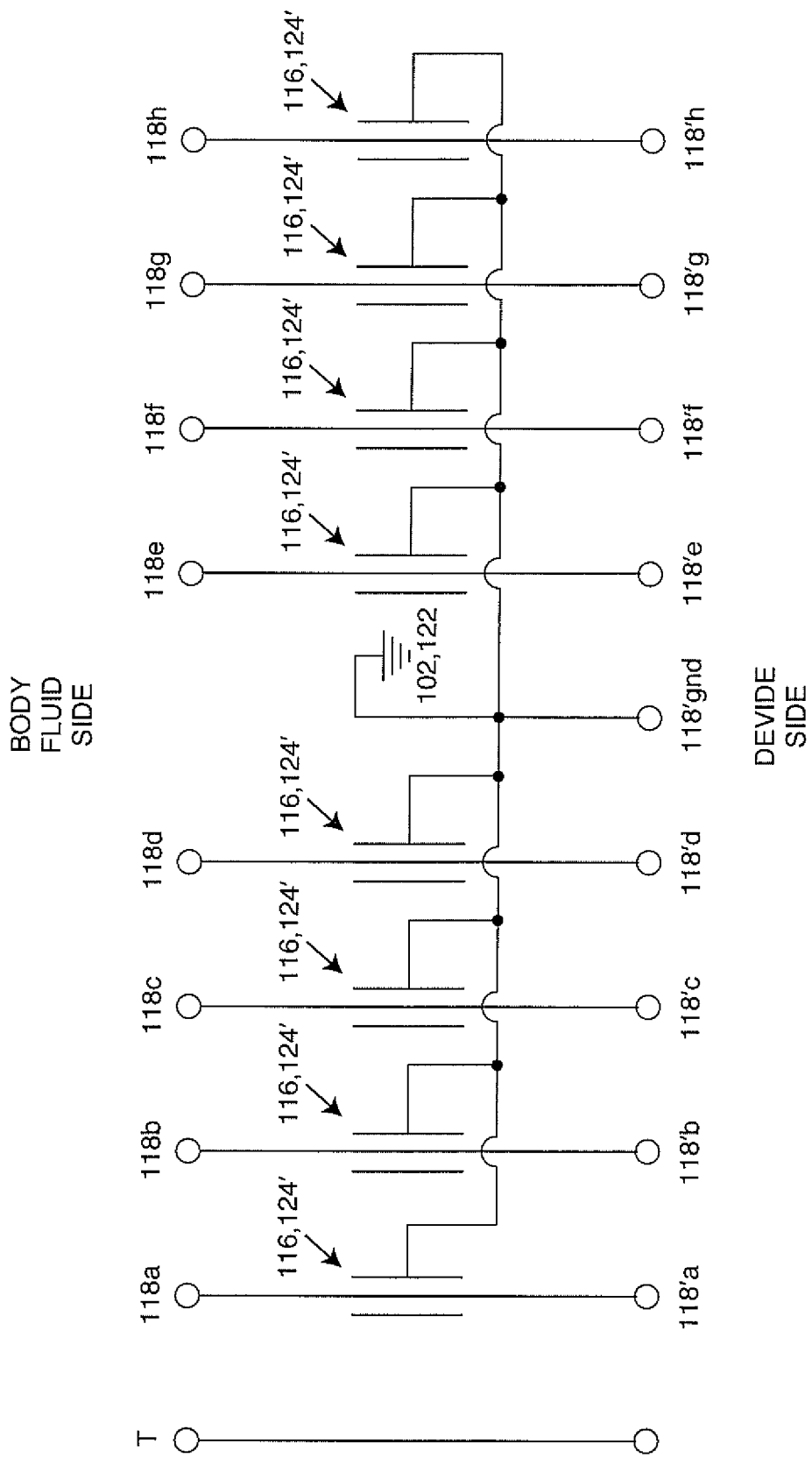
Figure 122:
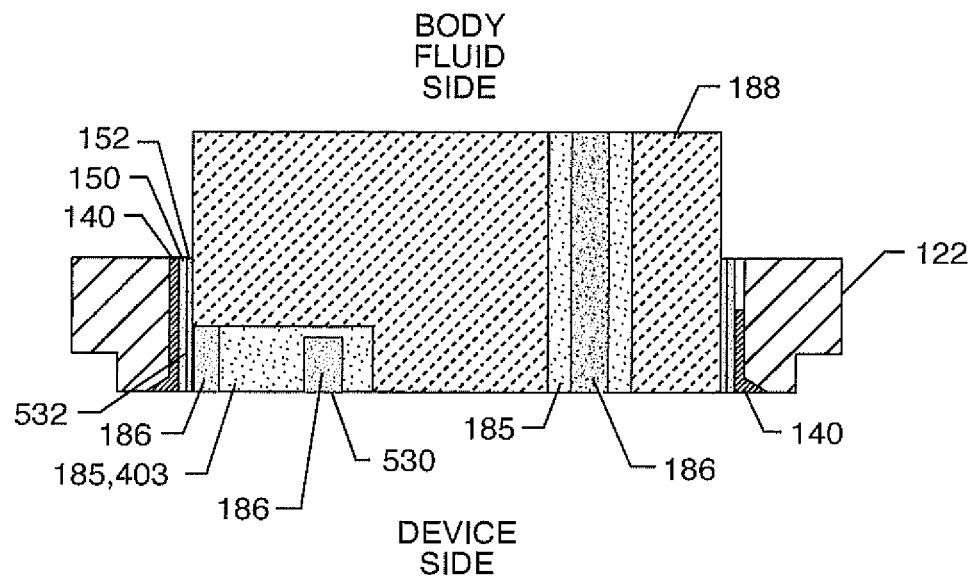
Figure 123:
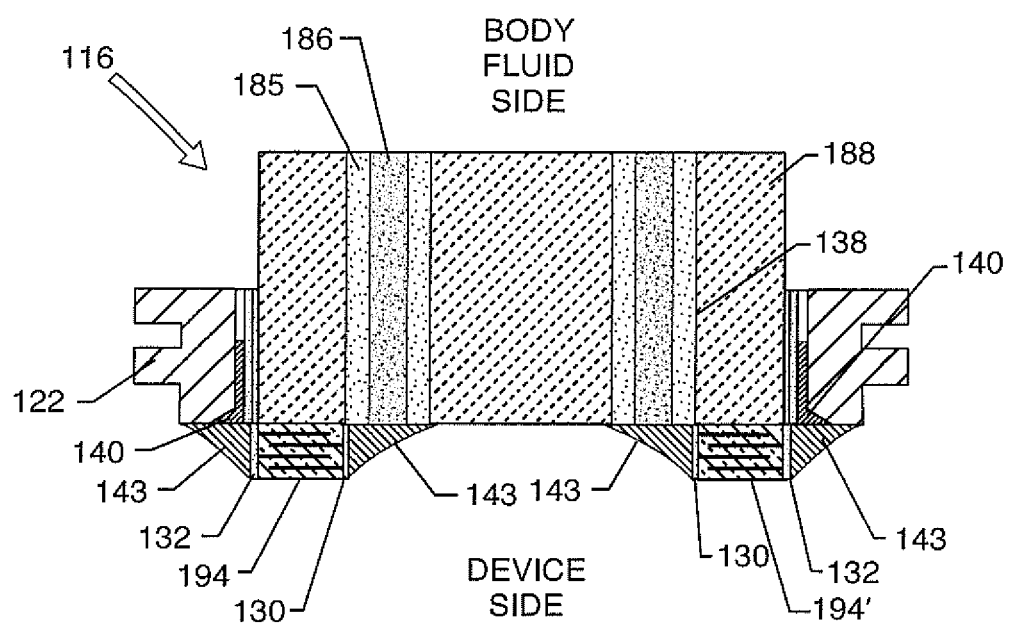
Figure 124:
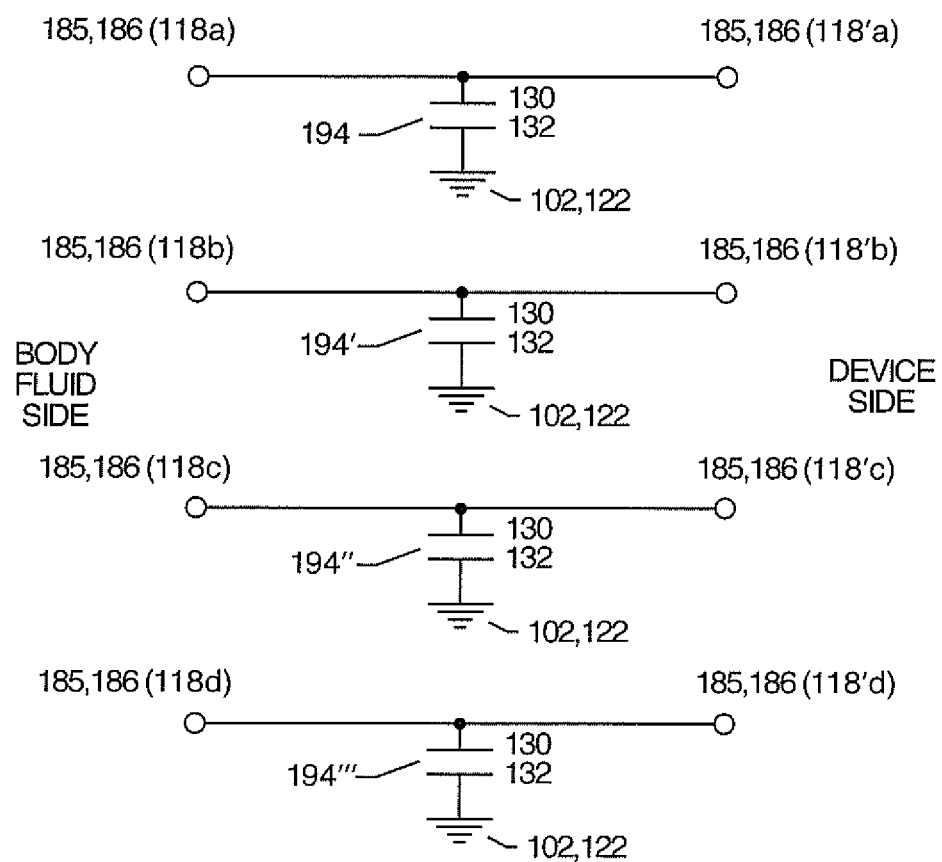
Figure 125:
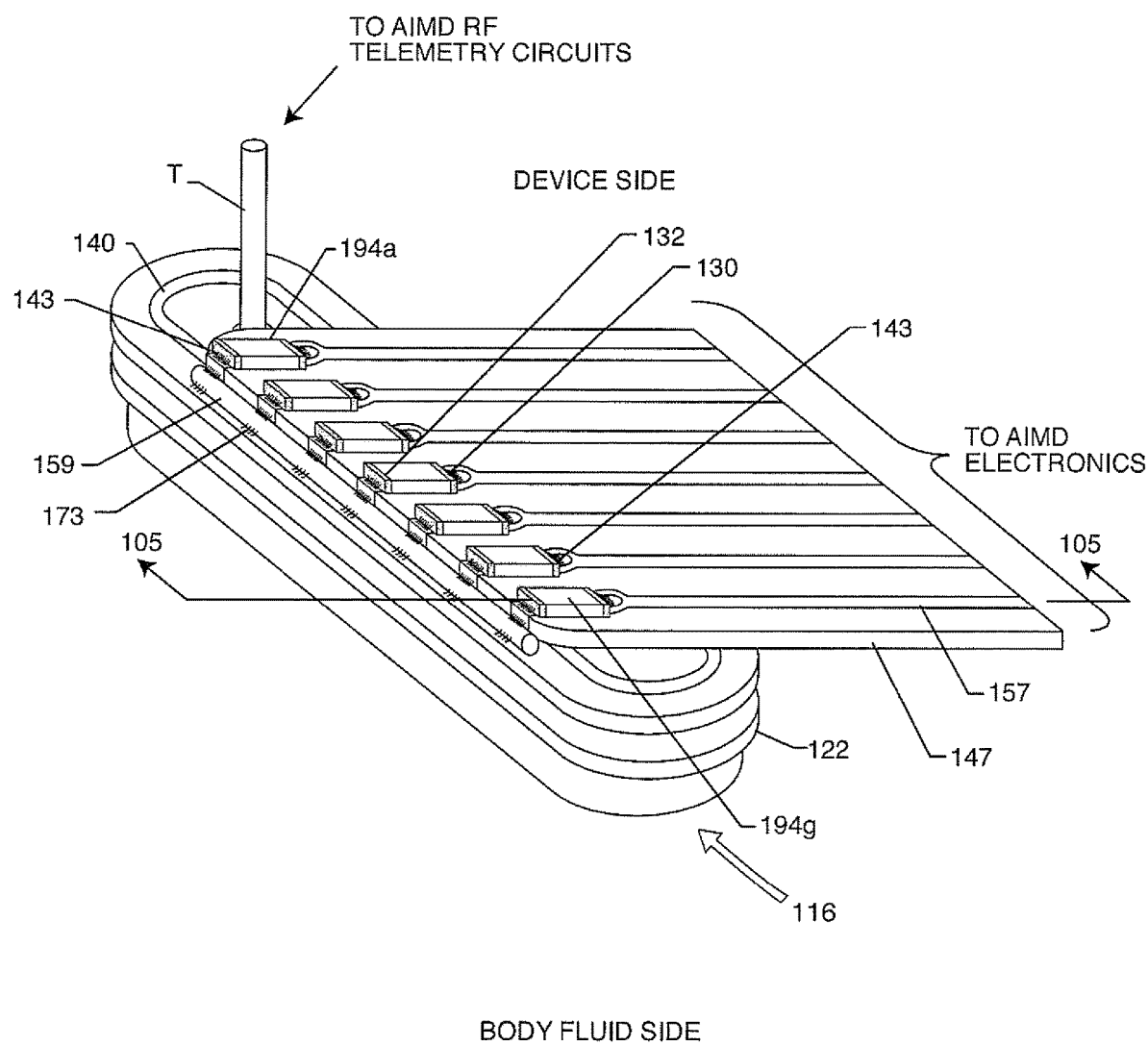
Figure 126:
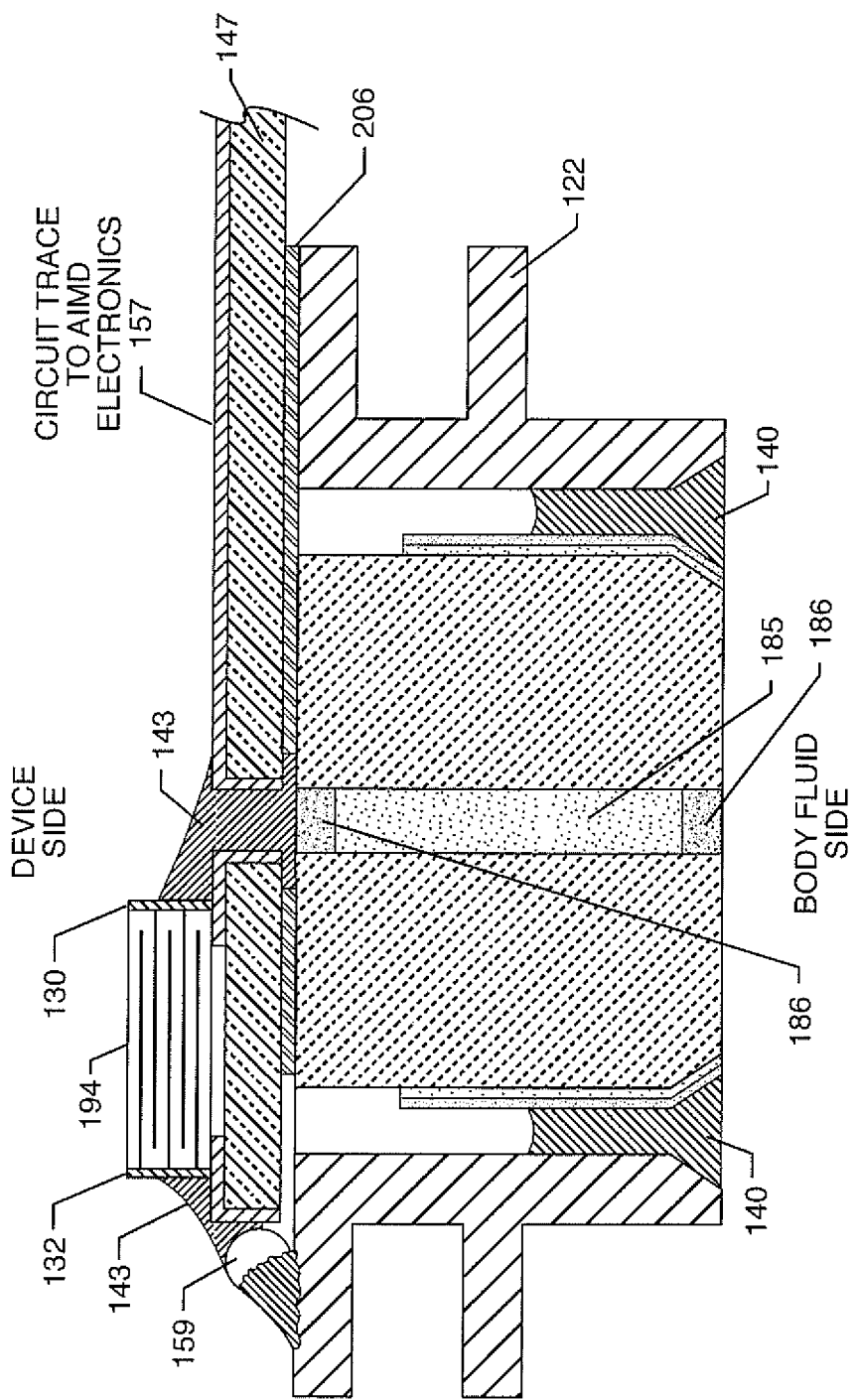
Figure 127:
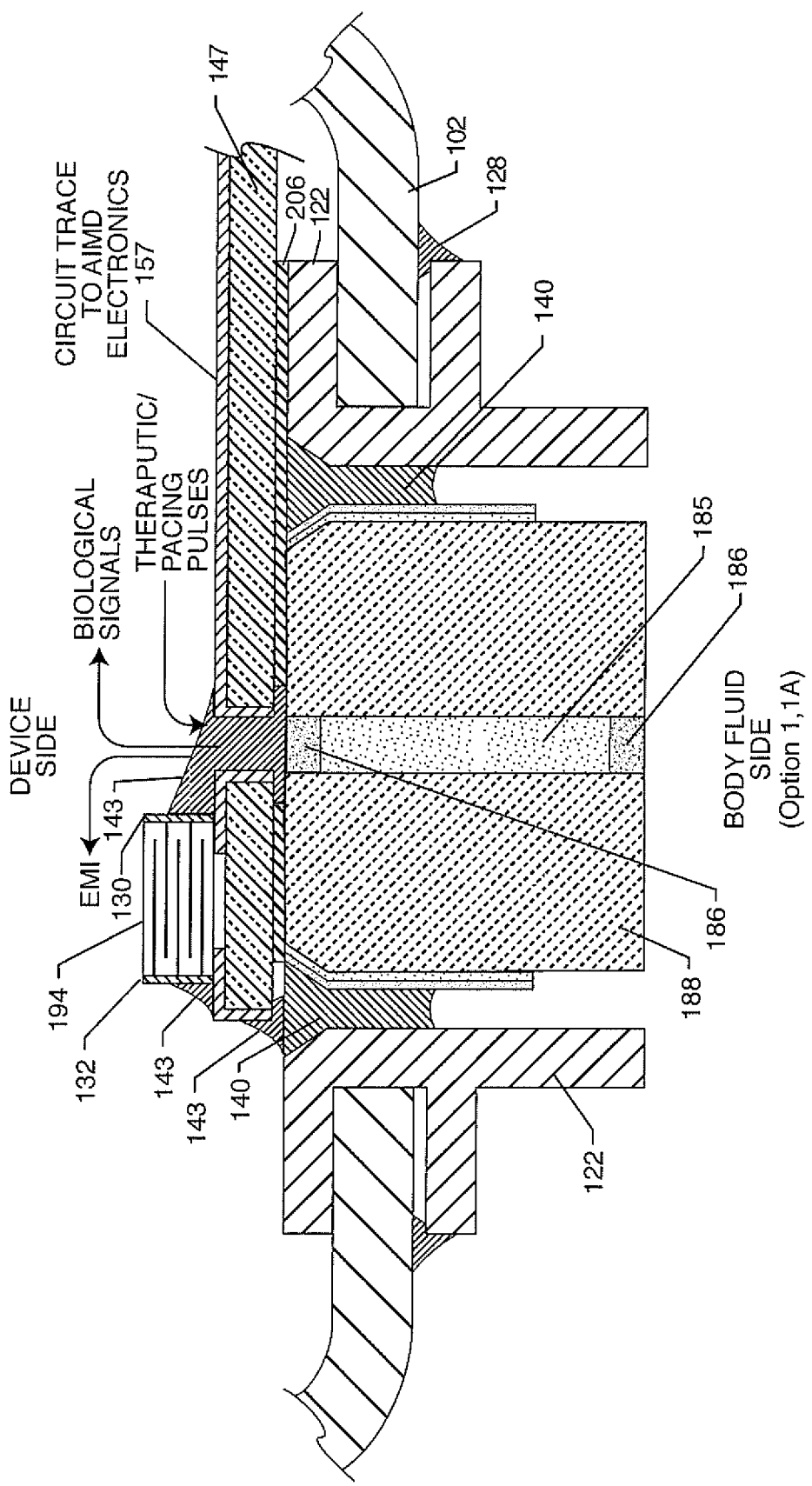
Figure 128:
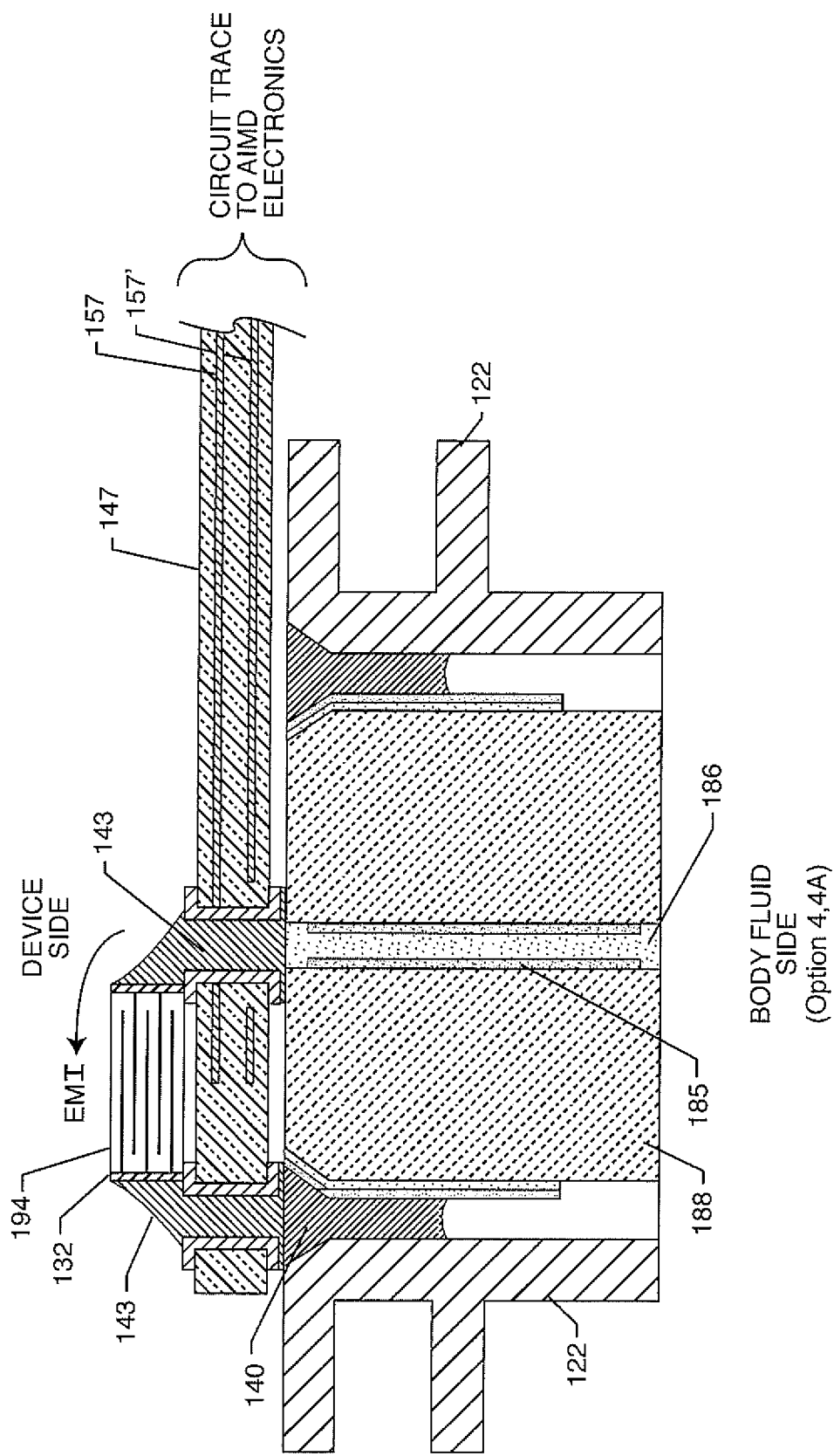
Figure 129:
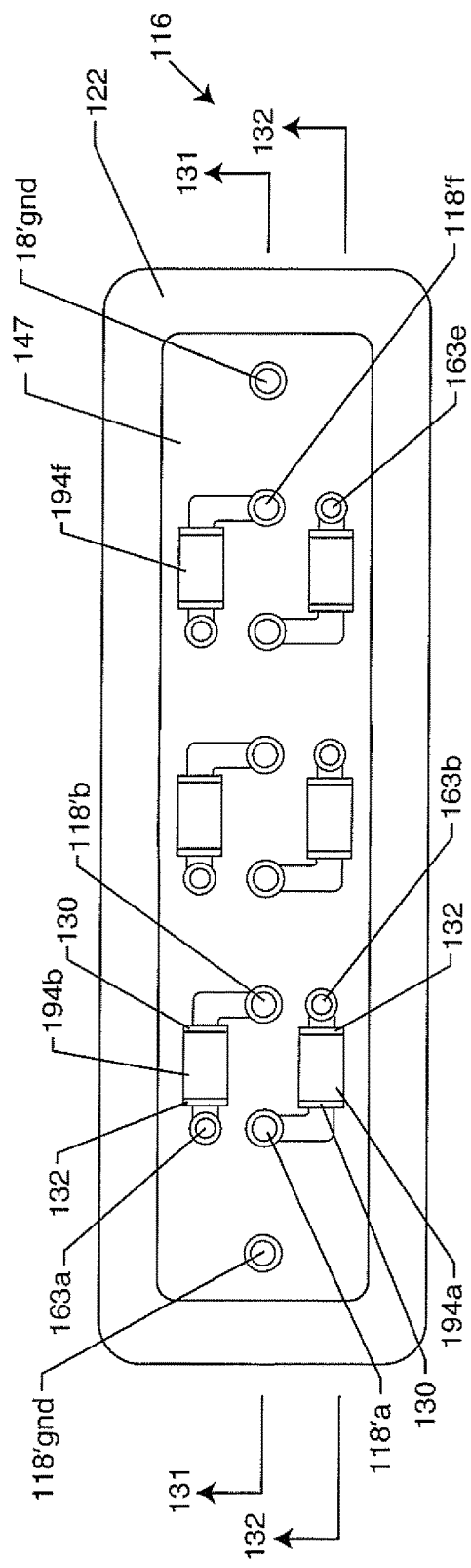
Figure 130:
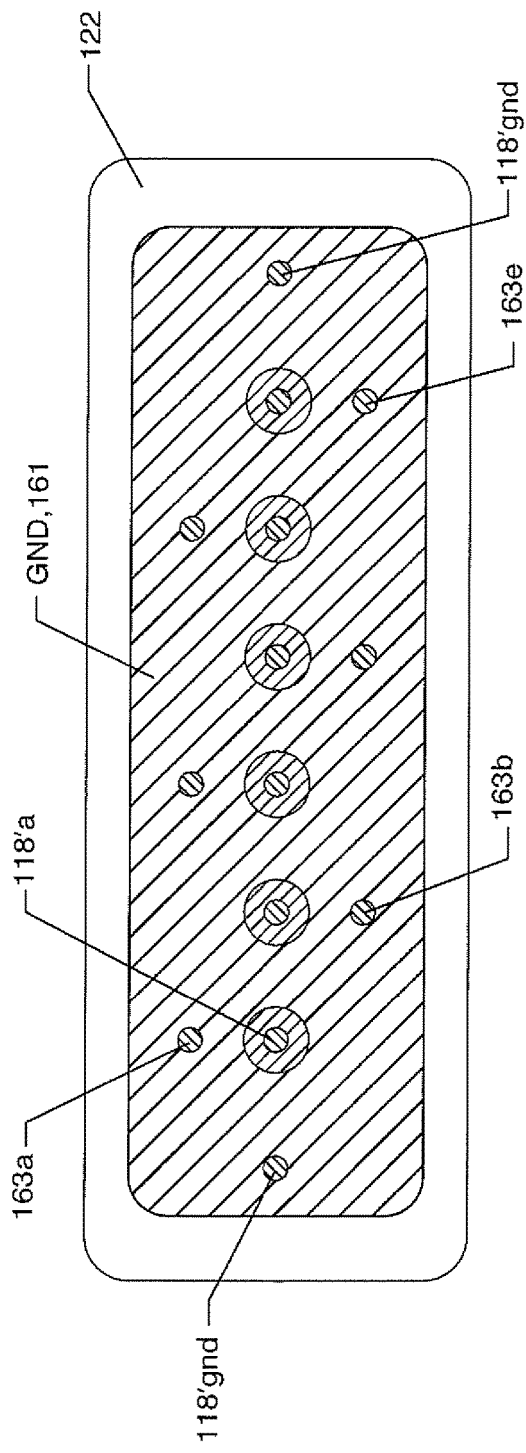
Figure 133:
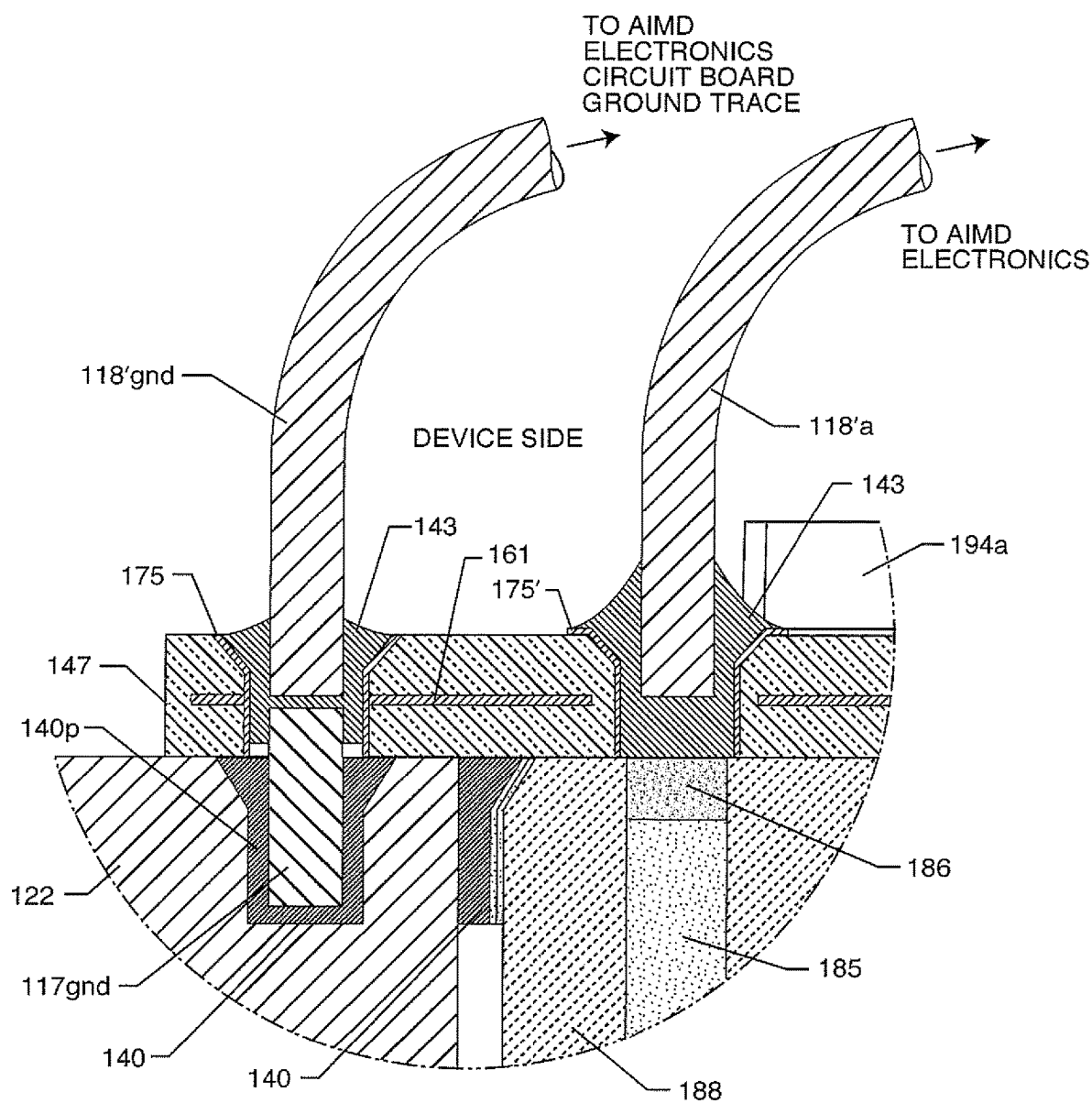
Figure 134:
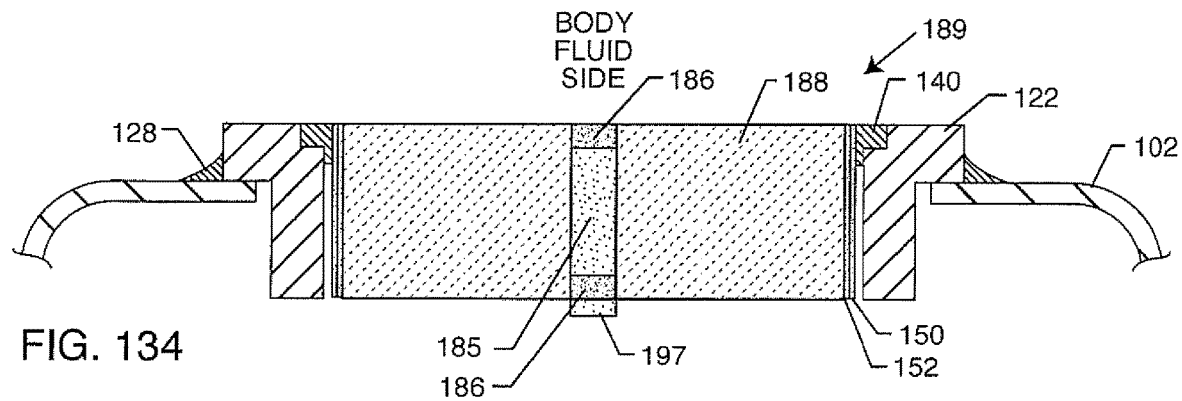
Figure 135:
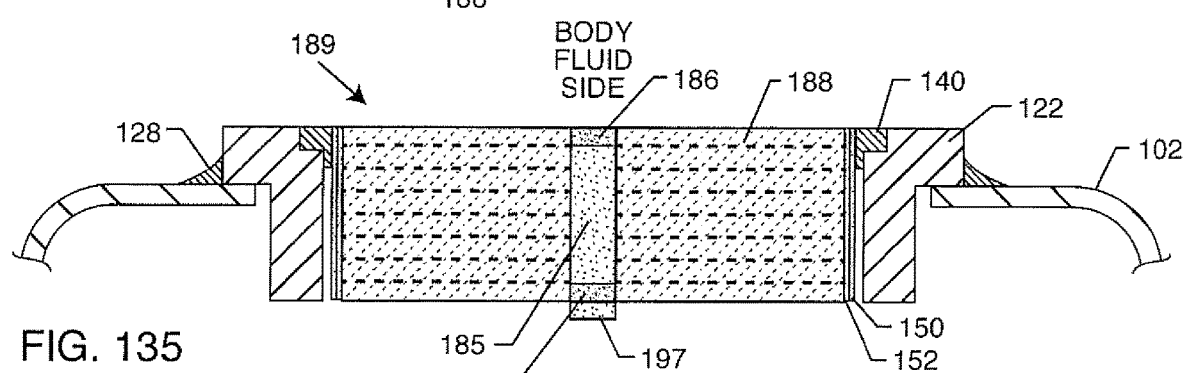
Figure 136:
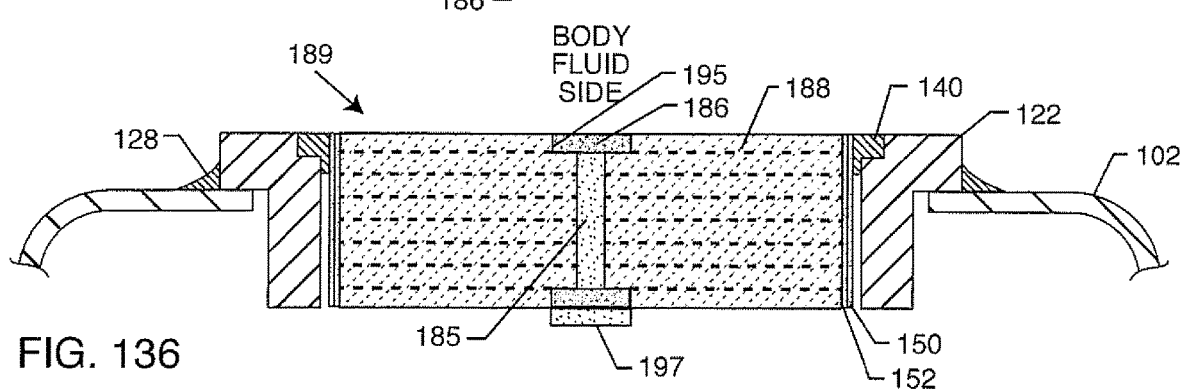
Figure 137:
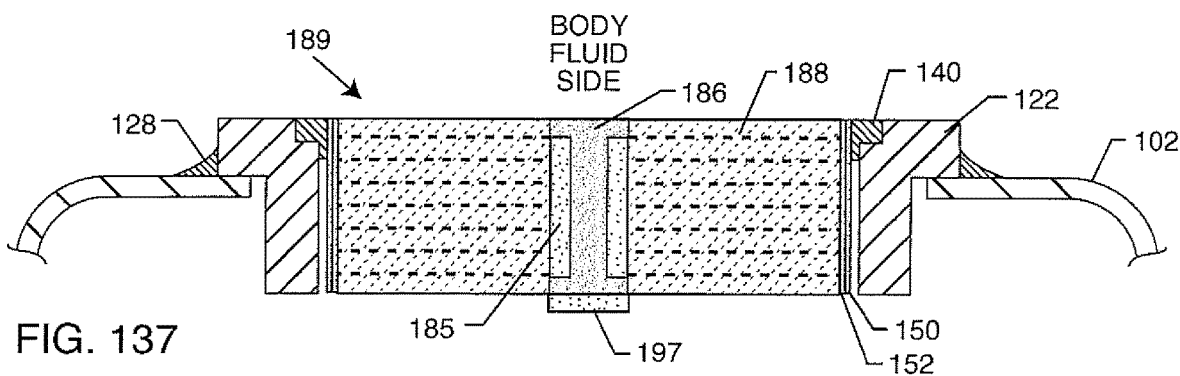
Figure 138:
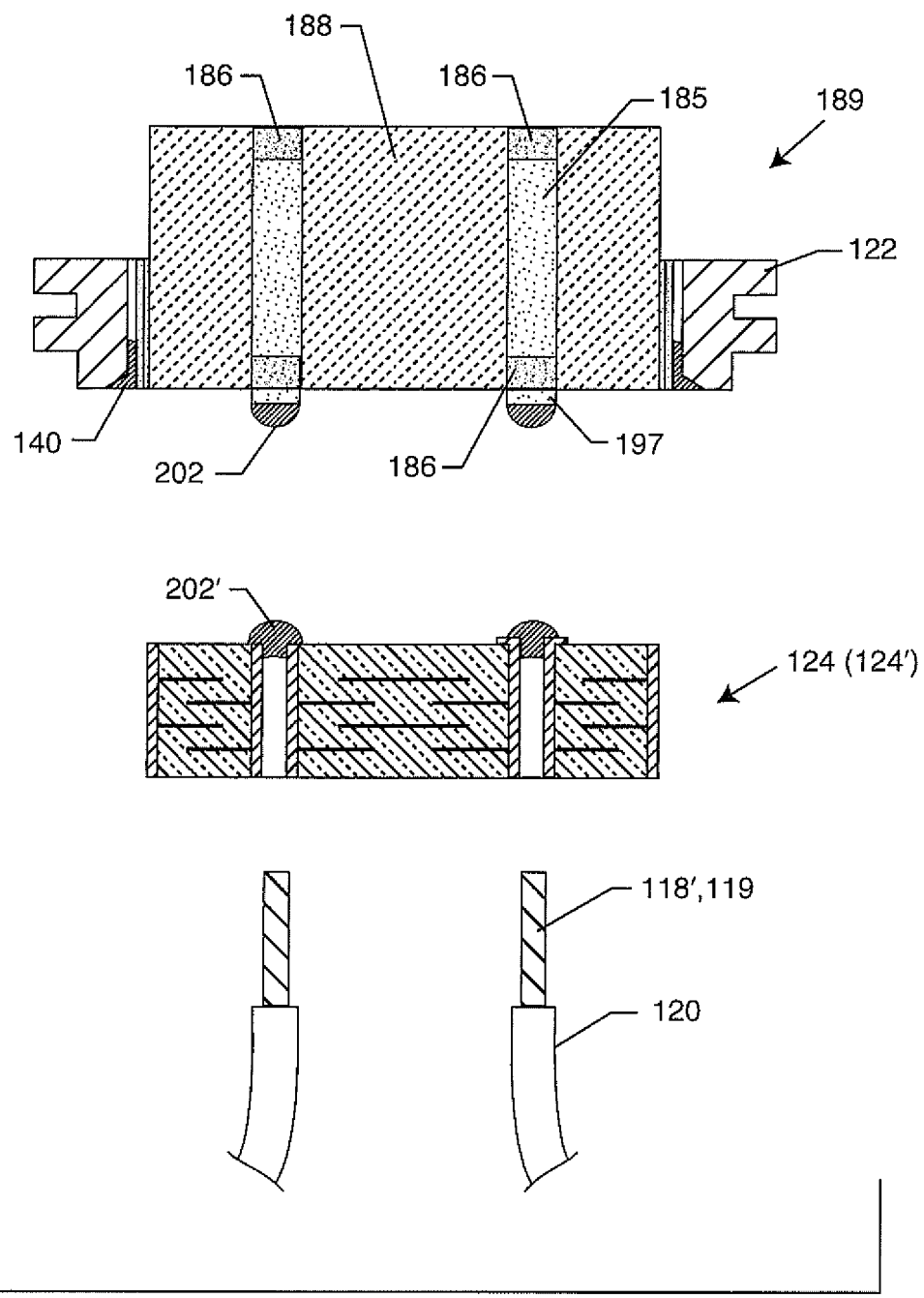
Figure 139:
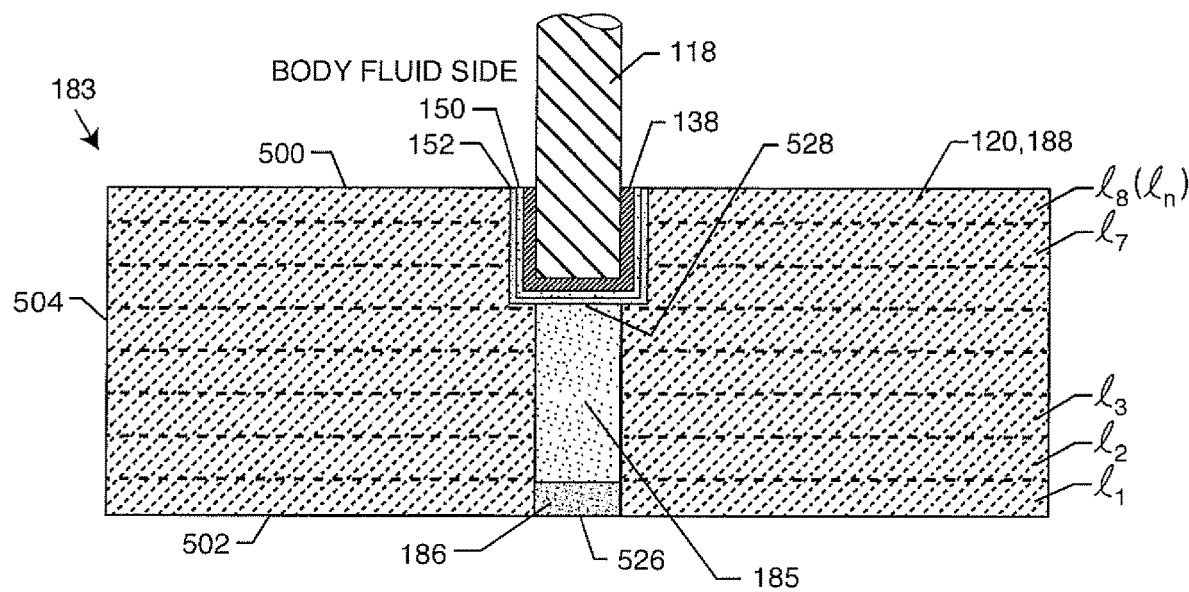
Figure 140:
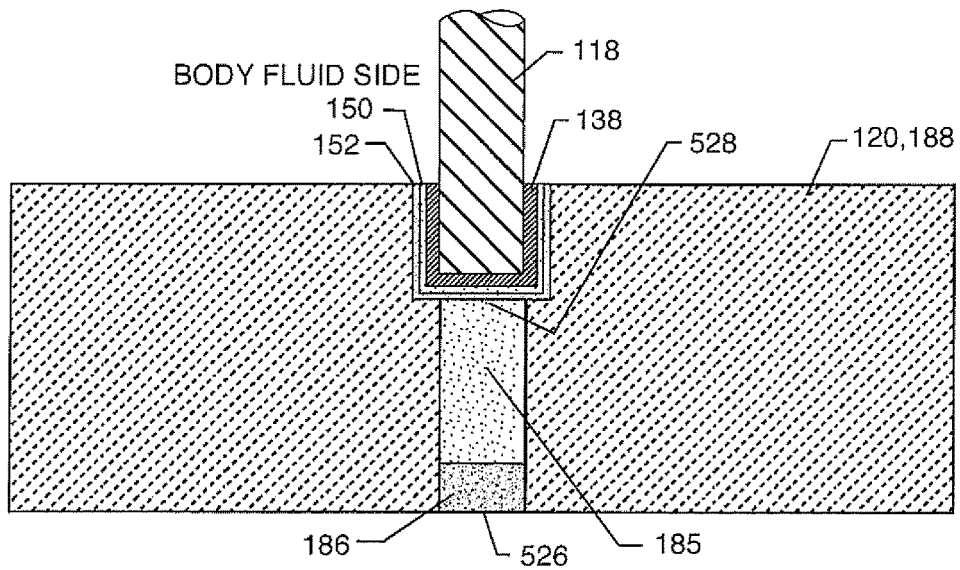
Figure 141:
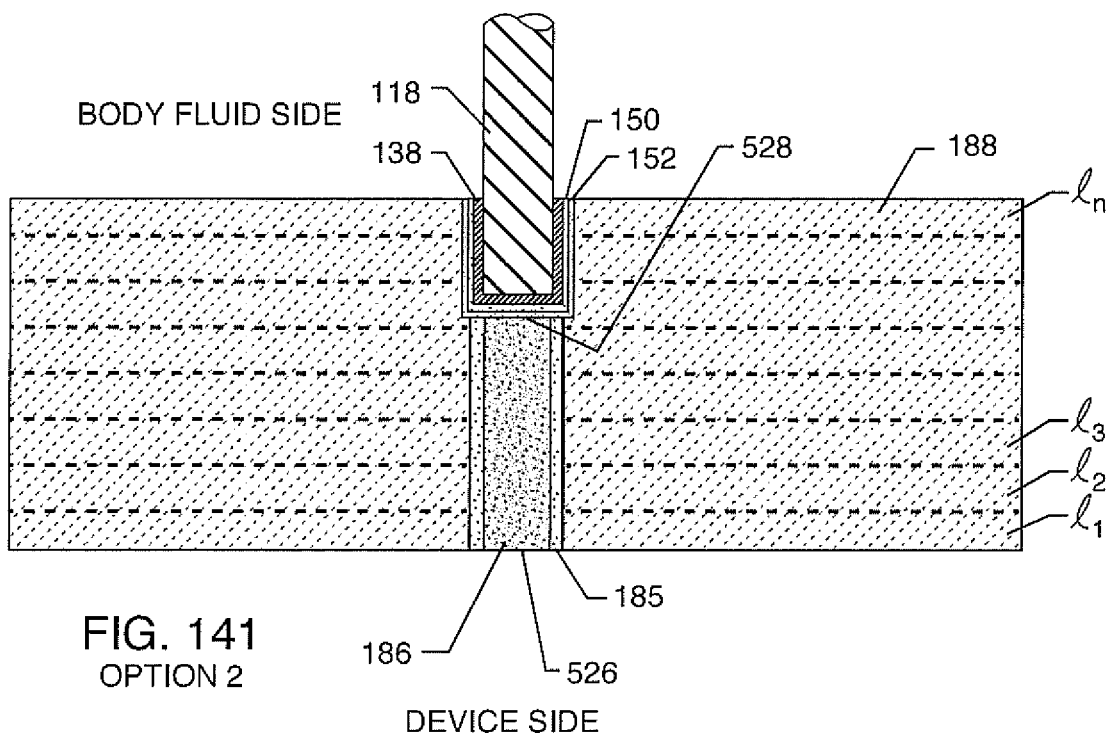
Figure 142:
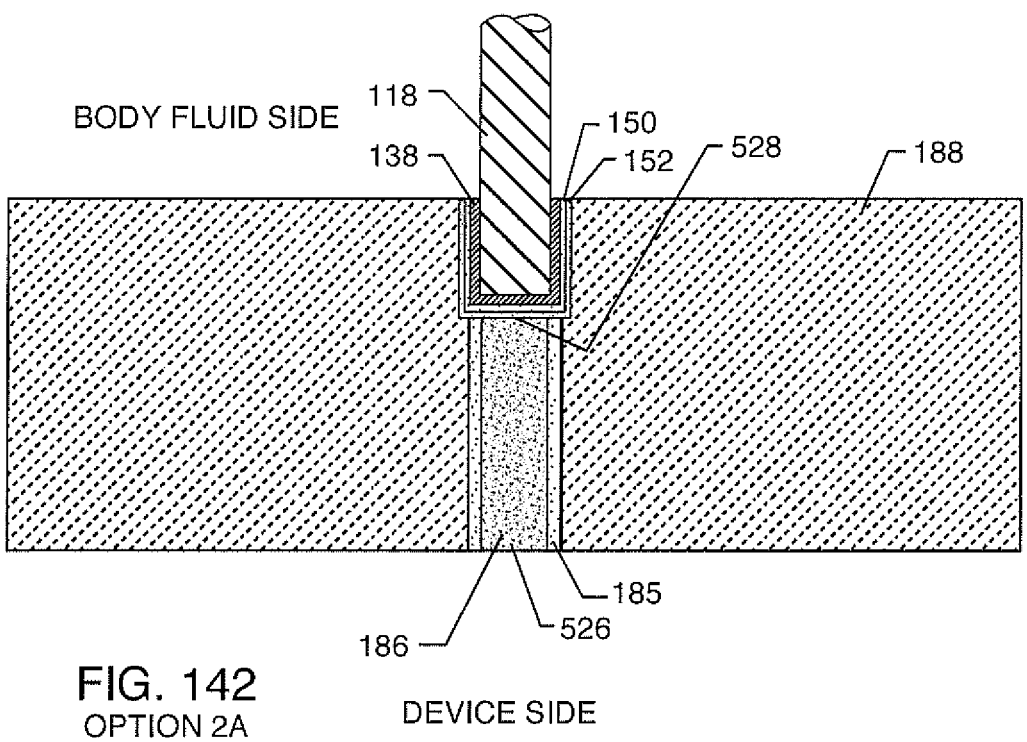
Figure 143:
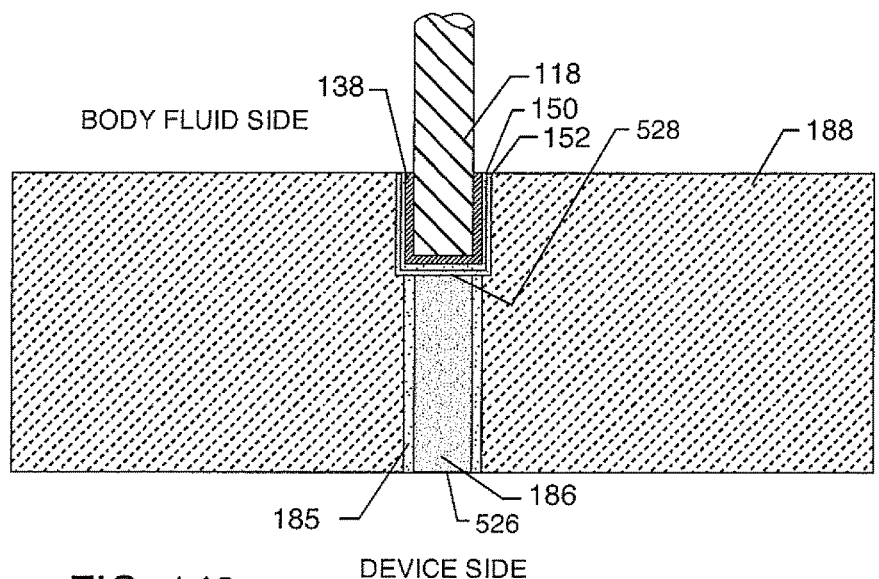
Figure 143A:
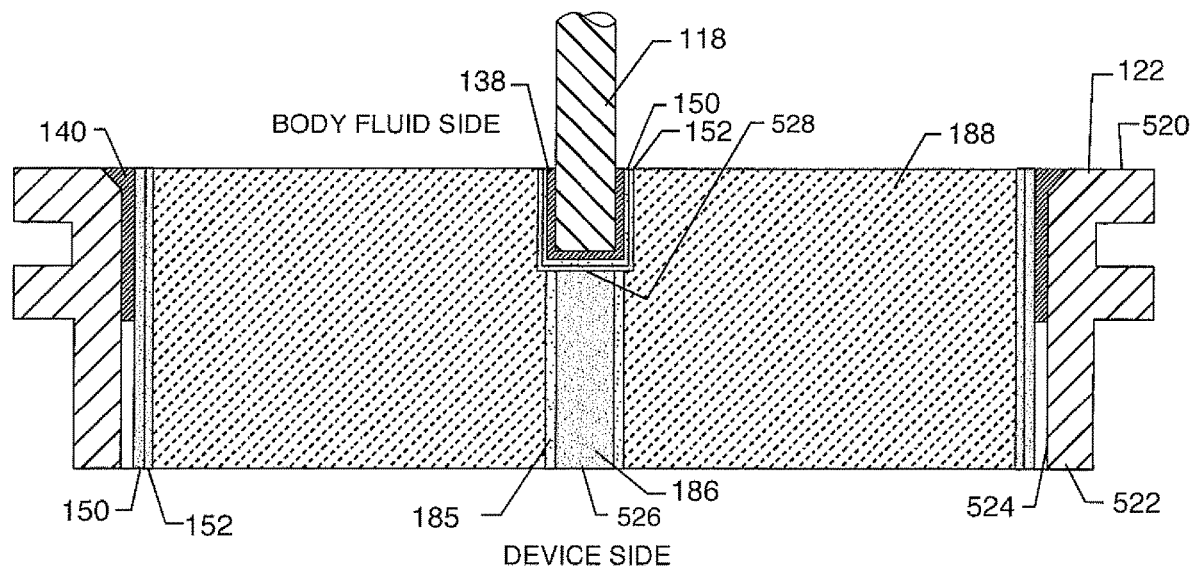
Figure 144:
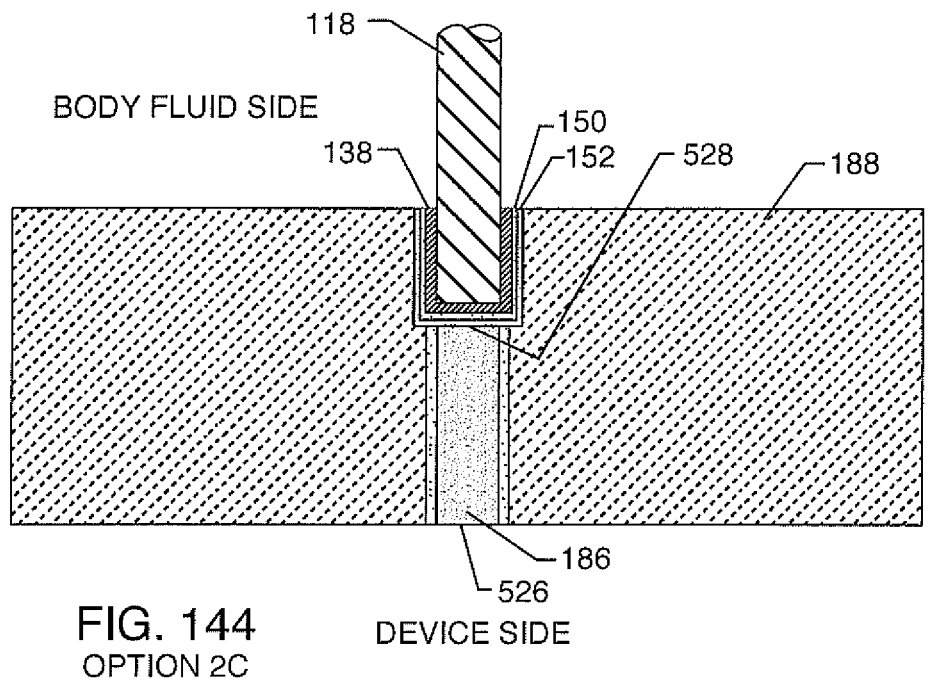
Figure 144A:
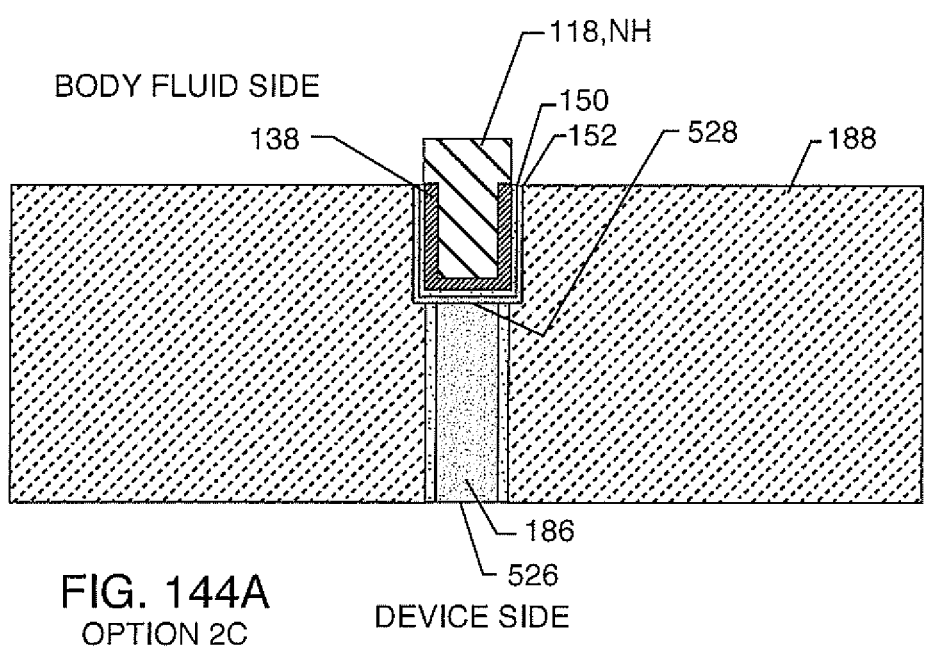
Figure 145:
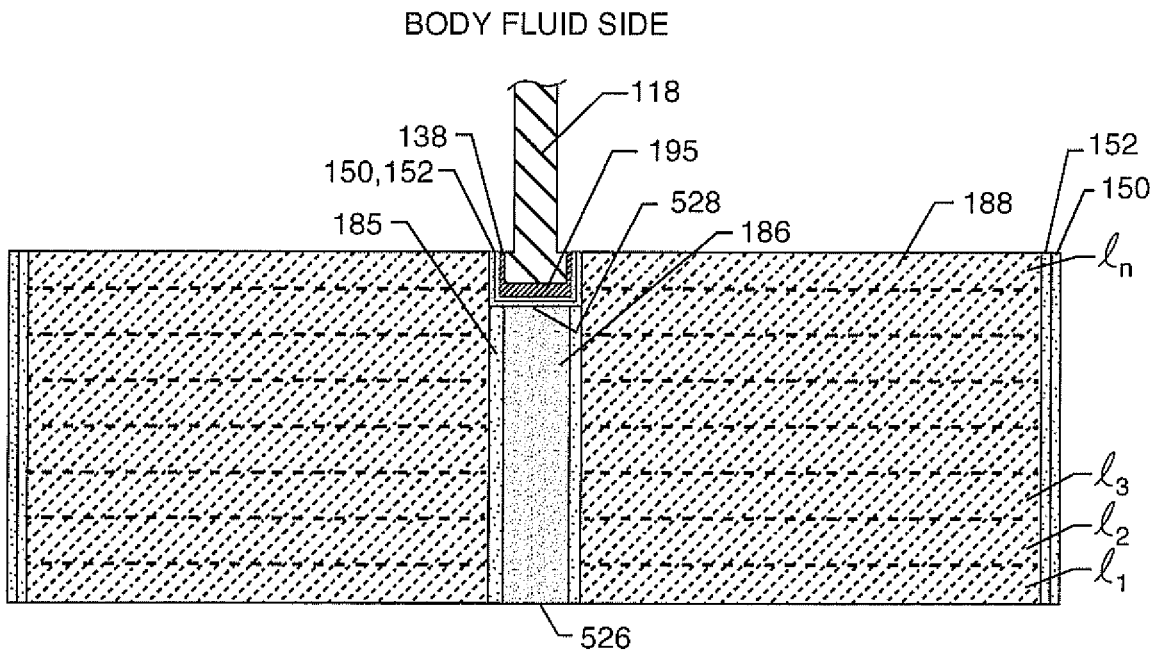
Figure 146:
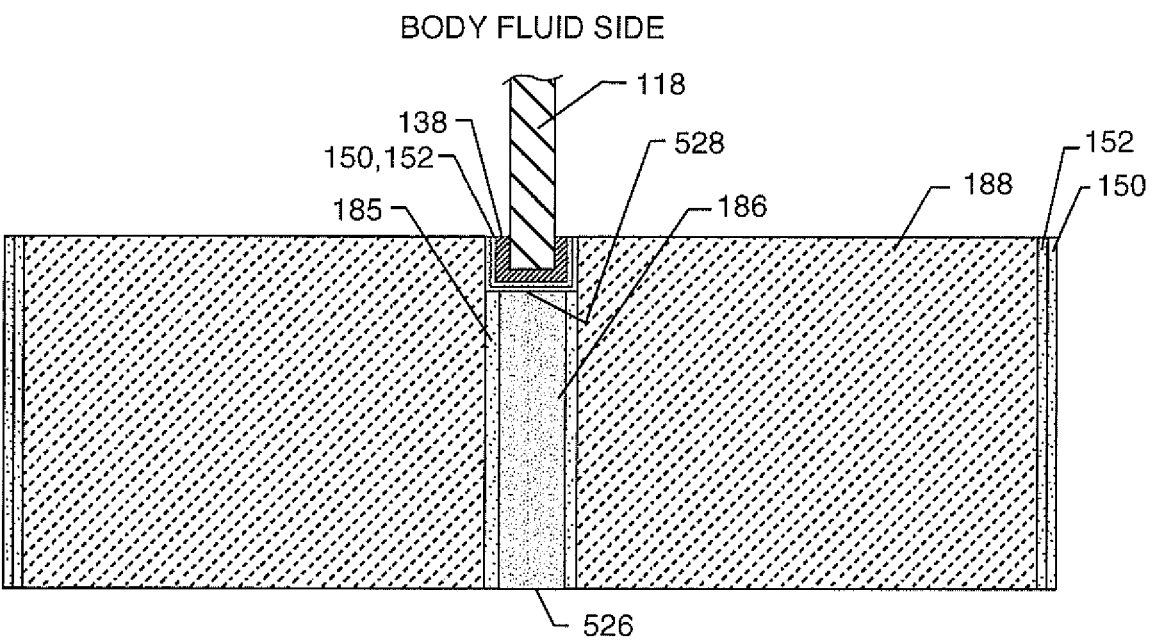
Figure 147:
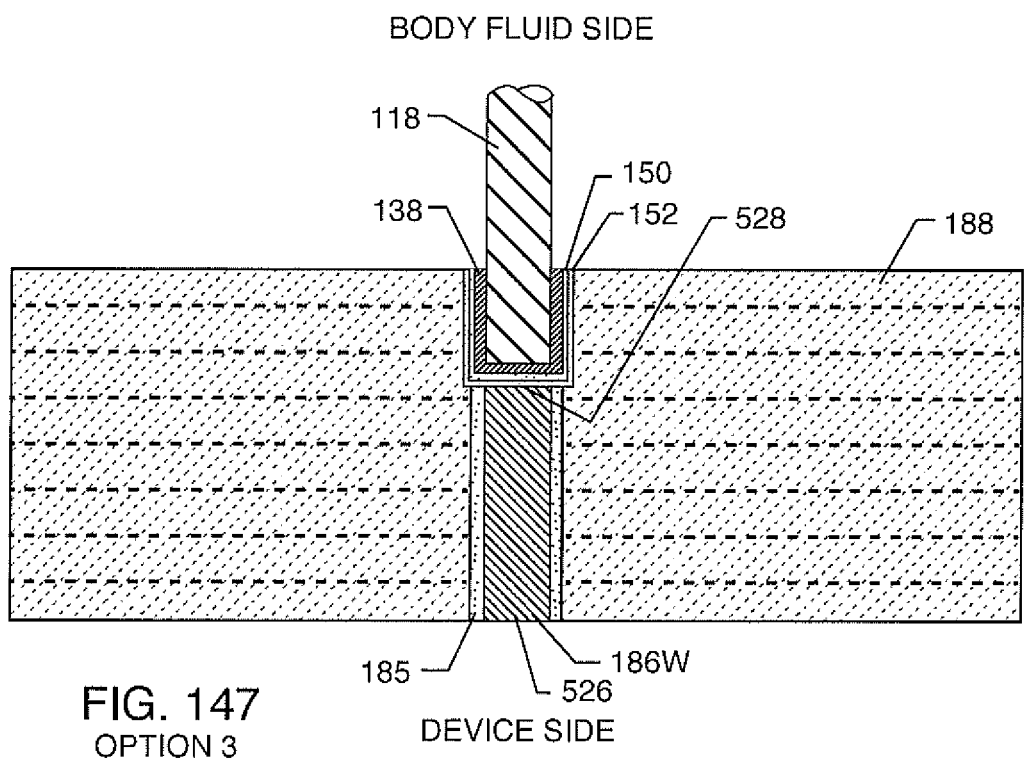
Figure 148:
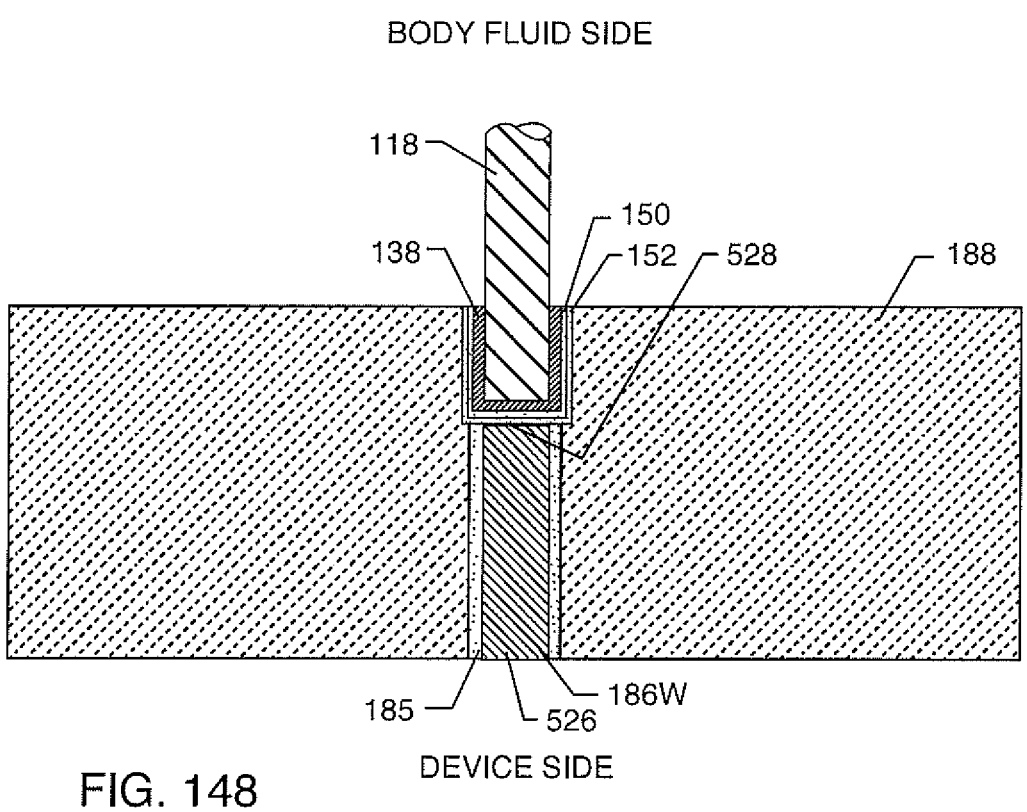
Figure 149:
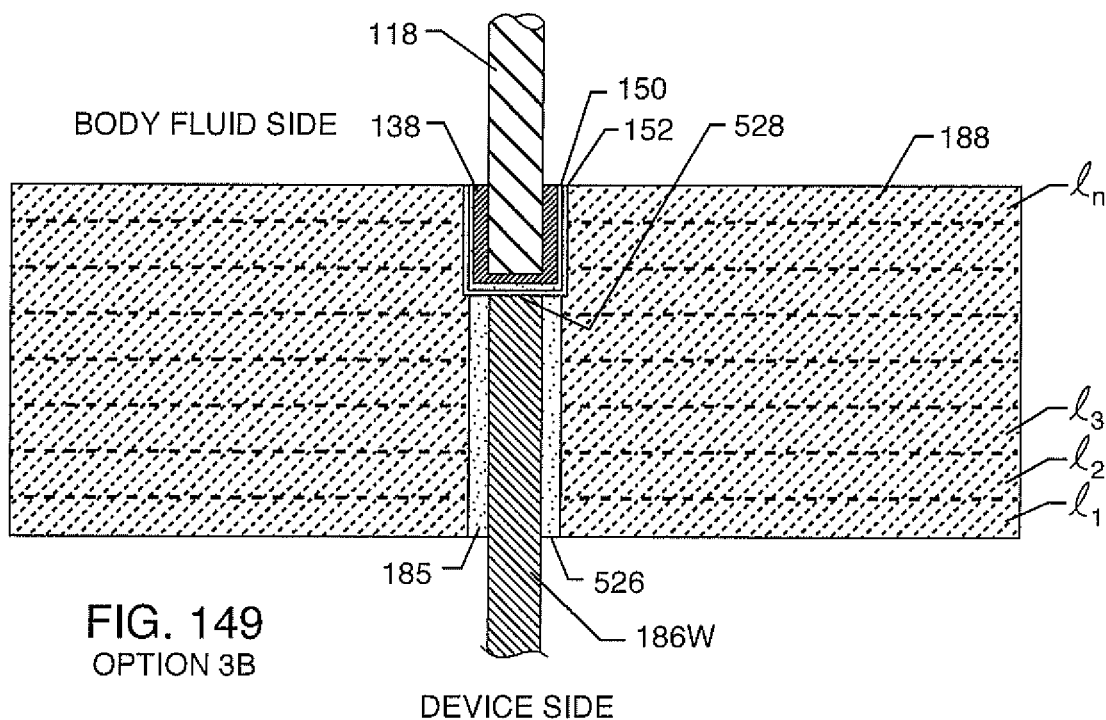
Figure 150:
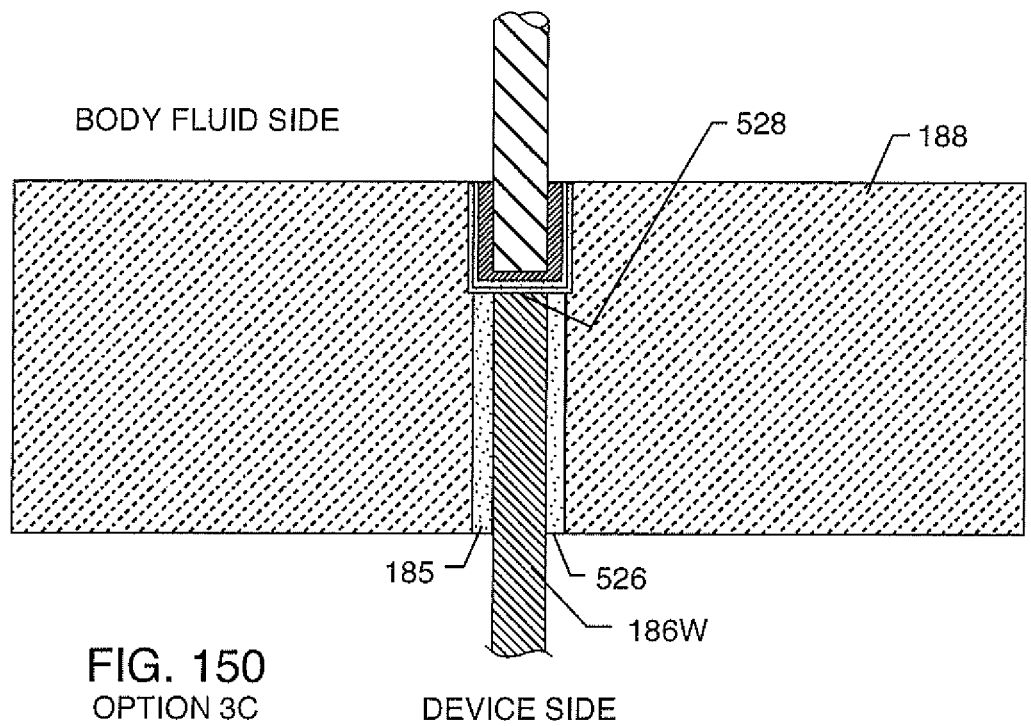
Figure 151:
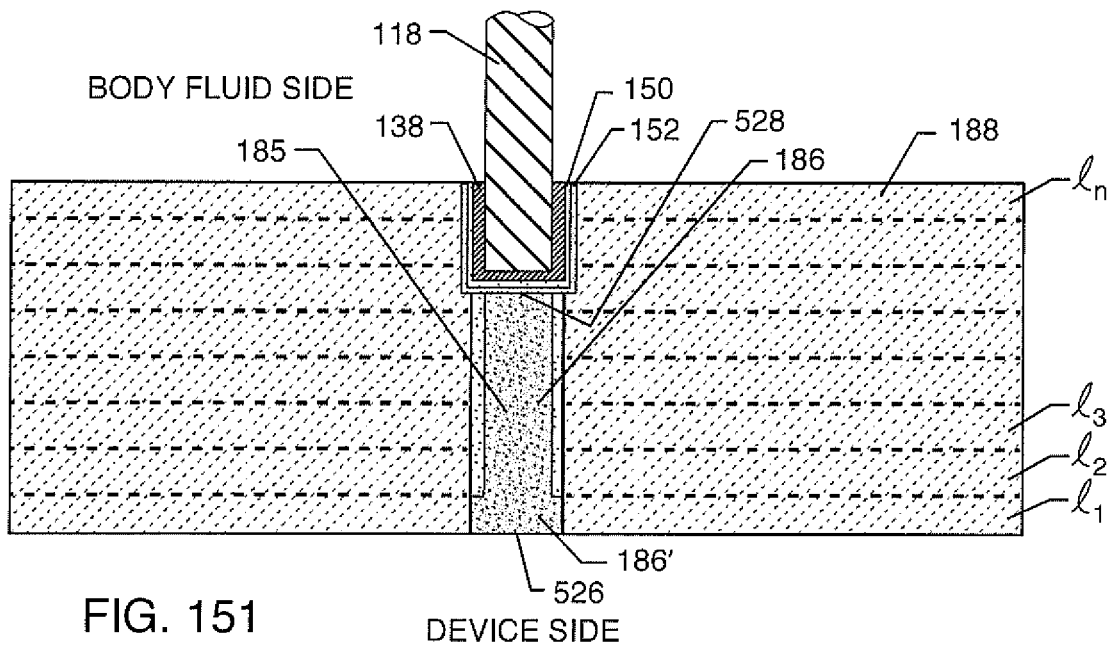
Figure 152:
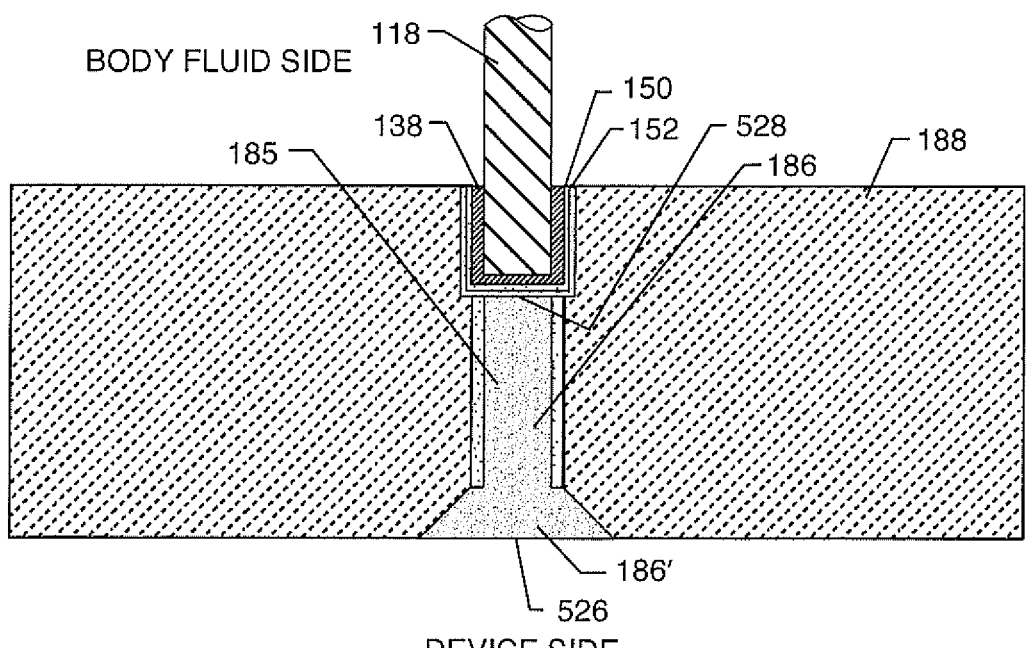
Figure 153:
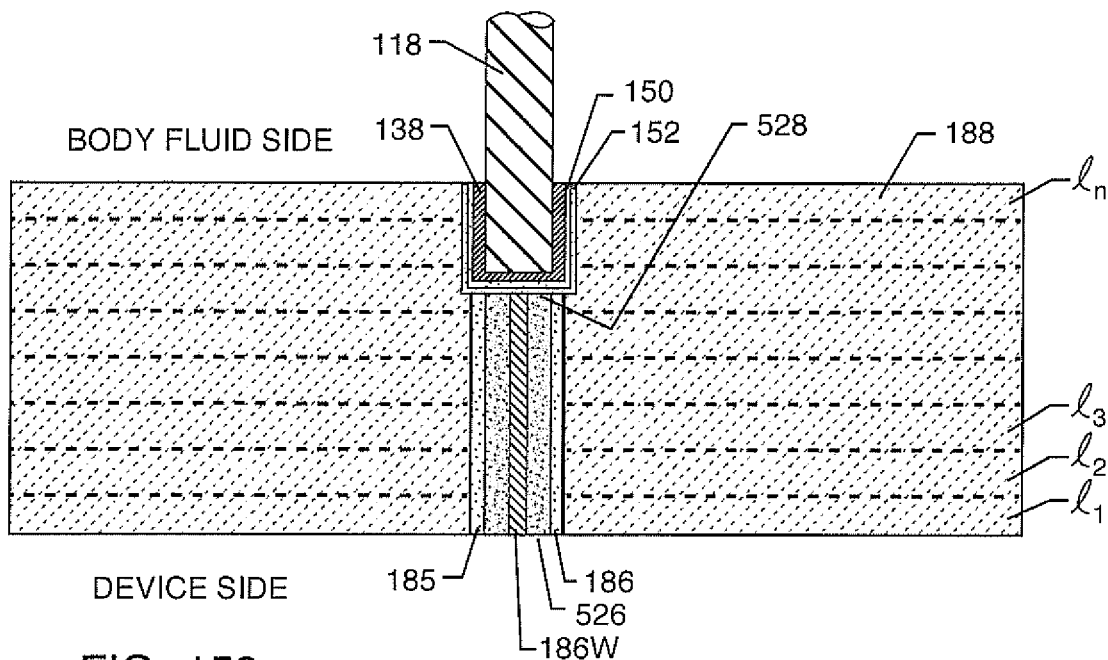
Figure 154:
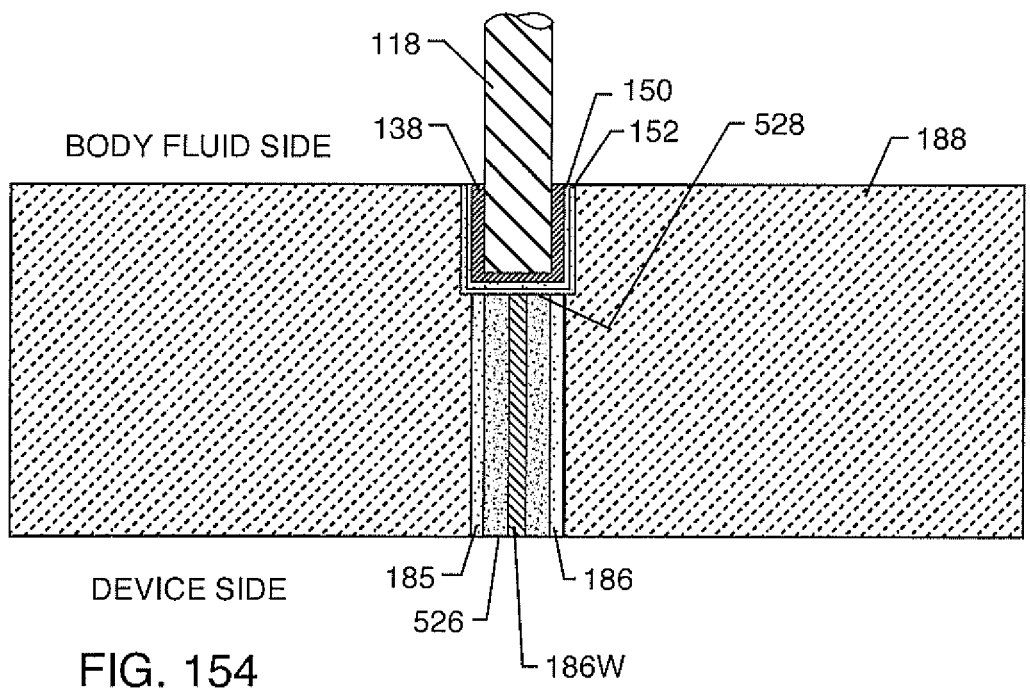
Figure 155:
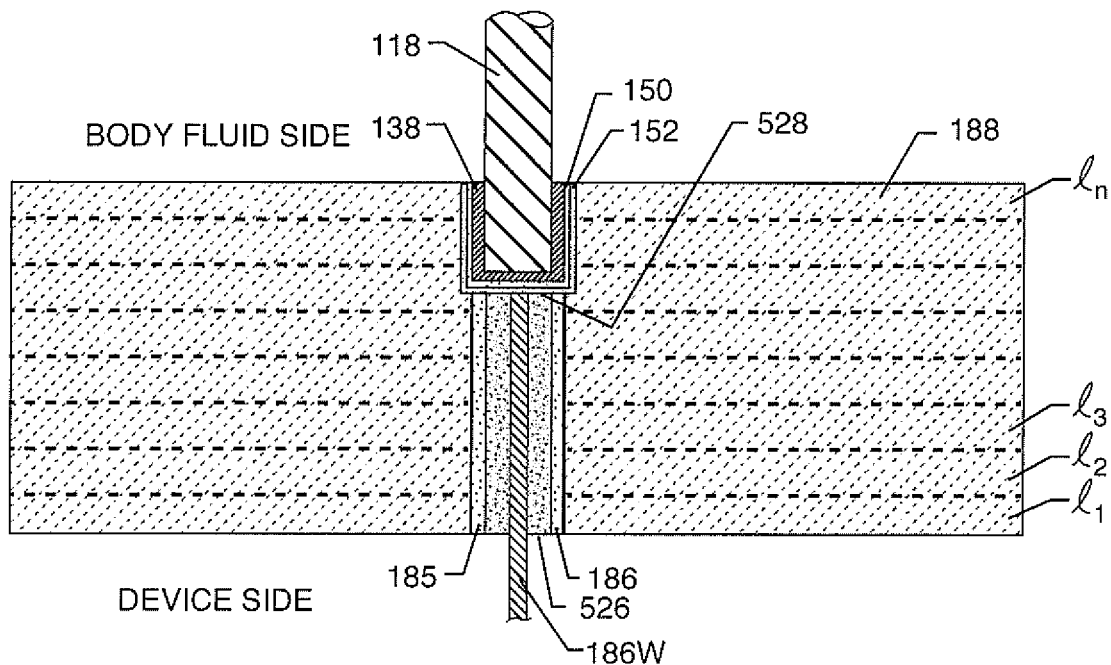
Figure 156:
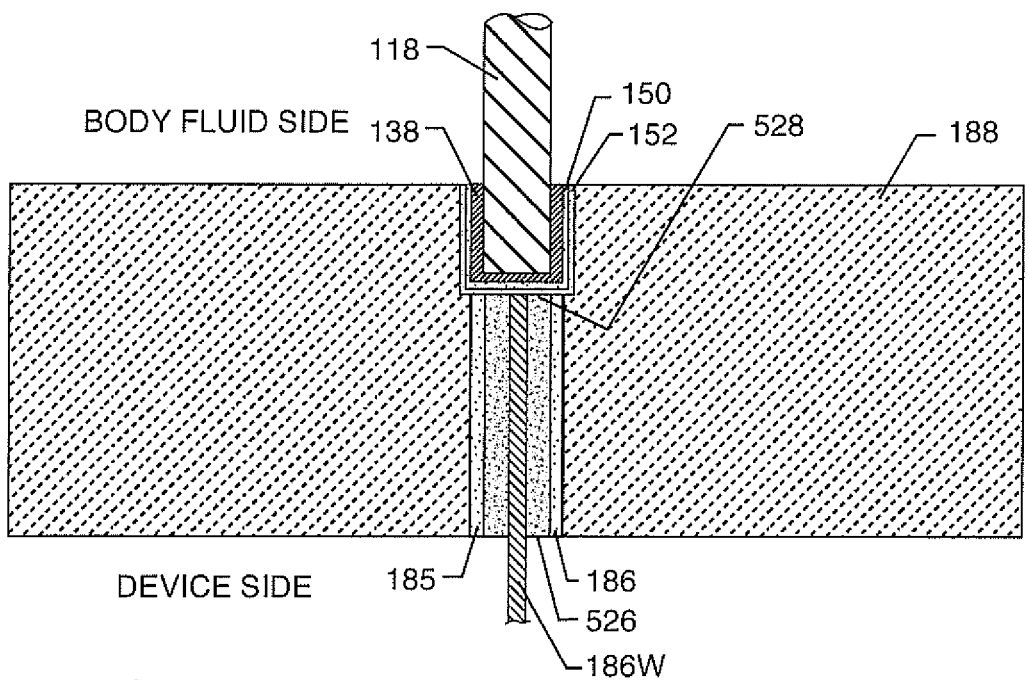
Figure 157:
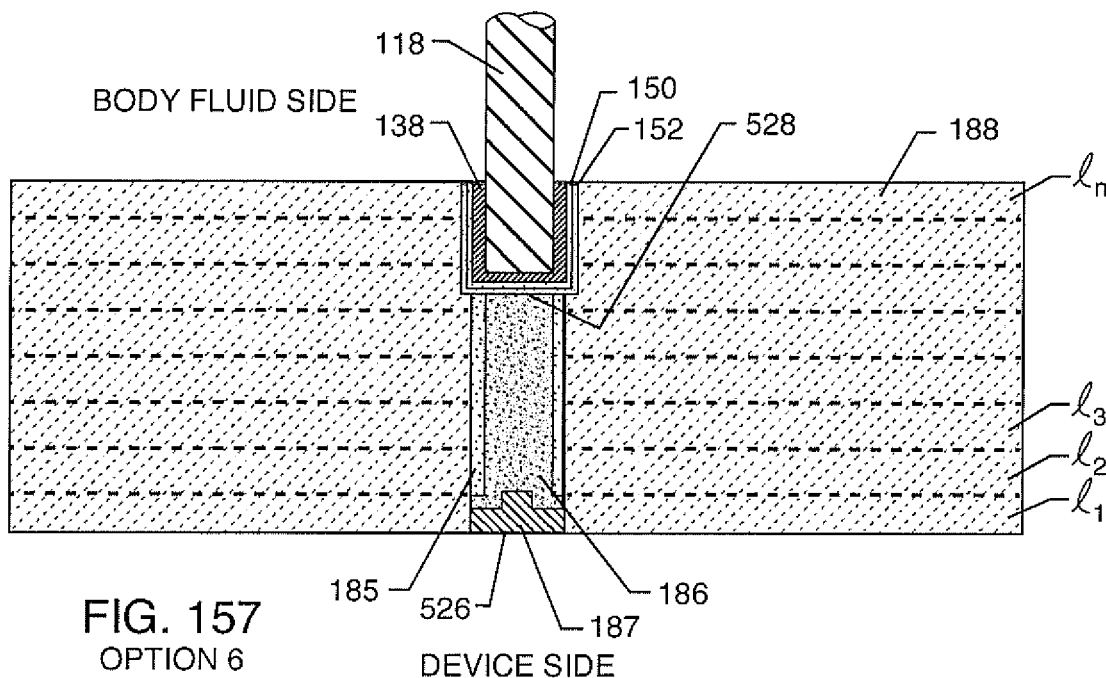
Figure 158:
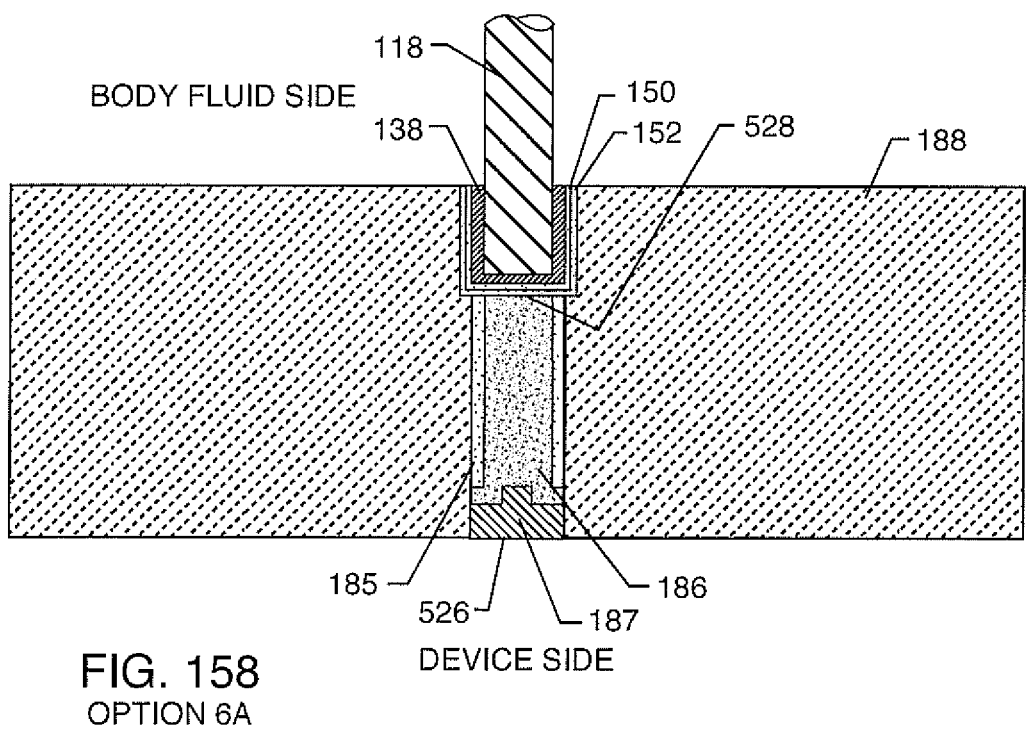
Figure 159:
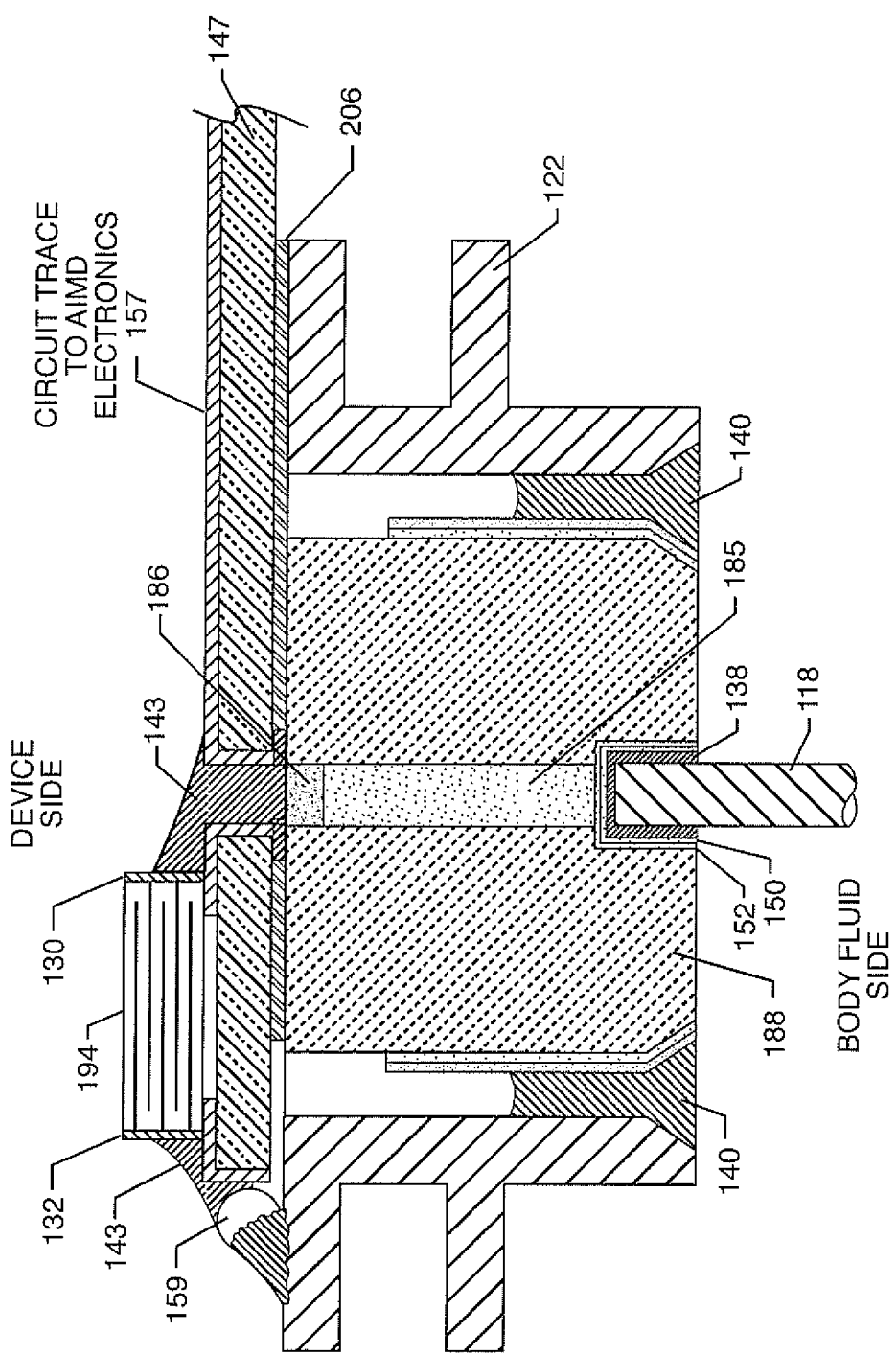
Figure 160:
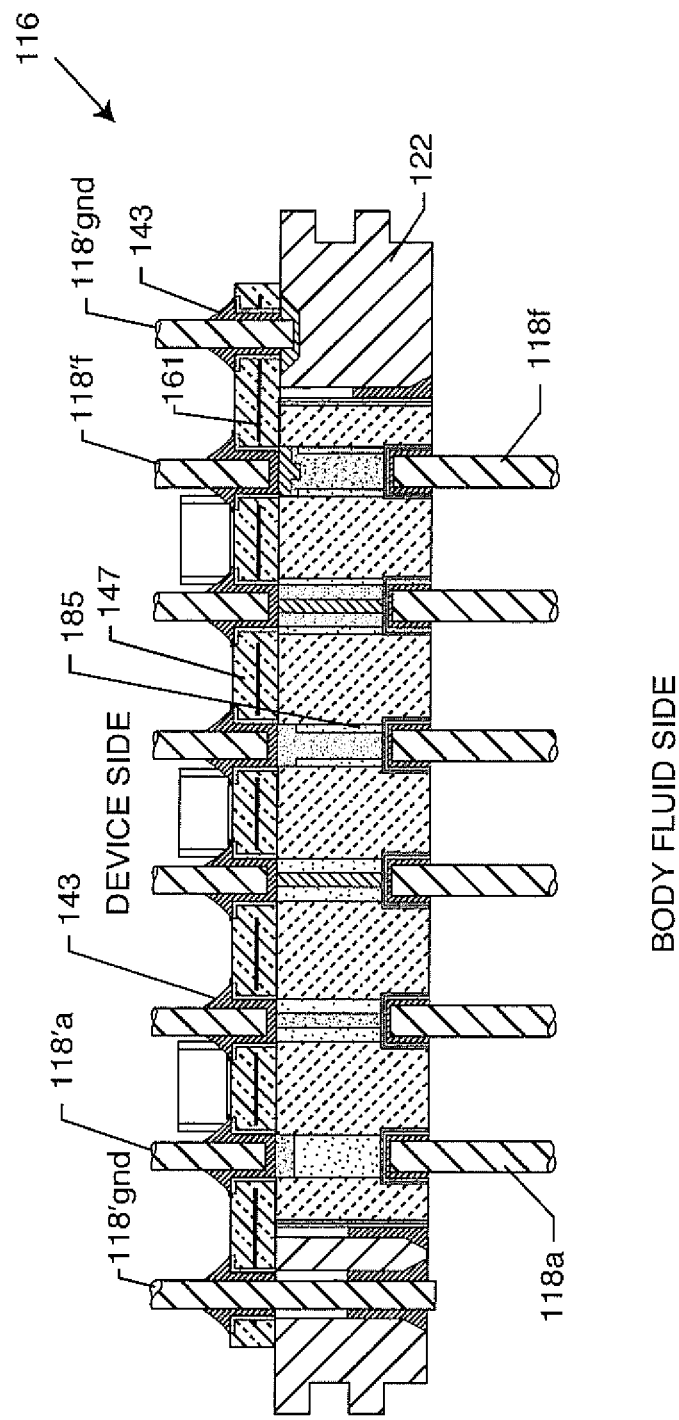
Figure 161:
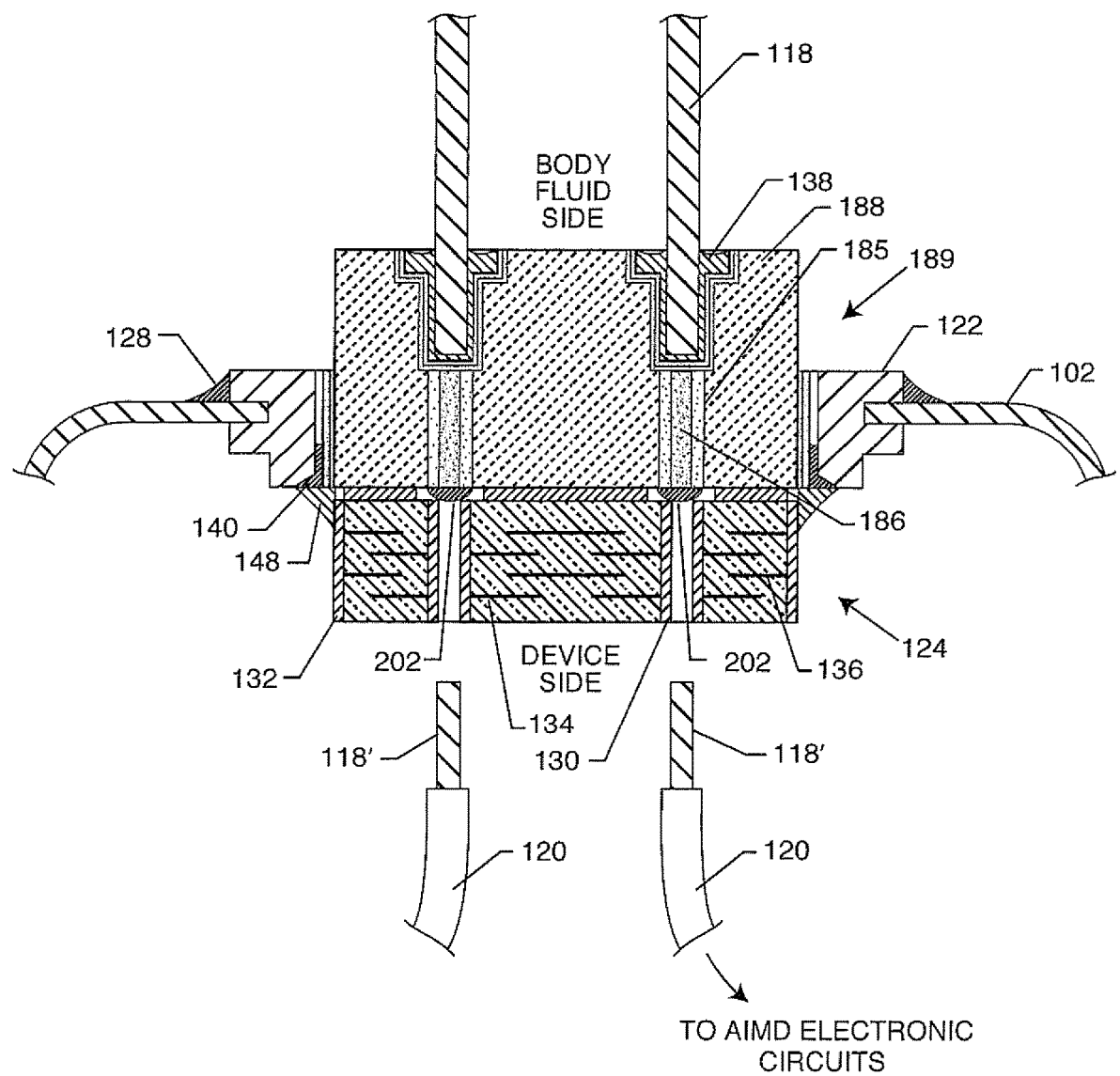
Figure 161A:
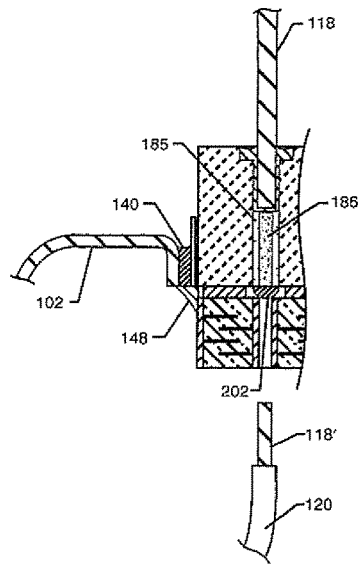
Figure 161B:
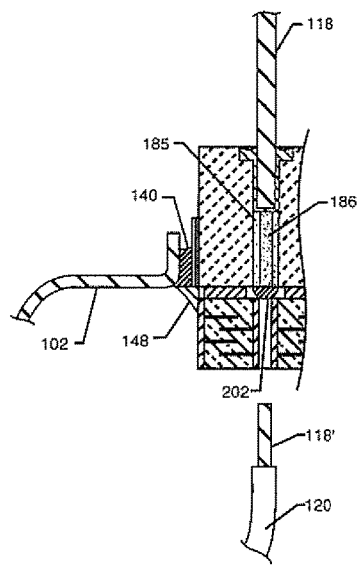
Figure 161C:
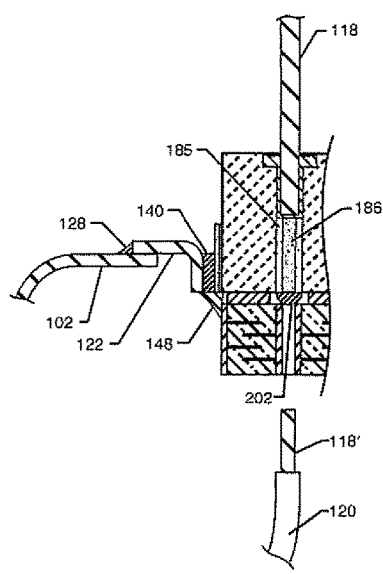
Figure 161D:
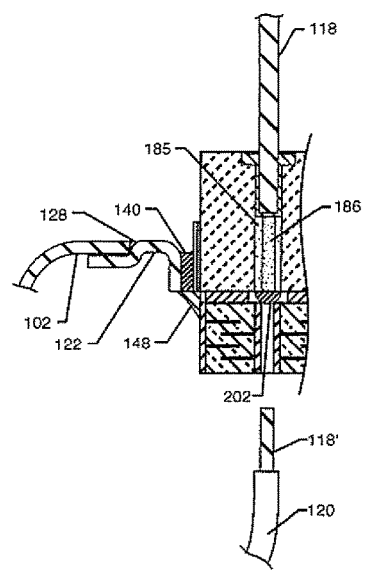
Figure 161E:
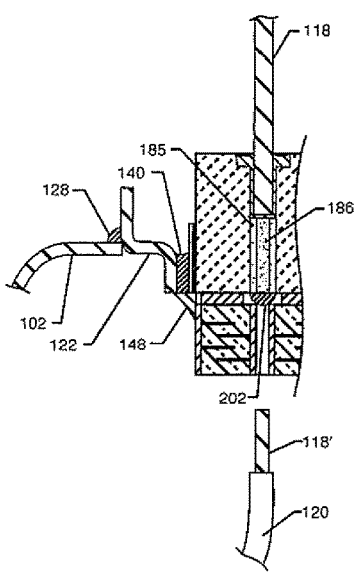
Figure 162:
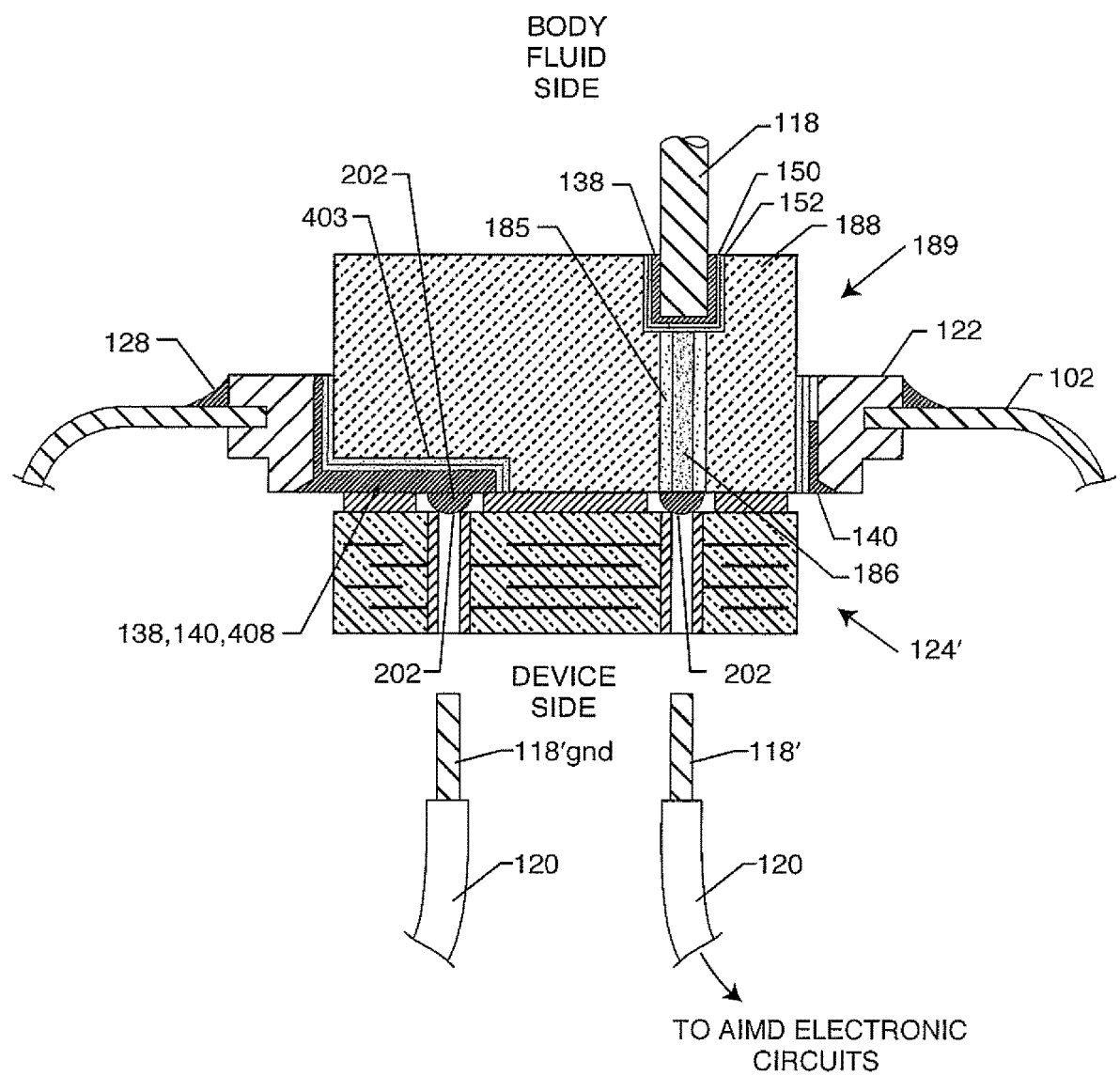
Figure 163:
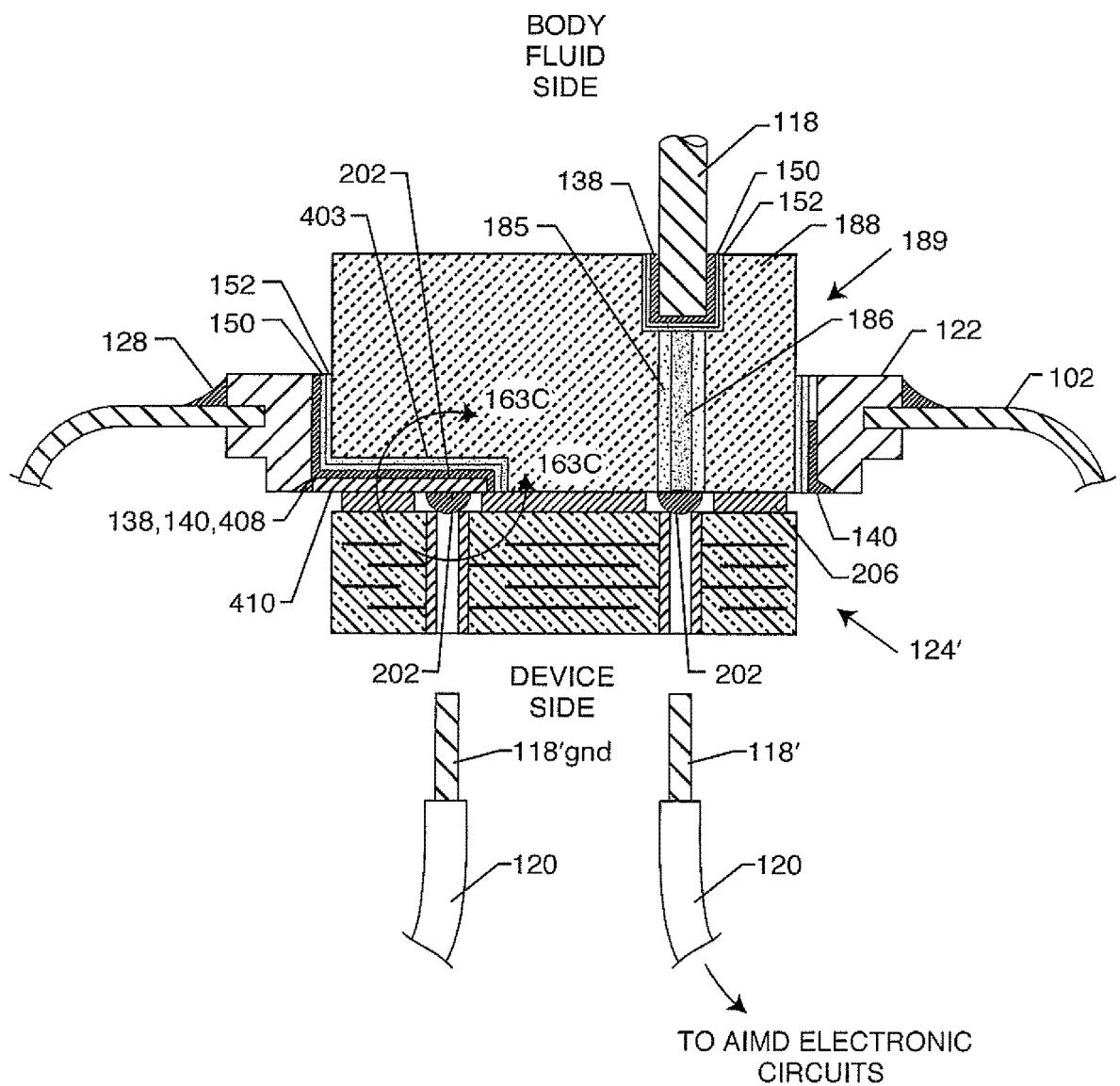
Figure 163A:
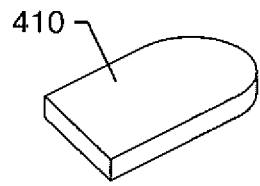
Figure 163B:
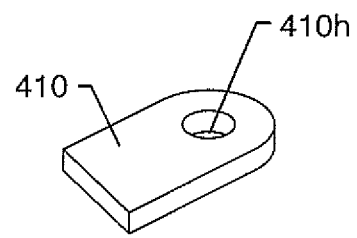
Figure 163C:
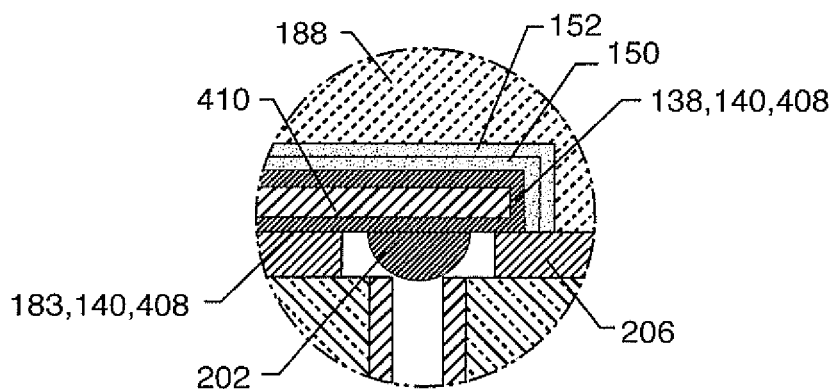
Figure 163D:
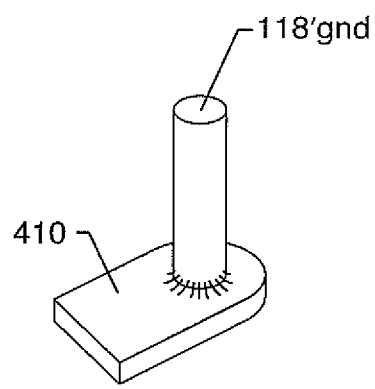
Figure 164:
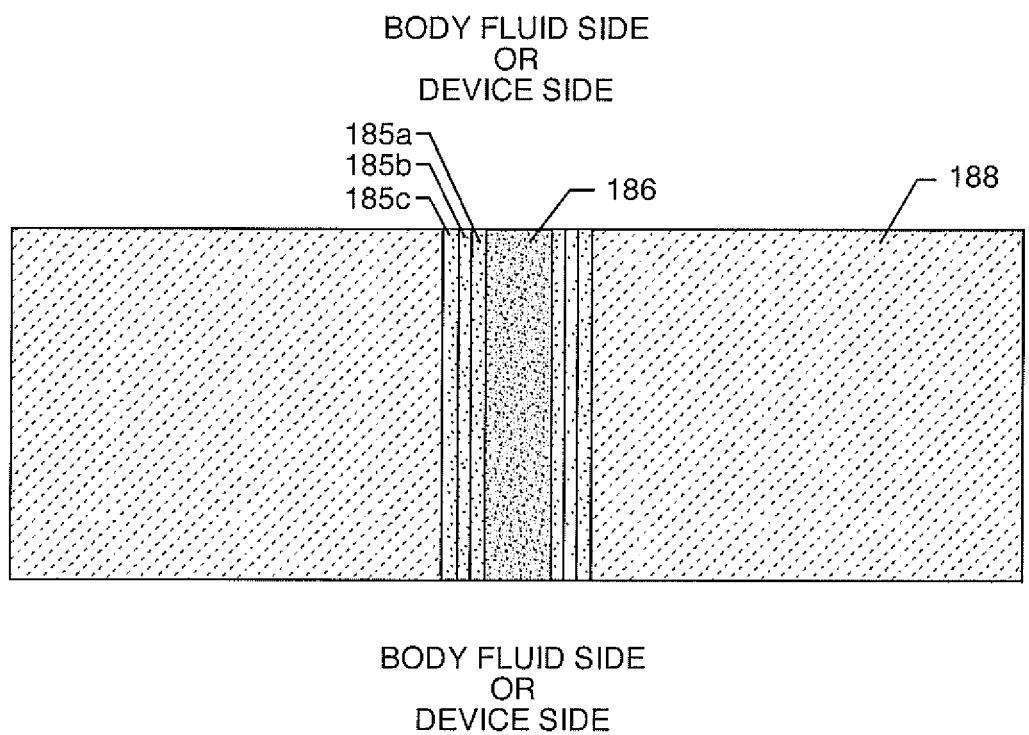
Figure 165:
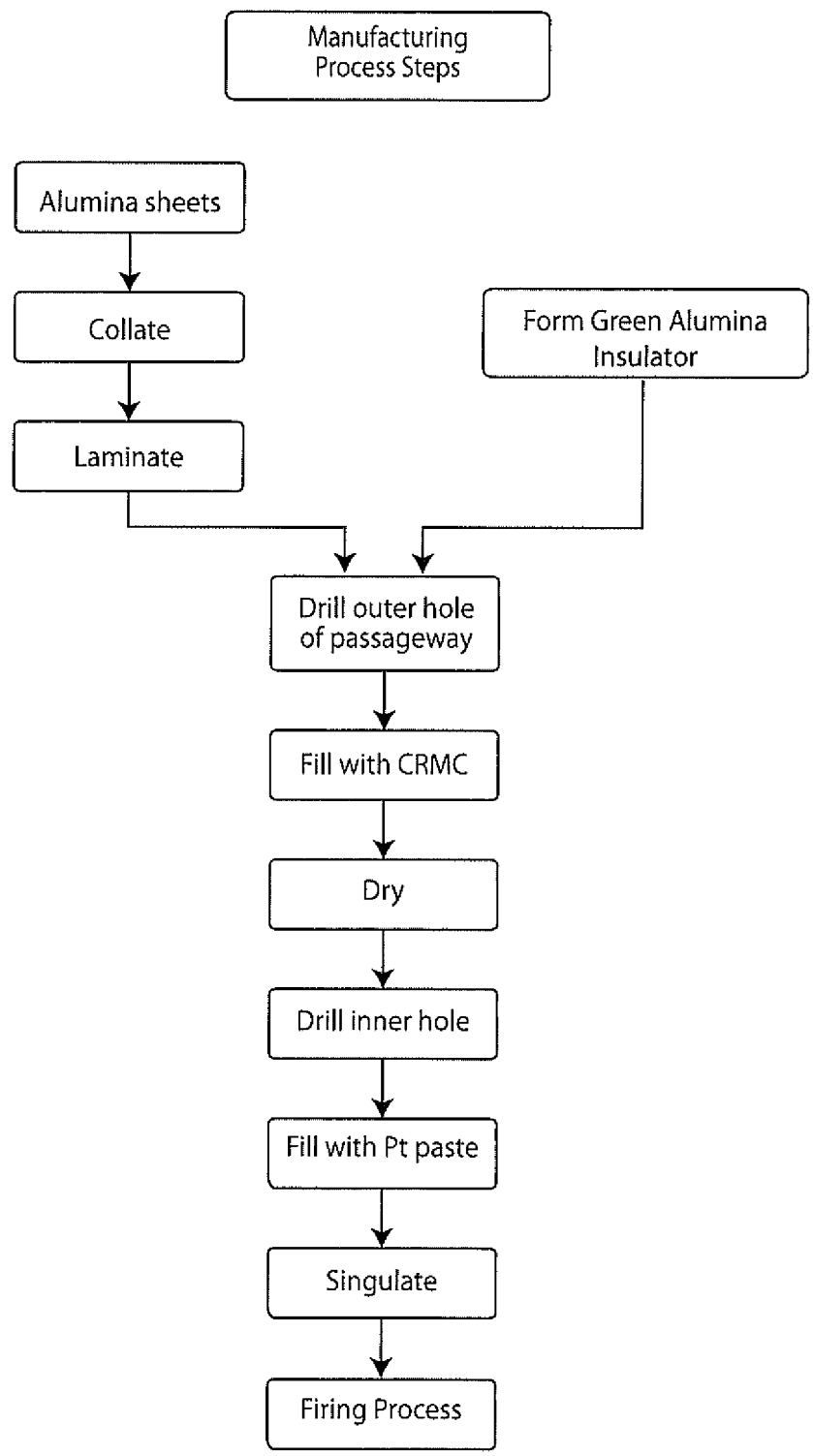
Figure 166:
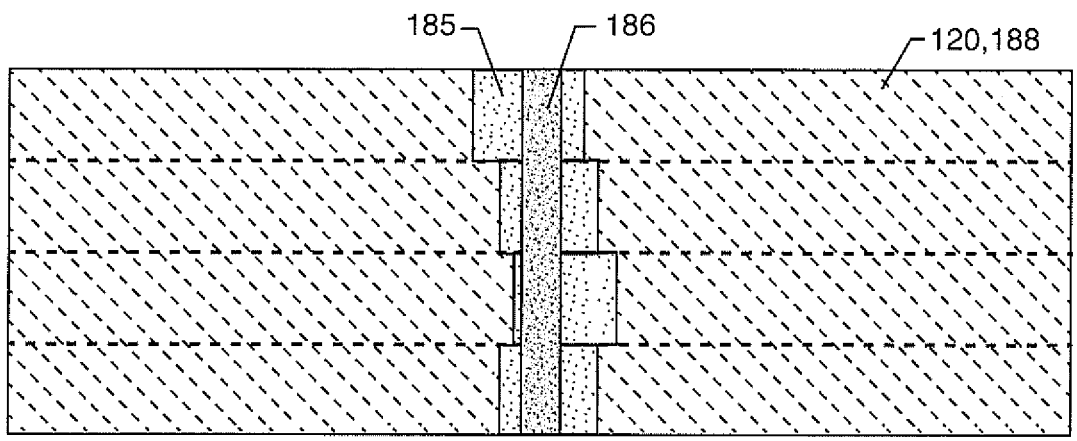
Figure 167:
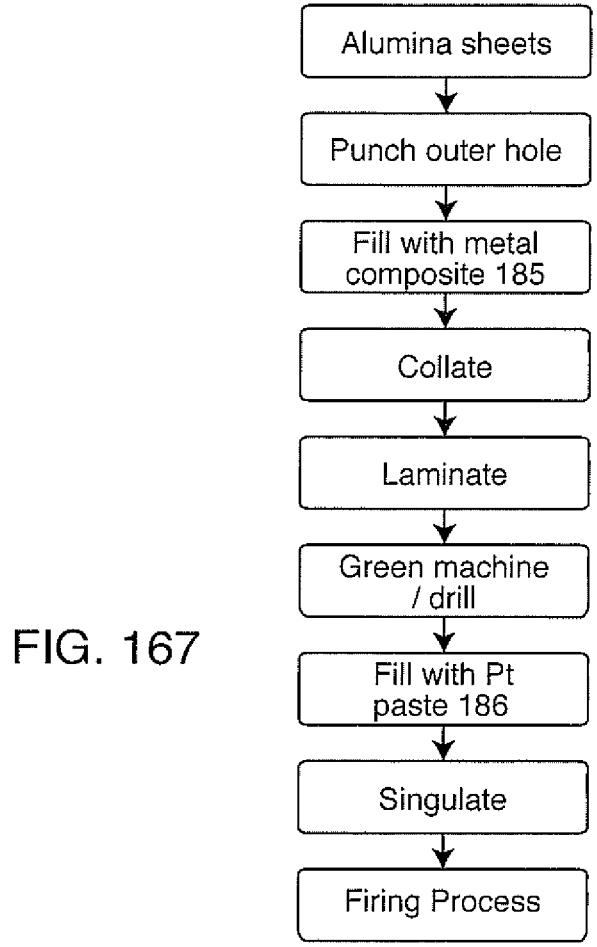
Figure 168:
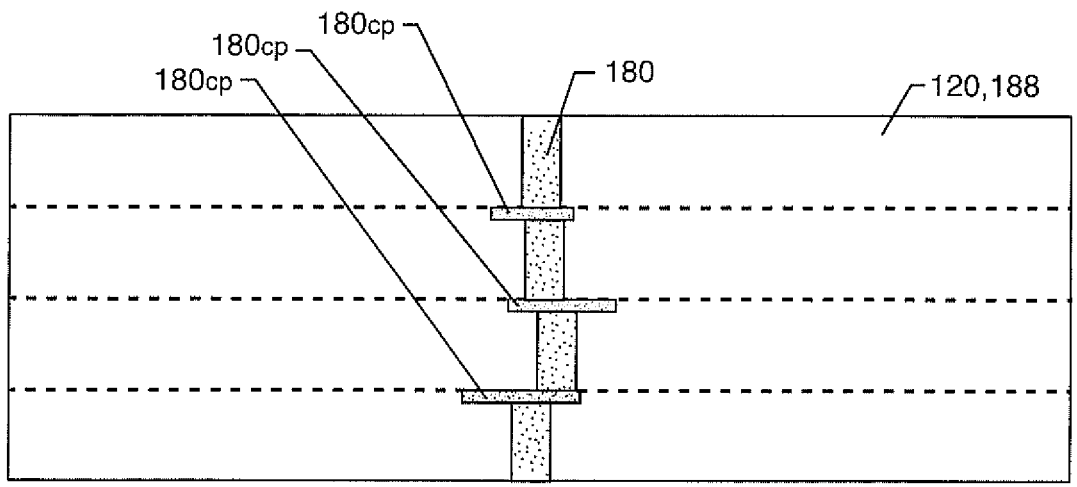
Figure 169:
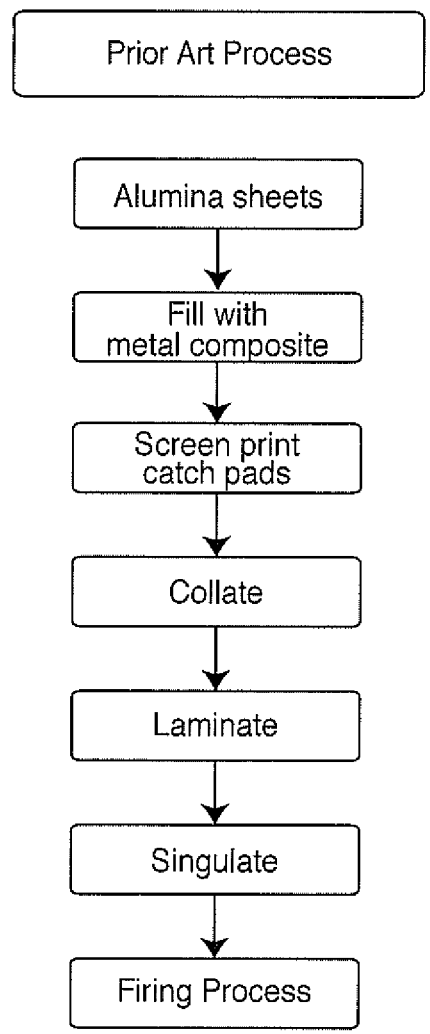
Figures 170, 170A:
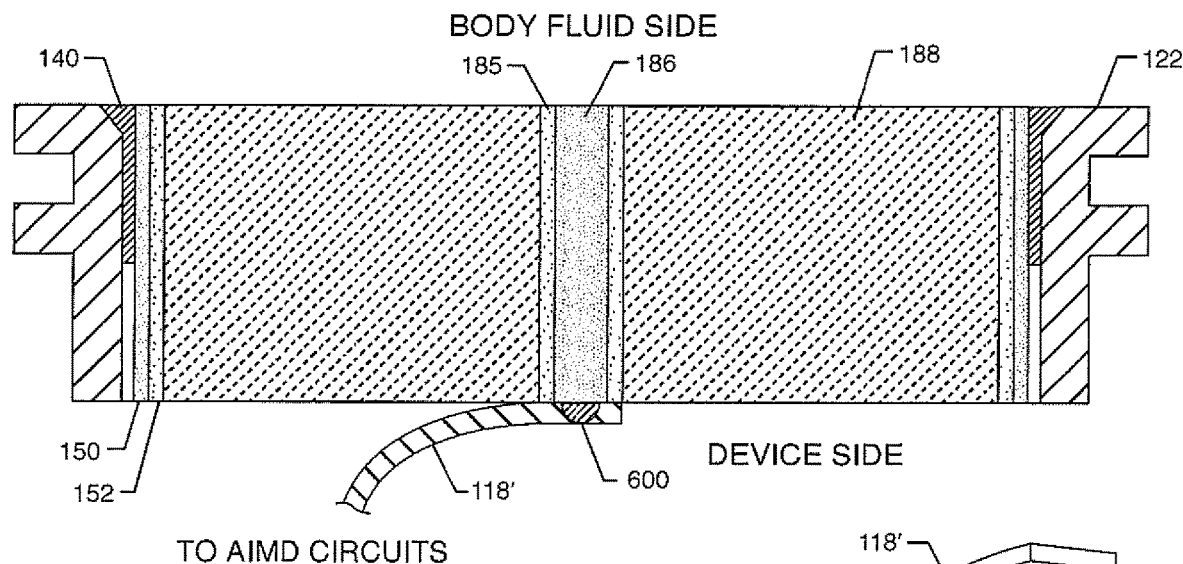
Figures 171, 171A:
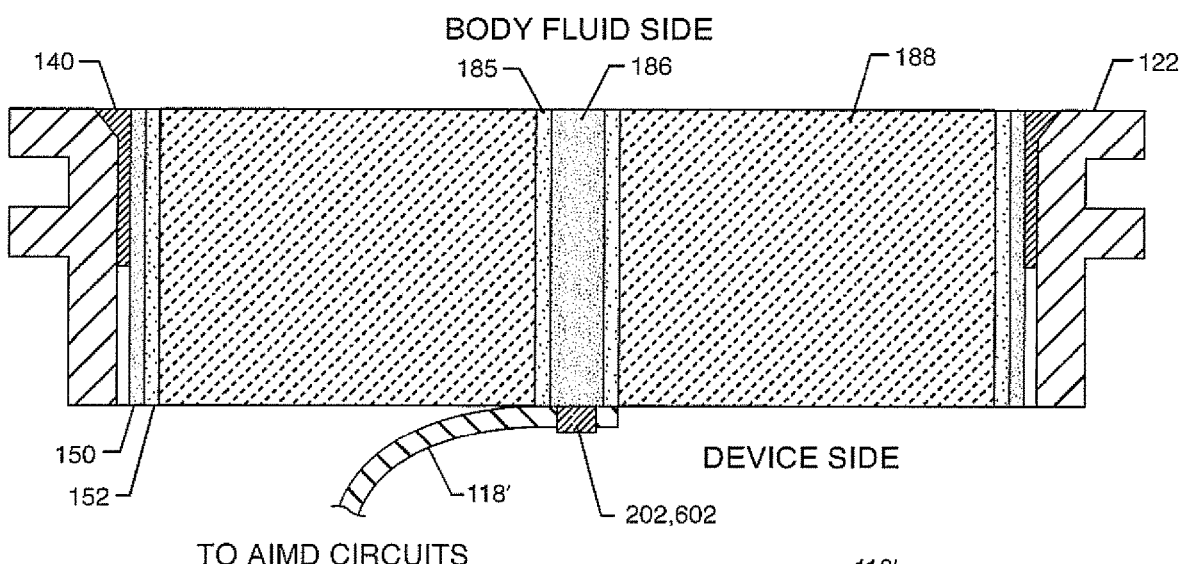
Figure 176:
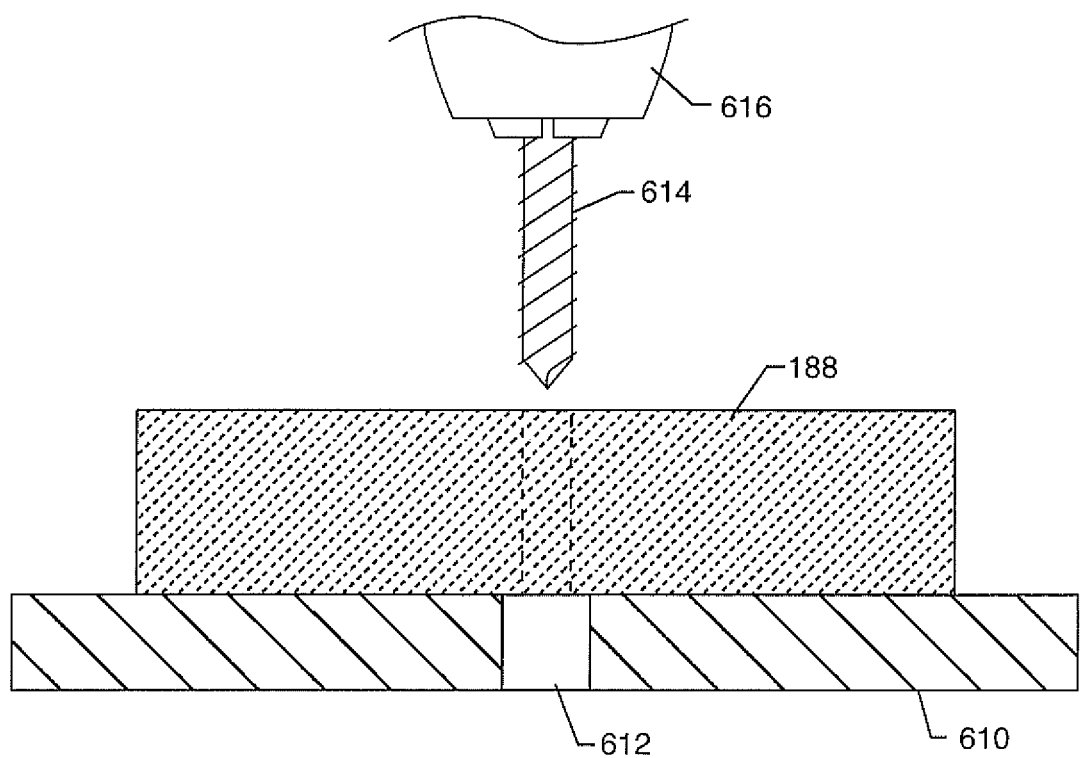

FIG. 110 illustrates the insulator 188 after it's been sintered and sputter layers 150 and 152 have been applied;

FIG. 111 illustrates the device side of the insulator 188 shown in FIG. 110;

FIG. 112 illustrates an alternative embodiment of the present invention;

FIG. 113 is a cross-sectional view taken from section 113-113 from FIG. 112 illustrating that the slot 403 is filled with platinum;

FIG. 114 illustrates a novel milled or micro-blasted slot exposing the side of the slot which may be filled with platinum as shown, or a Cermet or CRMC material;

FIG. 115 illustrates the sputter layers can be applied to the side of the insulator, as shown, but also importantly, the sputter layer would also be applied to the exposed part of the platinum fill of slot;

FIG. 116 illustrates the insulator of FIG. 115 gold brazed into an AIMD ferrule;

FIG. 117 illustrates that the grounding slot may be replaced by a slot filled with a Platinum-Alumina Cermet CRMC or platinum of the present invention;

FIG. 117A is taken from partial section 117A-117A from FIG. 117 and illustrates a different embodiment, in that, sputter layers have been eliminated and the gold braze is shown wetting between the ferrule and the CRMC material;

FIG. 118 is very similar to FIG. 74 illustrating that the Platinum-Alumina Cermet (CRMC) filled slot may also include a layer of pure platinum;

FIG. 119 is a sectional view showing a peninsula structure extending from the ferrule that has a gold braze for connection to a solder dot or the like;

FIG. 120 illustrates a feedthrough capacitor which includes one solid-filled capacitor feedthrough holes and one hollow-filled capacitor feedthrough hole;

FIG. 121 illustrates one possible electrical schematic of the internally grounded filtered hermetic feedthrough assembly of FIG. 120;

FIG. 122 is very similar to FIG. 117, except that slot filled with CRMC includes a counterbore, including pure platinum of the present invention;

FIG. 123 illustrates a hermetic insulator of the present invention with MLCC chip capacitors electrically attached between the active vias and to the ferrule and ferrule gold;

FIG. 124 is one possible electrical schematic of the filtered capacitor structure with MLCC chips illustrated in FIG. 123;

FIG. 125 illustrates a circuit board and MLCC capacitors that are attached through a metal addition to the ferrule;

FIG. 126 illustrates circuit board with circuit trace routed from the active via hole to the device electronics;

FIG. 127 illustrates a direct electrical connection on the left-hand side on the MLCC capacitor;

FIG. 128 is very similar to FIG. 127, except that in this case, the active circuit traces are embedded within circuit board;

FIG. 129 illustrates a circuit board mounted to the ferrule of a hermetic terminal subassembly for an AIMD;

FIG. 130 is a sectional view taken from section 130-130 from FIG. 131 of the ground plane of the circuit board of FIG. 129;

FIG. 131 is a sectional view taken from section 131-131 from FIG. 129;

FIG. 132 illustrates section 132-132 from FIG. 129 showing how the MLCC capacitors are connected to the ground trace and are grounded through via holes;

FIG. 133 is an enlarged view generally taken from section 133-133 from FIG. 131 illustrating how the leadwire is co-joined with electrical connection material to the platinum end of the via hole, including the Cermet CRMC;

FIG. 134 illustrates Option 1 and 1A of the present invention with a composite platinum-alumina via fill CRMC with platinum conductor end fills co-fired into a feedthrough with a device side solder coat;

FIG. 135 is similar to FIG. 134 however the insulator was multilayered;

FIG. 136 is similar to FIG. 135 however the platinum ends have been widened to facilitate ease of electrical attachment;

FIG. 137 is similar to FIG. 136 however now the platinum ends are connected with a center portion of platinum, which corresponds to Option 4;

FIG. 138 is similar to Option 1 and 1A, now showing a solder coat for facilitating an oxide resistant attachment of solder bump;

FIG. 139 is very similar to FIG. 29 now showing a body fluid side leadwire brazed and electrically coupled to the composite fill;

FIG. 140 is similar to FIG. 139 now showing a monolithic insulator;

FIG. 141 is very similar to FIG. 31 now showing a body fluid side leadwire brazed and electrically coupled to the composite fill;

FIG. 142 is similar to FIG. 141 now showing a monolithic insulator;

FIG. 143 is very similar to FIG. 33 now showing a body fluid side leadwire brazed and electrically coupled to the composite fill;

FIG. 143A is similar to FIG. 143 now showing a second gold braze hermetically sealing it to the ferrule;

FIG. 144 is very similar to FIG. 34 now showing a body fluid side leadwire brazed and electrically coupled to the composite fill;

FIG. 144A is similar to FIG. 144 now showing a nail head leadwire;

FIG. 145 is very similar to FIG. 139 now showing a body fluid side leadwire brazed and electrically coupled to the composite fill;

FIG. 146 is similar to FIG. 145 now showing a monolithic insulator;

FIG. 147 is very similar to FIG. 43 now showing a body fluid side leadwire brazed and electrically coupled to the composite fill;

FIG. 148 is similar to FIG. 147 now showing a monolithic insulator;

FIG. 149 is very similar to FIG. 45 now showing a body fluid side leadwire brazed and electrically coupled to the composite fill;

FIG. 150 is similar to FIG. 149 now showing a monolithic insulator;

FIG. 151 is very similar to FIG. 53 now showing a body fluid side leadwire brazed and electrically coupled to the composite fill;

FIG. 152 is similar to FIG. 151 now showing a monolithic insulator;

FIG. 153 is very similar to FIG. 55 now showing a body fluid side leadwire brazed and electrically coupled to the composite fill;

FIG. 154 is similar to FIG. 153 now showing a monolithic insulator;

FIG. 155 is very similar to FIG. 57 now showing a body fluid side leadwire brazed and electrically coupled to the composite fill;

FIG. 156 is similar to FIG. 155 now showing a monolithic insulator;

FIG. 157 is very similar to FIG. 59 now showing a body fluid side leadwire brazed and electrically coupled to the composite fill;

FIG. 158 is similar to FIG. 157 now showing a monolithic insulator;

FIG. 159 is very similar to FIG. 126 now showing a body fluid side leadwire brazed and electrically coupled to the composite fill with a circuit board on the device side;

FIG. 160 is very similar to FIG. 131 now showing a body fluid side leadwire brazed and electrically coupled to the different embodiments of the composite fills previously shown and described;

FIG. 161 illustrates a feedthrough having a body fluid side leadwire brazed and electrically coupled to a cermet (CRMC);

FIG. 161A illustrates a partial sectional view of another embodiment of the present invention with a ferrule-less connection to an AIMD housing;

FIG. 161B illustrates a partial sectional view of another embodiment of the present invention with a ferrule-less connection to an AIMD housing;

FIG. 161C illustrates a partial sectional view of another embodiment of the present invention with a stamped ferrule connection to an AIMD housing;

FIG. 161D illustrates a partial sectional view of another embodiment of the present invention with a stamped ferrule connection to an AIMD housing;

FIG. 161E illustrates a partial sectional view of another embodiment of the present invention with a stamped ferrule connection to an AIMD housing;

FIG. 162 is very similar to FIG. 161 now showing a gold braze extending inwards on the device side such that an electrical connection can be made to a device side leadwire facilitating the use of an internally grounded feedthrough capacitor;

FIG. 163 is very similar to FIG. 162 now showing a clip disposed within the gold braze thereby facilitating proper formation of the gold braze due to capillary action with the clip;

FIG. 163A is a perspective view of an exemplary clip similar to that in FIG. 163;

FIG. 163B is a perspective view of another exemplary clip similar to that in FIG. 163;

FIG. 163C is an enlarged view taken along lines 163C-163C of FIG. 163 showing the clip surrounded by the gold braze on both sides;

FIG. 163D is a perspective view of another exemplary clip similar to that in FIG. 163 now having a post attached to the clip;

FIG. 164 shows a multiple drilling and filling method of manufacturing with varying percentages of ceramic to metal pastes being layered around a center metallic paste;

FIG. 165 illustrates in a block form diagram one embodiment of the present invention;

FIG. 166 shows a variation of the present invention wherein misregistered sheets with CRMC fill are simultaneously drilled and filled;

FIG. 167 illustrates in block form diagram the embodiment of FIG. 166;

FIG. 168 shows a prior art structure having misregistered filled via holes with catch pads;

FIG. 169 illustrates in block form diagram the embodiment of FIG. 168;

FIG. 170 shows a device side wire connected to the sintered metal paste;

FIG. 170A is a perspective view of the device side wire of FIG. 170 showing its shape in more detail;

FIG. 171 shows a device side wire connected to the sintered metal paste;

FIG. 171A is a perspective view of the device side wire of FIG. 171 showing its shape in more detail;

FIG. 172 shows a device side wire about to be connected to the sintered metal paste;

FIG. 172A is a perspective view of the device side wire of FIG. 172 showing its shape in more detail;

FIG. 173 is similar to FIG. 172, now showing the device side wire connected to the sintered metal paste;

FIG. 173A is a perspective view of the device side wire of FIG. 173 showing its shape in more detail;

FIG. 174 shows a device side wire connected to the sintered metal paste;

FIG. 174A is a perspective view of the device side wire of FIG. 174 showing its shape in more detail;

FIG. 175 shows a device side wire connected to the sintered metal paste;

FIG. 175A is a perspective view of the device side wire of FIG. 175 showing its shape in more detail; and FIG. 176 is a sectional view of a dielectric body being drilled using a backing plate.

DETAILED DESCRIPTION OF THE PREFERRED EMBODIMENTS

As previously described in-whole or in-part within U.S. provisional applications 62/443,011, 62/450,187, 62/461,872, 62/552,363 and 62/613,500 filed Jan. 6, 2017, Jan. 25, 2017, Feb. 22, 2017, Aug. 30, 2017 and Jan. 4, 2018 respectively, the present invention now includes various embodiments of different options. The following detailed description is now for 110 sheets of drawings, which are labeled FIG. 1 through FIG. 176. Certain FIGURES illustrate one option while other FIGURES illustrate another option. Some FIGURES illustrate several options in just one figure. It will be understood that any of the FIGURES that describe the present invention are applicable to any of the options. In other words, the FIGURES illustrate a variety of ways in which the various options can be reduced to practice.

Figure 1:
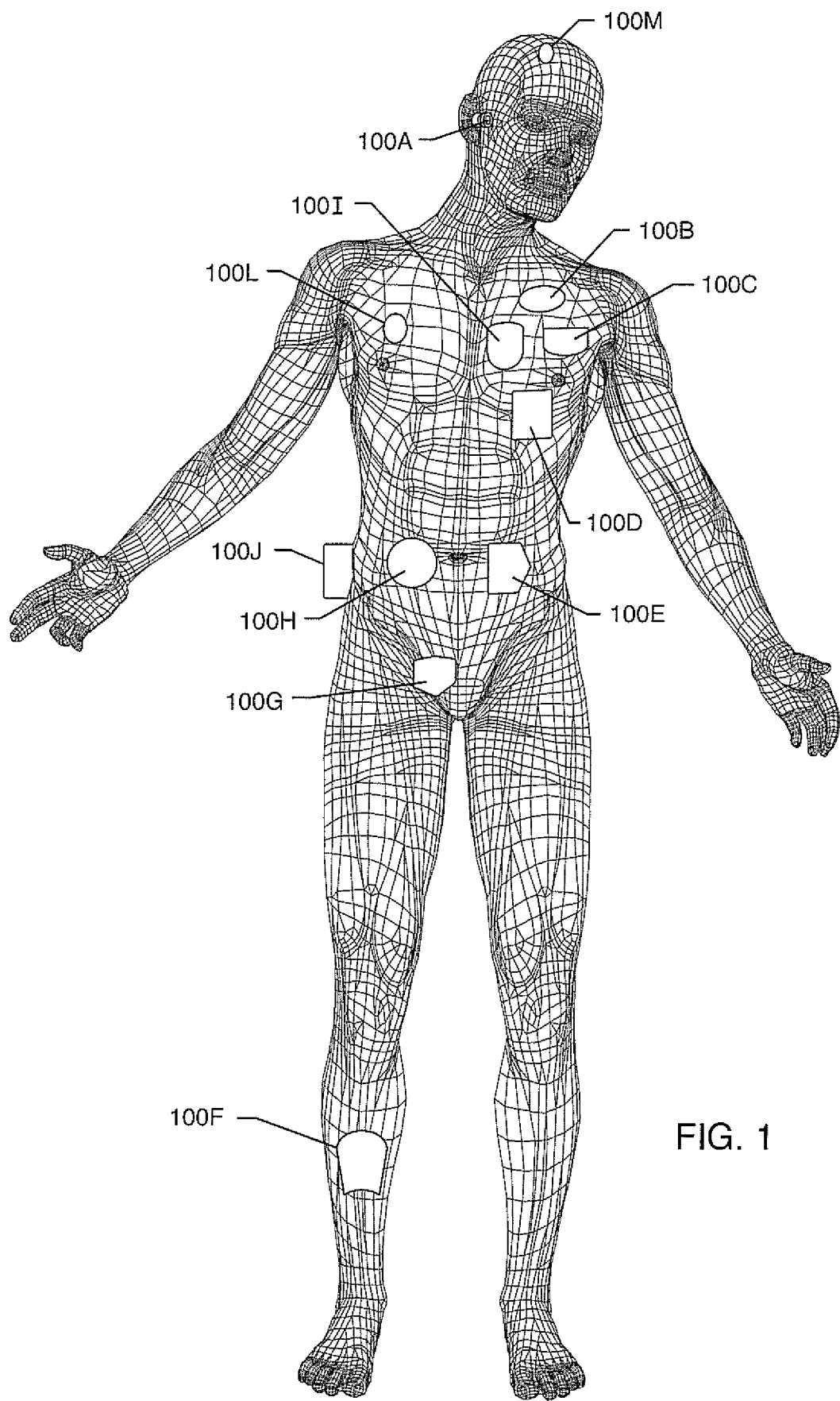
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker, which is well-known in the art, may have endocardial or epicardial leads. Implantable pacemakers may also be leadless. The family of cardiac pacemakers 100C includes the cardiac resynchronization therapy devices (CRT-D pacemakers) and leadless pacemakers. CRT-D pacemakers are unique in that, they pace both the right and left sides of the heart. The family also includes all types of implantable loop recorders or biologic monitors, such as cardiac monitors. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators. ICDs, as used herein, include subcutaneous defibrillators and also CRT-D devices. CRT devices are cardiac resynchronization therapy devices that could also provide high-voltage defibrillation. In summary, as used herein, the term AIMD includes any device implanted in the human body that has at least one electronic component.

Figure 2:
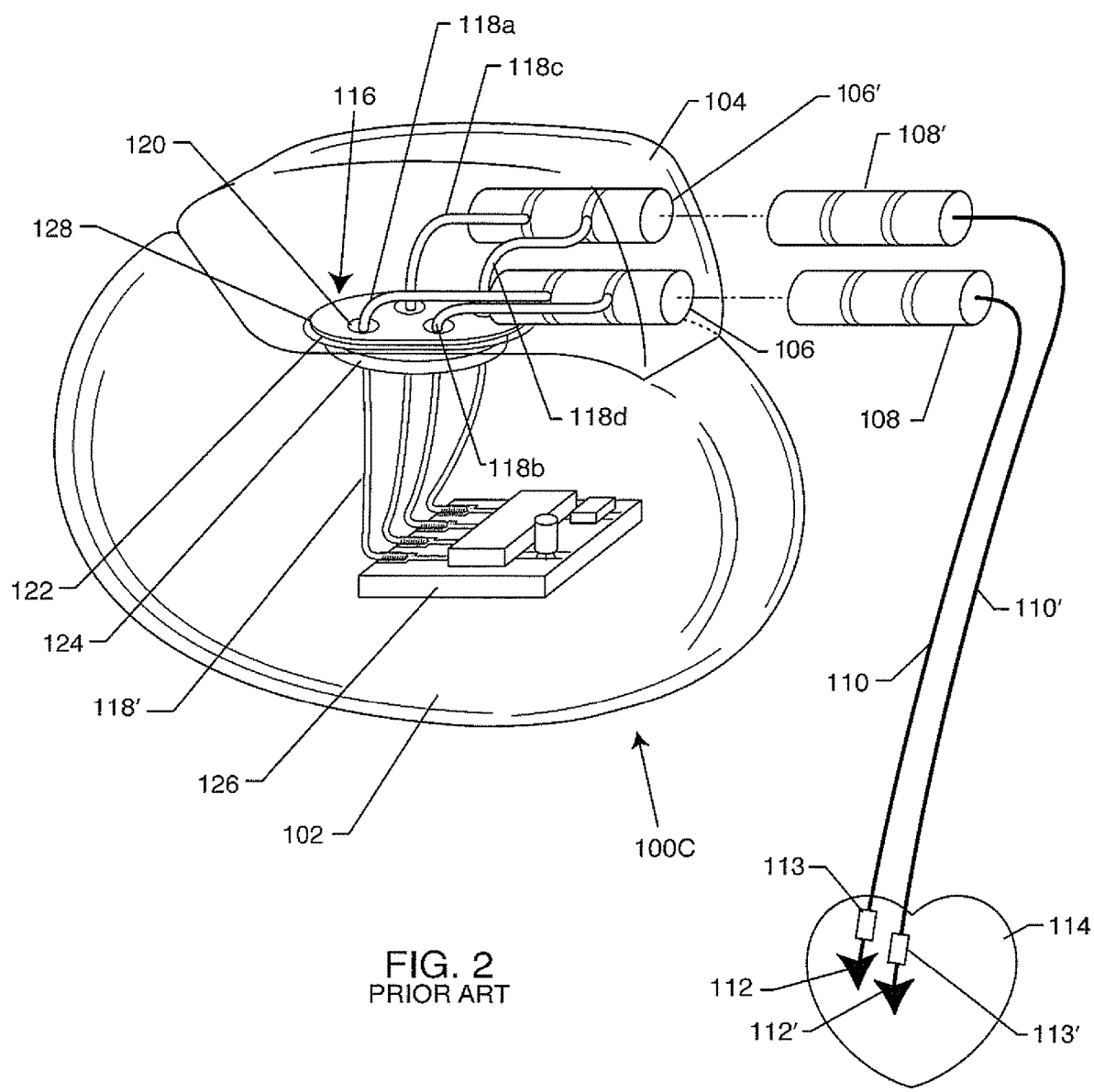
FIG. 2 is a side view of a prior art cardiac pacemaker.

FIG. 2 illustrates a prior art cardiac pacemaker 100C showing a side view. The pacemaker electronics are housed in a hermetically sealed and conductive electromagnetic shield 102 (typically titanium). There is a header block assembly 104 generally made of thermal-setting non-conductive plastic, such as Tecothane®. This header block assembly 104 houses one or more connector assemblies generally in accordance with ISO Standards IS-1, IS-2, or more modern standards, such as IS4 or DF4. These header block connector port assemblies are shown as 106 and 106'. Implantable leadwires 110, 110' have proximal plugs 108, 108' and are designed to insert into and mate with these header block connector cavities 106 and 106', or, in devices that do not have header block assemblies built directly into the pulse generator itself.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace. As described herein, composite conductive sintered paste filled vias passing through an insulator in nonconductive relation with a ferrule electrically acts the same as leadwire, lead wire, or pin. These sintered paste filled vias may also incorporate co-fired solid leadwires. As used herein, the term paste generally refers to pastes, inks, gels, paints, Cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

Figure 3:
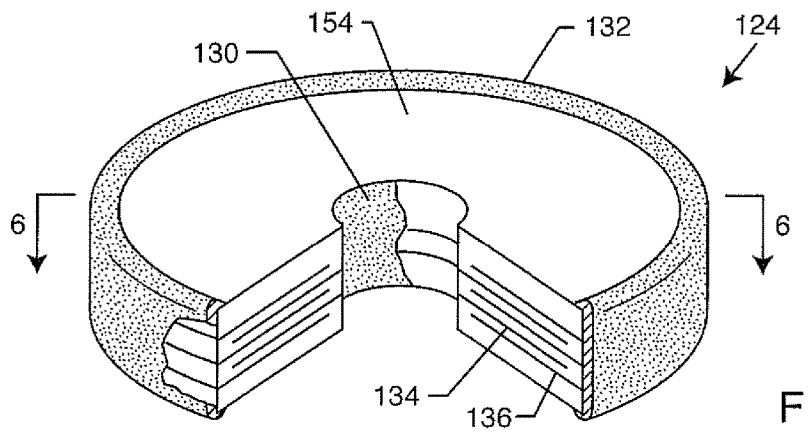
FIG. 3 is a perspective partial cutaway view of a unipolar capacitor.

FIG. 3 illustrates an isometric cut away view of a unipolar feedthrough capacitor. Shown, in cut away view, are active electrode plates 134 and ground electrode plates 136 both disposed within a capacitor dielectric 171. There is a feedthrough hole (passageway) 176, including metallization 130. There is also an outside diameter metallization 132.

Figure 4:
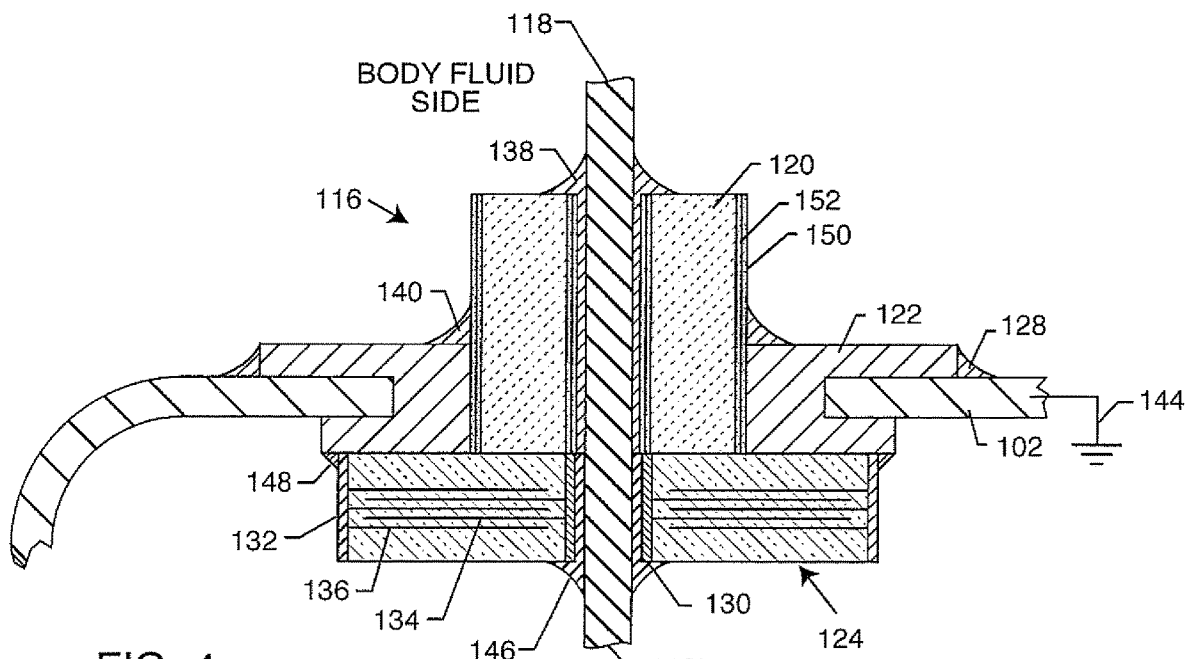
FIG. 4 is a side sectional view of a similar unipolar capacitor of FIG. 3 now mounted to a hermetic feedthrough for an active implantable medical device.

FIG. 4 shows the unipolar capacitor of FIG. 3 in section, mounted to the ferrule 122 of a hermetic seal subassembly 116 for an active implantable medical device. As shown, the ferrule 122 is configured to be laser welded 128 into an opening of an AIMD housing previously illustrated in FIG. 2 as element 102. The AIMD housing is generally of titanium or other biocompatible conductive material and forms an overall electromagnetic shield to help protect AIMD electronics from electromagnetic interference emitters, such as cell phones and the like. Accordingly, referring back to FIG. 4, we see the ground symbol 144 representing that EMI signals that may be coupled onto the body side of the lead 118, can be decoupled or diverted through the feedthrough capacitor 124 to the equipotential shield. When high frequency electromagnetic signals are diverted from lead 118 to the AIMD housing 102, they circulate around the shield and are converted into meaningless heat (just a few milli or microwatts).

Figure 5:
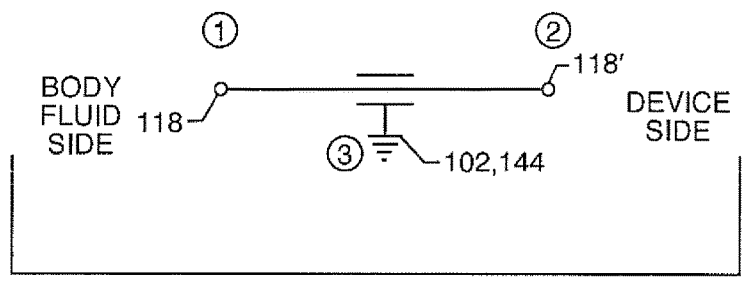
FIG. 5 is an electrical schematic representation of the unipolar filtered feedthrough assembly previously illustrated in FIG. 4.

FIG. 5 is the schematic diagram for the feedthrough capacitor of FIGS. 3 and 4. One can see that this is known as a three-terminal device and that there is significant high frequency attenuation along the length of the leadwire between 118 and 118'. Accordingly, the first terminal is on the body fluid side 118 and the second terminal is on the device side 118', the third terminal being the ground 102, 144, where undesirable electromagnetic interference is diverted to the AIMD housing. It is known in the art that three-terminal feedthrough capacitors have very little to no parasitic series inductance and are therefore, are very broadband low pass filters. This means that low frequency signals, such as therapeutic pacing pulses or biologic signals pass along from the body fluid side of the lead conductor 118 to the device side 118' without degradation or attenuation. However, at high frequencies, the capacitive reactance drops to a very low number and ideally, high frequency signals are selectively shorted out from the lead conductor 118, 118' to the ferrule 122 and in turn, to the conductive housing 102.

Figure 6:
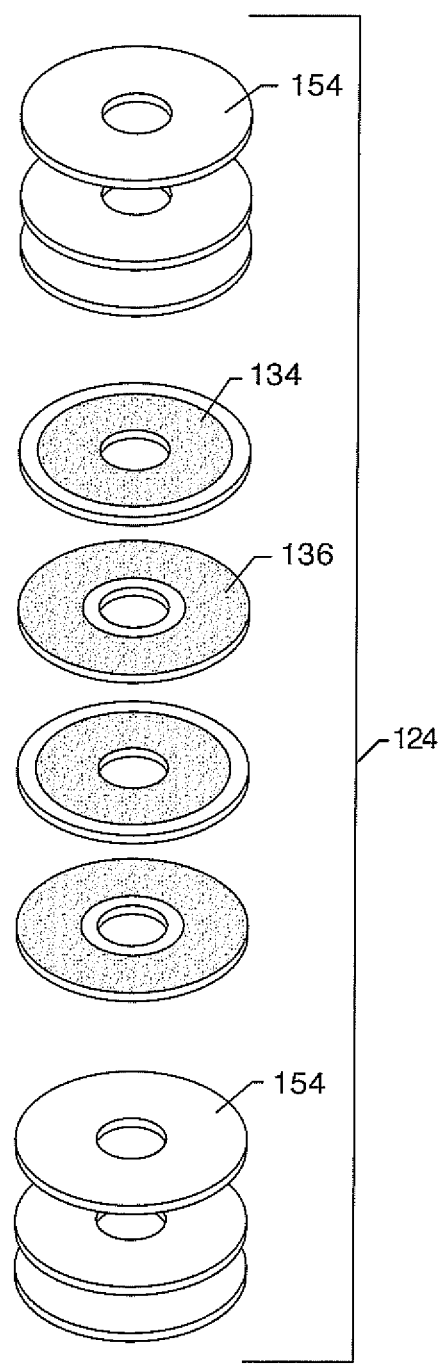
FIG. 6 is generally taken along lines 6-6 from FIG. 3 and is an exploded perspective view of the electrode layer stack up.

FIG. 6 is an exploded view of the unipolar capacitor of FIG. 3 showing that it has ceramic cover plates 154, active electrode plates that are interleaved with ground electrode plates 136 and one or more cover sheets disposed on the other end 154. In ceramic engineering, the ceramic dielectrics would typically be of BX or X7R having a dielectric constant of approximately 2000 or higher. It will also be appreciated that NP0, which is generally a low k dielectric with a dielectric constant below 200, could also be used, as taught in U.S. Pat. No. 8,855,768, the contents of which are fully incorporated herein by reference.

Figure 7:
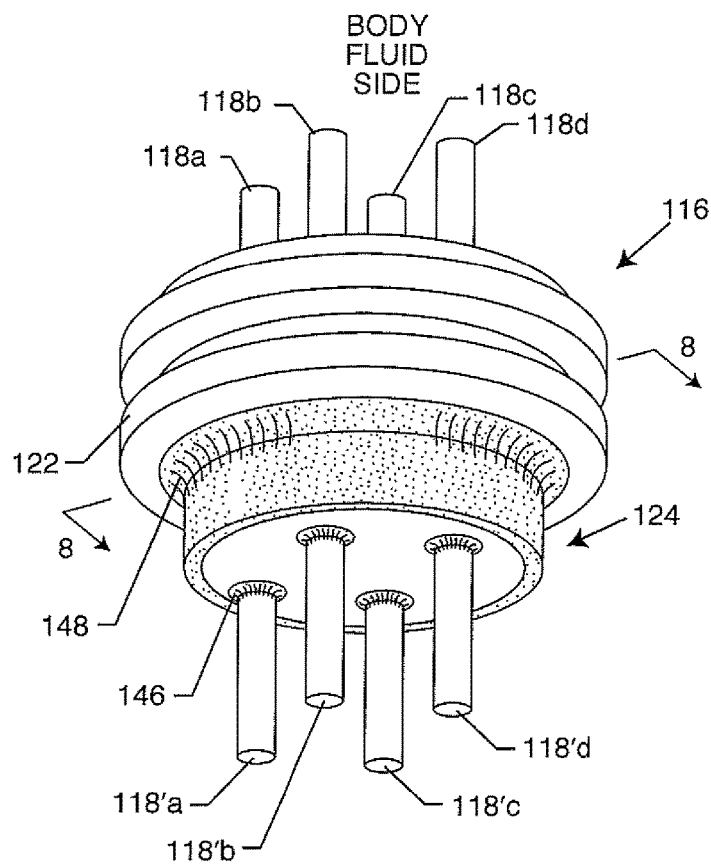
FIG. 7 is a perspective view of a quadpolar feedthrough capacitor and hermetic terminal assembly.

FIG. 7 illustrates a quadpolar feedthrough capacitor and hermetic terminal subassembly 116 where it has four leadwires 118*a*-118*d* and four feedthrough holes (quadpolar). It has a metallic ferrule 122 generally of titanium which is ready for laser welding 128 into the AIMD housing 102 (not shown).

Figure 8:
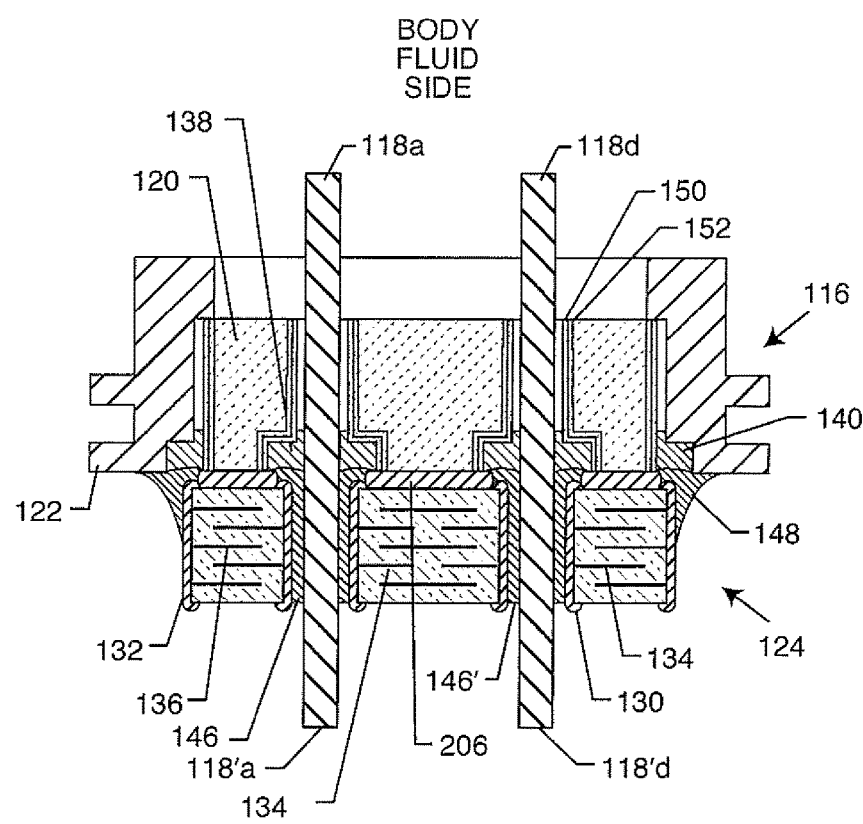
FIG. 8 is a sectional view of the feedthrough and hermetic terminal assembly of FIG. 7 taken along lines 8-8.

FIG. 8 is a prior art sectional view taken generally from section 8-8 from FIG. 7. This illustrates the hermetic terminal subassembly leadwires 118*a-d* passing through the hermetic terminal subassembly insulator 120 in non-conductive relationship and also through the feedthrough capacitor 124 wherein the active electrode plates 134 are electrically connected 146 to the hermetic terminal subassembly leadwire 118 and wherein the feedthrough capacitor ground electrode plates 136 are electrically connected 148 to the hermetic terminal subassembly ferrule 122 and gold braze 140.

Referring once again to FIGS. 7 and 8, in each case it is seen that the hermetic terminal subassembly leadwires 118*a-d* pass all the way through the entire structure, namely, the hermetic terminal subassembly 116 and the feedthrough capacitor 124. In general, these hermetic terminal subassembly leadwires 118*a-d* are electrically and mechanically continuous (single material) and pass through from the body fluid side to the inside of the device 100 housing 102. Because the hermetic terminal subassembly leadwires 118*a-d* pass through from the body fluid side to the inside of the device housing by way of header block connector assembly 104 or the like, it is very important that these hermetic terminal subassembly leadwire 118 materials be biocompatible, biostable and non-toxic. Generally, in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material ductility and to enable the hermetic terminal subassembly leadwire to sustain bending stresses.

Figure 9:
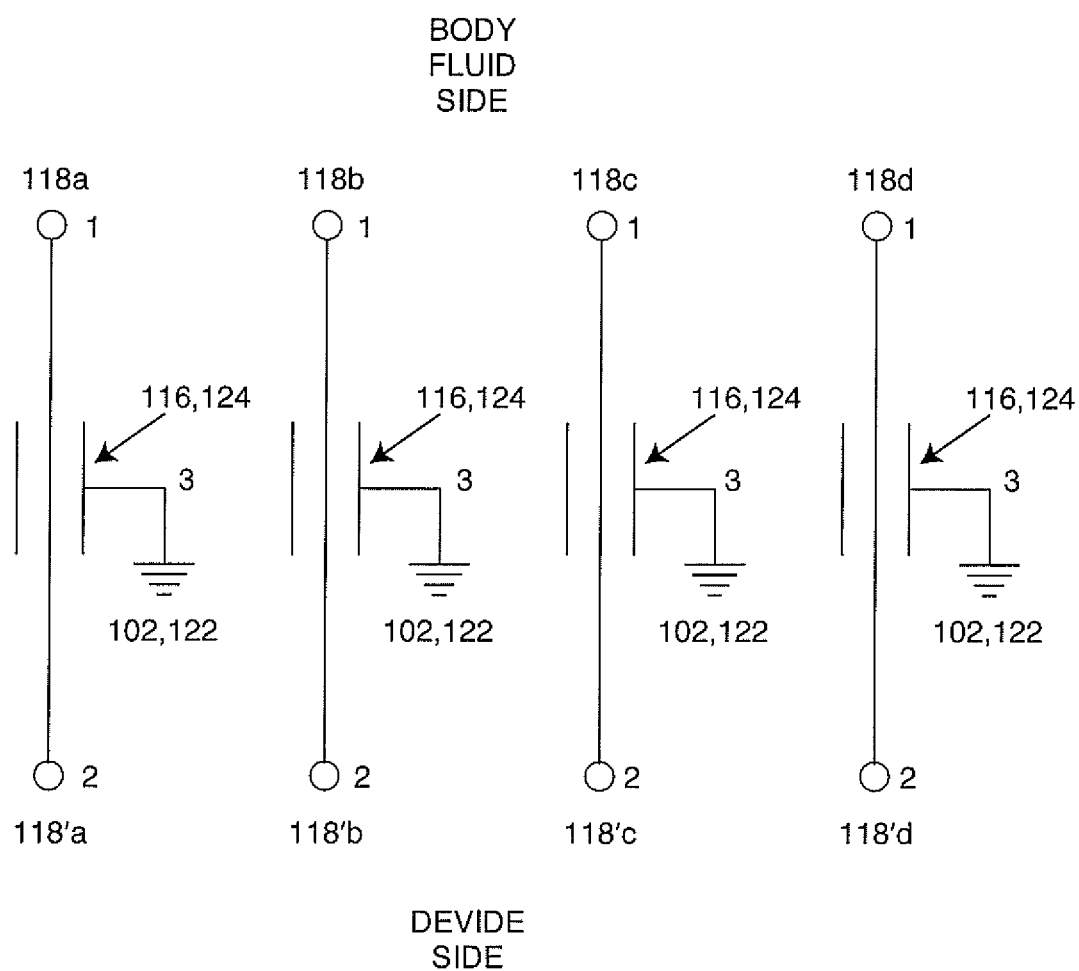
FIG. 9 is an electrical schematic representation of the quadpolar filtered feedthrough assembly as previously illustrated in FIGS. 7 and 8.

FIG. 9 is an electrical schematic representation of the quadpolar filtered feedthrough assembly 116, 124, as previously illustrated in FIGS. 7 and 8. Referring once again to FIG. 4C, one can see that these are feedthrough capacitors and are three-terminal devices. For example, feedthrough capacitor 116, 124 has a first terminal 118*a*, a second active terminal 118'*a* and a ground terminal 102, 122. In the art, feedthrough capacitors are known as broadband low pass filters. They have practically zero series inductance and are desirable in that, they work over a very wide range of frequencies. In general, feedthrough capacitors and their internal electrode geometries are well known in the prior art. In this case, the feedthrough capacitor is a diverter element, in that, it diverts RF signals on all four leads to the AIMD housing as previously described. This is important for the capacitance reactance formula. At very low frequencies, such as biologic sensing frequencies or biologic therapy frequencies, the capacitor impedance is extremely high and the capacitor acts like it's not present. However, at very high frequencies, such as frequencies around the area of a cell phone (950 MHz), the capacitor tends to look more like a short circuit and diverts those undesirable signals to the AIMD housing. One is referred to U.S. Pat. Nos. 4,424,551; 5,333,095; 5,978,204; 6,643,903; 6,765,779 all of which are fully incorporated herein by reference.

Figure 10:
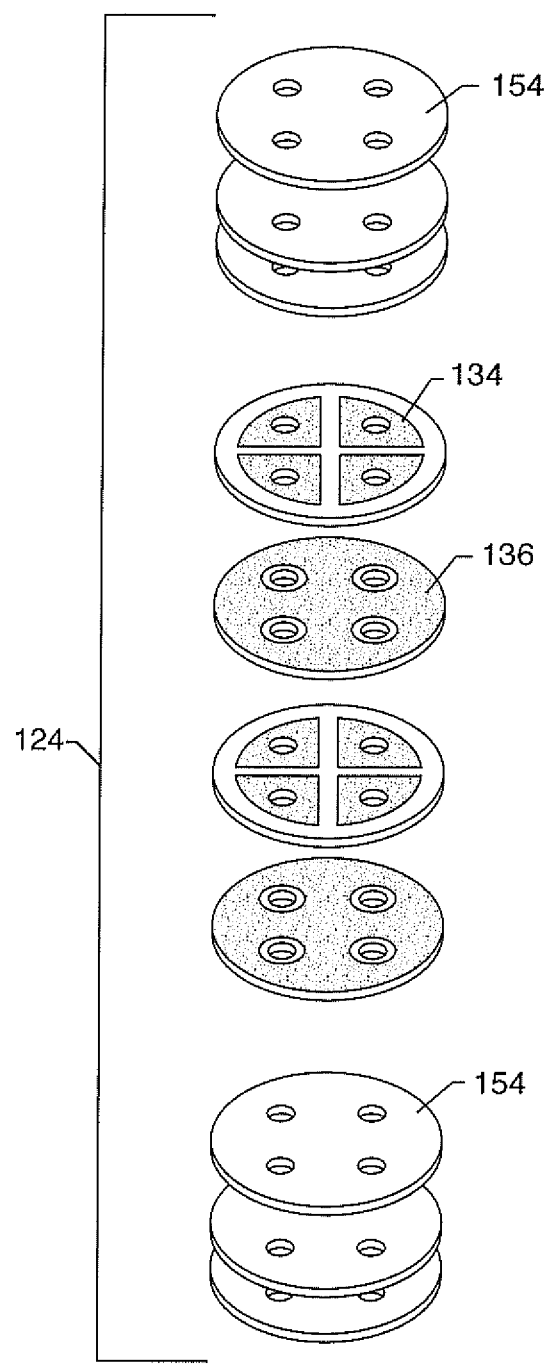
FIG. 10 is an exploded perspective view of the electrode layer stack up of the structure of FIGS. 7 and 8.

FIG. 10 is an exploded view of the quad polar capacitor 132 of FIG. 7. In the exploded view, you can see that there are four active electrode plates 134 and one ground plate 136. The effective capacitance area comes from the overlap of the active electrode 134 with the ground electrode 136. The greater this overlap area is, the higher the capacitance of the feedthrough capacitor becomes. One can also say that it is a multilayer structure. In FIG. 10, there are two active and ground plates shown. This has the effect of increasing the capacitor's effective capacitance area. It will be appreciated that as many as 400 or more ground and active layers could be used.

FIGS. 11A, 11B and 11C illustrate an internally grounded prior art feedthrough capacitor. In general, internally grounded feedthrough capacitors are known in the prior art with reference to U.S. Pat. Nos. 5,905,627; 6,529,103; 6,765,780 and the like, all of which are fully incorporated herein by reference. Referring once again to FIG. 11A, one can see an internally grounded feedthrough capacitor, which is octopolar (eight active leads). The eight active leads are labeled 118*a* through 118*h* on the body fluid side and on the inside of the AIMD housing they are labeled 118'*a* through 118'*h*. The ferrule 122 has a peninsula structure 139, which is connected to an internal ground pin 118*gnd*. Referring now to the octopolar feedthrough capacitor active electrode plates 134, they are designed to overlay in a sandwich fashion the ground electrode plates 136. One skilled in the art will realize that one can stack up as many of these interleaved layers as is required in order to achieve the required capacitance value and other design factors. The internal ground lead 118*gnd* is electrically connected to the ground electrode plate layers 136. The active electrodes 134*a* through 134*h* are each electrically connected through their respective leadwires 118'*a* through 118'*h*. The overlap between the active electrodes 134 and the ground electrodes 136 create what is known as effective capacitance area (or ECA). The active and ground electrode layers may be interleaved with additional ceramic layers to build up the dielectric thickness (not shown). In general, the monolithic ceramic feedthrough capacitor 124, as shown in FIG. 6 as element 124, is a result of laminating the various electrode layers together and then sintering them at a high temperature to form a rigid monolithic ceramic block. This is known as a single feedthrough capacitor that is multipolar (in this case these are octopolar or eight active filtered circuits). One can see that there is a perimeter metallization 132 on the outside of the round capacitor from FIGS. 3 and 7 whereas, in this case in FIG. 6, there is no perimeter metallization 132 at all.

There are several major advantages to internal grounding and removal of the perimeter or diameter metallization 132. This is best understood by referring back to FIGS. 3 through 8. In contrast to FIG. 4, with internal grounding there is no longer a need to apply a diameter metallization 132 as shown in FIGS. 11A, 11B and 11C. In addition, the electrical connection 148 has been entirely eliminated between the capacitor diameter metallization 132 and the gold braze 140 and ferrule 122. The elimination of this electrical connection 148 also makes the capacitor structure 124' much more resistant to mechanical damage caused by subsequent laser welding 128 of the hermetic seal assembly 116 into the AIMD housing 102. A significant amount of heat is produced by laser welding 128 and there is also a mismatch in thermal coefficient of expansion materials. By elimination of the electrical connection material 148, the capacitor 124' is free to float and is therefore, much more resistant to such stresses. Referring once again to FIG. 11B, one can see that the internal ground lead 118'gnd makes a low impedance connection from the capacitor's internal electrode plates 136 to the ferrule 122. This is what eliminates the need for the electrical connection material 148, as previously illustrated in FIG. 4. It will be appreciated that only one ground pin is shown in FIG. 6, but some designs may require a multiplicity of ground pins spaced apart such that, there is a very low impedance connection effectively grounding the capacitor internal electrodes 136 at multiple points.

Referring once again to FIG. 11B, one can see the ceramic capacitor subassembly 124' ready to be installed onto the hermetic terminal subassembly 189. These are shown joined together in FIG. 11C resulting in a hermetically sealed feedthrough capacitor filter assembly 116.

Referring back to FIG. 11B, it is important to clarify some confusion as terms of art. The feedthrough capacitor 124' can also be described as a three-terminal feedthrough capacitor with multiple via holes or feedthrough holes. In a confusing manner, the hermetic terminal subassembly 189 is often referred to in the art as a hermetic feedthrough. Therefore, we have the term feedthrough applying both to the feedthrough capacitor and to the hermetic terminal assembly. As used herein, these are two separate and distinct subassemblies, which are joined together in FIG. 11C to become a feedthrough filter hermetic terminal assembly 116 ready for installation into an opening of an AIMD housing. Referring once again to FIGS. 11A and 11B, one will appreciate that leadwires or lead conductors 118', 118 are continuous leadwires. In other words, on the body fluid side, the leadwire is of the same material as on the device side. This is typical in the prior art. Referring once again to FIG. 11B, one can see that the internal ground lead 118'gnd does not extend through to the body fluid side of the hermetic terminal feedthrough subassembly 189. It will be appreciated that it could be easily and readily extended to the body fluid side, but in most embodiments, it is not necessary.

An issue with the use of platinum for hermetic terminal subassembly leadwires 118a-d is that platinum has become extremely expensive and may be subject to premature fracture under rigorous processing such as ultrasonic cleaning or application use/misuse, possibly unintentional damaging forces resulting from Twiddler's Syndrome. Accordingly, what is needed is a filtered structure like a feedthrough capacitor assembly 116 which eliminates these high-priced, platinum, platinum-iridium or equivalent noble metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995, 7,310,216, 7,327,553, 7,489,495, 7,535,693, 7,551,963, 7,623,335, 7,797,048, 7,957,806, 8,095,224, 8,179,658 the contents of all of which are fully incorporated herein by reference.

Figure 11D:
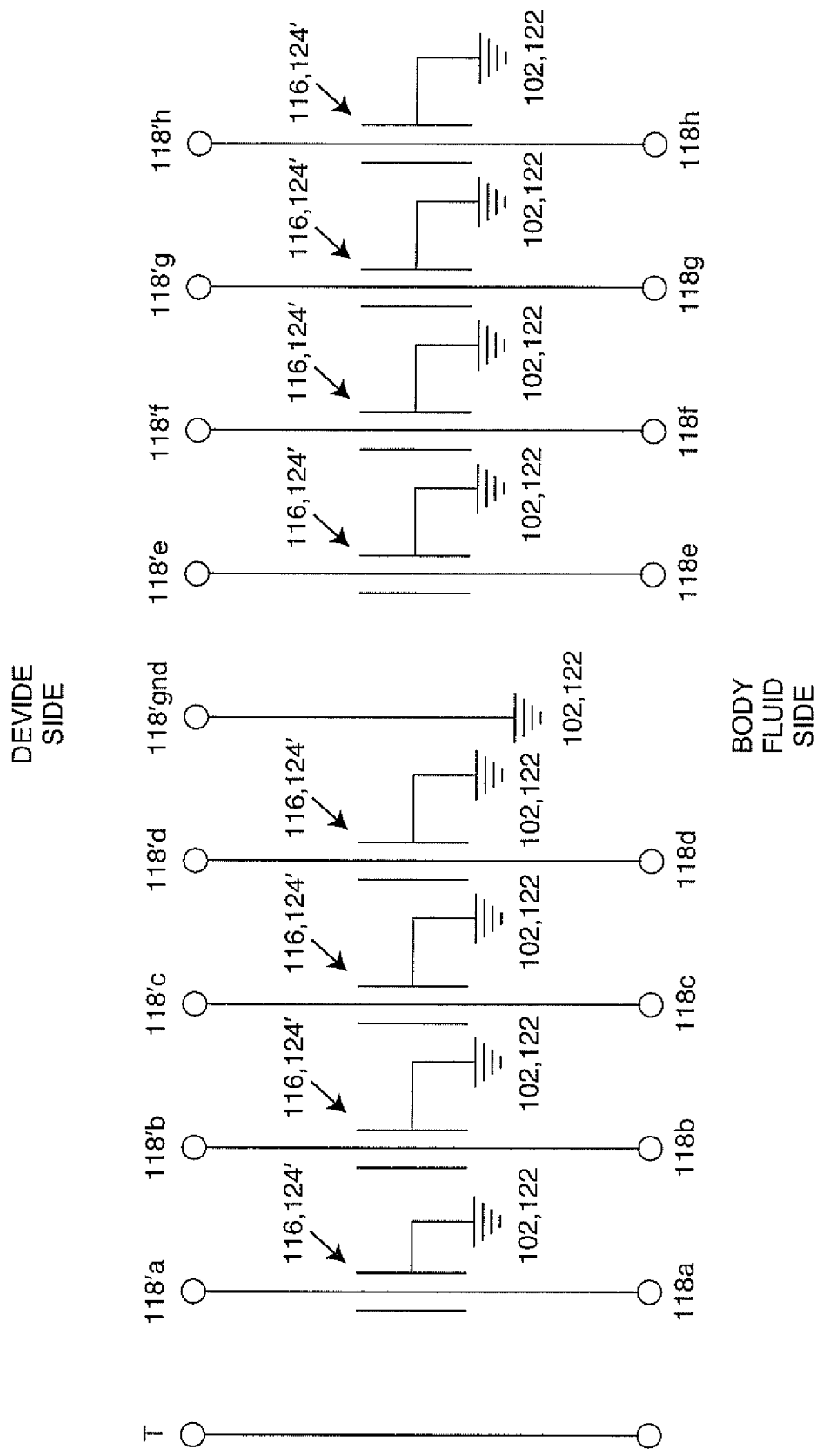
FIG. 11D is the electrical schematic for the feedthrough filtered hermetic terminal previously described in FIGS. 11A, 11B and 11C.

FIG. 11D is the electrical schematic for the feedthrough filtered hermetic terminal 116 previously described in FIGS. 11A, 11B and 11C. Referring once again to FIG. 11D, one can see the telemetry pin T, which passes through the filtered hermetic terminal assembly 116 without any appreciable capacitance to ground. In other words, it would be undesirable to have any high frequency filtering of the telemetry terminal since this would preclude the ability to recover stored information or program the AIMD device remotely. Leadwires 118a through 118h all have feedthrough capacitor hermetic terminal assemblies 116, 124 as shown. The internal ground pin 118gnd is shown only on the device side of the hermetic terminal subassembly 189. Referring once again to FIGS. 11A, 11B, 11C and 11D, it will be noted that the feedthrough filter hermetic seal subassembly has been inverted with reference to FIGS. 2, 3 and 4. It should also be noted that the capacitor 124 is still on the device side; it's just drawn inverted.

Figure 12:
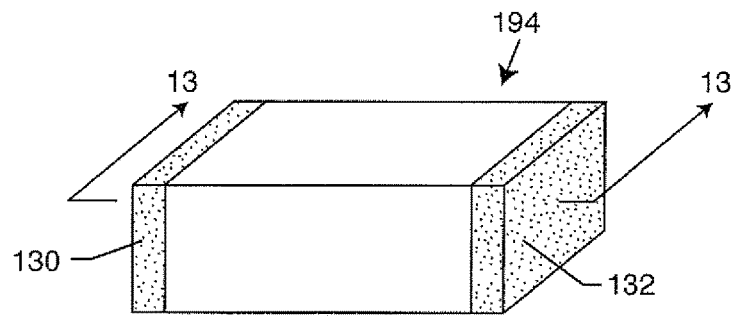
FIG. 12 illustrates a prior art monolithic ceramic capacitor.

FIG. 12 illustrates a prior art monolithic ceramic capacitor 194. These are otherwise known as MLCCs. Monolithic ceramic capacitors are very well known in the prior art and are produced daily in the hundreds of millions. It will be appreciated that MLCCs are also commonly referred to as multilayer ceramic capacitors. MLCCs are common components in every electronic device, including computers, modern smart phones and the like. It should be noted here that not all rectangular 2-terminal capacitors, as illustrated in FIG. 12, must be ceramic. As used herein, MLCC or monolithic ceramic capacitors shall also include all kinds of stacked tantalum, stacked film and other dielectric type capacitors that form 2-terminal rectangular shapes. It will also be appreciated that any of the 2-terminal capacitors in the art, including ceramic, film and tantalum could also have other shapes other than rectangular, including cylindrical and the like.

Figure 13:
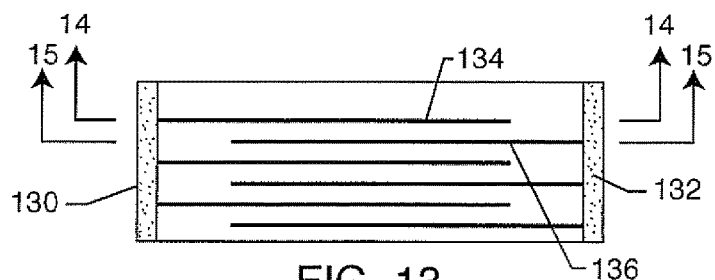
FIG. 13 is taken from section 13-13 from FIG. 12, illustrating a cross-section of an MLCC capacitor.
Figure 14:
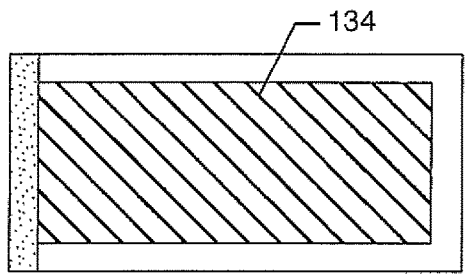
FIG. 14 is a sectional view taken along lines 14-14 from FIG. 13.
Figure 15:
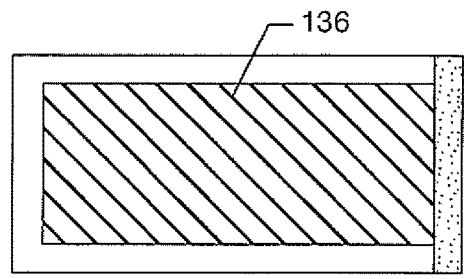
FIG. 15 is a sectional view taken along lines 15-14 from FIG. 13.

FIG. 13 taken from section 13-13 from FIG. 12, illustrates a cross-section of an MLCC capacitor. As can be seen, the prior art MLCC is a two-terminal device having a metallization on the left 130 and a metallization on the right 132. It has overlapping electrodes as illustrated in FIGS. 14 and 15. It has an effective capacitance area ECA created by the overlap of the left-hand electrodes 134 with the right-hand electrodes 136.

Figure 16:
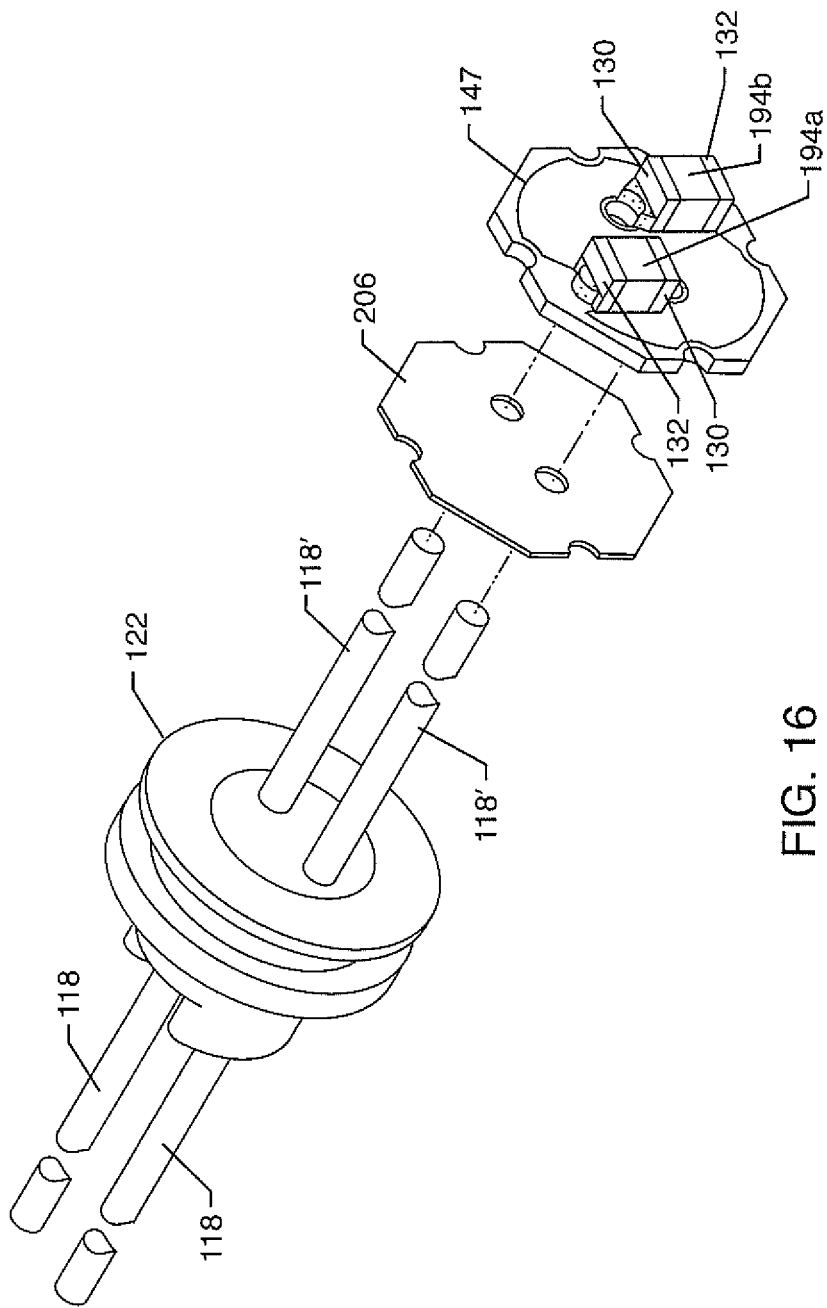
FIG. 16 illustrates a prior application of an MLCC capacitors attached to hermetic seal subassembly of an active implantable medical device.
Figure 17:
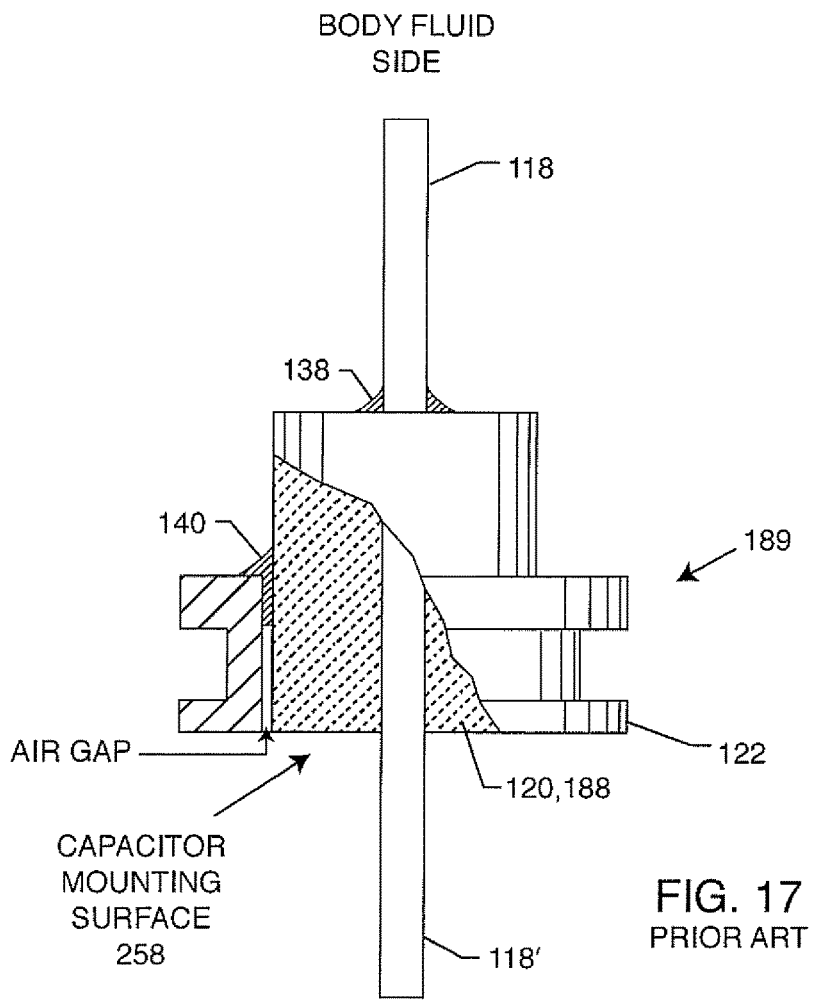
FIG. 17 illustrates a prior application of an MLCC capacitors attached to hermetic seal subassembly of an active implantable medical device.
Figure 18:
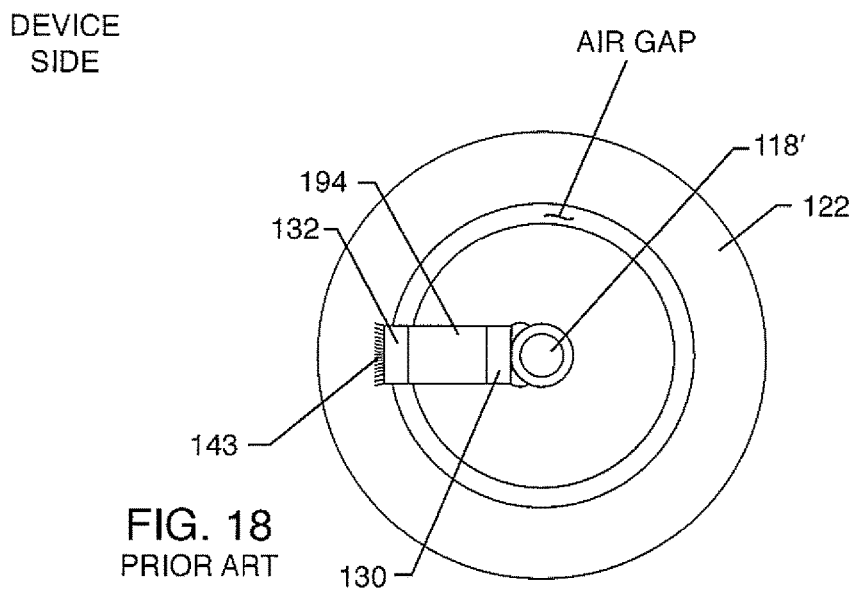
FIG. 18 illustrates a prior application of an MLCC capacitors attached to hermetic seal subassembly of an active implantable medical device.

FIGS. 16, 17 and 18 illustrate prior applications of MLCC capacitors 194 attached to hermetic seal subassemblies of active implantable medical devices. These patents include: U.S. Pat. Nos. 5,650,759; 5,896,267; 5,959,829 and 5,973,906, the contents of which are fully incorporated herein by reference. Referring once again to FIG. 17, one can see that there is a hermetic seal insulator 120,188 disposed within a ferrule 122. In this FIG., the insulator 120,188 is hermetically sealed by a gold braze 140 between the insulator 120,188 and ferrule 122. There is also a leadwire 118, which on the body fluid side is labeled 118 and on the device side is labeled 118'. This leadwire is continuous from the body fluid side to the device side. There is also a hermetic seal gold braze 138, which hermetically seals the leadwire 118 to the insulator 120,188. Throughout this specification, it will be understood that the insulator 120,188 is sometimes single-numbered as 120, sometimes single-numbered as 188 or in some cases, is labeled 120,188. It will also be appreciated that the gold braze insulator is typically of a high purity alumina ceramic. It will also be appreciated that the insulator could include a glass seal in which case, the gold brazes 138 and 140 would not be necessary.

Figure 19:
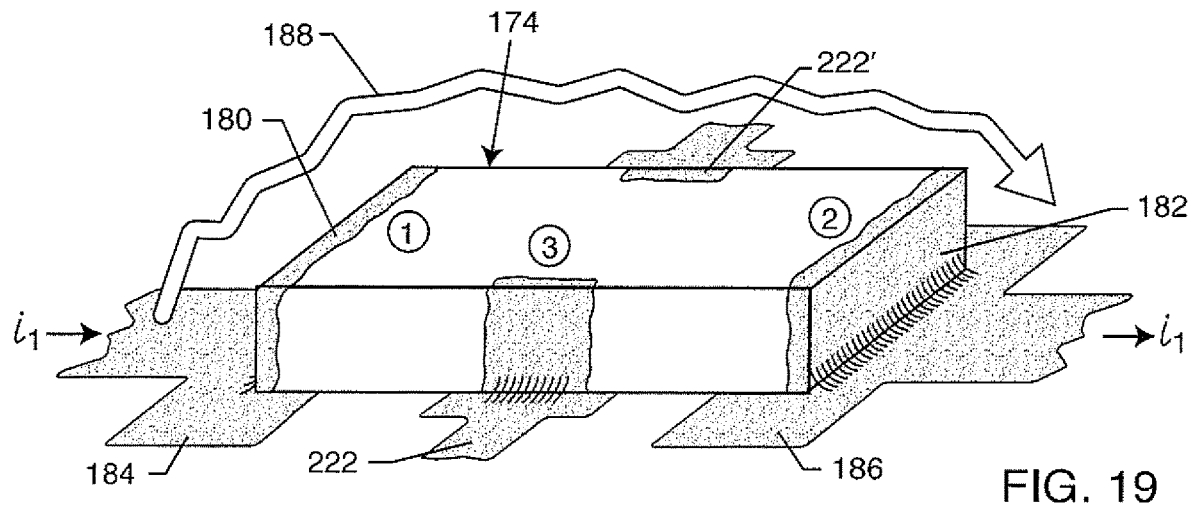
FIG. 19 illustrates a prior art flat-through capacitor.
Figure 20:
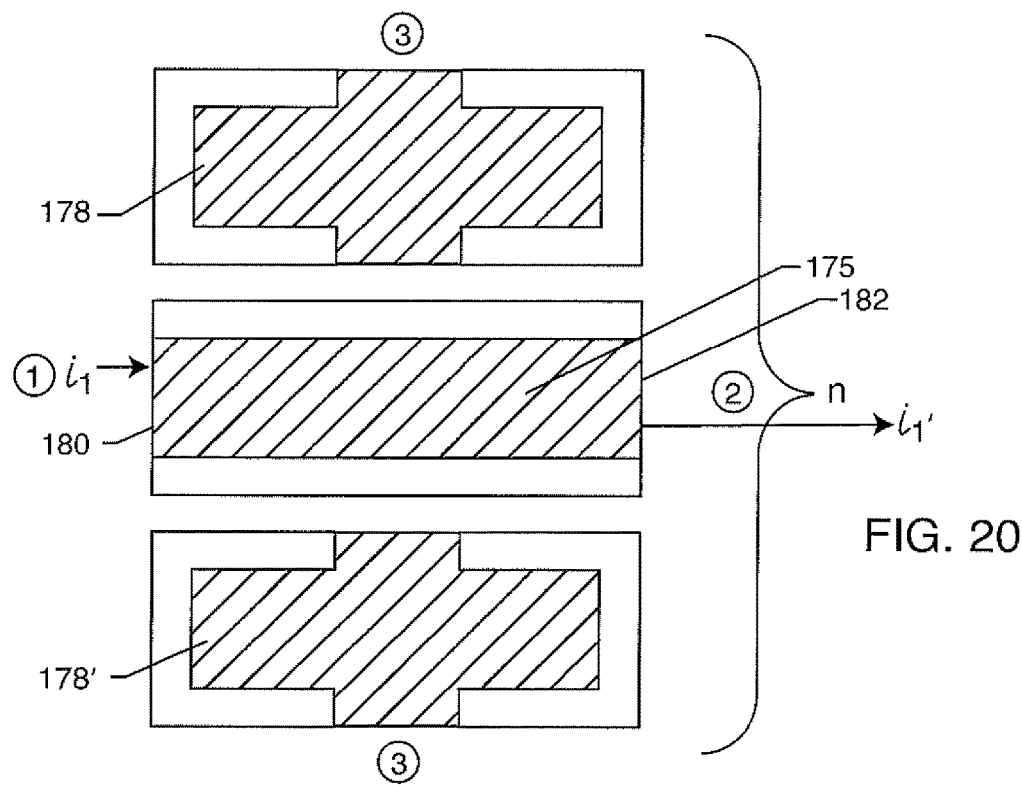
FIG. 20 is a multiple sectional view of the electrode plate stack-up of the structure of FIG. 19.

FIG. 19 illustrates a prior art flat-through capacitor. This is better understood by referring to its internal electrode plates as illustrated in FIG. 20. This is also known as a three-terminal capacitor because there is a circuit current it that passes through its electrode plate 175 from the first terminal 180. If there is a high frequency electromagnetic interference signal being conducted along this electrode plate, then it comes out the other side at a second terminal 182. Referring back to FIG. 19, there is a general disadvantage to such capacitors in that, at very high frequency EMI 188 can cross-couple from the left side of the MLCC capacitor to the right side.

Figure 21:
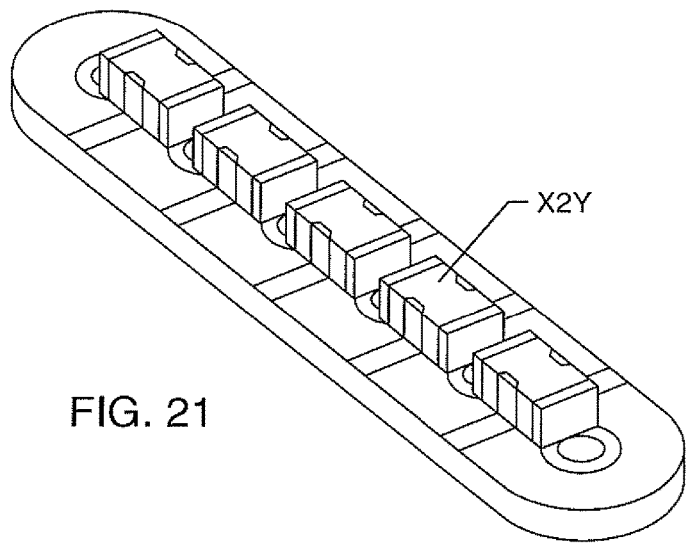
FIG. 21 illustrates a three-terminal capacitor that is also known in the industry as X2Y attenuator.
Figure 22:
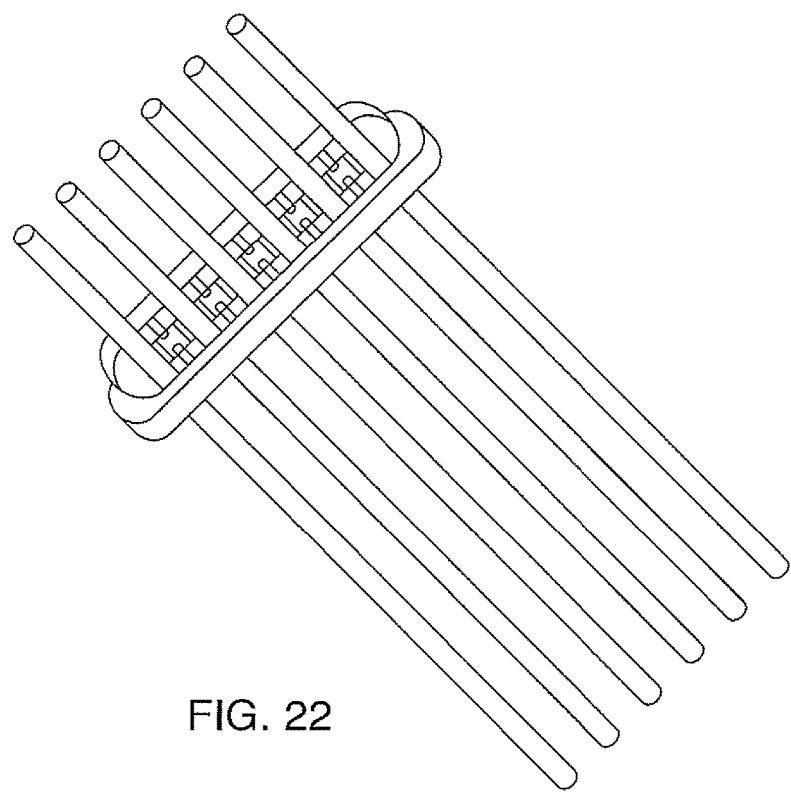
FIG. 22 illustrates a three-terminal capacitor that is also known in the industry as X2Y attenuator.
Figure 23:
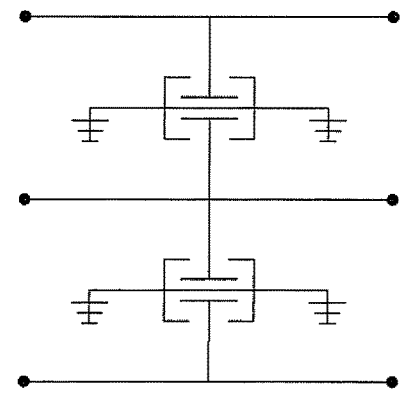
FIG. 23 illustrates an electrical schematic of the three-terminal capacitors of FIGS. 21 and 22.

FIGS. 21, 22 and 23 illustrate a three-terminal capacitor that is also known in the industry as X2Y attenuator. These are well known in the prior art. It will be appreciated by one skilled in the art, that any of these flat-thru or X2Y attenuators can be applied to the present invention.

Figure 24:
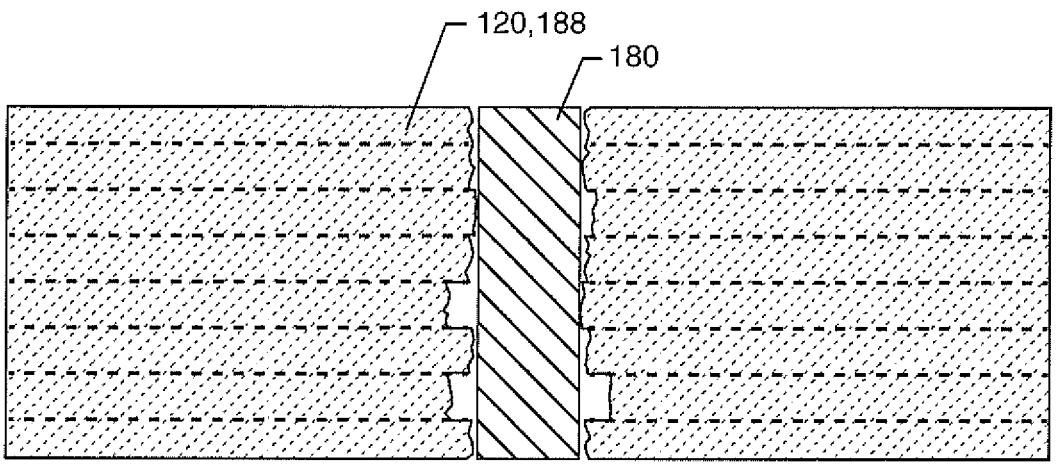
FIG. 24 is a sectional view taken from prior art FIG. 9 of U.S. Pat. No. 9,492,659, hereinafter referred to as the '659 patent.
Figure 25:
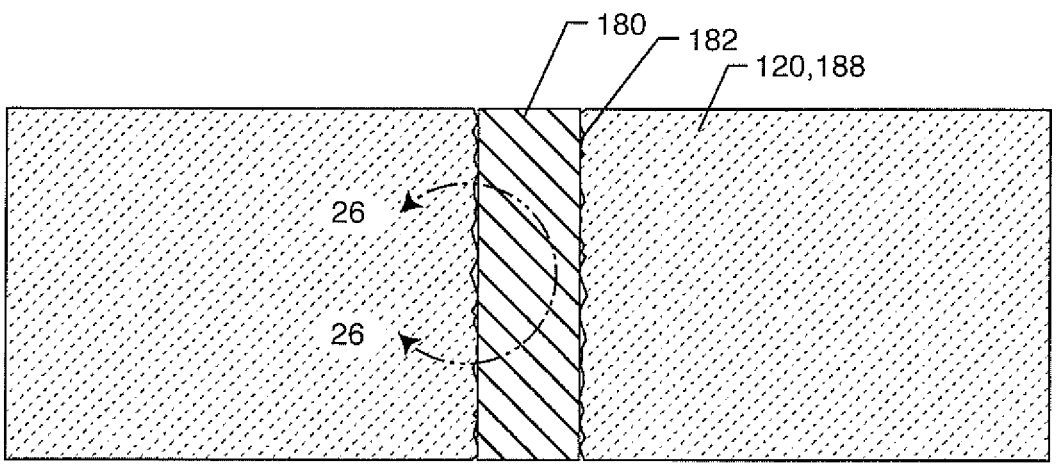
FIG. 25 is a sectional view taken from prior art FIG. 10 of the '659 patent.
Figure 26:
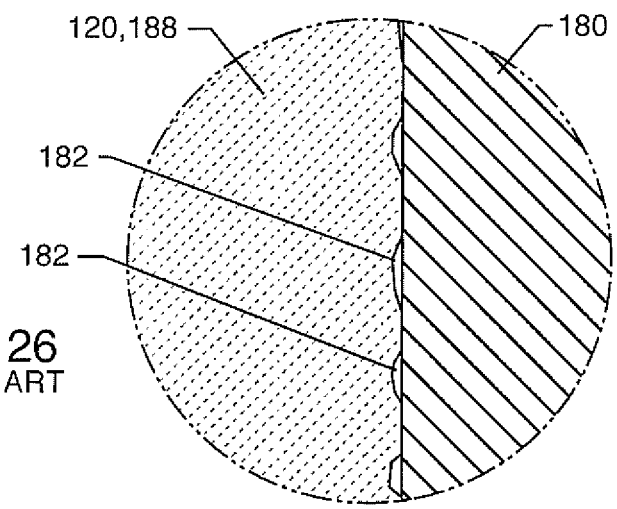
FIG. 26 is an enlarged sectional view taken along lines 26-26 which is from prior art FIG. 10A of the '659 patent.

FIGS. 24, 25 and 26 are taken from prior art FIGS. 9, 10 and 10A of U.S. Pat. No. 9,492,659, which is incorporated in full with this reference.

Figure 27:
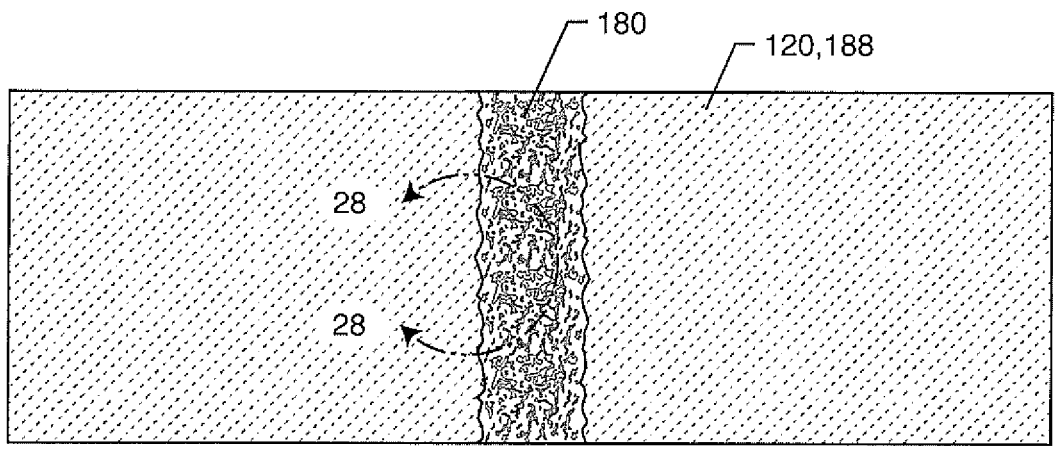
FIG. 27 is a sectional view taken from prior art FIG. 11 of the '659 patent.
Figure 28:
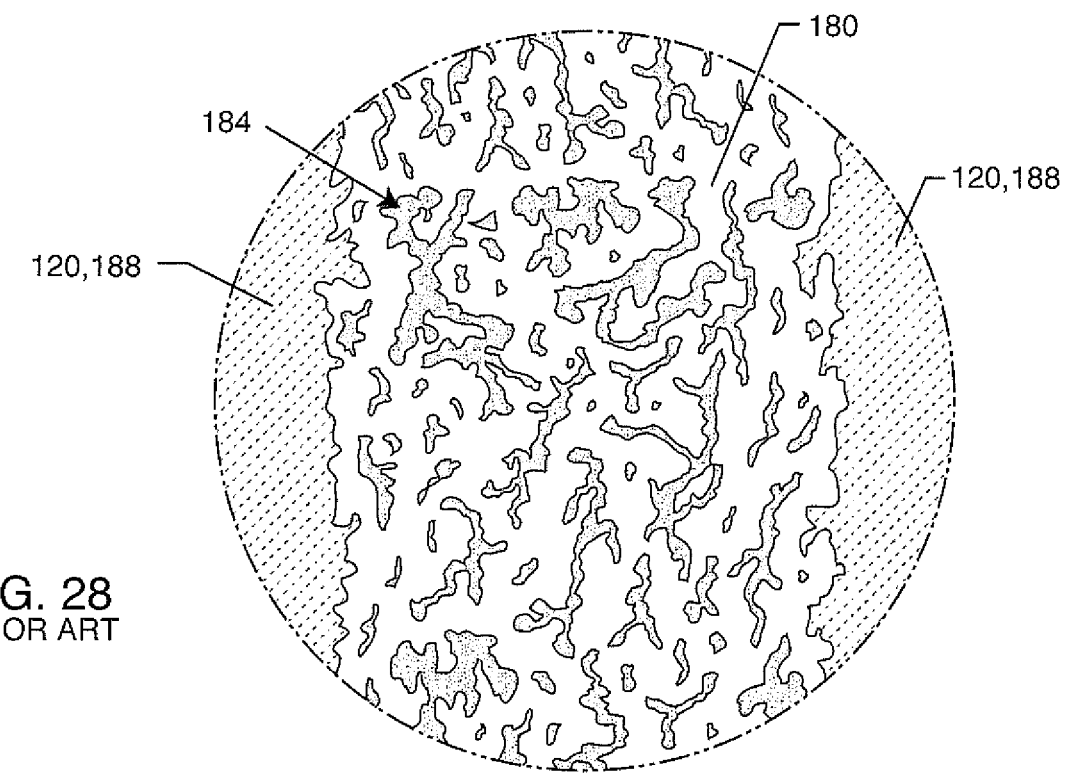
FIG. 28 is an enlarged sectional view taken along lines 28-28 which is from prior art FIG. 11A of the '659 patent.

FIGS. 27 and 28 are taken from prior art FIGS. 11 and 11A of the '659 patent. In FIGS. 11 and 11A of the '659 patent, the alumina insulator was designated by the number 120. However, now in FIGS. 27, 28 and all following drawings, the alumina insulator will be referred to by the number 188.

FIG. 29 is generally taken from prior art FIG. 14 of the '659 patent and has been modified to illustrate Option 1 of the present invention. PAC is a Platinum-Alumina Cermet and is numbered as element 185.

In this application we will refer to this Platinum-Alumina Cermet PAC (which prior to sintering is a paste or ink) as a Ceramic Reinforced Metal Composite or CRMC. A CRMC is specifically intended to have a CTE between that of a substantially pure metal and a substantially pure insulator, the CRMC comprising at least 15% of pure ceramic by weight or by volume. Alternatively, the CRMC may comprise a range between 20% to 80% ceramic by weight or by volume. More than one layer of CRMC may be used, each layer having a CTE so that transition from the substantially pure metal CTE to the substantially insulator CTE mitigates undesirable residual stresses induced by CTE mismatch during sintering. CRMC are noted herein as element 185. As used herein, substantially pure metal 186 is at least 90%, 95%, 98% and 99% pure metal by weight or by volume. Substantially pure ceramic 188 as used herein is at least 96%, 98%, 99% and 99.99% pure ceramic by weight or by volume. An example of substantially pure metal includes substantially pure platinum 186, and an example of substantially pure ceramic includes substantially pure alumina 188. An example of a CRMC 185 would include 20% alumina 80% platinum by weight or by volume. Alternatively, another example of a CRMC 185 would include 80% alumina 20% platinum by weight or by volume. It will be understood that any combination within these ranges are possible. The above discussion is applicable to all the embodiments disclosed herein. As will be described later on, CRMC may comprise a wide variety of different types of ceramics and metal fills. This CRMC paste is disposed within laminates $L_2$ through $L_7$. Laminates $L_1$ and $L_8$ comprise a via fill of substantially pure platinum (Pt) 186. It will be appreciated that any number of laminate layers $L_n$ may be used. It will also be understood throughout this patent that when Cermets, Platinum-Alumina Cermets or even pure platinum are referred to, that in general, these are pastes or inks which will have solvents and binders that will be baked out during sintering processes. The structure of FIG. 29 is laminated all together and then co-fired to form a solid monolithic structure. Substantially, pure platinum end caps 186 are disposed on the top and bottom of the via, as shown. The structure offers a number of very important advantages. The CRMC very closely matches the thermal coefficient of expansion of the alumina substrate 188. This results in a very good hermetic seal between the CRMC and the alumina insulator 188. The substantially pure caps 186 on the tops and bottoms provide for a very high conductivity. Under certain processing conditions Cermets may form a thin glass layer or even an alumina layer over the via ends. It may be necessary therefore that an additional manufacturing step, such as acid etch, lapping or mechanical abrasion, may be necessary to remove this formed layer. The present invention offers a substantial advantage over the prior art by co-firing substantially pure platinum end caps 186. By removing the alumina from these end caps, one avoids the glassy phases that may degrade resistivity. In the case of the specific structure of FIG. 29, the pure platinum/Cermet interface at the ends of the via will inherently provide a concentration gradient along the longitudinal axis of the via, extending from the Cermet through the platinum cap. A concentration gradient will also exist along the length of the platinum extending through the via. Concentration gradients at ceramic/metal interfaces have been thoroughly discussed in Kingery with predictive models for degree of concentration dating back to Becker's 1938 bond count method. Referring to Claim 1 of U.S. Pat. No. 8,841,558, the contents of which are incorporated herein fully by reference, a concentration gradient is claimed. It should be noted that nowhere in the '558 specification is a concentration gradient discussed. Moreover, as taught by Kingery and others, concentration gradients are inherent when sintering ceramics to metals. The inherency follows physical and chemical laws of nature and has been demonstrated through research efforts as discussed in the Karbasi dissertation which specifically discusses the platinum/alumina interface.

Referring back to FIG. 29, the alumina insulator body 188 may be defined as having a first insulator side 500 opposite a second insulator side 502. The first insulator side and second insulator side then are separated and connected by at least one outside perimeter surface 504 of the alumina insulator body.

Figure 30:
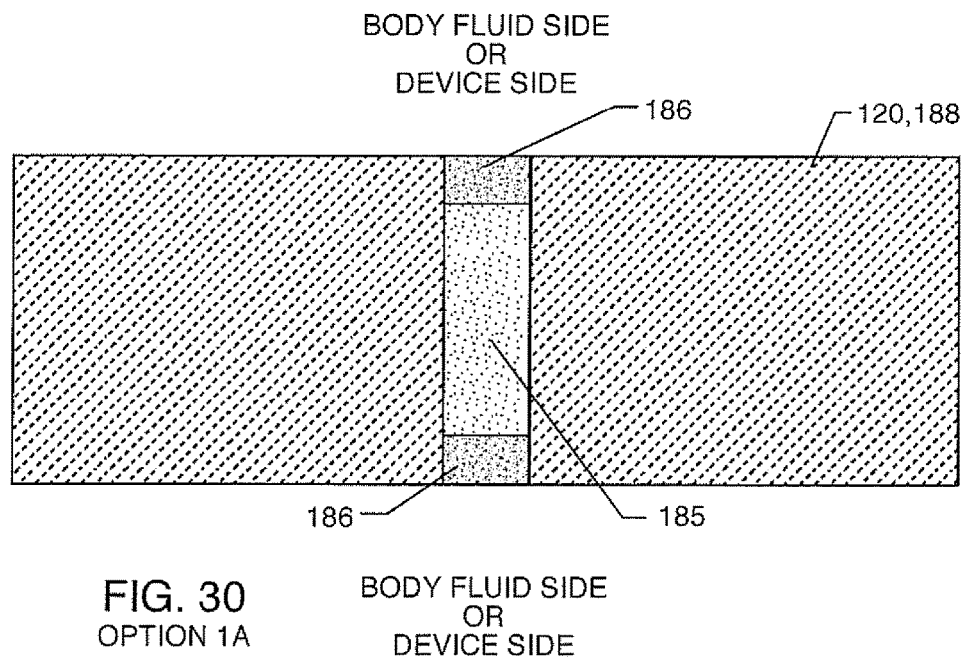
FIG. 30 is generally taken from prior art FIG. 13 of the '659 patent and has been modified to show Option 1A of the present invention.

FIG. 30 is generally taken from prior art FIG. 13 of the '659 patent and has been modified to show Option 1A of the present invention. In this case, the alumina body 188 is formed as a solid pellet and not of layers as previously discussed in FIG. 29. As used herein the word "pellet" is synonymous with a single body of green ceramic (pre-sintered). A ceramic pellet can be formed by pressing ceramic paste into a mold or other such forming apparatus. In contrast, multilayer ceramics comprise stacking of layers that are then pressed and co-sintered to create a solid body. One method of manufacturing the device of Option 1A would be to fill the entire via bore with the CRMC and then use drilling, machining or other processes to remove a top and bottom portion, which is then filled with substantially pure platinum 186. After firing (otherwise known as sintering), the Option 1A version (solid pellet) becomes indistinguishable over the Option 1 (multilayer) version. The Option 1A version, accordingly, has all of the advantages described for Option 1.

Figure 30A:
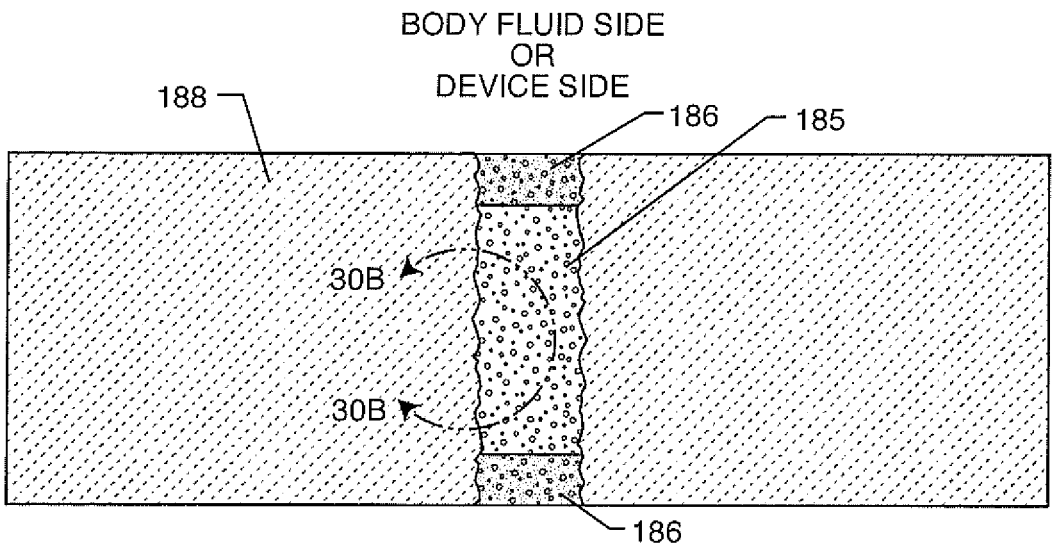
FIG. 30A is generally taken from prior art FIG. 15 of the '659 patent and illustrates Option 1A of the present invention post sintering.

FIG. 30A is generally taken from prior art FIG. 15 of the '659 patent and illustrates Option 1A of the present invention post sintering.

Figure 30B:
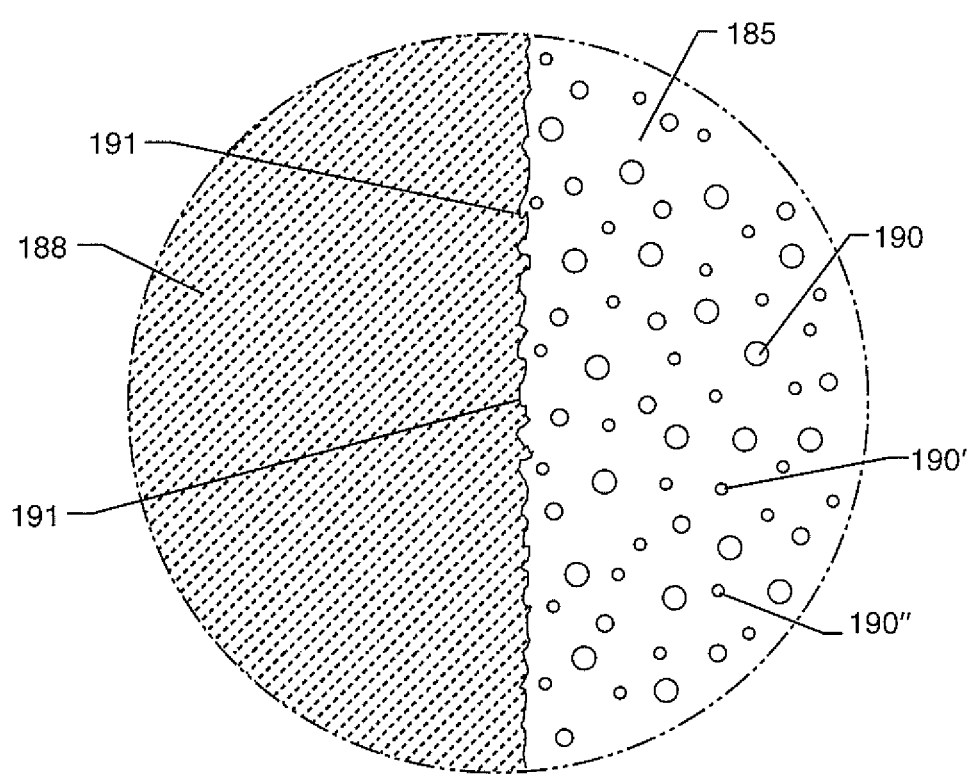
FIG. 30B is generally taken from prior art FIG. 16 of the '659 patent and is a sectional view taken from section 30B-30B from FIG. 30A illustrating how the CRMC forms a very tight knit interlaced surface structure with the alumina ceramic insulator.

FIG. 30B is generally taken from prior art FIG. 16 of the '659 patent and is a sectional view taken from section 30B-30B from FIG. 30A illustrating how the CRMC 185 forms a very tight knit interlaced surface structure 191 with the alumina ceramic insulator 188. As previously discussed, the present invention provides for a highly reliable hermetic structure in the interface of the CRMC and a ceramic insulator structure 188 while at the same time, providing for a very low resistive and highly conductive pure platinum end cap 186 on the top and bottom.

Referring once again to FIG. 30B, one can see that there is porosity as indicated by 190, 190' and 190". Some porosity is normal and even desirable as this porosity, not only is stress absorbing, but also tends to deter crack formation.

FIG. 31 is generally taken from prior art FIG. 14 of the '659 patent, but has been modified to show Option 2 of the present invention. In this case, the insulator 188 is multilayer and the entire via hole is first filled with the CRMC paste 185 and then, in the green state, the inner diameter is drilled out so that it can be filled with pure platinum 186. A layer of CRMC 185 which surrounds the pure platinum 186, forms a buffer during sintering and subsequent thermal shock, such that, there is a gradation of the differential and coefficient of thermal expansion. The thickness of the CRMC 185 can be adjusted along with the diameter of the pure platinum 186 such that during co-firing, no stress cracks are induced in the alumina body 188.

A partial solid wire, nailhead, crimp posts and the like can be co-fired within the via structure to optimize via conductivity and/or connectability as shown in various FIGS. provided by U.S. publication 2015/0314131 and the '659 patent which are incorporated herein in full by reference.

Figure 32:
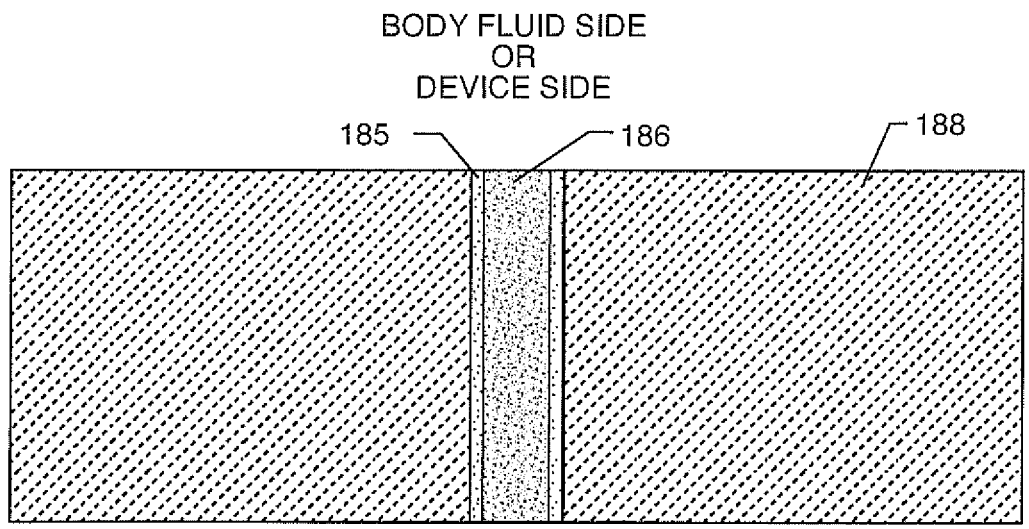
FIG. 32 illustrates Option 2A of the present invention which is generally taken from prior art FIG. 13 of the '659 patent and is very similar to FIG. 31, except in this case, the pre-sintered alumina insulator body 188 is not multilayer.

FIG. 32 illustrates Option 2A which is generally taken from prior art FIG. 13 of the '659 patent and is very similar to FIG. 31, except in this case, the pre-sintered alumina insulator body 188 is not multilayer.

FIG. 33 (Option 2B) is very similar to FIGS. 31 and 32, except that a body fluid side counterbore 195 (or device side) has been added into the CRMC 185 and the 186 material. It is important to note that the counterbore 195 drilling has left a thin layer of the CRMC material on the inside walls of the bore in the via hole. Providing a thin layer of CRMC material will allow gold braze 138 to wet without the need for the previously described sputtering layers 150 and 152.

Figure 33A:
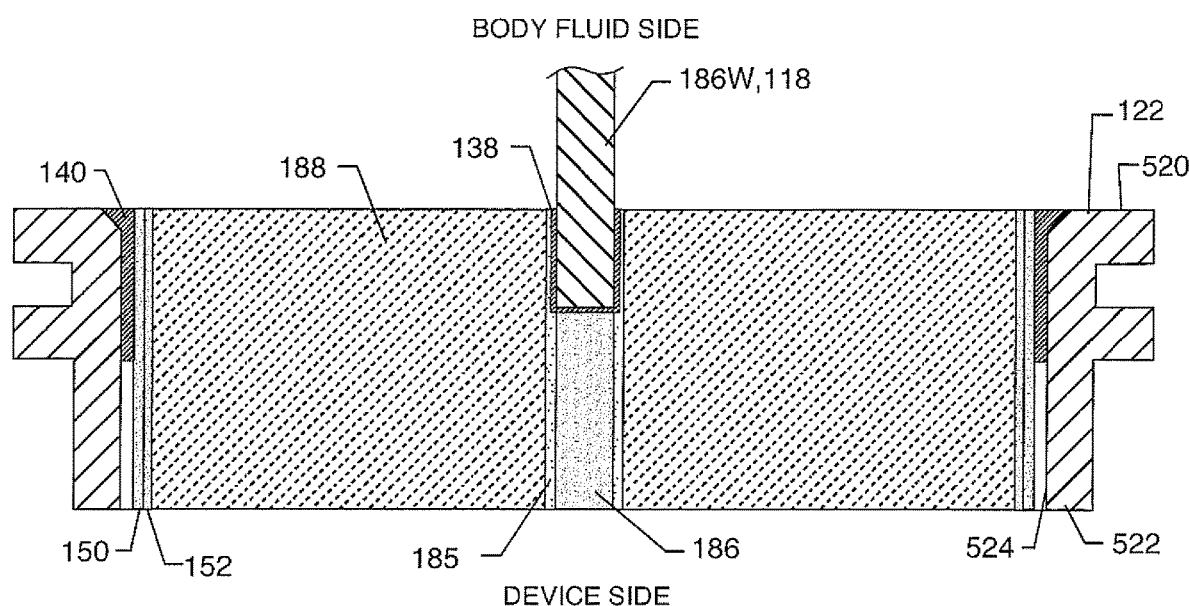
FIG. 33A illustrates the alumina ceramic insulator assembly of FIG. 33 showing that the insulator is gold brazed into ferrule.

FIG. 33A (Option 2B) illustrates the alumina ceramic insulator assembly 188 of FIG. 33 showing that the insulator is gold brazed 140 into ferrule 122. Generally, during the same gold brazing operation a second gold braze 138 is formed in the counterbore 195 of FIG. 33. A solid leadwire 186W is inserted and is co-brazed 138 into the inside of this counterbore 195. The gold braze 138 wets and flows to the CRMC material on the inside of the counterbore and also to the end of the pure platinum fill 186. Referring back to FIG. 33, the insulator assembly, consisting of insulator 188, CRMC 185 and platinum fill 186, are generally co-sintered (also known as co-firing) at a high temperature forming a strong monolithic structure. It is then ready for co-brazing at a lower temperature, as described in FIG. 33A. Referring once again to FIG. 33, the counterbore 195 is easily formed in the green state. In ceramic engineering terms, "green" means "before firing." Green materials are generally relatively soft and still contain binders and solvents, making them pliable and easy to machine. Alternatively, referring back to FIGS. 31, 32 and 33, the insulator structure 188 could have been sintered at high temperature and then the counterbore 195 of FIG. 33 could be formed by machining the hard, sintered ceramic materials.

Referring back to FIGS. 33 and 33A, it will be appreciated that the body fluid side leadwire 186W could be alternatively placed on the device side or even on both the body fluid and device side.

Furthermore, the conductive ferrule body 122 may be defined as having a first ferrule side 520 opposite a second ferrule side 522. A ferrule opening 524 is then between and through the first and second ferrule sides. This means the alumina insulator body is at least partially disposed within the ferrule opening.

FIG. 34 (Option 2C) represents a body fluid side leadwire 186W which will be routed to an implanted lead or an AIMD header block (not shown). The insulator could be drilled all the way through or even drilled with a counterbore (as shown) and then completely filled with CRMC material 185. Then a hole is drilled through so that the platinum fill 186 can be accomplished leaving room for a leadwire, such as a platinum solid leadwire 186W. This is then sintered at very high temperatures wherein, the CRMC material forms a strong hermetic seal between the alumina insulator 188 and also the solid leadwire 186W, which would generally be of platinum or other high-temperature, biocompatible materials. By having the pure platinum fill 186 be very close to or abut the solid leadwire 186W, one is assured that a very low resistance connection is made from the body fluid side to the device side, which is very important for high current applications, such as those from a high voltage shock from an implantable cardioverter defibrillator.

Figure 34A:
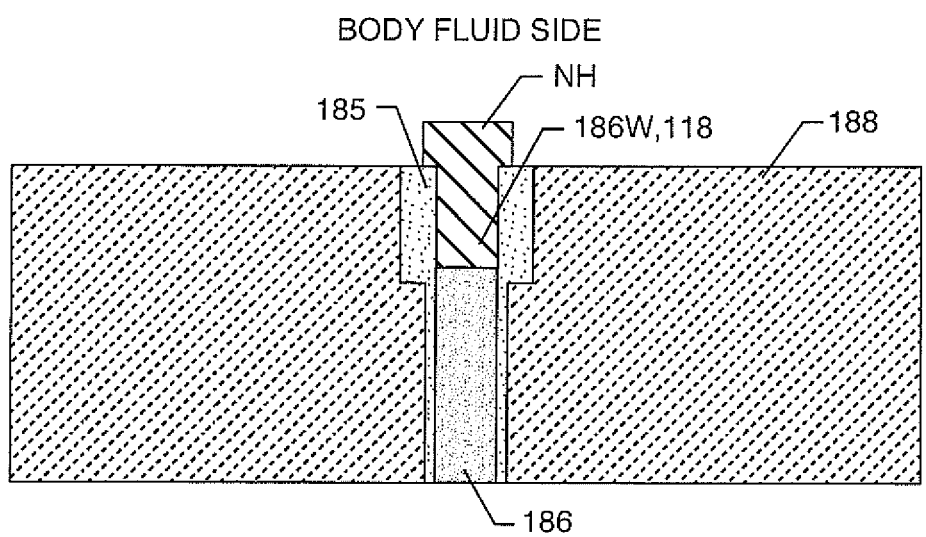
FIG. 34A illustrates Option 2C which is very similar to FIG. 34 now illustrating that leadwire may include a nail-headed solid lead.

FIG. 34A illustrates Option 2C which is very similar to FIG. 34 illustrating that leadwire 186W may include a nailheaded solid lead 186W. The nailhead NH feature aids in pull strength and overall mechanical strength of the package.

Figure 35:
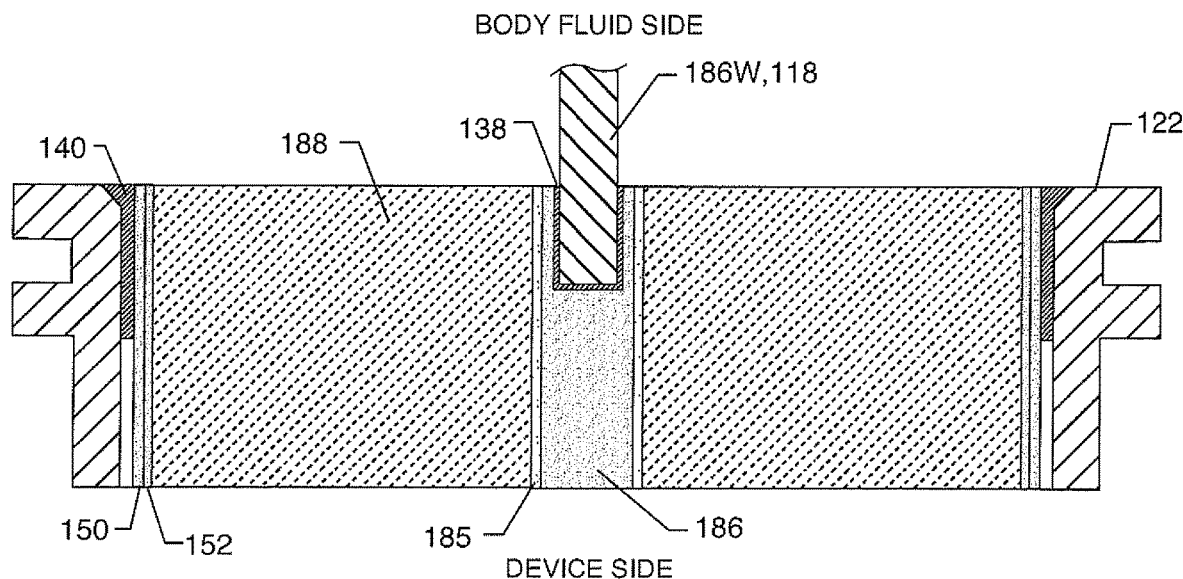
FIG. 35 is similar to the structures illustrated in FIGS. 33 and 33A, except in this case, the counterbore is into the platinum fill.

FIG. 35 is similar to the structures illustrated in FIGS. 33 and 33A, except in this case, the counterbore is into the platinum fill 186, as illustrated. Also illustrated is a gold braze 138. Ideally, the hole drilled to accommodate leadwire 186 would be perfectly aligned, as illustrated in FIG. 35, thereby allowing the gold braze to wet directly to the platinum fill 186. However, the inventors have discovered that it is not always possible to perfectly align the counterbore hole with the platinum fill 186.

Figure 36:
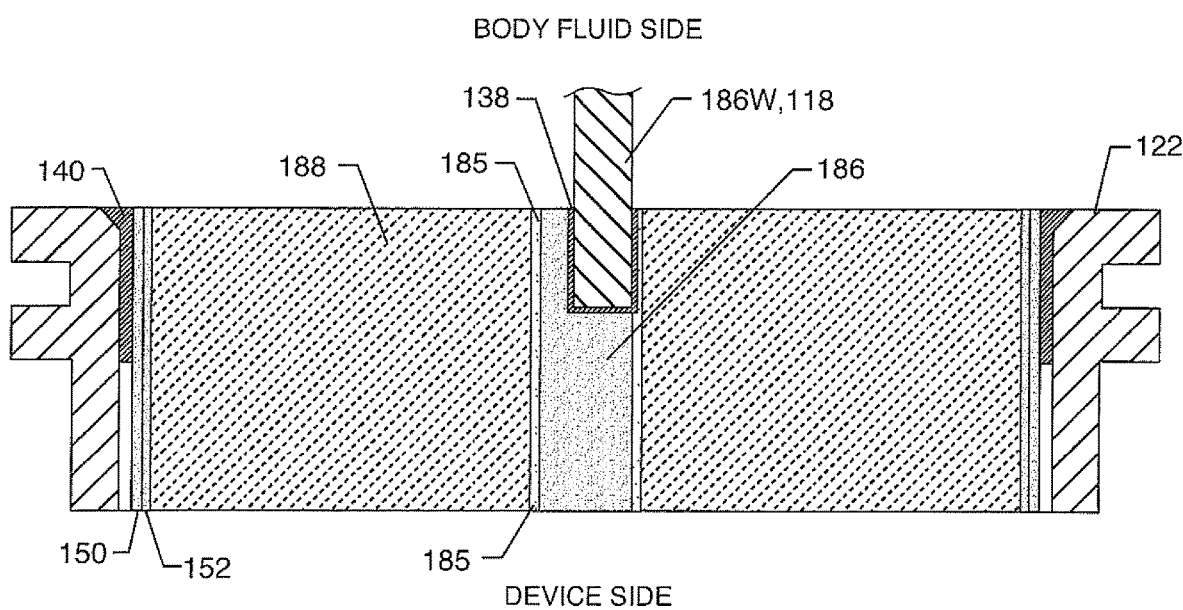
FIG. 36 illustrates option 2D of FIG. 35 wherein, the counterbore hole to accommodate body fluid side leadwire is not perfectly centered or aligned with the platinum.

FIG. 36 illustrates option 2D of FIG. 35 wherein, the counterbore hole to accommodate body fluid side leadwire 186W is not perfectly centered or aligned with the platinum. This is not a problem, in fact, the hole can be so misaligned that it encounters the platinum on part of the hole 186 and CRMC on another portion as shown. The gold braze 138 will still wet both to the platinum 186 and to the now exposed off-centered CRMC material 185. In both cases, we end up with a mechanically robust and high integrity hermetic seal on the device side. As previously described, in any of these drawings, leadwire 186W could also be placed on the device side or even on both the device side and the body fluid side.

Figure 37:
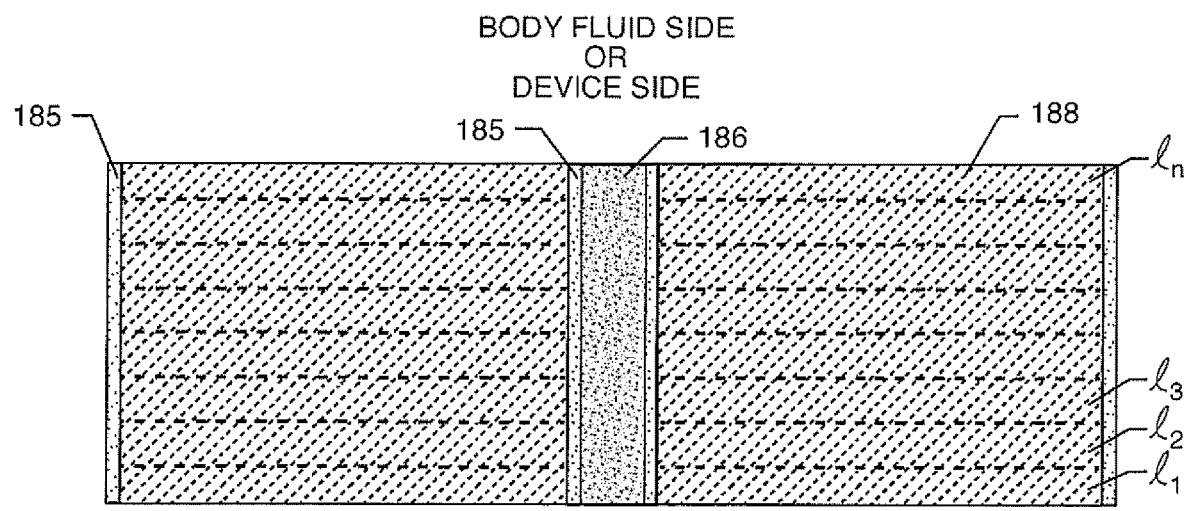
FIG. 37 illustrates Option 2E, which is very similar to Option 2, except that CRMC material has been added to the outer diameter or perimeter of the alumina insulator.

FIG. 37 illustrates Option 2E, which is very similar to Option 2, except that CRMC material 185 has been added to the outside diameter or perimeter of the alumina insulator 188. The co-firing of the CRMC material 185 on the outside diameter or perimeter of the hermetic seal eliminates the need for sputter layers 150 and 152. The CRMC layer is intended so that gold braze can wet directly to it.

Figure 38:
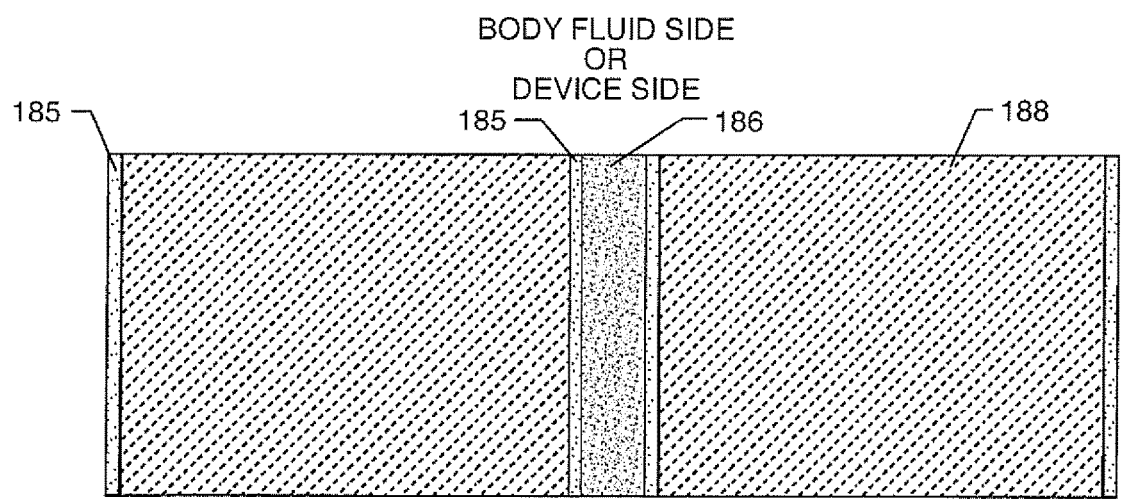
FIG. 38 illustrates Option 2F which is the same as FIG. 37, except that in this case, the alumina insulator is formed with a solid pellet of ceramic rather than multilayer, as illustrated in FIG. 37.

FIG. 38 illustrates Option 2F which is the same as FIG. 37, except that in this case, the alumina insulator 188 is formed with a solid pellet of ceramic rather than multilayer, as illustrated in FIG. 37.

As previously mentioned, the pellet can be formed by pressed alumina ceramic powders. It should also be appreciated that solid slabs of green alumina can be machined to form a solid pellet 188.

Figure 39:
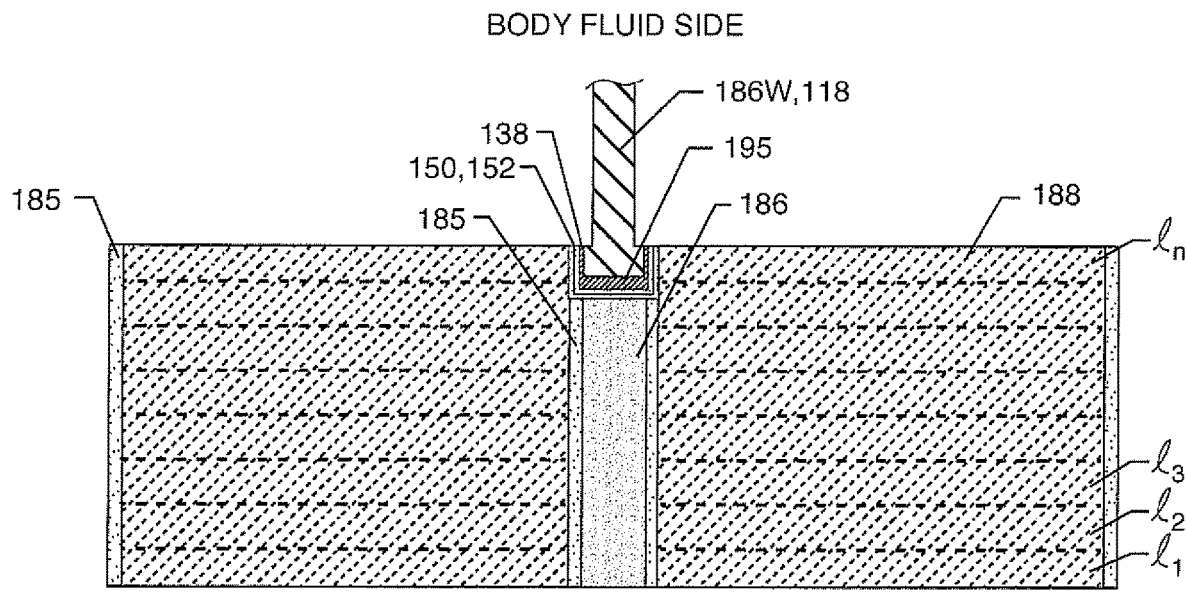
FIG. 39 illustrates Option 2G where the via hole is first solid filled with CRMC material.

FIG. 39 illustrates Option 2G wherein, the via hole is first solid filled with CRMC material 185. The via hole is then drilled and is completely filled with the platinum paste 186. Then both the CRMC 185 and the platinum fill 186 are counterbored. As can be seen, there is also a perimeter or diameter CRMC 185. It will be appreciated that the outside diameter or perimeter CRMC layer 185 could be replaced by adhesion and wetting layers 150 and 152, as previously described. Referring once again to FIG. 39, one can see that after sintering, the inside diameter and sides and bottom of the counterbore hole are sputtered 150, 152. Then in a subsequent co-brazing operation (with a ferrule 122 not shown), nailhead or straight leadwire 186W, 118 are co-brazed 138 to the sputter layers as indicated.

Figure 40:
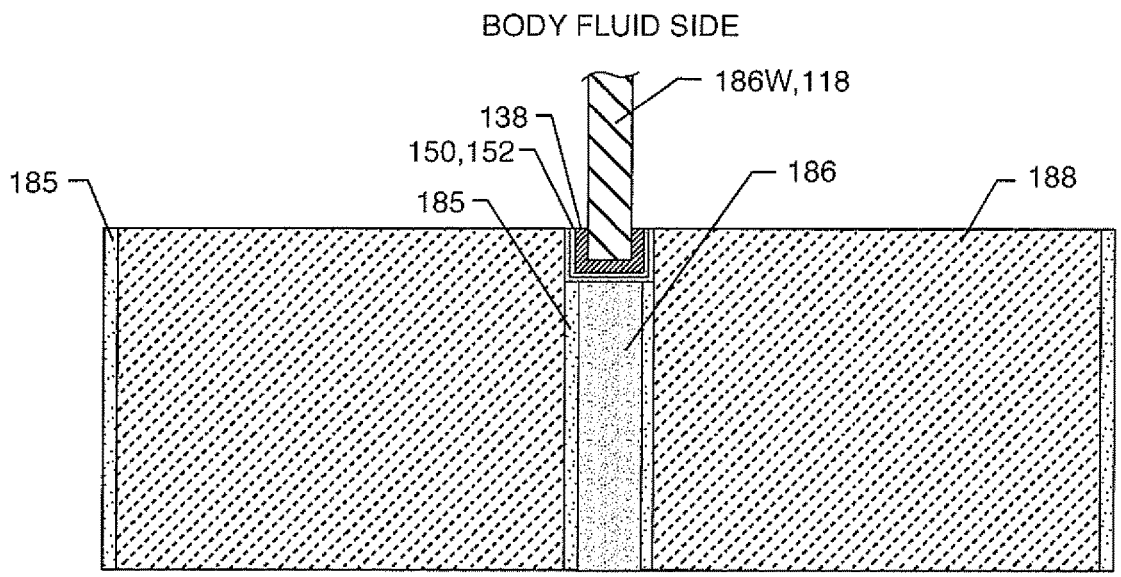
FIG. 40 is very similar to FIG. 39, except that the nailhead has been eliminated and leadwire is straight.

FIG. 40 is very similar to FIG. 39, except that the nailhead has been eliminated and leadwire 186W, 118 is straight. Again, it will be appreciated that the outside diameter or outside perimeter CRMC material 185 could be replaced by one or more sputter layers to facilitate adhesion and wetting of gold.

Figure 41:
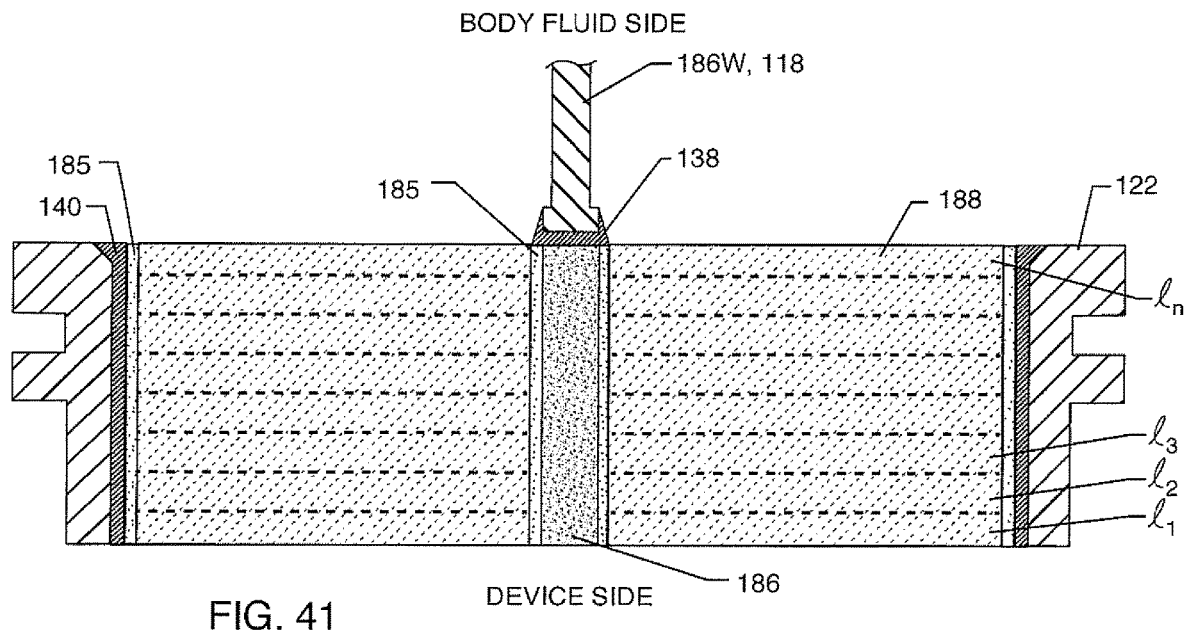
FIG. 41 illustrates Option 2I, which takes the insulator previously described in FIG. 31 and places it within a ferrule.

FIG. 41 illustrates Option 2I, which takes the insulator previously described in FIG. 31 and places it within a ferrule 122. In general, the alumina insulator 188 and platinum fill 186 and CRMC 185 have already been sintered at a very high temperature forming a solid monolithic structure. It will also be appreciated that the outside diameter or perimeter of the insulator 188 also embodies a CRMC surface 185, which would be co-brazed 140 into the ferrule 122, as previously described. In an optional lower temperature gold brazing operation, a gold braze 140 is formed between ferrule 122 and the CRMC layer 185 on the insulator structure 188. Alternatively, at the same time during the, a lead 186W, 118 is co-brazed 138 to the end of the via hole consisting of platinum fill 186 and CRMC material 185. Mechanically strong hermetic seals are thereby formed between the insulator material 188 and ferrule 122. A hermetic seal has been previously formed during the sintering of the insulator 188 between the CRMC material 185 and its fill 186. By using gold braze material 138, one achieves a very low resistance and strong mechanical connection between the body fluid side leadwire 118 and the via hole fill 186.

Referring once again to FIG. 41, it will be appreciated that the outside diameter or perimeter gold braze 140 can be formed at the same time as the gold braze attachment between the lead and the CRMC 185/platinum fill 186 in a conventional high temperature gold brazing furnace process.

Figure 42:
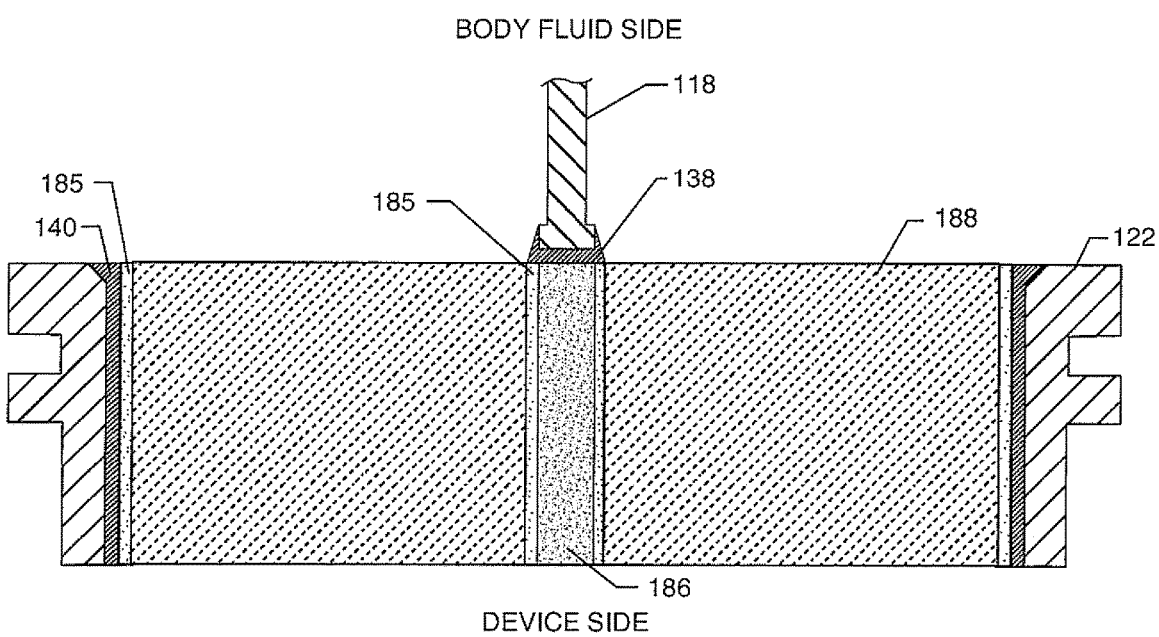
FIG. 42 illustrates Option 2J which is exactly the same as previously illustrated in FIG. 41, except in this case, the alumina insulator is a solid pellet instead of multilayer.

FIG. 42 illustrates Option 2J which is exactly the same as previously illustrated in FIG. 41, except in this case, the alumina insulator is a solid pellet instead of multilayer.

FIG. 43 illustrates Option 3 which is generally taken from prior art FIG. 14 of the '659 patent and has been modified to illustrate Option 3 of the present invention. FIG. 43 is very similar to FIG. 31, except that the substantially pure platinum paste 186 has been replaced by a substantially pure platinum solid wire 186W. The platinum wire 186W is surrounded by the novel CRMC layer of the present invention and the entire structure is co-fired along with insulator 188.

Figure 44:
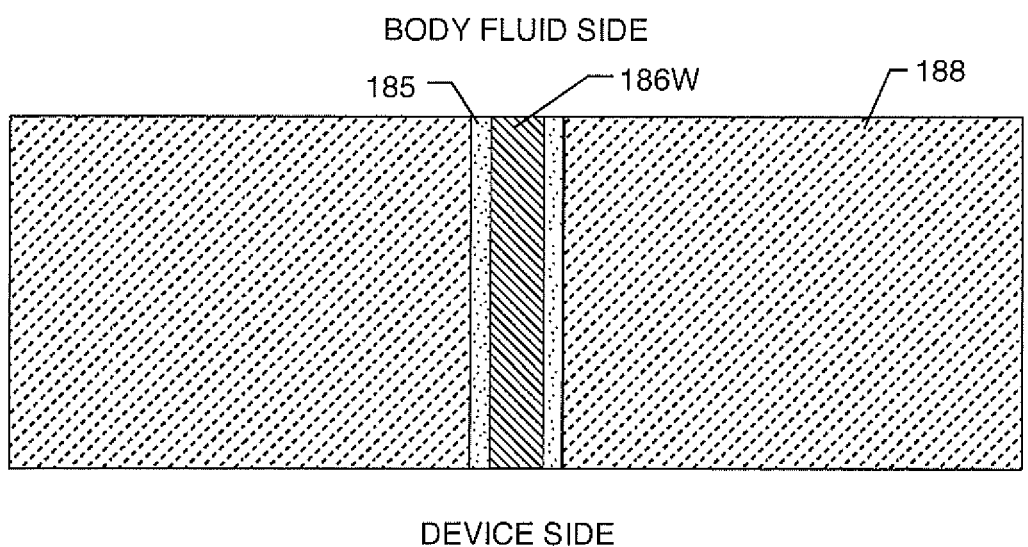
FIG. 44 illustrates Option 3A which is taken from prior art FIG. 13 of the '659 patent and illustrates the structure of FIG. 43 except that it is not multilayered.

FIG. 44 illustrates Option 3A which is taken from prior art FIG. 13 of the '659 patent and illustrates the structure of FIG. 43 except that it is not multilayered.

It will be appreciated throughout the drawing descriptions of this invention that the words "sintering" and "firing" are synonymous. It will also be appreciated that, to those skilled in the art, there could be lower temperature solvent and binder bake-out processes that are then fired by a higher temperature firing or sintering operation. The objective is to remove the volatiles, such as solvents and binders and then sinter the alumina insulator into a solid monolithic and dense, hard structure.

FIG. 45 illustrates Option 3B wherein, the leadwire 186W, previously described in FIGS. 43 and 44, can be extended or lengthened into the body fluid side or into the device side or both. By lengthening this leadwire on the body fluid side, one could connect it, for example, to header block connectors. By extending it into the body fluid side, it could then be routed to an AIMD electronic circuit board.

Figure 46:
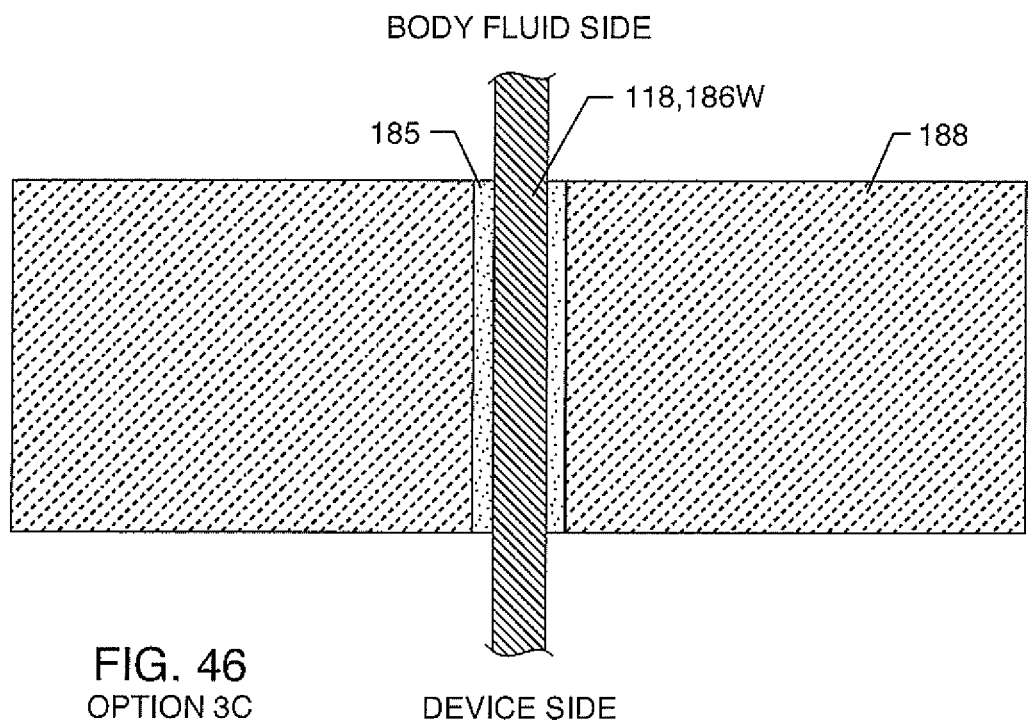
FIG. 46 illustrates Option 3C which is the same as FIG. 45, except that in this case, the insulator is a solid pellet instead of multilayer.

FIG. 46 illustrates Option 3C which is the same as FIG. 45, except that in this case, the insulator 188 is a solid pellet instead of multilayer.

Figure 47:
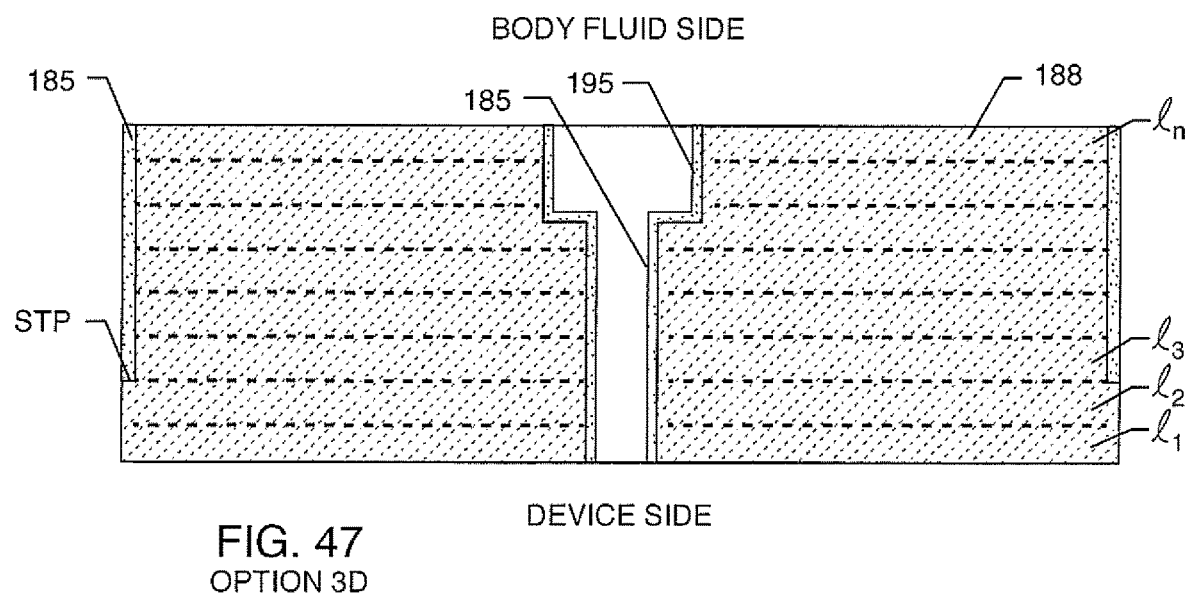
FIG. 47 illustrates Option 3D wherein, the insulator has been drilled and then counterbored in the green state.

FIG. 47 illustrates Option 3D wherein, the insulator 188 has been drilled and then counterbored 195 in the green state. Then a CRMC layer 185 has been added to the inside surfaces of the via hole and counterbore, as shown, and a layer of CRMC material 185 has also been added to a portion of the outside or perimeter of the insulator. It is noted that the outside diameter or perimeter of the insulator can be stepped STP as shown in order to better support that CRMC material during high temperature sintering. This step feature STP is considered optional.

Figure 48:
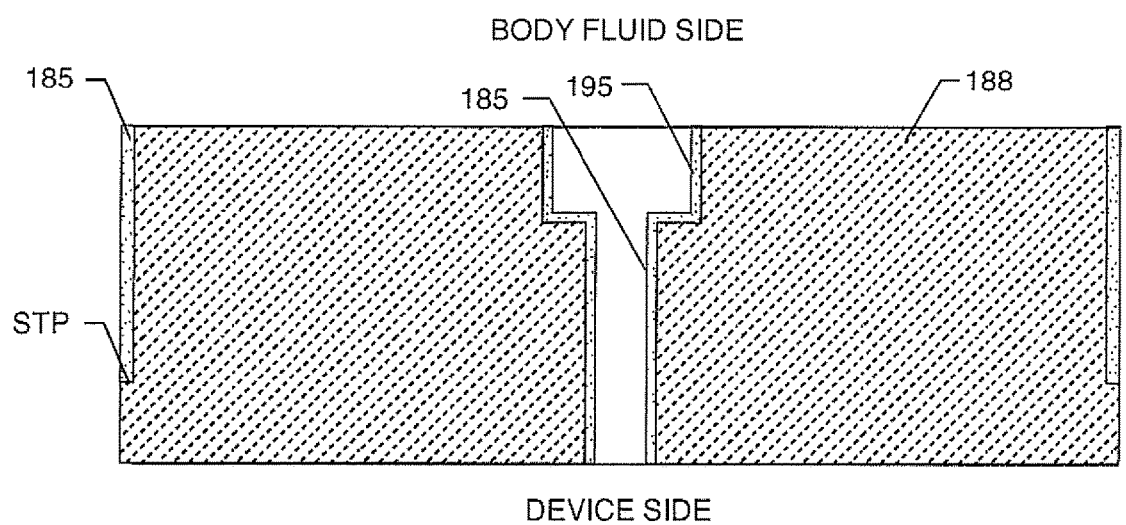
FIG. 48 illustrates Option 3E which is the same as FIG. 47, except that the insulator is a solid pellet instead of multilayer.

FIG. 48 illustrates Option 3E which is the same as FIG. 47, except that the insulator 188 is a solid pellet instead of multilayer.

Figure 49:
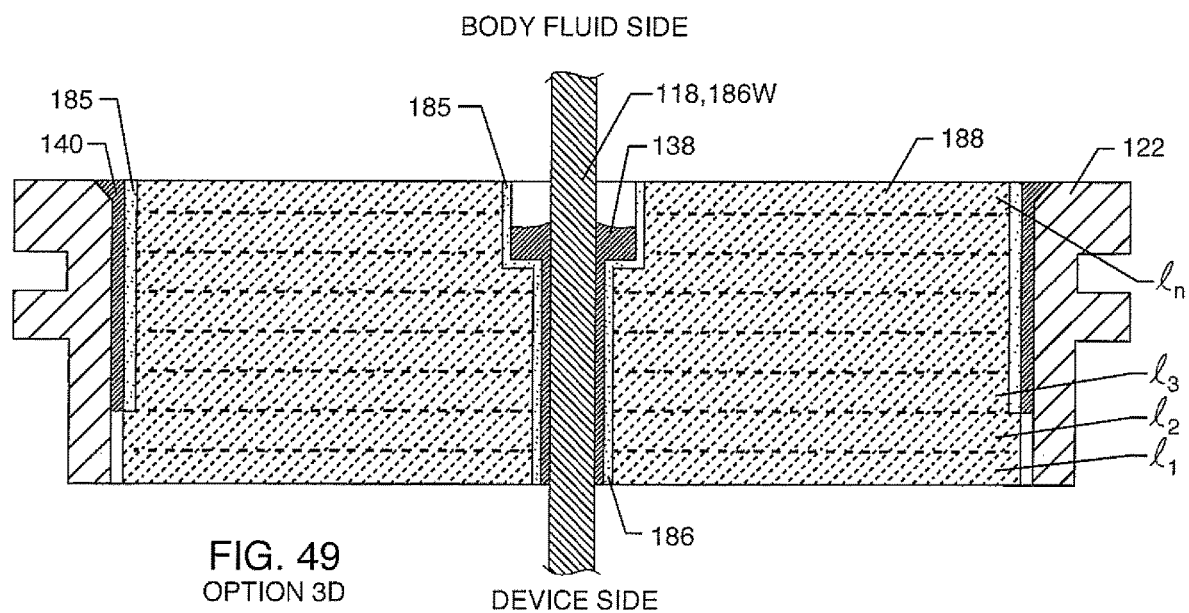
FIG. 49 illustrates Option 3D wherein, the insulator of FIG. 47 has been placed at least partially within a ferrule while at the same time, a leadwire has been placed through the center of the via hole.

FIG. 49 illustrates Option 3D wherein, the insulator of FIG. 47 has been placed at least partially within a ferrule 122 while at the same time, a leadwire 118,186W has been placed through the center of the via hole. Gold brazes 138 and 140 are generally formed at the same time in a brazing furnace. Mechanically strong and hermetic bonds are formed between the gold braze material 138 and the CRMC material 185 of the via as well as the lead 118,186W. In this case, since the lead 118,186W is exposed on the body fluid side, the use of biocompatible or noble materials are required. For example, lead 118,186W could be platinum, palladium, tantalum, titanium or the like. A mechanically strong hermetic seal 140 is also formed by gold brazing between the ferrule structure 122 (which is generally titanium) and the CRMC layer 185 as shown.

Figure 50:
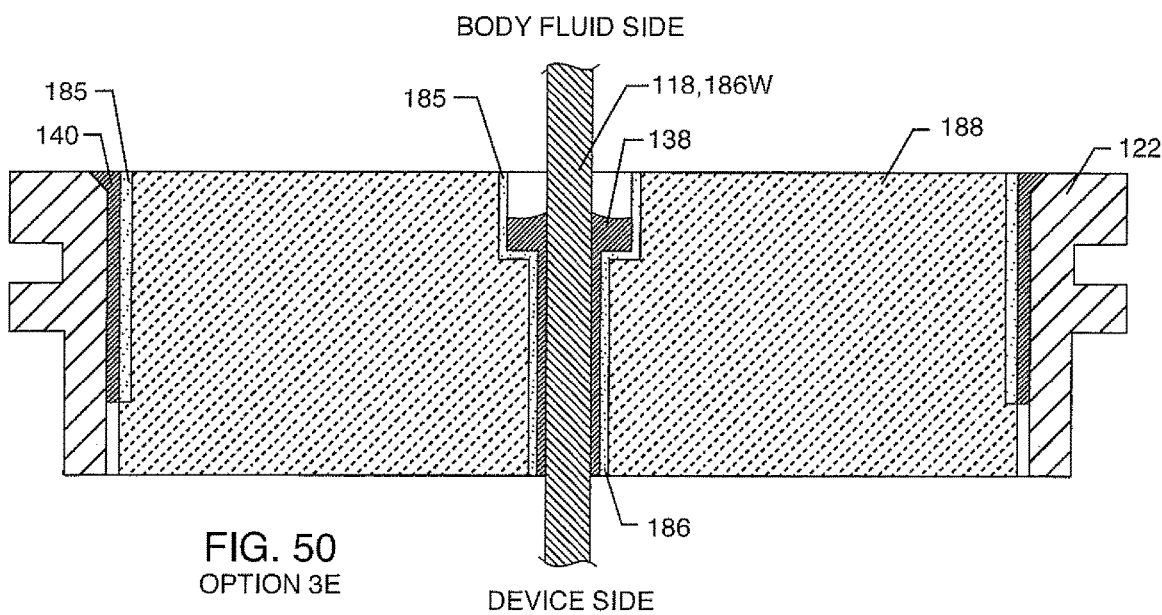
FIG. 50 illustrates Option 3E which is the same as FIG. 49, except in this case, the insulator 188 is a solid pellet instead of multilayer.

FIG. 50 illustrates Option 3E which is the same as FIG. 49, except in this case, the insulator 188 is a solid pellet instead of multilayer.

Figure 51:
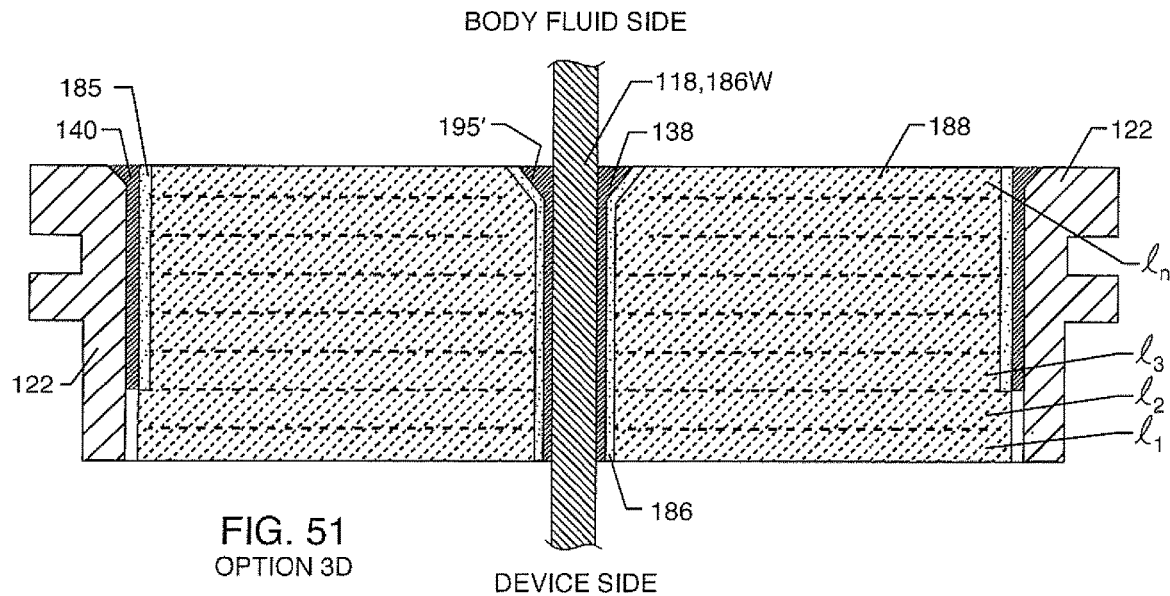
FIG. 51 illustrates Option 3D which is very similar to FIG. 49 except the counterbore has been replaced by relatively smaller countersink to hold the gold braze preform.

FIG. 51 illustrates Option 3D which is very similar to FIG. 49 except the counterbore has been replaced by relatively smaller countersink 195' to hold the gold braze preform 138.

Figure 52:
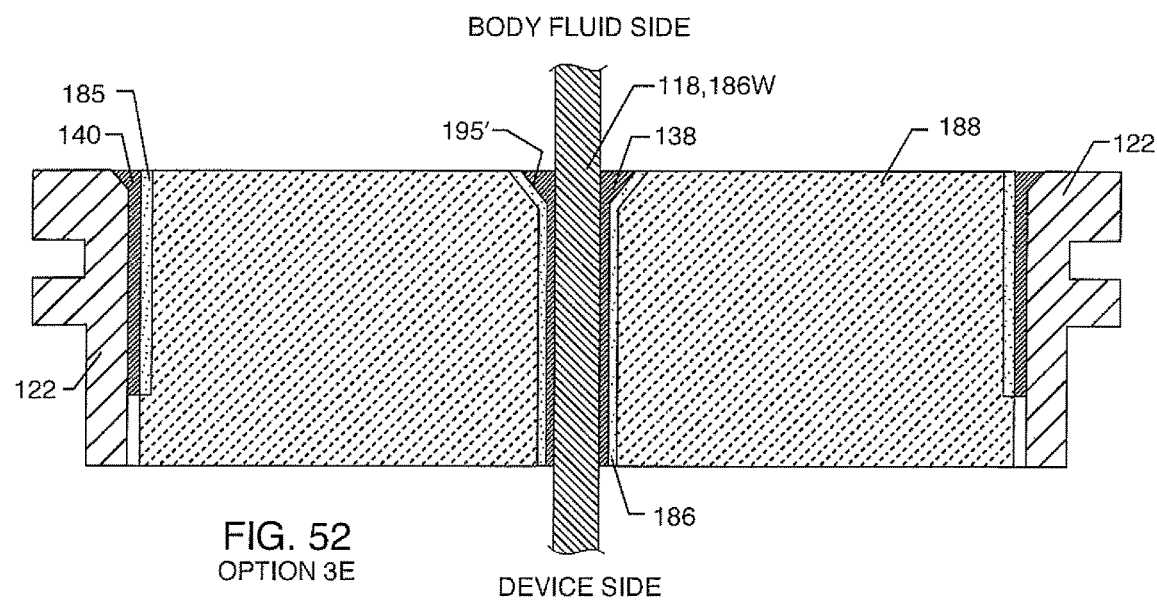
FIG. 52 illustrates Option 3E which is the same as FIG. 51, except the insulator is a solid pellet instead of multilayer.

FIG. 52 illustrates Option 3E which is the same as FIG. 51, except the insulator 188 is a solid pellet instead of multilayer.

FIG. 53 illustrates Option 4 which is taken from prior art FIG. 17B of the '659 patent and illustrates Option 4 of the present invention. FIG. 53 is very similar to FIG. 31 herein, except that there are counterbores 195 disposed on the top and bottom of the via so that a pure platinum larger end cap 186' is formed on both the body fluid side and the device side. It will be understood that depending on the application, this counterbore 186' could be disposed on either side, either just the body fluid side or just the device side or both, as required for the application. Referring once again to FIG. 53, one can see that there is a CRMC layer 185 disposed throughout the center of the via to grade the thermal coefficient of expansion and enhance hermetic sealing of the assembly.

Figure 53A:
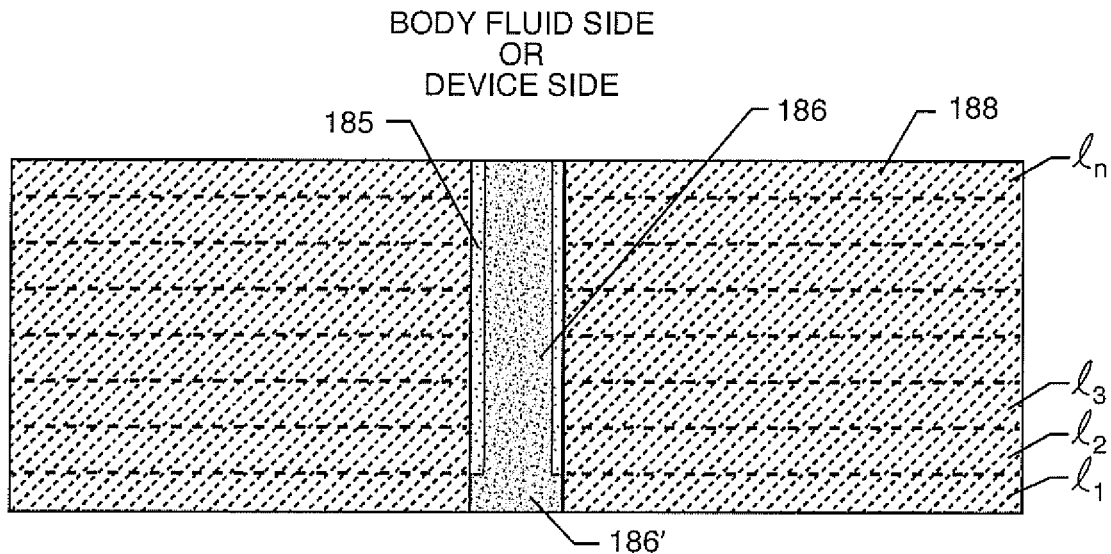
FIG. 53A is very similar to FIG. 53, except in this case, the enlarged platinum nailhead fill is disposed on just one side.

FIG. 53A is very similar to FIG. 53, except in this case, the enlarged platinum nailhead fill 186 is disposed on just one side. As shown, it can be disposed on the body fluid side or the device side. The insulator of FIG. 53A is multilayer, including layers $L_1$ through $L_n$.

Figure 54:
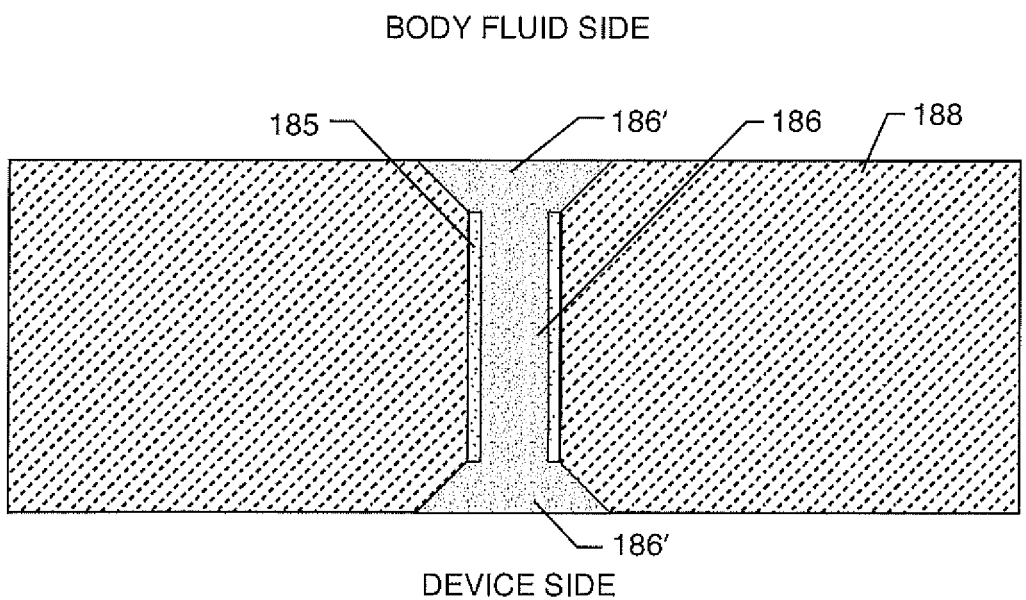
FIG. 54 is taken from prior art FIG. 13 of the '659 patent and illustrates Option 4A of the present invention wherein the insulator is a solid pellet instead of multilayer.

FIG. 54 is taken from prior art FIG. 13 of the '659 patent and illustrates Option 4A of the present invention wherein the insulator 188 is a solid pellet instead of multilayer.

Figure 54A:
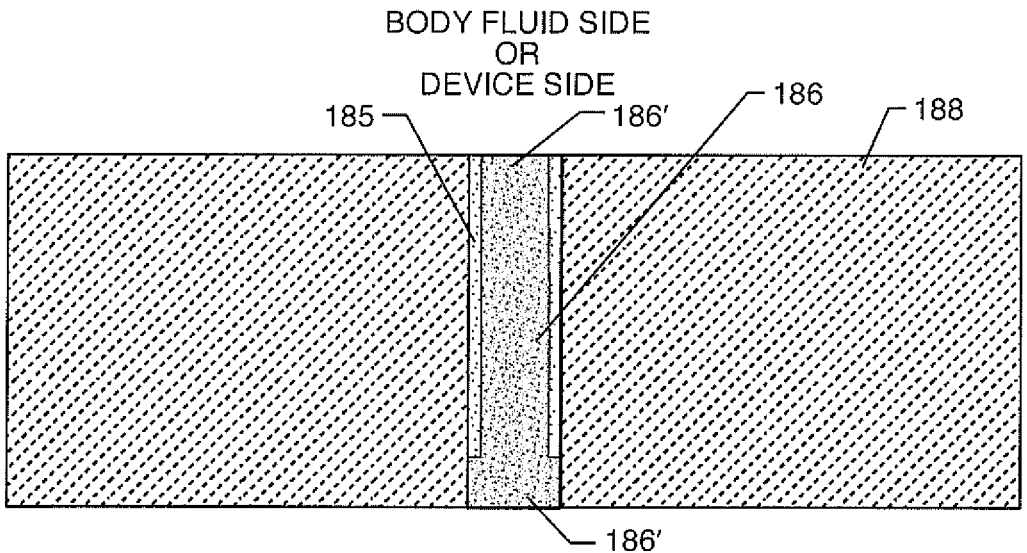
FIG. 54A is the same as FIG. 53A, except in this case, the ceramic is formed from a solid pellet.

FIG. 54A is the same as FIG. 53A, except in this case, the ceramic 188 is formed from a solid pellet.

FIG. 55 illustrates Option 5 which is taken from prior art FIG. 14 of the '659 patent and is very similar to FIG. 43 herein, except that the pure platinum wire 186W is surrounded by two different layers. In this case, the entire via bore hole is first filled with the CRMC paste 185. Then, it is drilled out and filled with a substantially pure platinum paste 186, then the substantially pure platinum paste is drilled out and a thin pure platinum wire 186W is inserted, and then co-fired along with the overall multilayer alumina insulator 188.

Figure 56:
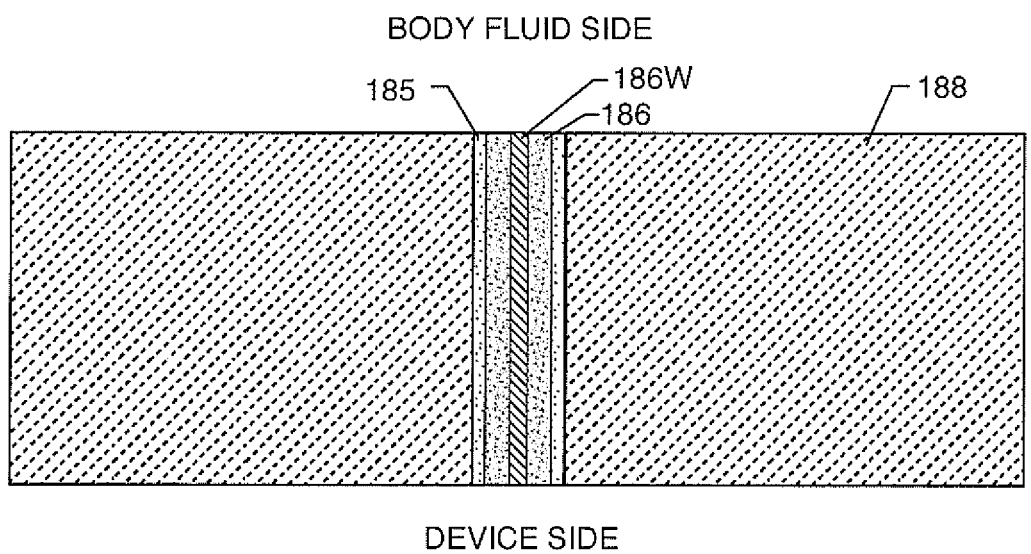
FIG. 56 illustrates Option 5A which is taken from prior art FIG. 13 of the '659 patent and illustrates the structure of FIG. 55 except that the insulator is not multilayer.

FIG. 56 illustrates Option 5A which is taken from prior art FIG. 13 of the '659 patent and illustrates the structure of FIG. 55 except that the insulator 188 is not multilayer.

FIG. 57 illustrates Option 5B which is very similar to FIG. 55, except that it shows that the solid leadwire 186W can be extended into the body fluid side or into the device side or both.

Figure 58:
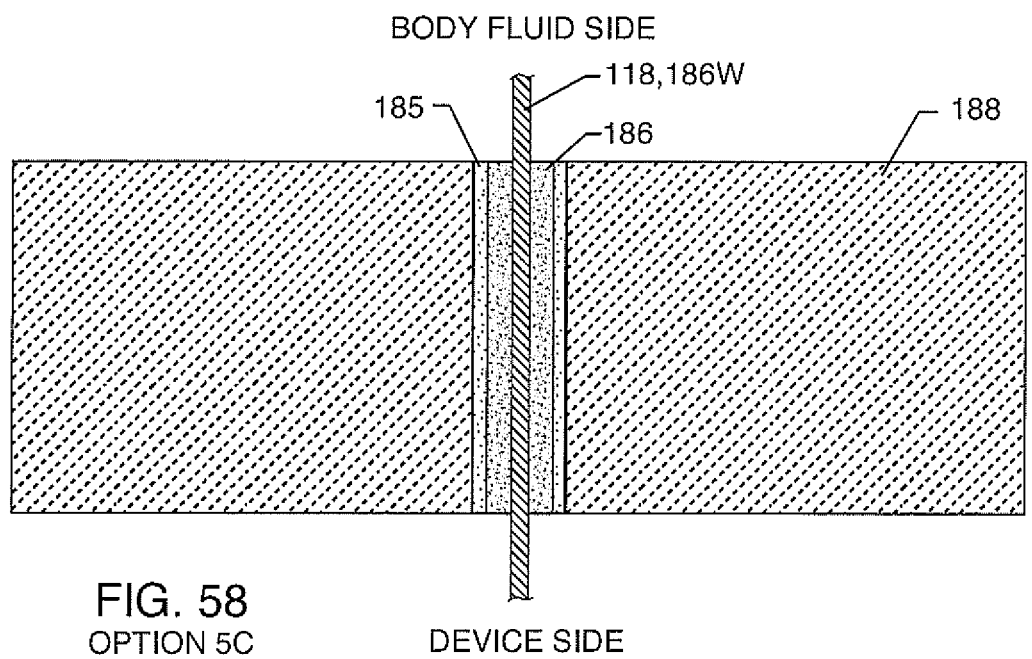
FIG. 58 illustrates Option 5C which is the same as FIG. 57, except that in this case, the ceramic insulator is a solid pellet instead of multilayer.

FIG. 58 illustrates Option 5C which is the same as FIG. 57, except that in this case, the ceramic insulator 188 is a solid pellet instead of multilayer.

FIG. 59 illustrates Option 6 which is taken from prior art FIG. 14 of U.S. Pat. No. 9,492,659 hereinafter referred to as the '659 patent. This FIG. is very similar to FIG. 53 herein, except that machined pure platinum solid metal end caps 187 have been co-fired into the pure platinum 186. An advantage to the pure platinum cap 187 illustrated in FIG. 59 is that it provides for a very flat wire bonding surface for later assembly operations. It will also be appreciated that any of the structures previously illustrated in the present invention, could be lapped on the top and bottom thereby also providing a very flat and uniform surface. It will also be appreciated that end caps 187 could include other materials pending location (body fluid side or device side) and also may be achieved by other methods such as applying a gold containing solder or other biocompatible or oxide resistant material, swaging a gold or other appropriate metal preform, nickel, copper, into the cavity and the like.

Figure 60:
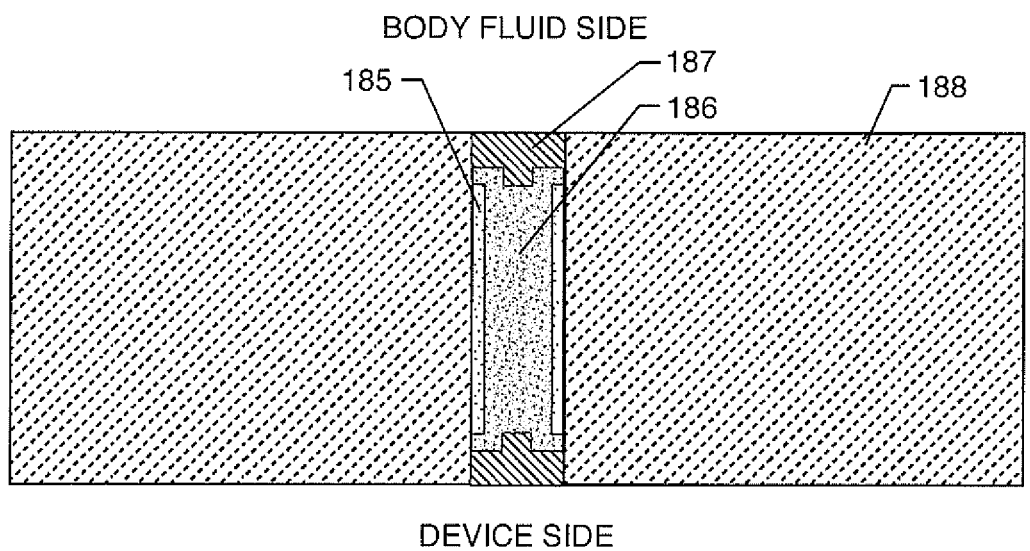
FIG. 60 illustrates Option 6A which is taken from prior art FIG. 13 of the '659 patent and illustrates that the structure of FIG. 59 does not require a multilayer alumina structure 188, but rather was made from a pellet.

FIG. 60 illustrates Option 6A which is taken from prior art FIG. 13 of the '659 patent and illustrates that the structure of FIG. 59 does not require a multilayer alumina structure 188, but rather was made from a pellet 188.

Figure 61:
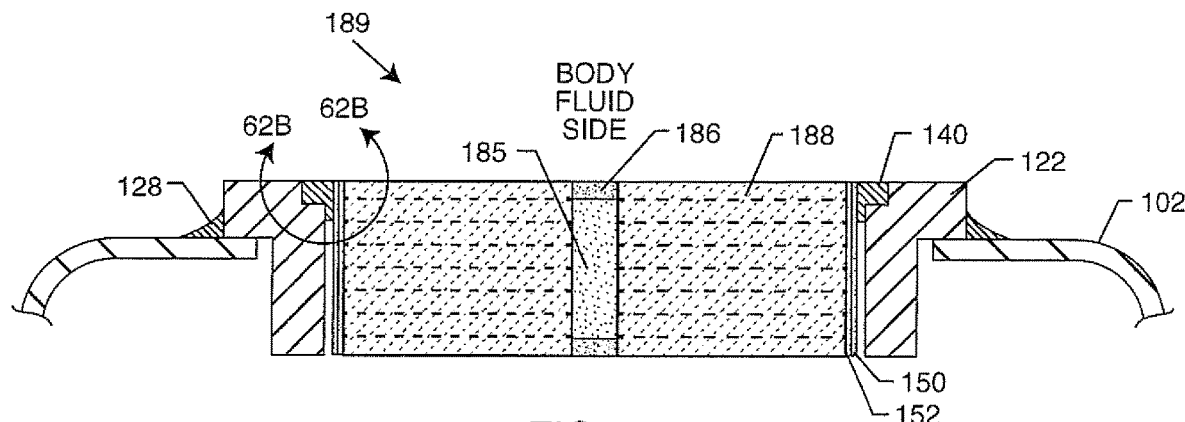
FIG. 61 is taken from prior art FIG. 17A of the '659 patent and illustrate an embodiment of the present invention where the alumina insulator, after sintering, can be sputtered, including an adhesion layer and a wetting layer, such that a gold braze to a titanium ferrule can be accomplished.
Figure 62:
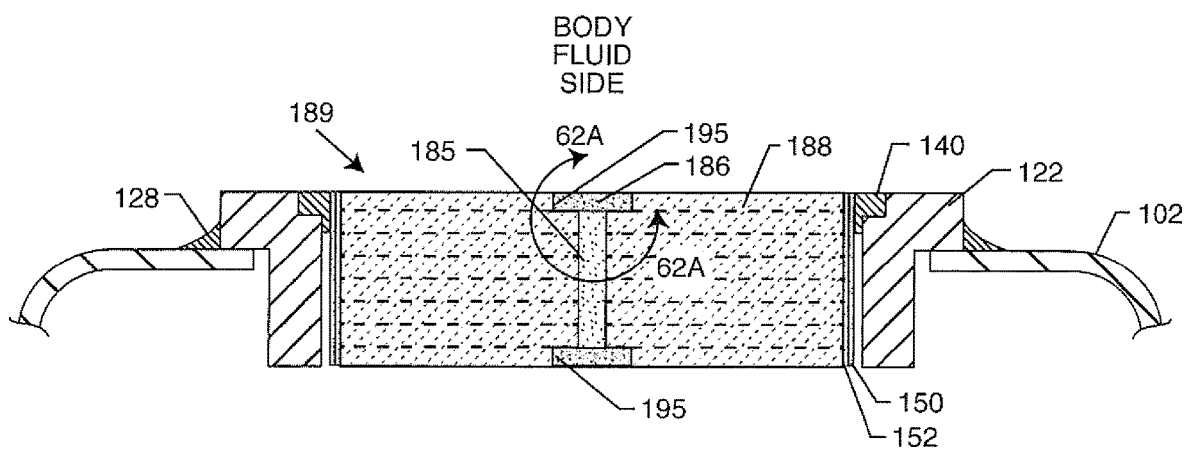
FIG. 62 is taken from prior art FIG. 17B of the '659 patent and illustrates an embodiment of the present invention where the alumina insulator, after sintering, can be sputtered, including an adhesion layer and a wetting layer, such that a gold braze to a titanium ferrule can be accomplished.
Figure 62A:
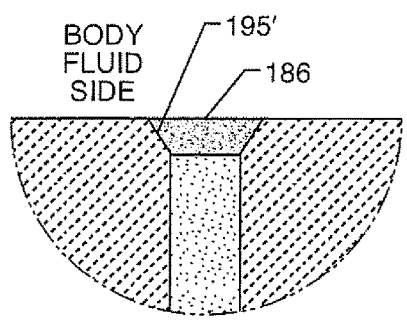
FIG. 62A is generally taken from section 62A-62A from FIG. 62 and it illustrates that the counterbore 195 may be a countersink.

FIGS. 61 and 62 are taken from prior art FIGS. 17A and 17B of the '659 patent and illustrate various embodiments of the present invention where the alumina insulator, after sintering, can be sputtered, including an adhesion layer 152 and a wetting layer 150, such that a gold braze 140 to a titanium ferrule 122 can be accomplished. Titanium ferrules 122 are well known in the prior art and is suitable for laser welding 128 into the housing of an AIMD 102. Referring now to FIGS. 62 and 62A, one can see that the diameter/width/size of the platinum via fill 186 at the surface of each end of the via has been extended beyond the CRMC 185 providing a larger electric contact/bonding area for connection to AIMD circuits on the device side and/or electrical leads on the body fluid side. FIG. 62 illustrates that the enlarged area may be a counterbore 195 and FIG. 62A may be a countersink 195'. It will be appreciated that the counterbore 195 of FIG. 62 and the countersink 195' of FIG. 62A may be on the body fluid side of the insulator 188 or the device side or both. It will also be appreciated that these features could be round as shown, but also may be square, rectangular, oval or other geometries.

FIG. 62A is generally taken from section 62A-62A from FIG. 62. It illustrates that the counterbore 195 may be a countersink 195'.

Figure 62B:
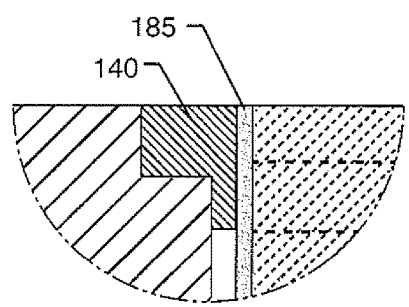
FIG. 62B is an enlarged sectional view 62B-62B taken from FIG. 61.

FIG. 62B is an enlarged sectional view 62B-62B taken from FIG. 61. FIG. 62B shows an optional embodiment where the sputtering layers 150, 152 are replaced by the CRMC material 185 on the outside diameter or perimeter of the insulator 188. It will be appreciated that the application of CRMC material on the outside diameter or perimeter of the insulator requires less labor, eliminates secondary operations such as vacuum sputtering, ion implantation and the like, making the manufacturing process more efficient.

Figure 63:
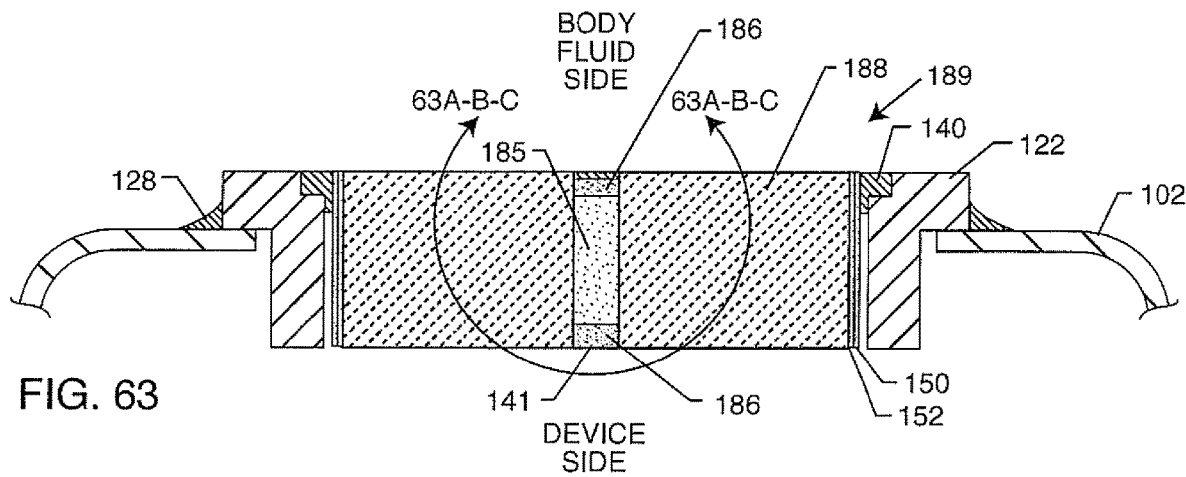
FIG. 63 is very similar to FIG. 30 except that a thin layer of gold is disposed on top of the body fluid side platinum via fill.

FIG. 63 is very similar to FIG. 30 except that a thin layer of gold 141 is disposed on top of the body fluid side platinum via fill 186. As shown, the platinum fill 186 is recessed below the body side surface of the insulator 188. Sputter layers 150, 152 are present but not shown. It would be preferred that 141 be a gold braze and be formed at the same time that gold braze 140 to the ferrule 122 is formed. It will be understood that gold braze 141 could be disposed on the body fluid side as shown or on the device side not shown or both.

Referring once again to FIG. 63, it will also be appreciated that the thin layer of gold braze 141 need not be flush with the surface of the insulator 188. In other words, it could stick up or be proud of the insulator (not shown).

Figure 63A:
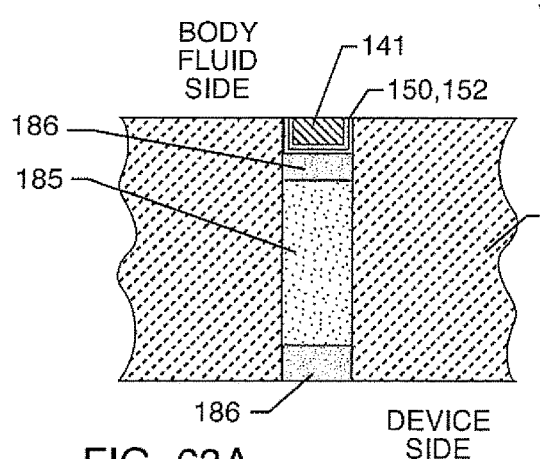
FIG. 63A is an enlarged sectional view taken from section 63A-63A from FIG. 63 illustrating gold braze layer on top of the platinum via fill.

FIG. 63A is an enlarged sectional view taken from section 63A-63A from FIG. 63 illustrating gold braze layer 141 on top of the platinum via fill 186. It will be appreciated that gold braze layer 141 can be added to any of the Options 1 through 6 as described herein. Now, one can see layers 150 and 152 to which one can attach to the gold braze 141.

Figure 63B:
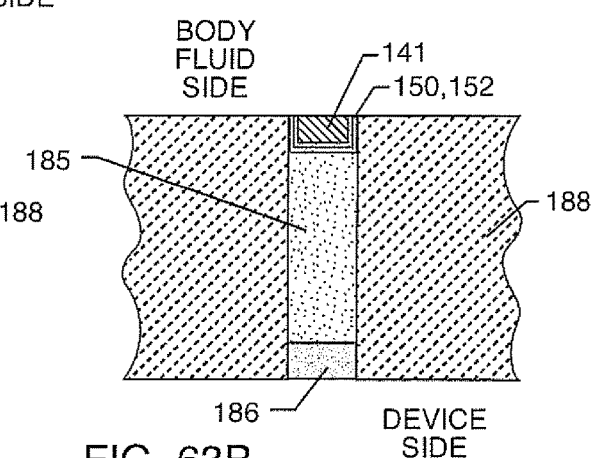
FIG. 63B is very similar to FIG. 63A except that the platinum end cap, on the body fluid side, has been eliminated and the gold braze has been directly brazed to the layers and then to the CRMC.

FIG. 63B is very similar to FIG. 63A except that the platinum end cap 186, on the body fluid side, has been eliminated and the gold braze 141 has been directly brazed to the layers 150, 152 and then to the CRMC.

Figure 63C:
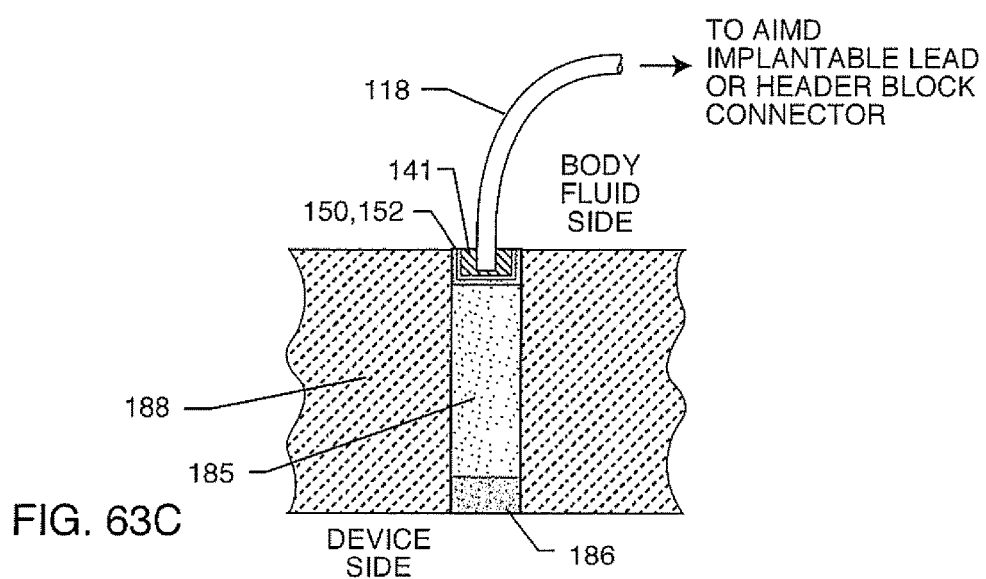
FIG. 63C is very similar to FIG. 43 except that a device side leadwire has been co-brazed on the body fluid side.

FIG. 63C is very similar to FIG. 43 except that a device side leadwire 118 has been co-brazed 141 on the body fluid side. This leadwire 118 could be routed to an AIMD header block 104, as shown in FIG. 2, and connector 106 or directly to an implanted lead 110.

It will be appreciated that for any of the above embodiments, the gold braze layer 141 and or the platinum fill layer 186 may be flush, sub-flush or proud of either the body side of the insulator 188, the device side of the insulator 188 or both.

Figure 64:
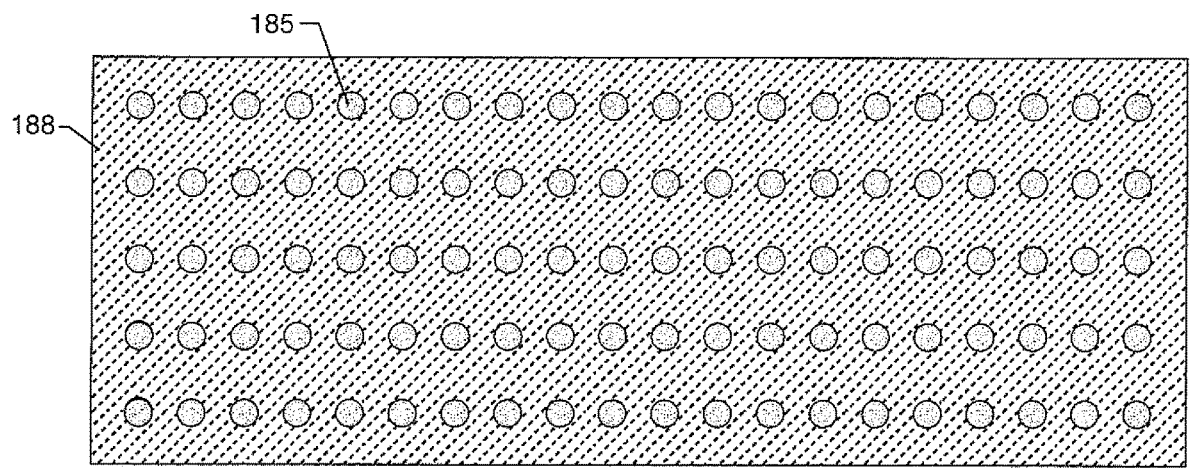
FIG. 64 is taken from prior art FIG. 19A of the '659 patent, illustrating that any of the options of the present invention lend themselves to very high density packaging.

FIG. 64 herein is taken from prior art FIG. 19A of the '659 patent, illustrating that any of the options of the present invention lend themselves to very high density packaging.

Figure 65:
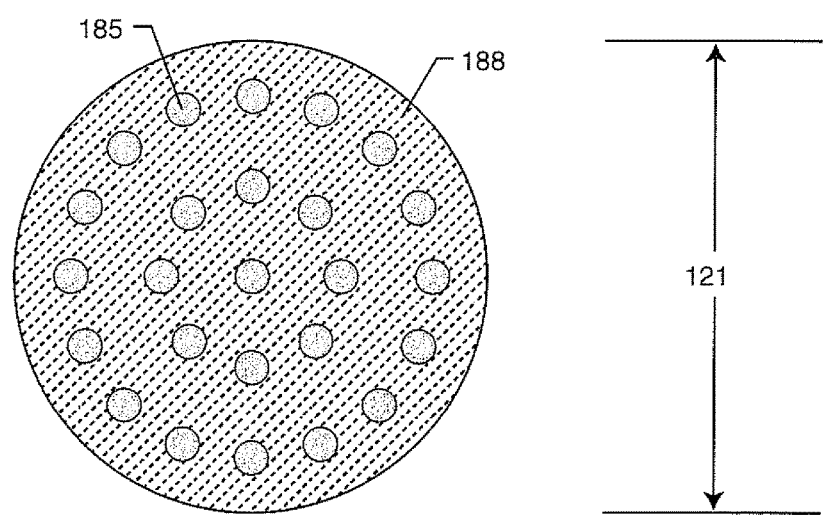
FIG. 65 is taken from prior art FIG. 19D of the '659 patent indicating that the alumina insulator of FIG. 64 can be round instead of rectangular.

FIG. 65 is taken from prior art FIG. 19D of the '659 patent indicating that the alumina insulator 188 of FIG. 64 can be round instead of rectangular. It will be known to one skilled in the art from this teaching that round and rectangular are not limiting in that any shape may be utilized to achieve a desired structure.

Referring back to FIGS. 64 and 65, it will be appreciated that the end view 185 of the CRMC layer, can be modified to incorporate any of the options as previously disclosed.

Figure 66:
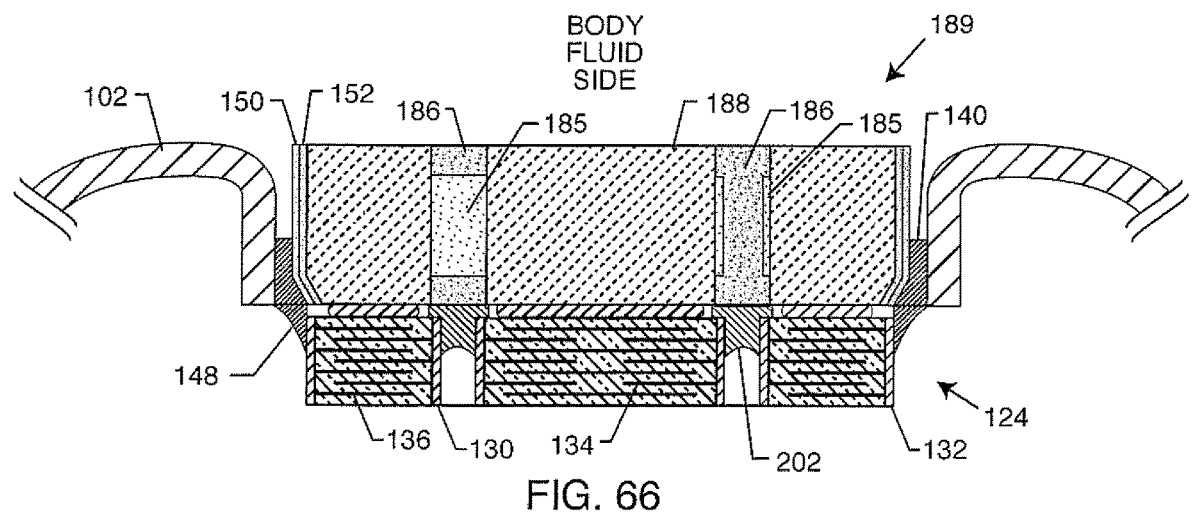
FIG. 66 is taken from prior art FIG. 22A of the '659 patent and illustrates that the present invention does not require a ferrule.

FIG. 66 is taken from prior art FIG. 22A of the '659 patent and illustrates that the present invention does not require a ferrule 122. In this case the insulator 188 is brazed 140 to an opening in the AIMD housing 102. Referring once again to FIG. 66, one can see that on the left hand side, the filled via comprises a CRMC 185 with platinum end caps 186, which is consistent with Option 1A of the present invention, as previously shown in FIG. 30. The right hand via hole, illustrated in FIG. 66, illustrates Option 4 of the present invention, as previously illustrated in FIG. 53. Referring once again to FIG. 66, one can see that a feedthrough capacitor 124, which has been manufactured in a completely separate manufacturing process, has been surface mounted to the device side of insulator 188. Electrical attachments 202 attach the feedthrough capacitor active electrodes to the platinum 186 of the via hole. Generally, electrical connection material 202 could be solder, including solder in the form of a ball grid array, solder paste or thermal-setting conductive adhesives (or even low temperature welds). The capacitor's ground electrodes are connected in parallel through the capacitor diameter or external perimeter metallization 132. There is an electrical connection 148 from the capacitor metallization 132 to at least a portion of the gold braze 140 of the AIMD housing 102 (or a ferrule 122 not shown). It will also be appreciated that the feedthrough capacitor can have one feedthrough hole (unipolar) or any other number of poles all the way to "n" poles. The feedthrough holes are metallized with metallization 130, which connects the active electrode plate sets. The active electrode plate sets overlap the ground plates thereby forming feedthrough capacitors.

Figure 67:
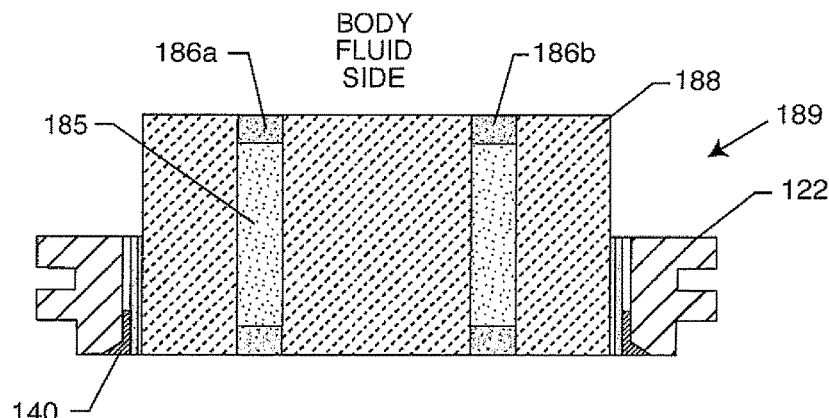
FIG. 67 illustrates that the feedthrough capacitor may be mounted to or adjacent the novel alumina ceramic insulator assembly of the present invention.
Figure 68:
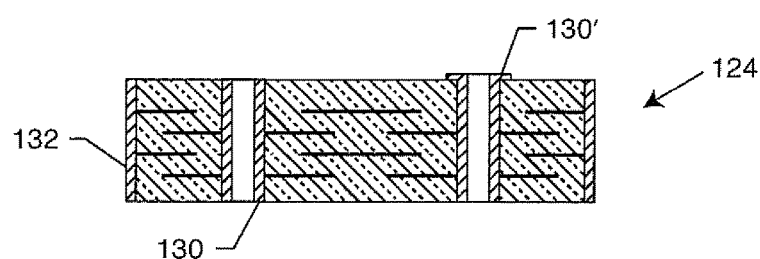
FIG. 68 illustrates that the feedthrough capacitor may be mounted to or adjacent the novel alumina ceramic insulator assembly of the present invention.

FIGS. 67 and 68 illustrate that the feedthrough capacitor 124 may be mounted to or adjacent the novel alumina ceramic insulator assembly 189 of the present invention. In general, when referring to FIGS. 67 through 74, the hermetic feedthrough assembly 189 can be built with any of the Options 1 through 6 of the present invention.

Figure 69:
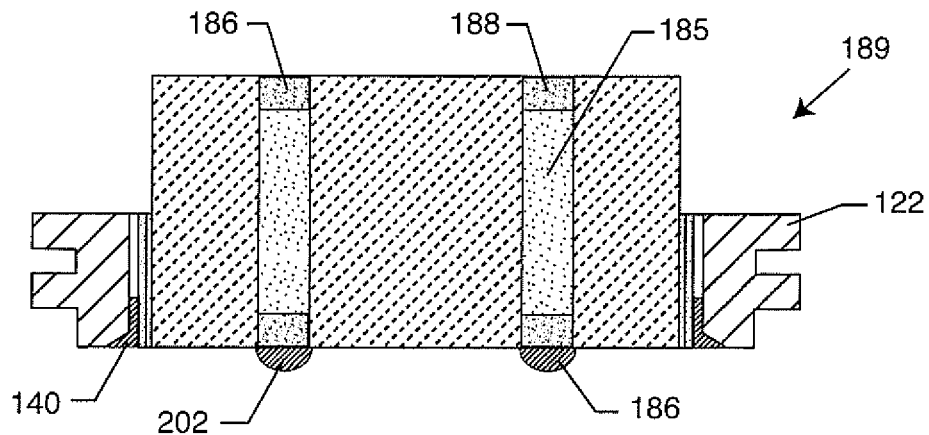
FIG. 69 illustrates that ball grid arrays can be used for mounting a feedthrough capacitor.
Figure 70:
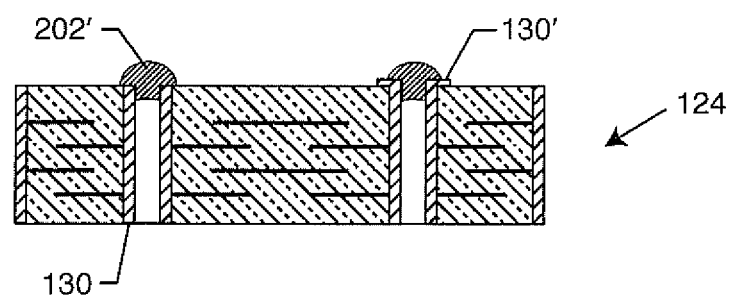
FIG. 70 illustrates that ball grid arrays can be used for mounting a feedthrough capacitor.
Figure 71:
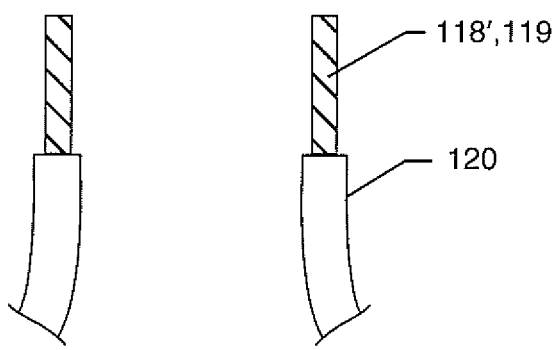
FIG. 71 illustrates that ball grid arrays can be used for mounting a feedthrough capacitor.

FIGS. 69, 70 and 71 illustrate that ball grid arrays 202 or 202' can be used for mounting a feedthrough capacitor 124. It is contemplated that the solder bumps may be applied to the insulator, to the capacitor, or to both.

Figure 72:
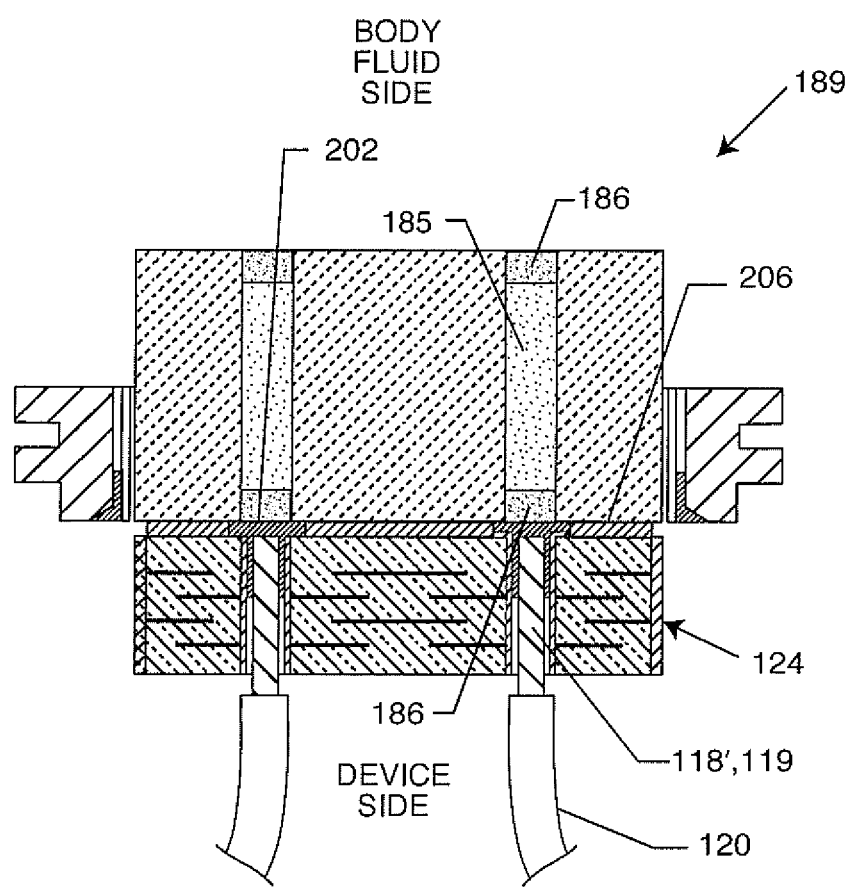
FIG. 72 illustrates the feedthrough capacitor after the ball grid array has been flowed and the feedthrough capacitor has therefore been soldered to the pure platinum end of the present invention.

FIG. 72 illustrates the feedthrough capacitor 124 after the ball grid array 202 has been flowed and the feedthrough capacitor has therefore been soldered to the pure platinum end 186 of the present invention.

Figure 73:
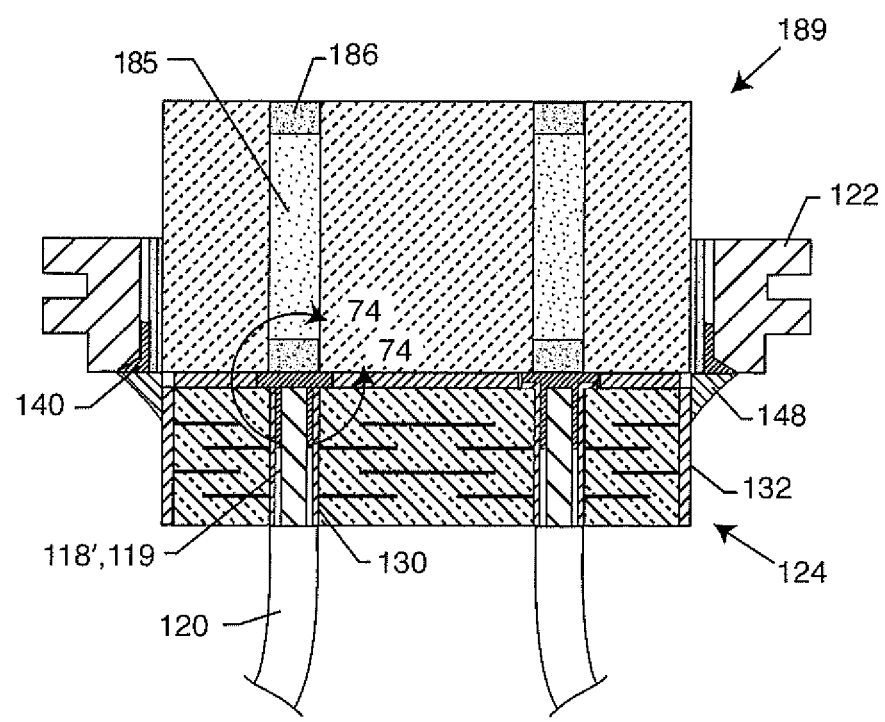
FIG. 73 illustrates that the conventional feedthrough capacitor must have an electrical connection from its outer diameter metallization to the ferrule.

FIG. 73 illustrates that the conventional feedthrough capacitor 124 must have an electrical connection 148 from its outside diameter metallization 132 to the ferrule 122.

FIG. 74 illustrates section 74-74 from FIG. 73 showing how the ball grid array solder 202 wets directly to the pure platinum fill 186.

Figure 75:
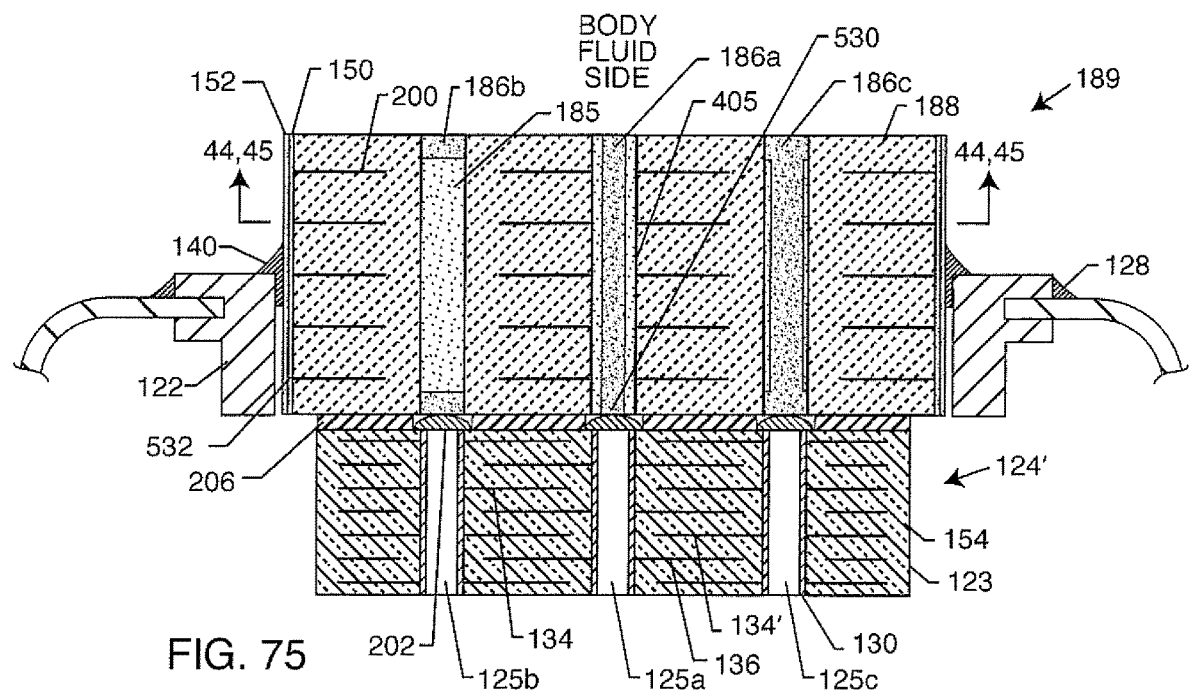
FIG. 75 illustrates an alternative embodiment of the present invention.
Figure 76:
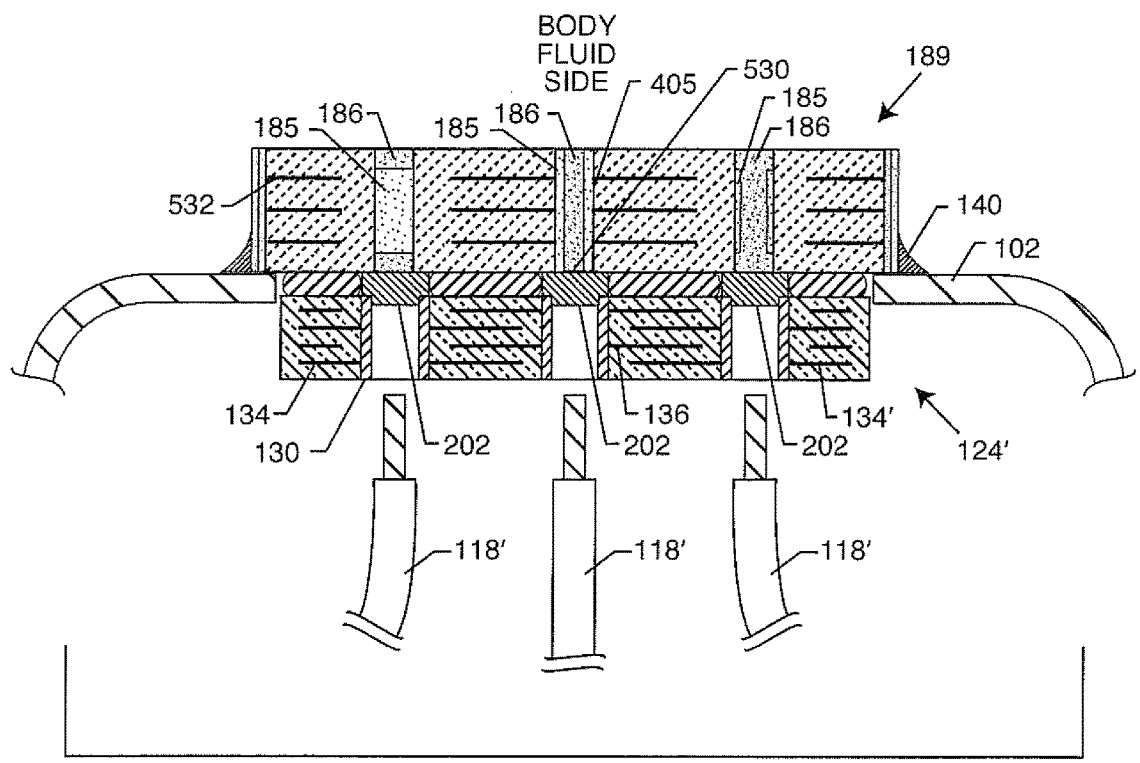
FIG. 76 illustrates an alternative embodiment of the present invention.

FIGS. 75 and 76 illustrate alternative embodiments of the present invention. Referring once again to FIG. 75, one can see that the left hand filled via represents Option 1 of the present invention, as previously illustrated in FIG. 30. The middle via hole illustrates Option 2, of the present invention, as previously illustrated in FIG. 32. The right hand via hole of FIG. 75 illustrates Option 4 of the present invention, as previously illustrated in FIG. 53. FIG. 76 best illustrates how low cost leadwires 118' can be co-soldered through ball grid array 202 to the internally grounded feedthrough capacitor 124' and also to the pure platinum end 186 of the novel vias of the present invention in the hermetic seal insulator 188. Referring once again to FIGS. 75 and 76 herein, the feedthrough capacitor 124' is internally grounded, meaning there is no need for an outside diameter or perimeter electrical connection 148 to the ferrule 122. Internally grounded feedthrough capacitors are well known in the prior art, as previously described in FIGS. 11A, 11B and 11C.

Figure 77:
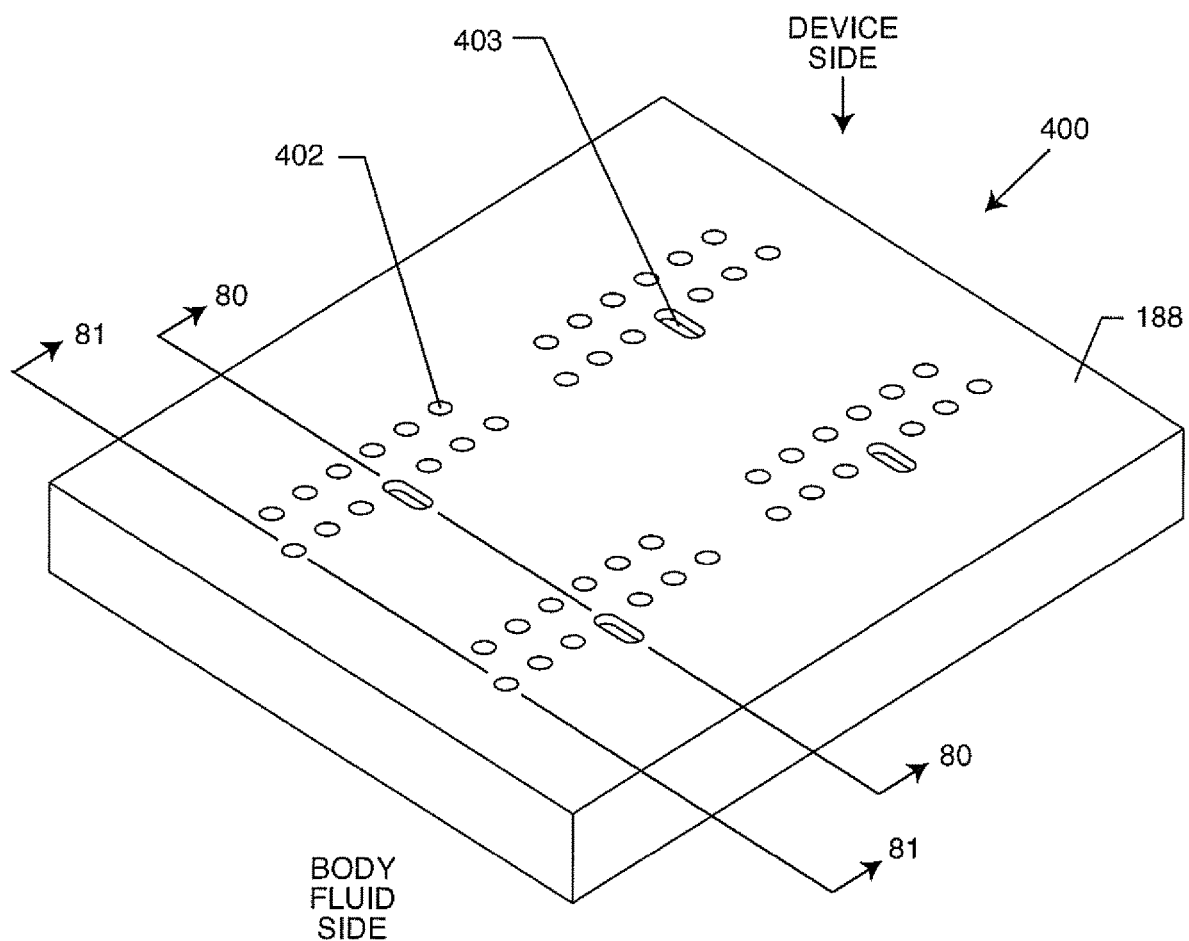
FIG. 77 shows a bar of ceramic material.

FIG. 77 shows a bar of ceramic material 400. In the green state, this bar is comprised principally of alumina ceramic and has a number of vehicles and binders making it relatively soft and pliable. In the green state, it is easily drilled. As will be seen, in this example, this will result in four ceramics used to produce a hermetic seal. It will be understood that high density bars may even include over a hundred hermetic seals. Referring back to FIG. 77, each of these have a ground slot 403 and 12 active pins. It will also be understood that any number of active pins or ground slots may be incorporated. In this case, the slots 403 do not go all the way through the thickness of the bar 400.

Figure 78:
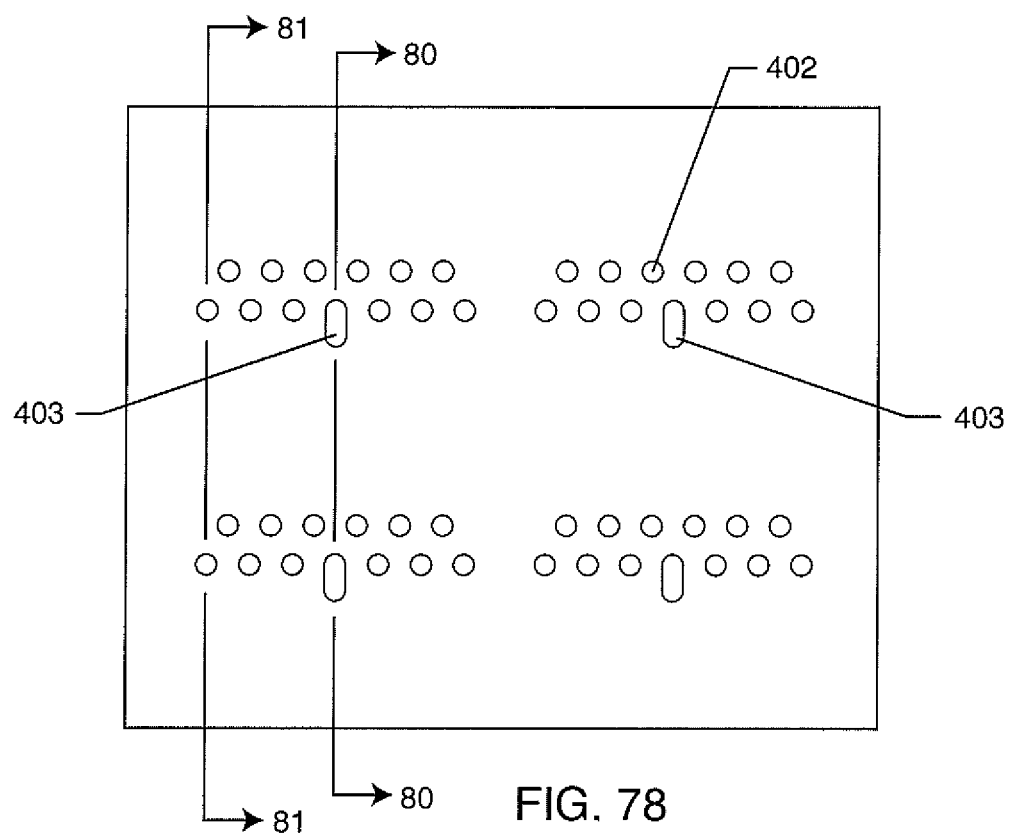
FIG. 78 illustrates the device side of the bar.

FIG. 78 illustrates the device side of the bar 400.

Figure 79:
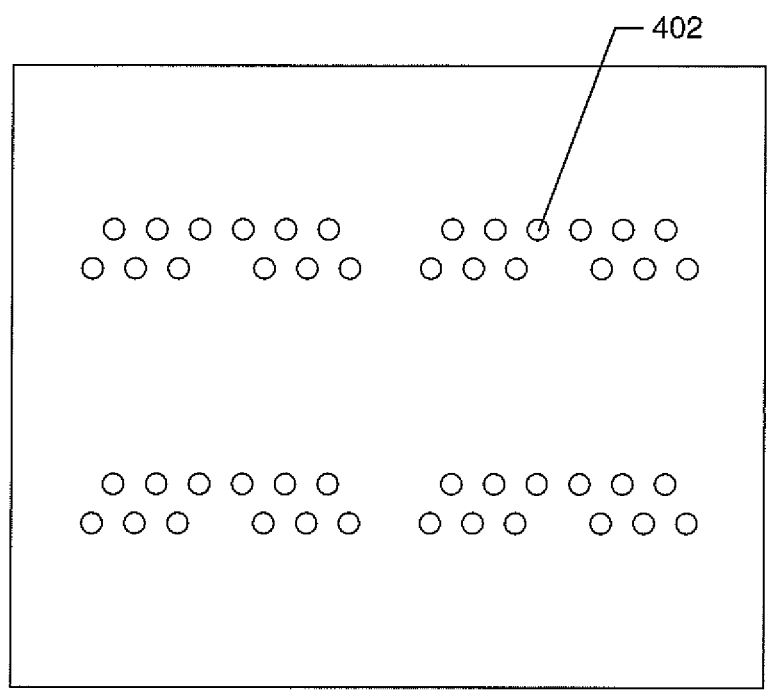
FIG. 79 illustrates the body fluid side of the bar.

FIG. 79 illustrates the body fluid side of the bar 400. Referring back to FIGS. 77 through 79, it will be appreciated that the holes 402 in the bar may also incorporate counterbores in accordance with any of the Options previously described in the present invention.

Figure 80:
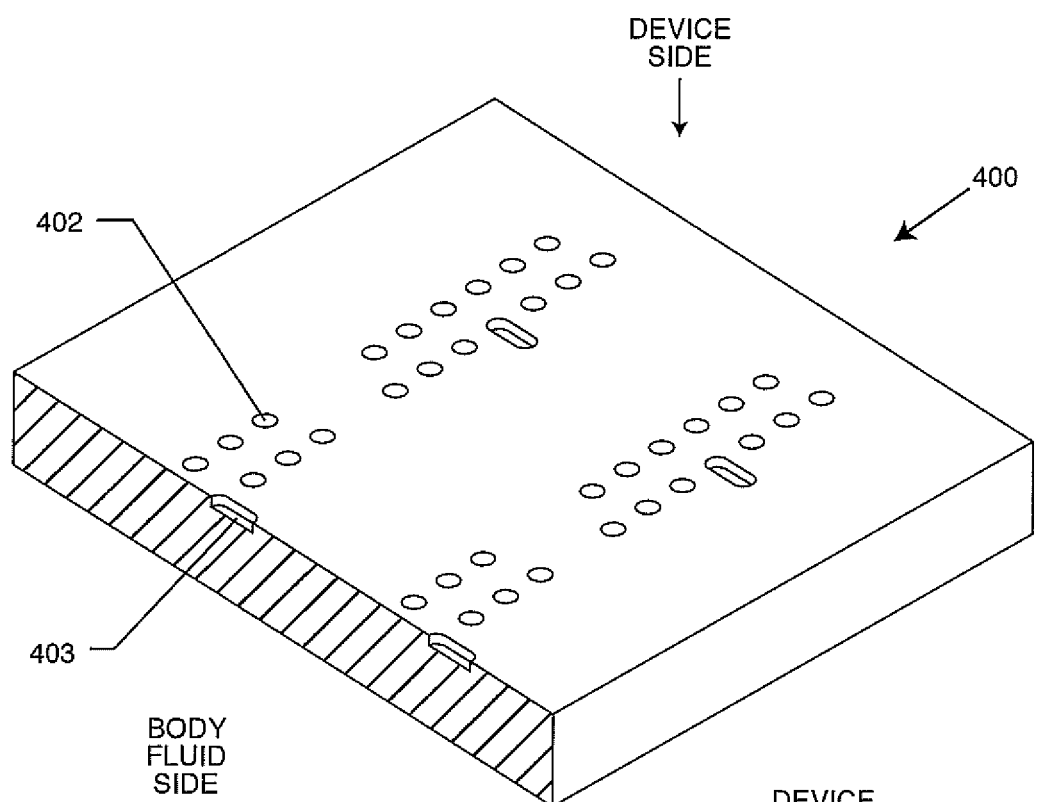
FIG. 80 is a sectional view taken from section 80-80 from FIGS. 77 and 78.

FIG. 80 is a sectional view taken from section 80-80 from FIGS. 77 and 78. As can be seen, the slot 403 only partially is disposed in the green ceramic bar 400 (in other words, it does not go all the way through).

Figure 81:
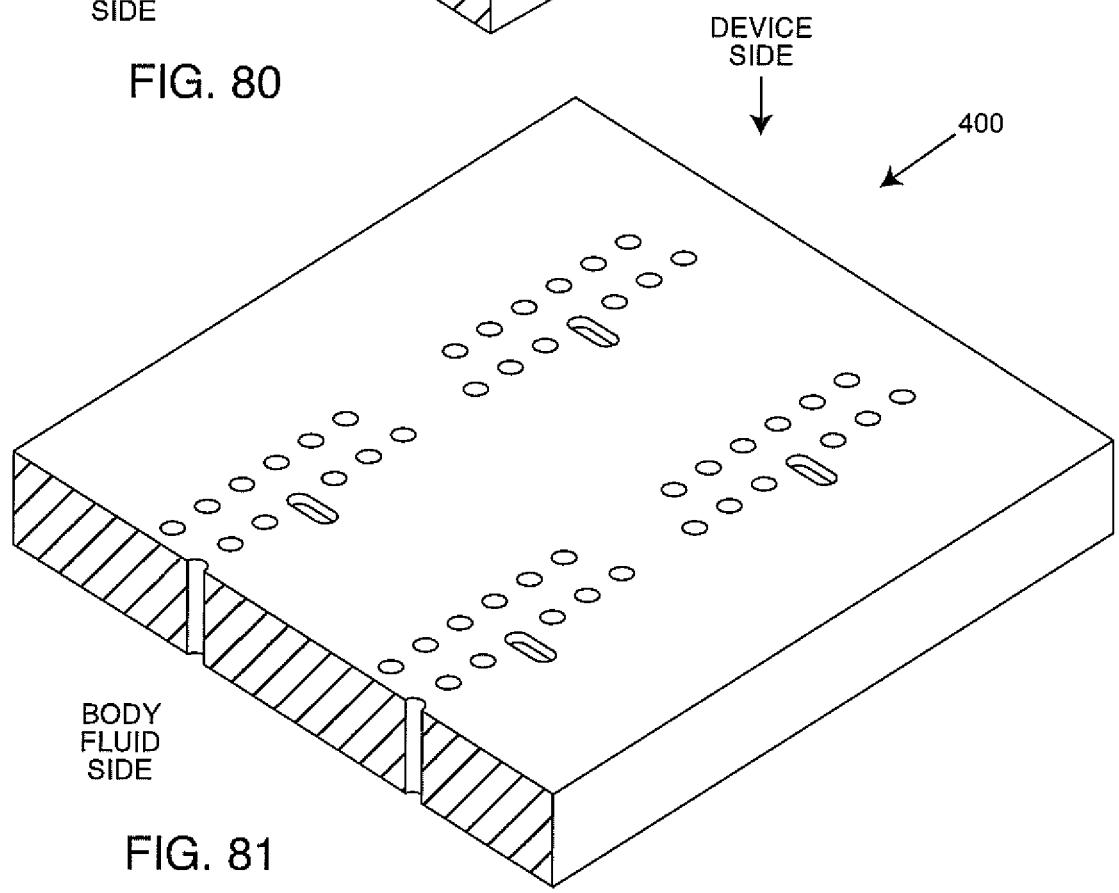
FIG. 81 is taken from FIGS. 77 and 78 along section 81-81.

FIG. 81 is taken from FIGS. 77 and 78 along section 81-81. This section is taken through two of the via holes 402. Again, it will be appreciated that one or more counterbores could be added in accordance with the present invention.

Figure 82:
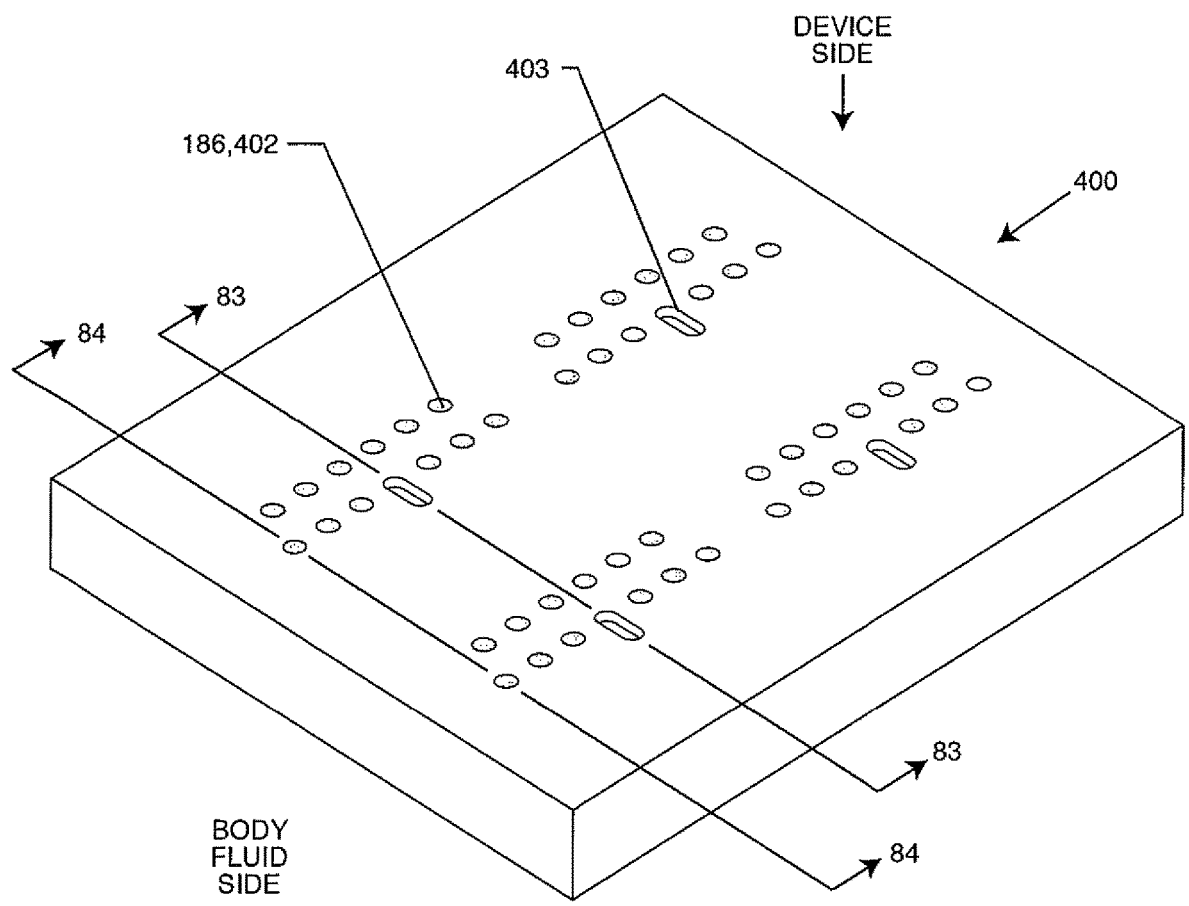
FIG. 82 shows that all of the via holes have been filled with a conductive deposit paste in accordance with the present invention.

FIG. 82 shows that all of the via holes 402 have been filled with a conductive deposit paste in accordance with the present invention. FIG. 82 illustrates Option 1; however, it will be appreciated that any of the other options described herein, may also be incorporated. Importantly, slots 403 do not penetrate through to the body fluid side and they are not filled with the conductive paste. One method of filling the via holes 402 with paste would be a vacuum pull, a pressure push, a squeegee fill or other equivalent process, which is well known in the prior art. In general, the conductive paste would comprise either a ceramic reinforced metal composite paste 185 and can be in combination, as previously described with a platinum paste 186. Again, any of the previously described options may be applied to FIG. 82.

Figure 83:
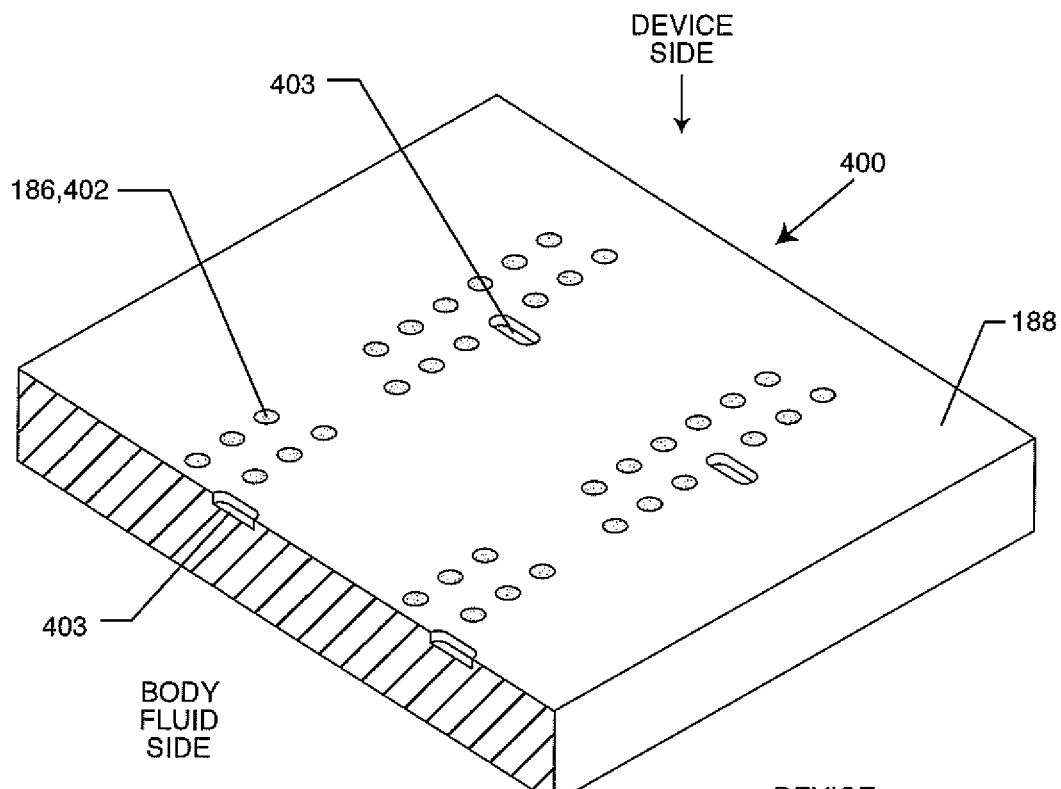
FIG. 83 is a sectional view taken generally along the line 83-83 from FIG. 82 and illustrates that the slots only penetrate a portion of the way into the green bar.

FIG. 83 is a sectional view taken generally along the line 83-83 from FIG. 82. FIG. 83 clearly illustrates that the slots 403 only penetrate a portion of the way into the green bar 400.

Figure 84:
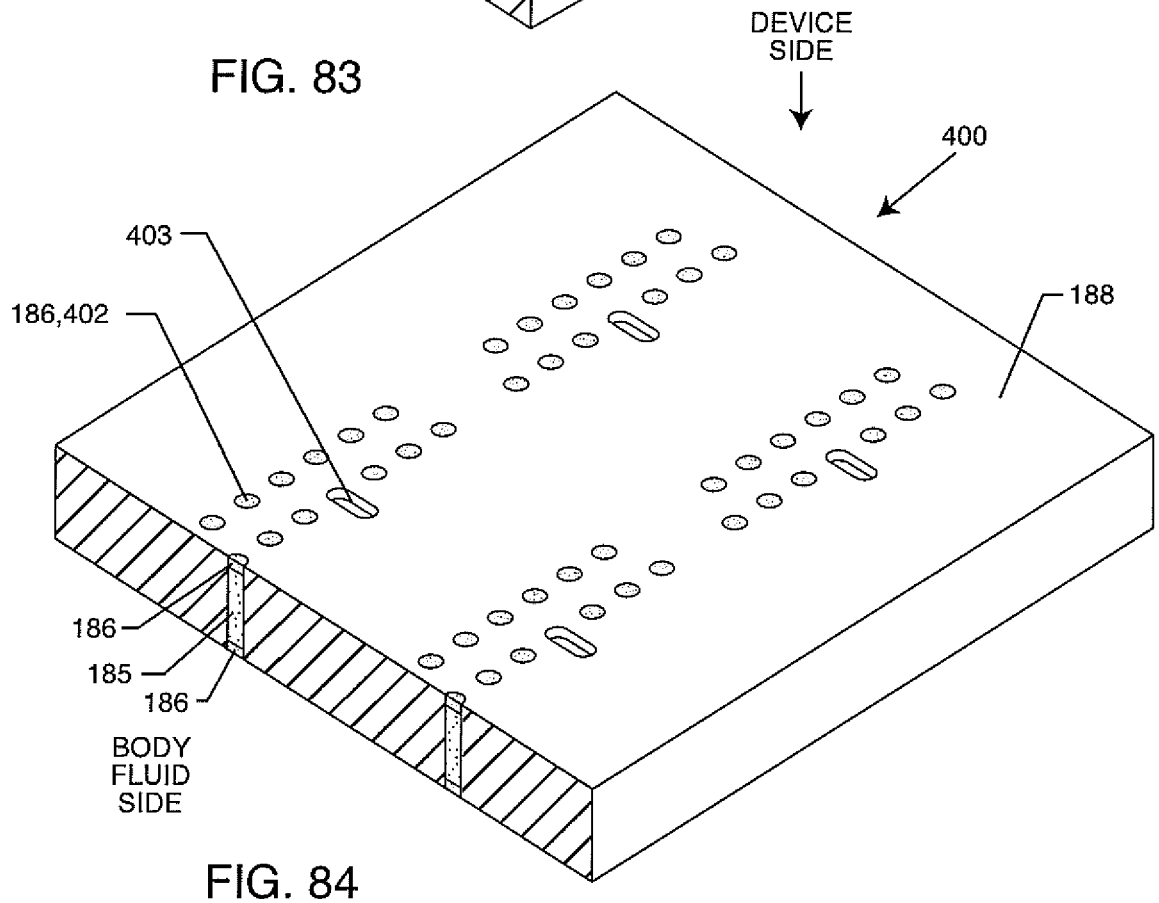
FIG. 84 is taken from section 84-84 from FIG. 82.

FIG. 84 is taken from section 84-84 from FIG. 82. The sectional view from FIG. 84 illustrates Option 1 of the present invention, but can be modified in accordance with any of the options of the present invention. Referring once again to FIG. 84, one can see that the pre-sintered CRMC paste 185 fills the via with pure platinum end caps 186. Again, this is in accordance with Option 1.

Figure 85:
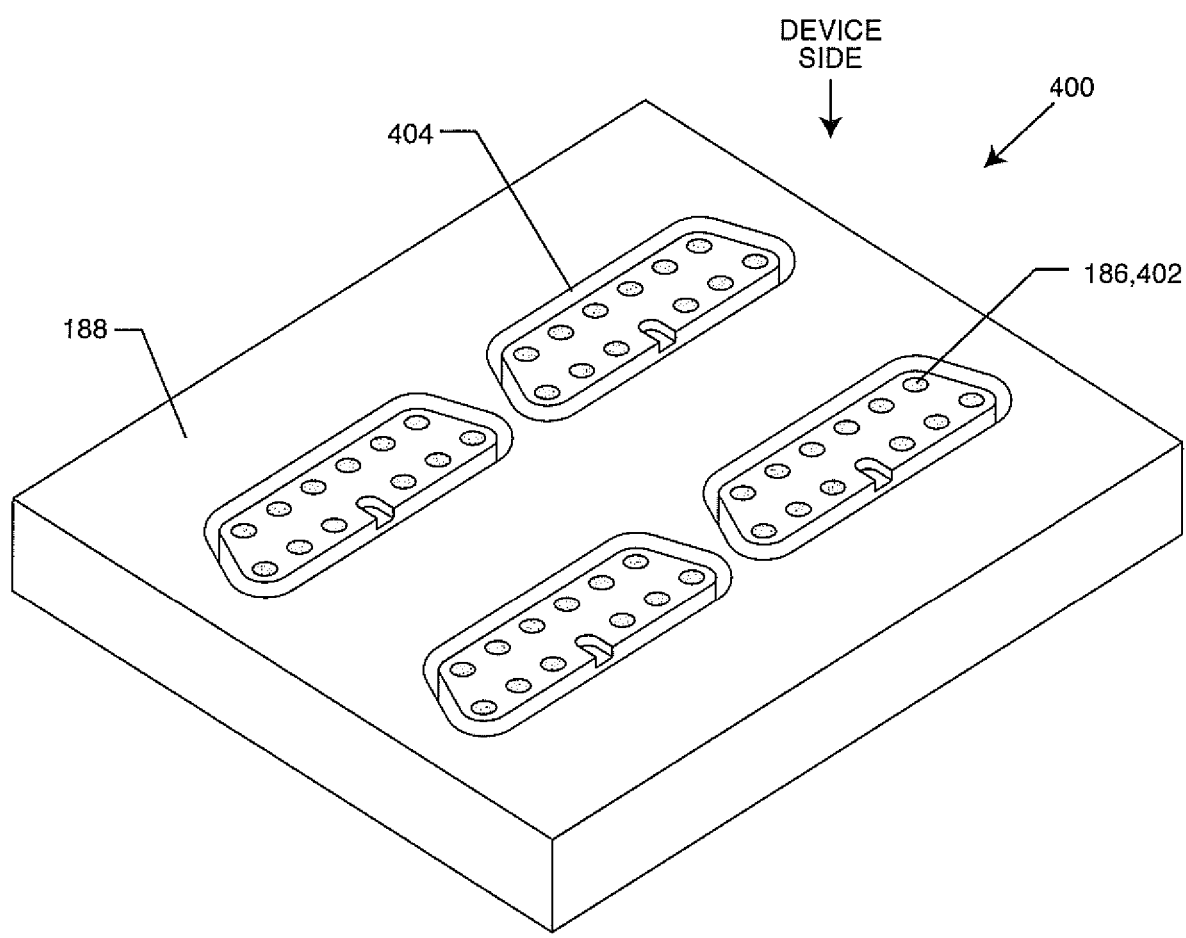
FIG. 85 illustrates the green ceramic bar previously described in FIGS. 77 through 84, illustrating how the four separate insulators have at least partially been milled out of the bar.

FIG. 85 illustrates the green ceramic bar 400 previously described in FIGS. 77 through 84, illustrating how the four separate insulators have at least partially been milled out of the bar. They can also be stamped (like a cookie cutter) or cut out using various machine tools. This step is known as separating the individual insulators from the bar 400.

Figure 86:
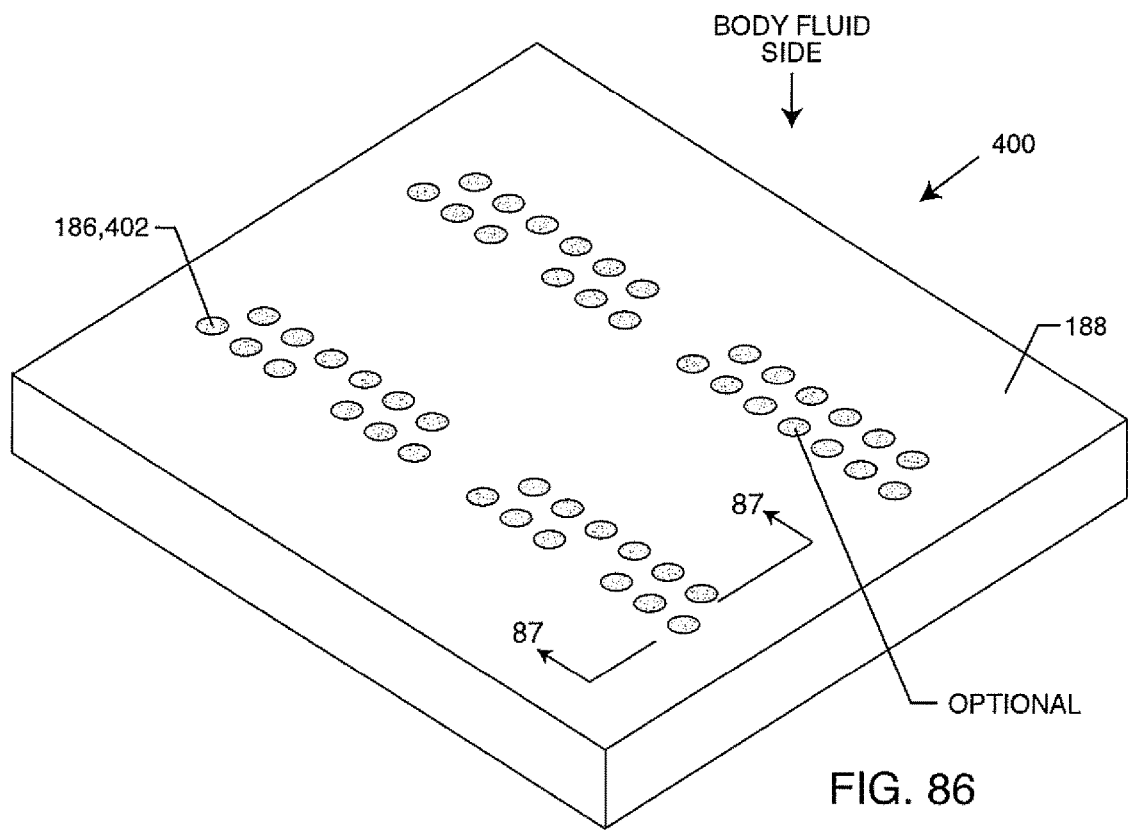
FIG. 86 illustrates the body fluid side as opposed to the device side as previously illustrated in FIG. 85 and illustrates that the individual insulators have not yet quite been cut out of the bar.

FIG. 86 illustrates the body fluid side as opposed to the device side as previously illustrated in FIG. 85. FIG. 86 illustrates that the individual insulators have not yet quite been cut out of the bar. This is best understood by referring to FIG. 87, which is a sectional view taken from section 87-87 of FIG. 86. Referring once again to FIG. 87, one can see that the individual insulators have almost been milled 404 all the way out of the bar. One common technique is to mill them almost all the way out of the bar and then simply break them loose from the bar.

Figure 87:
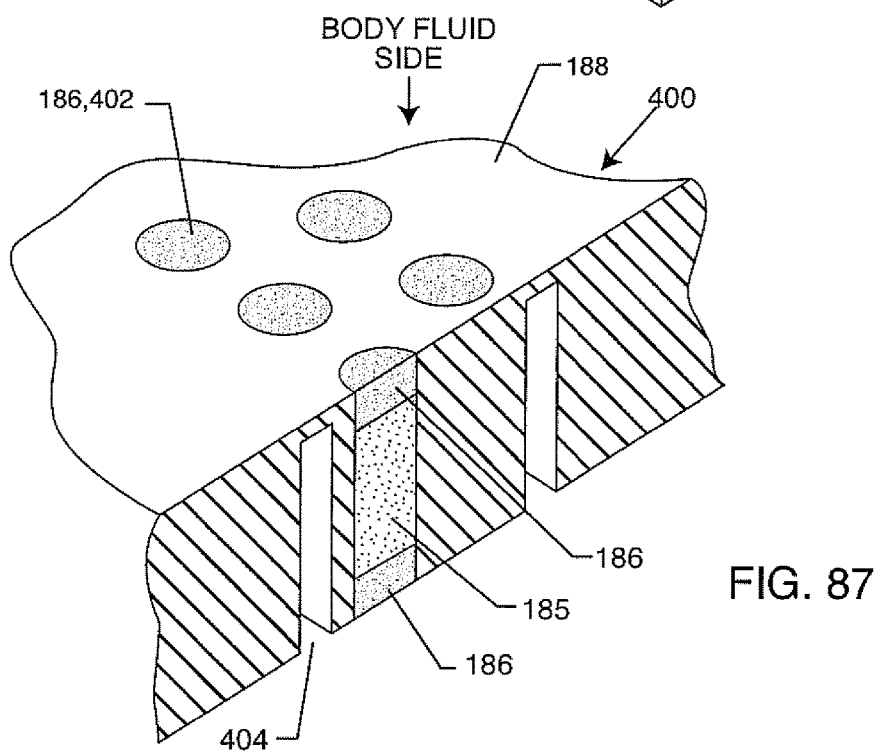
FIG. 87 is through section 87-87 from FIG. 86 showing the slot cut nearly all the way through the bar.

FIG. 87 is through section 87-87 from FIG. 86 showing the slot 404 cut nearly all the way through the bar 400.

Figure 88:
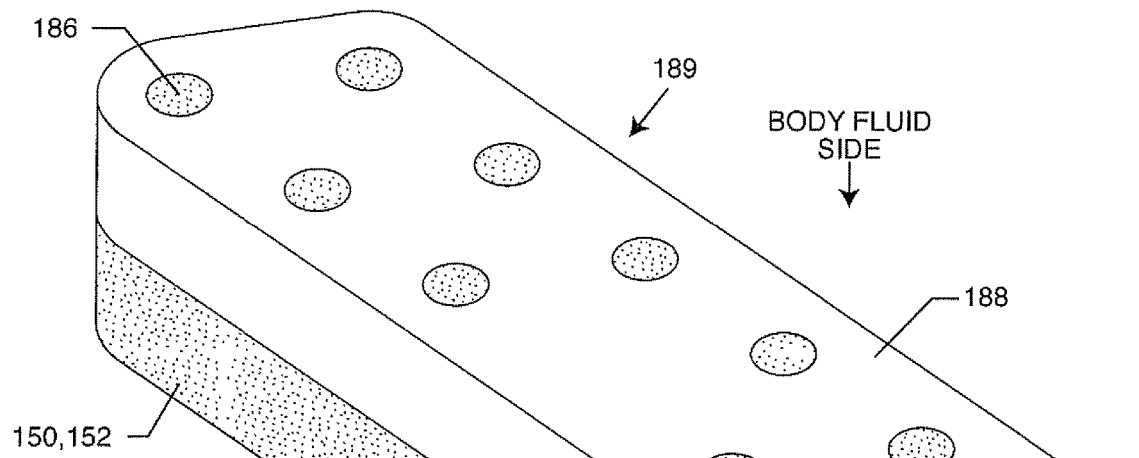
FIG. 88 illustrates the insulator after it is broken out of the bar in isometric view on the body fluid side.

FIG. 88 illustrates the insulator 188 after it is broken out of the bar 400 in isometric view on the body fluid side. Referring once again to FIG. 88, one will see that removal from the bar, the insulator 188 has been sintered at a high temperature to form a solid monolithic insulative body. Also shown are sputter layers, which include an adhesion layer 152 and a wetting layer 150 for acceptance to gold braze. As shown, the metallization is disposed approximately half way up the side of the insulator, but it will be appreciated that the metallization could extend all the way up the side or any portion of the side. In accordance with the present invention, the via holes are filled with platinum 186 in accordance with Option 1A of the present invention. It will be appreciated that the via holes could comprise any of the options of the present invention.

Figure 89:
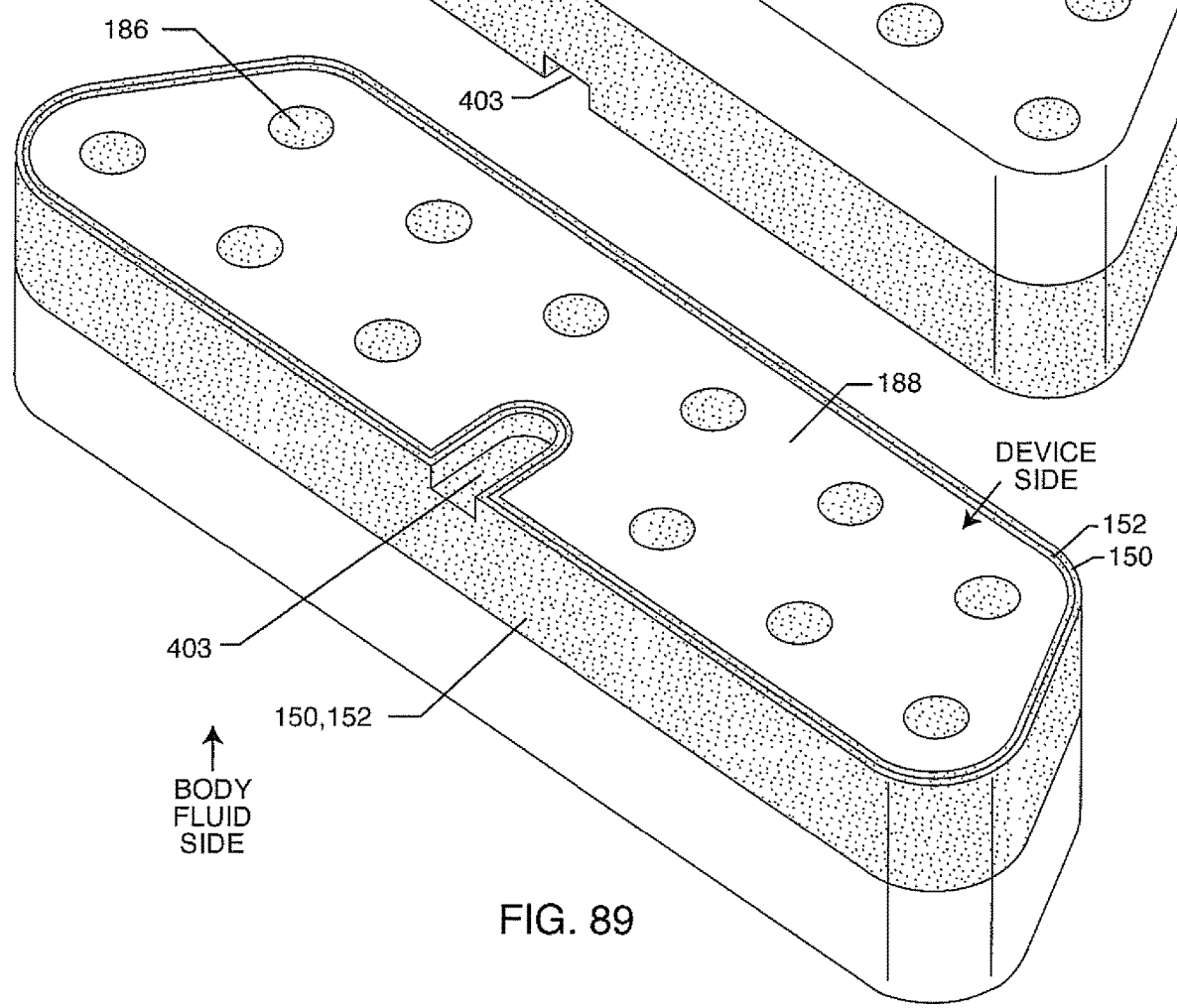
FIG. 89 is the same sintered insulator previously illustrated in FIG. 88, except that it has been inverted to show the device side instead of the body fluid side.

FIG. 89 is the same sintered insulator previously illustrated in FIG. 88, except that it has been inverted to show the device side instead of the body fluid side. Importantly, the sputter layer metallization 150, 152 extends into a novel slot 403, as shown. Again, in accordance with Option 1 of the present invention, the via hole fills are shown to be pure platinum 186, but again, these filled could be modified with any of the options of the present invention. As can be seen, the sputter layers, including the sputtering in slot 403, will accept a gold braze 140s as will be shown.

Figure 90:
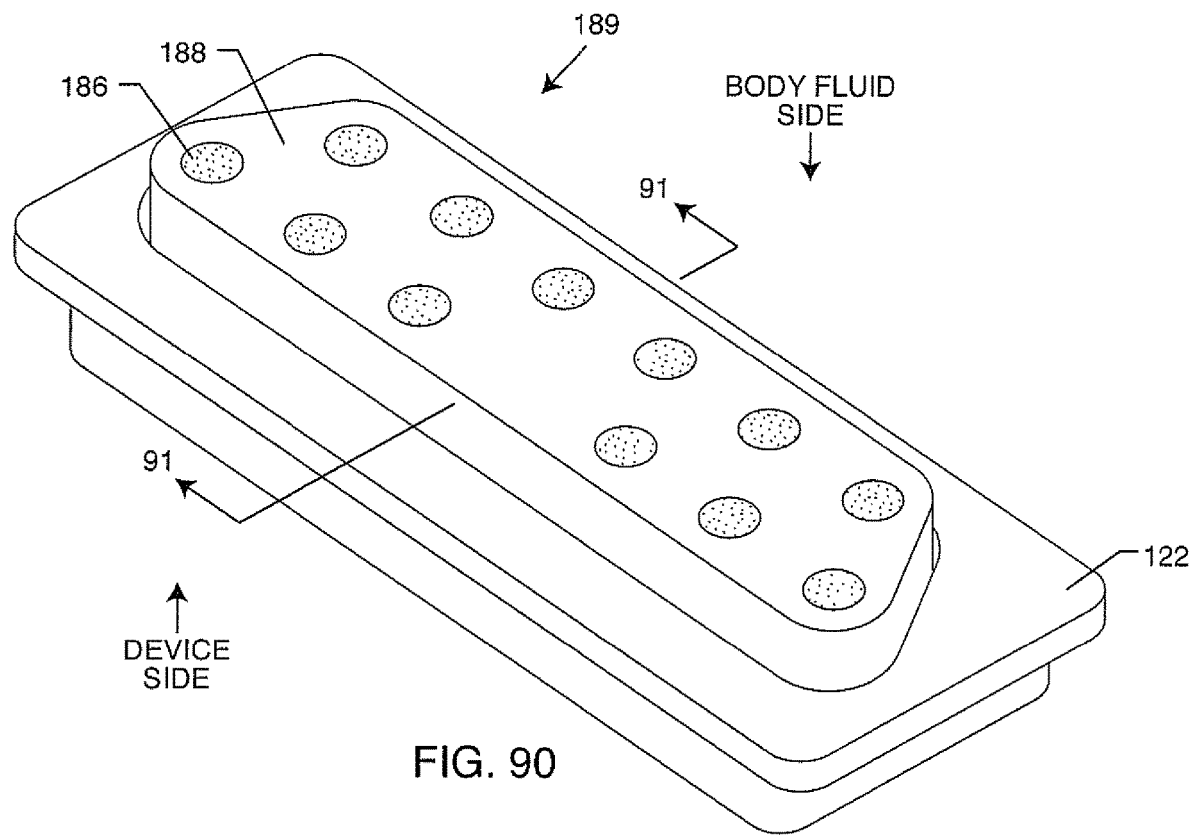
FIG. 90 illustrates the insulator of FIGS. 88 and 89 placed into an opening of a ferrule.

FIG. 90 illustrates the insulator of FIGS. 88 and 89 placed into an opening of a ferrule 122. As previously described, ferrule 122 is designed to be laser welded into an opening of an AIMD housing. The insulator, through its wetting sputter layer, has been gold brazed to the ferrule, but this is not doable in FIG. 90.

Figure 91:
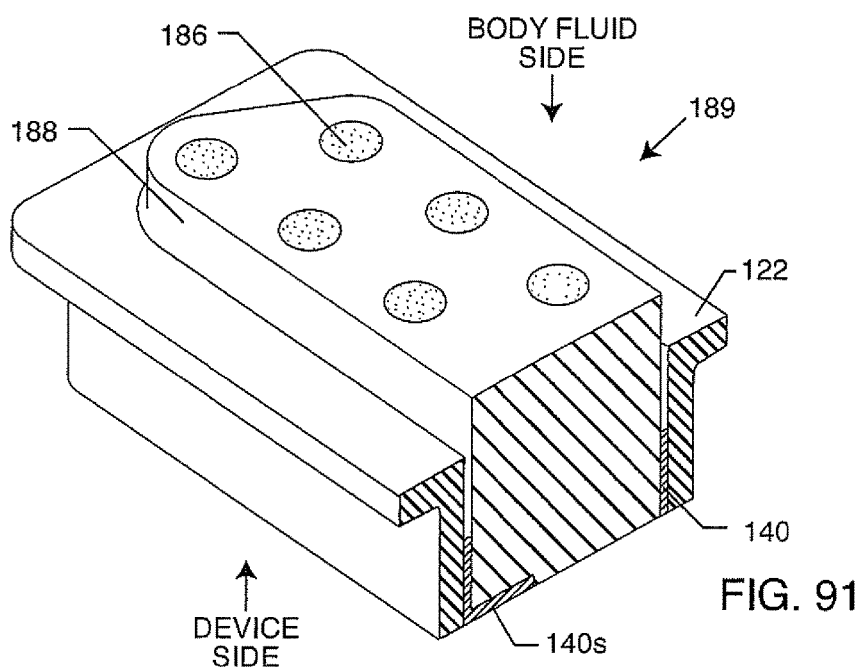
FIG. 91 is a cross-section 91-91 taken from FIG. 90.

FIG. 91 is a cross-section 91-91 taken from FIG. 90. Referring to the cross-section, one can see the gold braze 140s and 140. The metallization layers 150, 152 are not shown for simplicity, but are known to be present. Therefore, the gold braze 140 forms a strong mechanical and hermetic seal between the ferrule 122 and the insulator body 188. The gold braze also extends into slot 140s.

Figure 92:
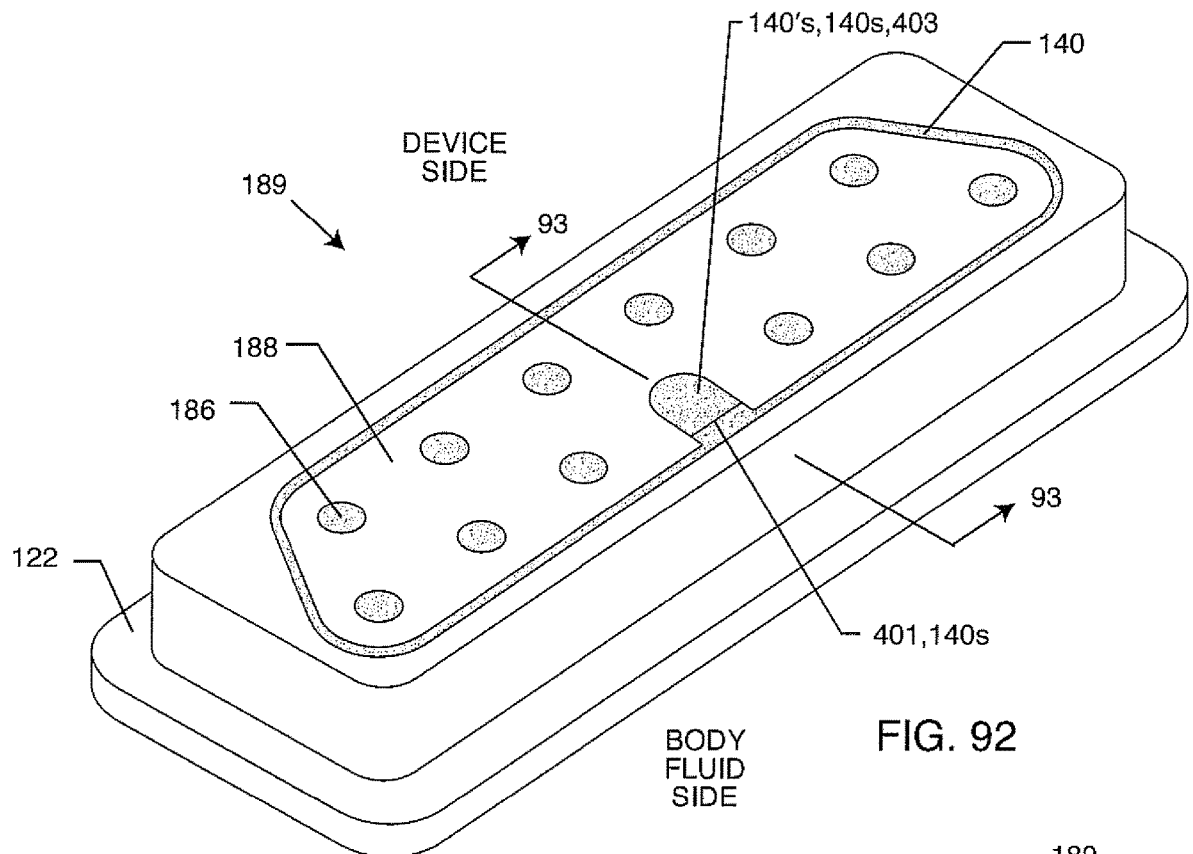
FIG. 92 illustrates the device side of the feedthrough terminal of FIG. 90, illustrating the gold braze.

FIG. 92 illustrates the device side of the feedthrough terminal of FIG. 90, illustrating the gold braze 140. The metallization layers 150, 152 on the alumina insulator 188 have been eliminated for clarity. It will be understood throughout the rest of these FIGS. that if the metallization layers are not shown, they will be present. In general, the surface of the alumina insulator 188 is flush with the top of the ferrule 122 as shown in FIG. 92. It will be appreciated that the insulator structure 188 could be recessed below the ferrule surface 122 or stand proud of it. It is preferred that the insulator be flushed to accommodate the mounting of a feedthrough capacitor 124' to be described later.

Referring once again to FIG. 92, one can see a demarcation line 401 separating gold braze 140 from the gold braze in the slot 140s. This demarcation line isn't necessarily a straight line, as shown, but does indicate that during the gold brazing operation, due to capillary action, the molten gold braze wants to flow out of the thin slot 403 and, instead, flow to the perimeter (or the circumference of round insulators not shown) gold braze 140. Actual experiments by the inventors have indicated that, in some cases, the gold braze and the slot 140s becomes very thin or has pulled away completely. Accordingly, in a secondary low temperature gold braze operation, an additional gold braze material 140's is added to adequately fill the gold braze slot 140's, 140s. Referring once again to FIG. 92, the secondary low temperature braze 140's does not need to be biocompatible since it is never exposed to body fluids. Accordingly, this braze material could consist of TiCuSil, CuSil or a number of other low temperature braze materials. In other words, this does not have to be of pure gold. Secondary low temperature gold braze 140's could comprise a substantially pure gold, such as a nano-gold material, which would reflow at a lower temperature. There are a number of other usable low temperature brazes (again, they do not need to be biocompatible).

Figure 93:
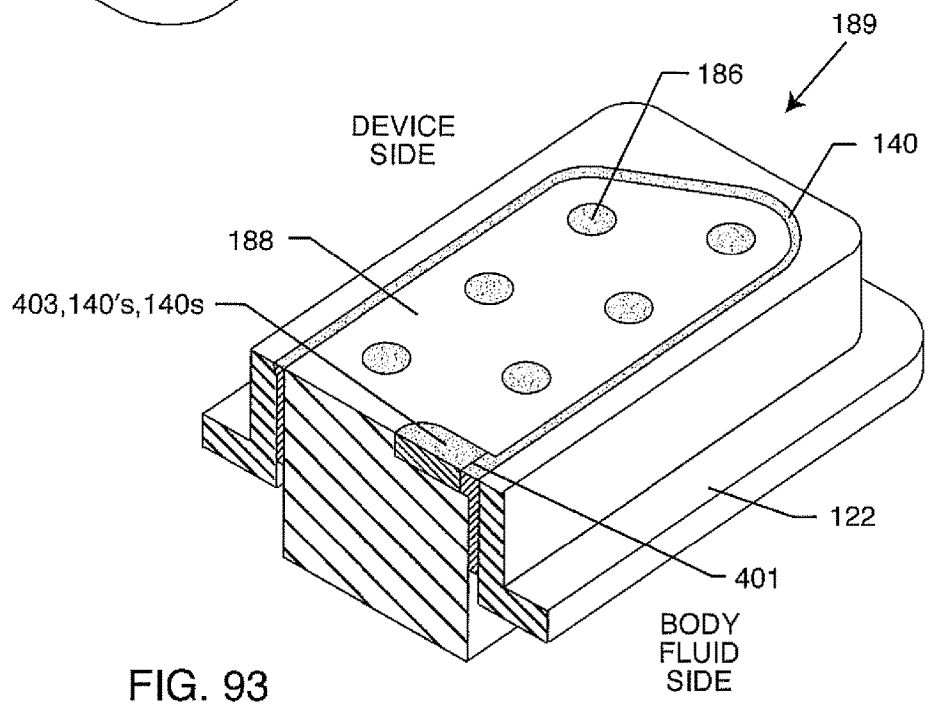
FIG. 93 is taken from section 93-93 from FIG. 92, which illustrates the slot with the gold braze in cross-section.

FIG. 93 is taken from section 93-93 from FIG. 92, which illustrates the slot 140's, 140s in cross-section. Again, demarcation line 401 is shown as a straight line for simplicity, but it could be a gradation of the gold braze 140s, which would be thinned in the slot, 140s or even a thin layer of the original gold braze 140s that's overlayed by the lower temperature braze 140's.

Figure 94:
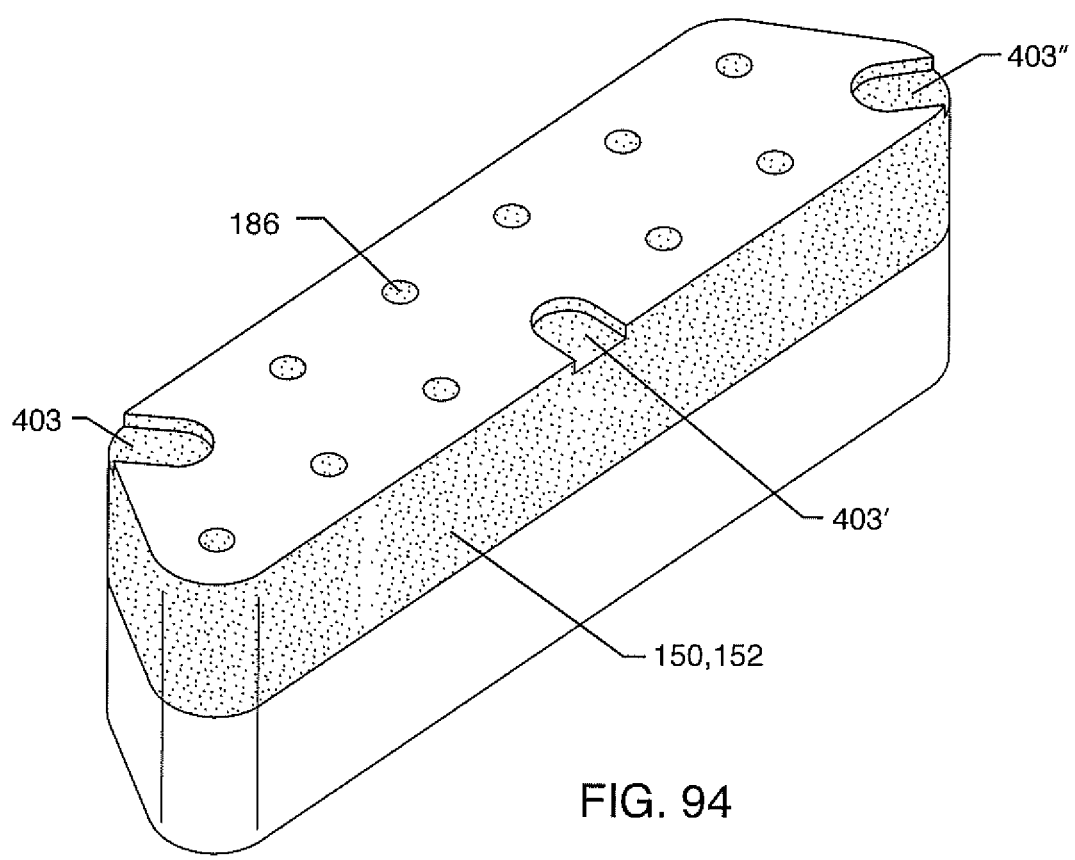
FIG. 94 is very similar to the insulator to FIG. 89 now with multiple novel slots.

FIG. 94 is very similar to the insulator to FIG. 89 with novel slot 403. In this case, there are three novel grounding slots 403, 403' and 403". It will be appreciated that this will allow for three grounding locations with gold braze 140s. Multiple grounding points are necessary as the active lead count goes up in order to provide a low impedance path across the internal ground electrode plates 134, 136 of the internally grounded feedthrough capacitor 124'. This is known as a multipoint grounding system and it ensures that each active pin of the filtered hermetic terminal will have a high insertion loss. Insertion loss is a measure of filter performance.

Figure 95:
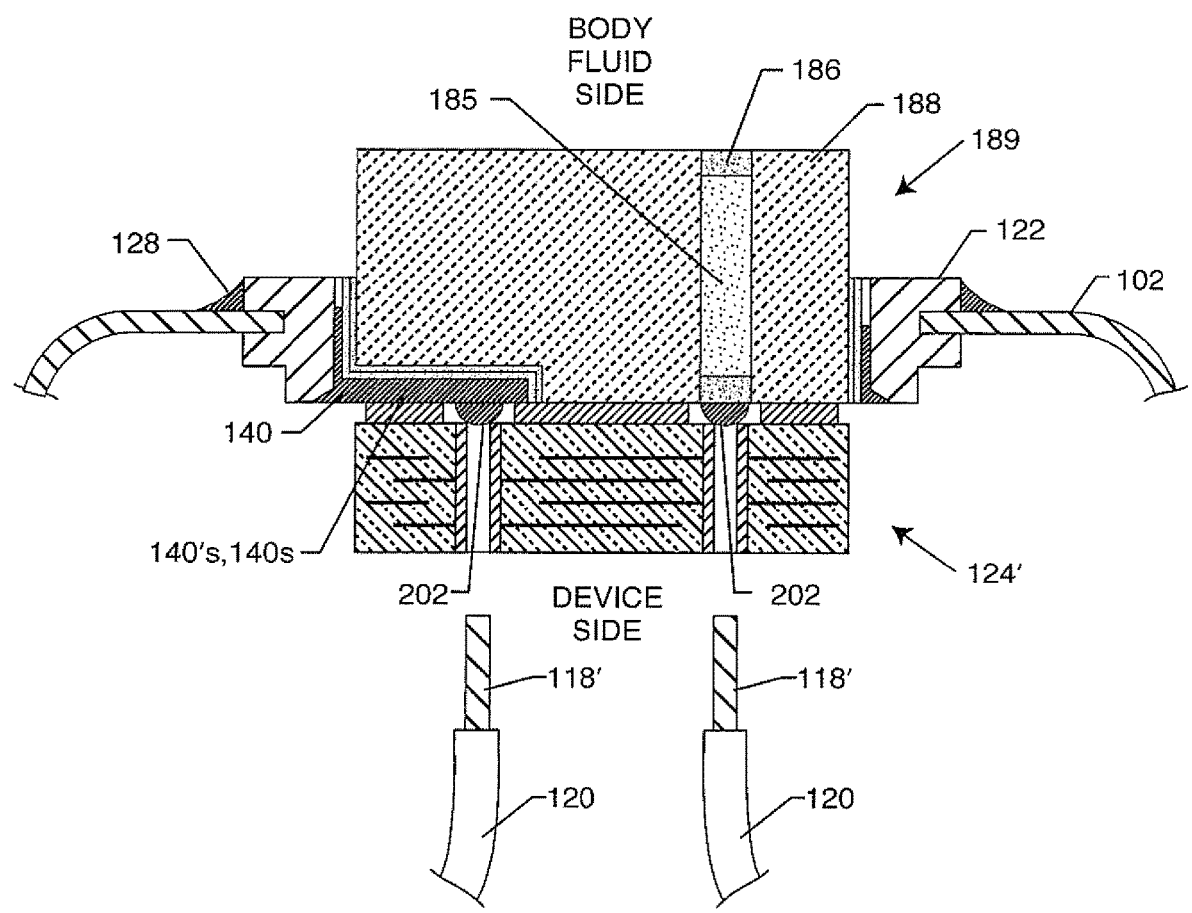
FIG. 95 is a sectional view showing how a gold braze fills the slots of FIGS. 88-94 and is connected to the ferrule.

FIG. 95 is a sectional view now showing how the slot of FIGS. 88-94 is filled with a gold braze. The gold braze electrically couples the ferrule 122 to the solder bump 202 which in turn is connected to the leadwire 118'. The internally grounded capacitor 124' is then able to dissipate electrical energy from its right-hand side lead 118' to the ferrule 122.

Figure 96:
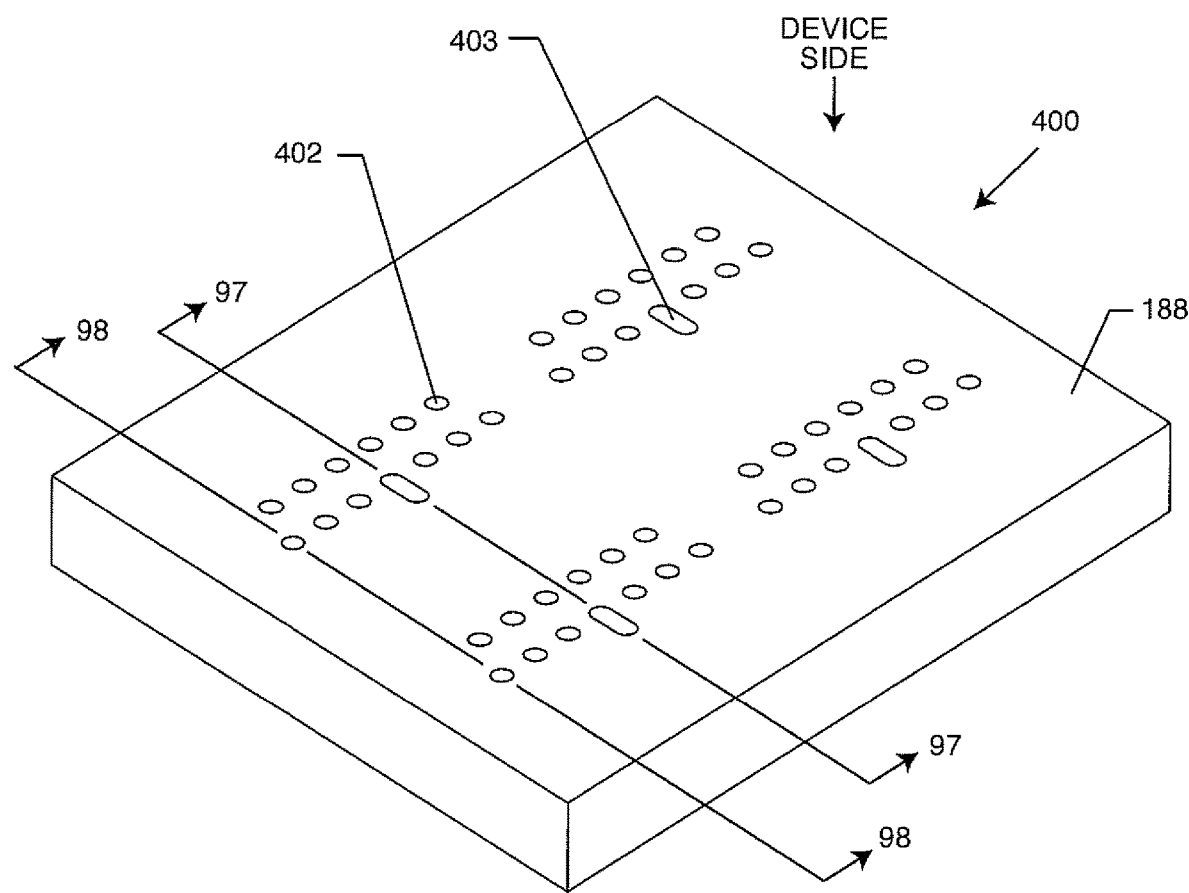
FIG. 96 is very similar to FIG. 77, except that the slots are deeper but do not penetrate all the way through the bar of the ceramic wafer.

FIG. 96 is very similar to FIG. 77, except that the slots 403 are deeper but do not penetrate all the way through the bar of the ceramic wafer 400, 188.

Figure 97:
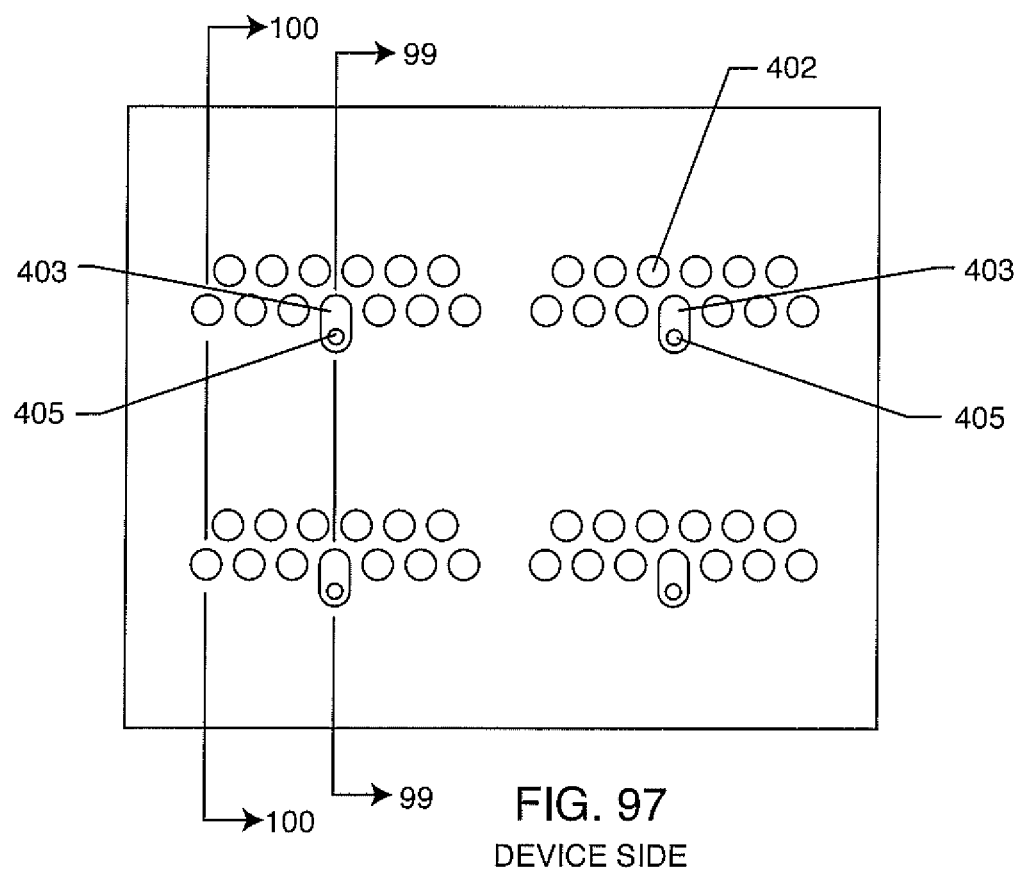
FIG. 97 is a top view of the device side of the ceramic bar of FIG. 96.

FIG. 97 is a top view of the device side of the ceramic bar 400 of FIG. 96. Referring once again to FIG. 97, one will see that the slot 403 also comprises a through-hole 405.

Figure 98:
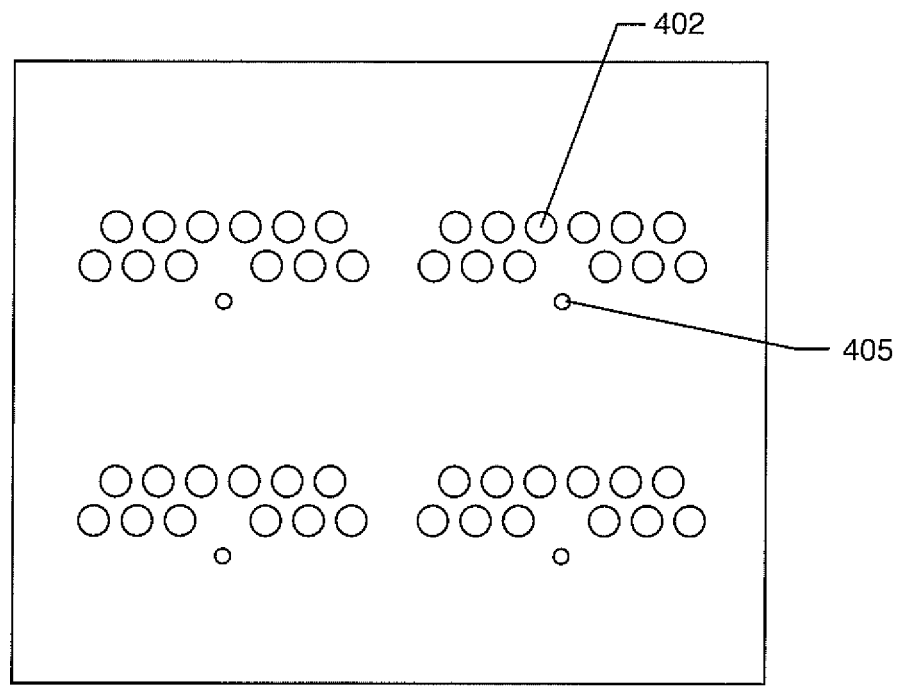
FIG. 98 is the body fluid side of the bar from FIG. 96.

FIG. 98 is the body fluid side of the bar from FIG. 96. It will be appreciated that studying FIGS. 97 and 98 indicate that the slot 403 does not go all the way through the bar 400, but the slot in addition to the through-hole 405 does penetrate all the way through. During the filling of the slot in the hole with CRMC and then subsequent platinum fills, in general requires a vacuum pull or a pressing of CRMC paste. The through-hole 405 is very important so that a pressure bubble is not formed and material can escape and completely fill the interior surfaces comprising 403, 405. If hole 405 didn't go all the way through the bar and you tried to brush a ceramic paste in from the device side, an air bubble would form, thereby preventing a full fill of the material.

Figure 99:
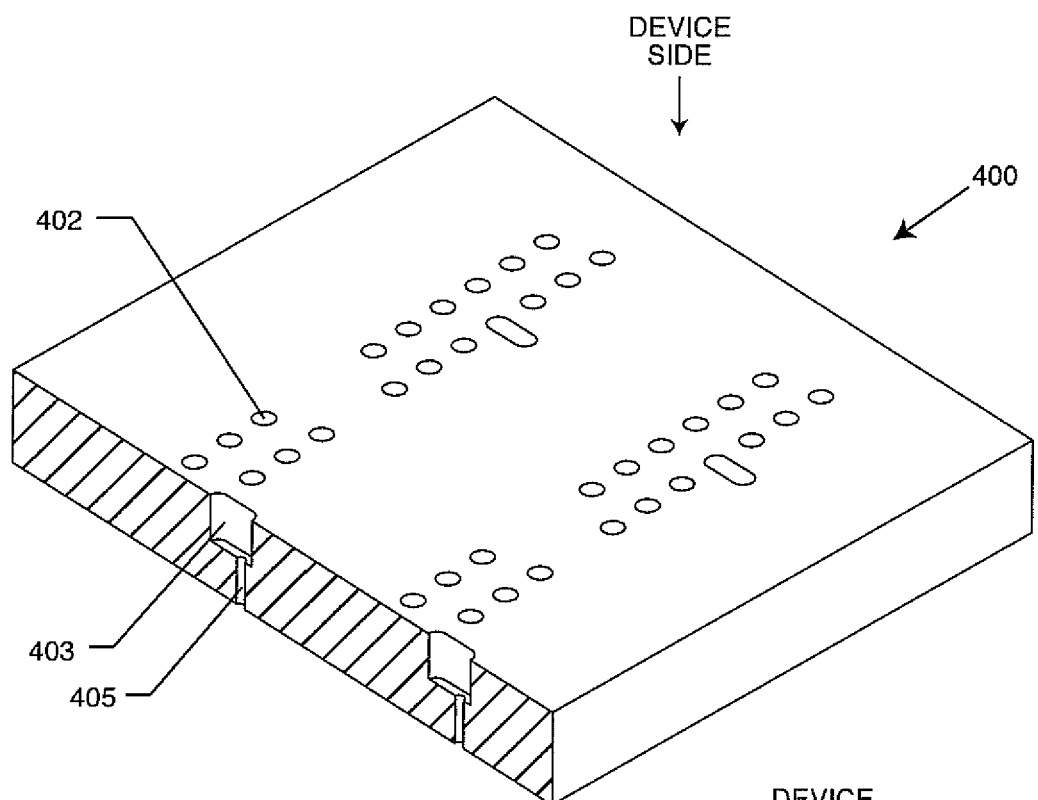
FIG. 99 is taken from section 99-99 from FIG. 97 showing the slot and the pull hole shown in cross-section.

FIG. 99 is taken from section 99-99 from FIG. 97 showing the slot 403 and the pull hole 405 shown in cross-section. Referring once again to FIG. 99, the individual insulators, when they are cut out of the bar, will be cut in a way that the through-hole 405 is eliminated and discarded. This is also better understood in FIG. 97, where one can see the through-hole 405. When the individual insulators are cut out of the bar, as shown in FIGS. 107 and 109, again, it will be appreciated that the through-hole of 405 is eliminated and is not part of the final insulator structure.

Figure 100:
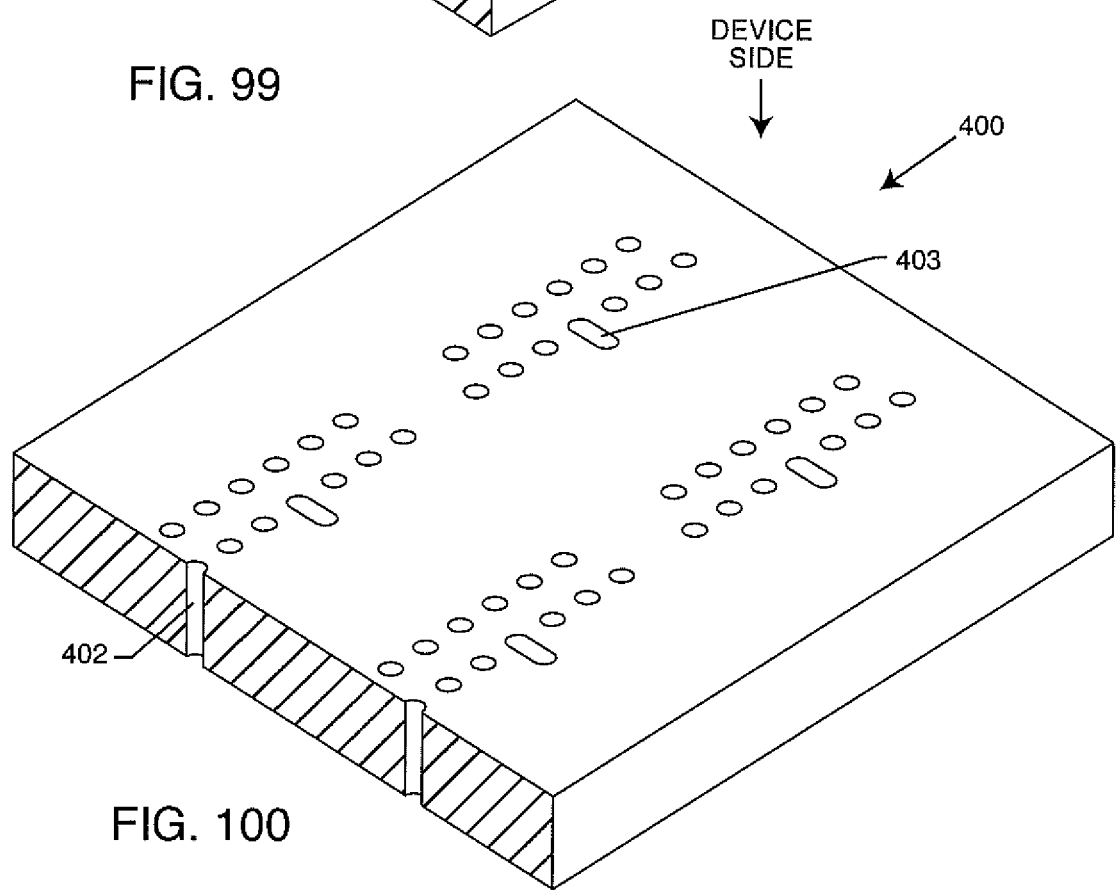
FIG. 100 is taken from section 100-100 from FIG. 97, showing one of the via holes.

FIG. 100 is taken from section 100-100 from FIG. 97, showing one of the via holes. It will be noted that the number of via holes 402 can vary anywhere from one via hole all the way to "n" via holes. As previously described, there could also be a number of ground slots 403, and relief holes 405.

Figure 101:
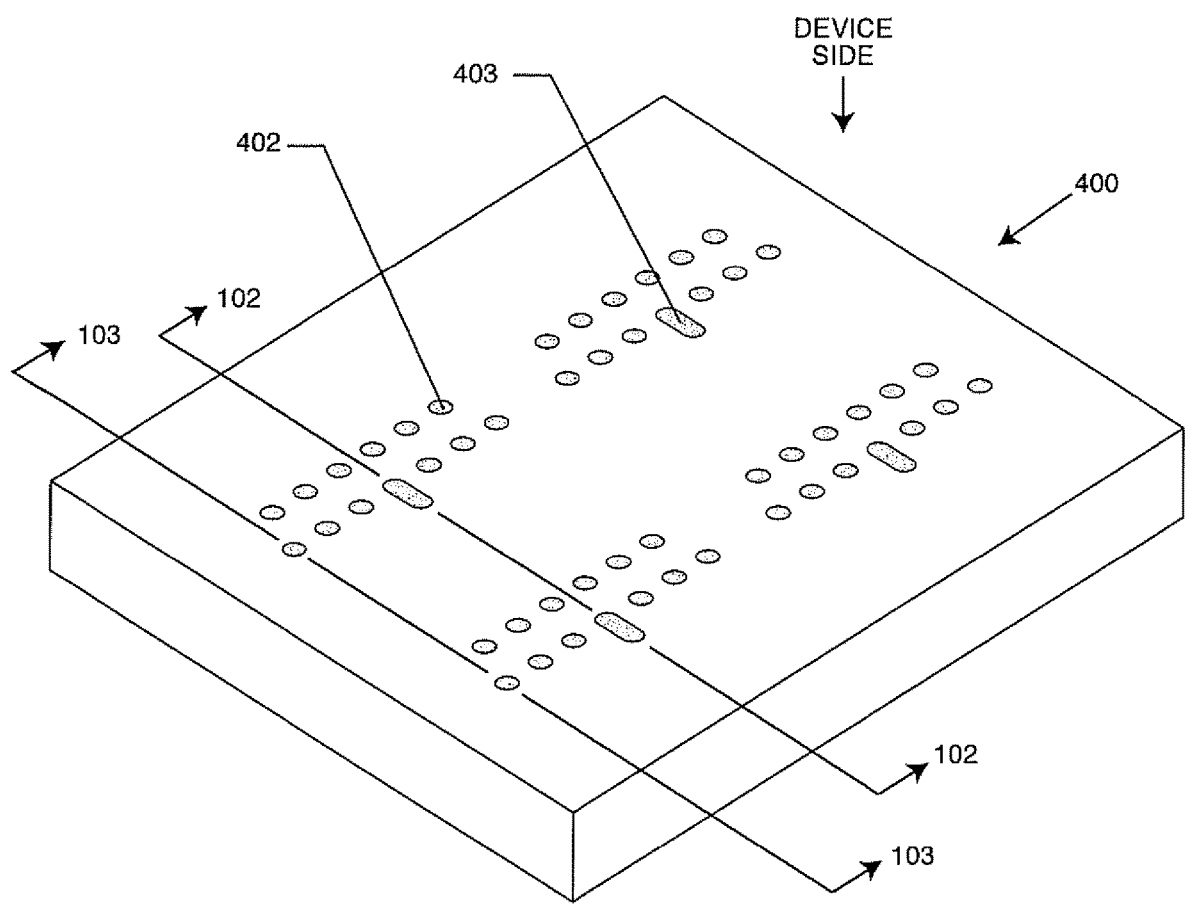
FIG. 101 illustrates the bar of FIG. 96 after holes and slots have been filled with a combination of paste and platinum, in accordance with any of the options of the present invention.

FIG. 101 illustrates the bar of FIG. 96 after holes 402 and slots 403 have been filled with a combination of paste and platinum, in accordance with any of the options of the present invention.

Figure 102:
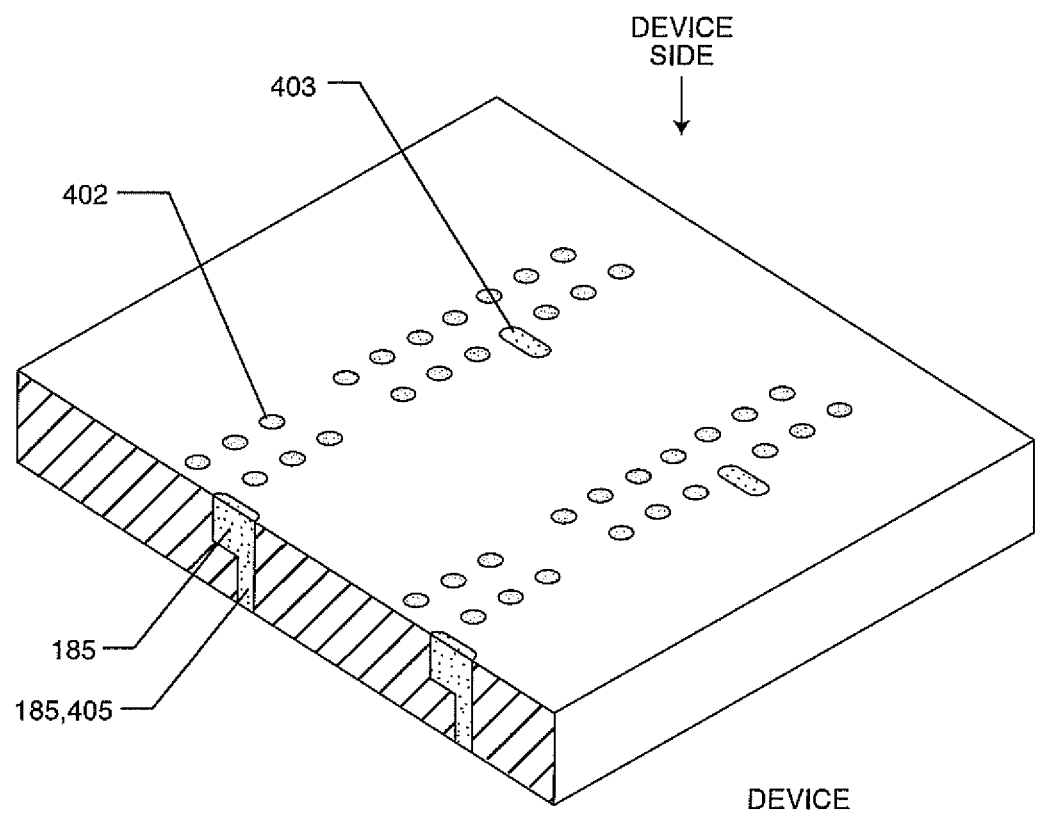
FIG. 102 is taken from section 102-102 from FIG. 101 illustrating the filled slot and filled pull through hole.

FIG. 102 is taken from section 102-102 from FIG. 101 illustrating the filled slot 403 and filled pull through hole 405. In this case, it will be noted that both the slot 403 and the through-hole 405 have been filled with CRMC material 185.

Figure 103:
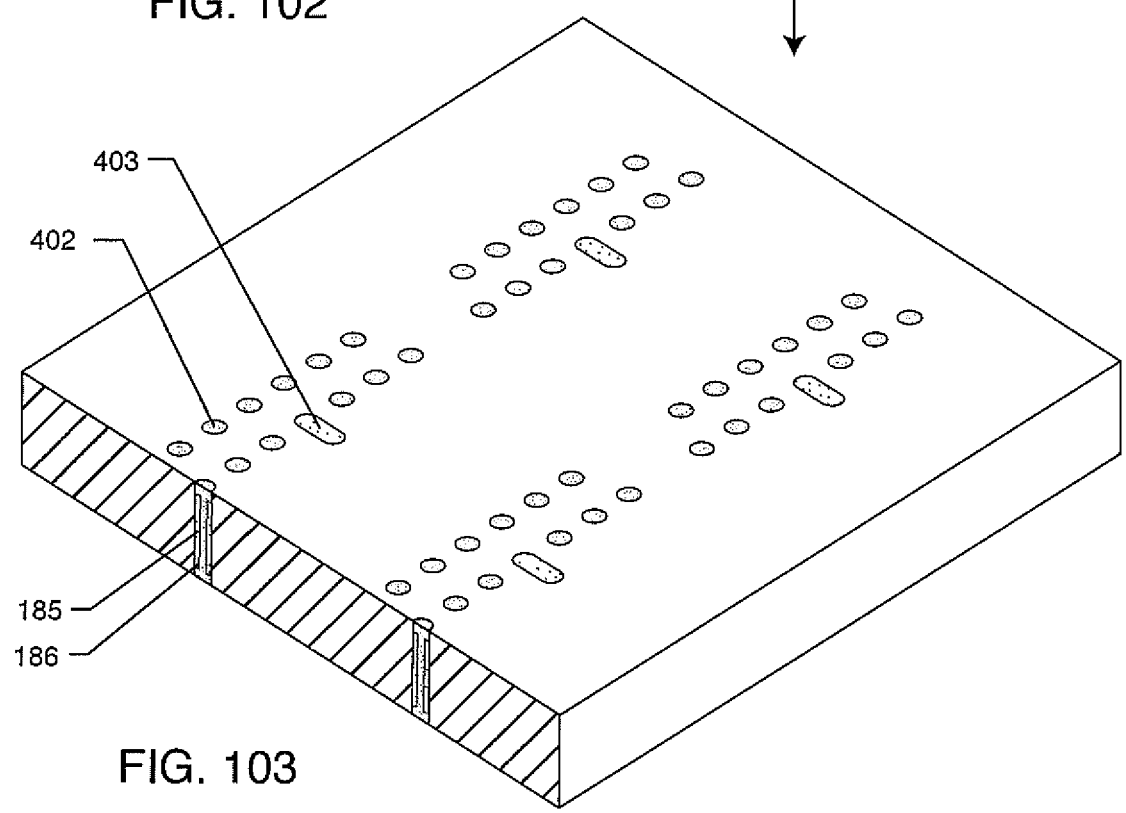
FIG. 103 is taken from section 103-103 from FIG. 101 illustrating two of the via holes in cross-section.

FIG. 103 is taken from section 103-103 from FIG. 101 illustrating two of the via holes 402 in cross-section. Referring to FIG. 103, one can see that the via holes 402 have been filled in accordance with Option 4 of the present invention, as previously illustrated in FIG. 53. Accordingly, there is a CRMC layer 185 and then a platinum fill 186, 186' forming the dumbbell shapes, previously illustrated in FIG. 53. In subsequent drawings, it will be explained how the fill of FIG. 103 is accomplished.

FIG. 104 through 106 explain the process as to how the filled via hole 402, illustrated in FIG. 103, is accomplished. Referring to FIG. 104, the via holes 402 are first filled completely with CRMC paste 185, which in the present invention, in one embodiment, is a platinum-ceramic paste, otherwise known as a CRMC.

FIG. 105 illustrates that a hole is drilled all the way through the CRMC 185. After drilling a hole all the way through, then counterbores are drilled or formed on the top and bottom, as illustrated.

In FIG. 106, in a subsequent operation, the through-hole and counterbores are filled with a pure platinum paste 186. This forms the Option 4 configuration, as previously illustrated in FIG. 3. Again, the alumina-ceramic bar 188 is still in the green state (in other words, not sintered) and the paste still contains solvents and binders, which during a subsequent sintering operation, will be baked out. Pending the viscosity of the fill material, a simple drying process may be used to prevent material loss prior to drilling, counterboring, cutting or other such material removal process.

Figure 107:
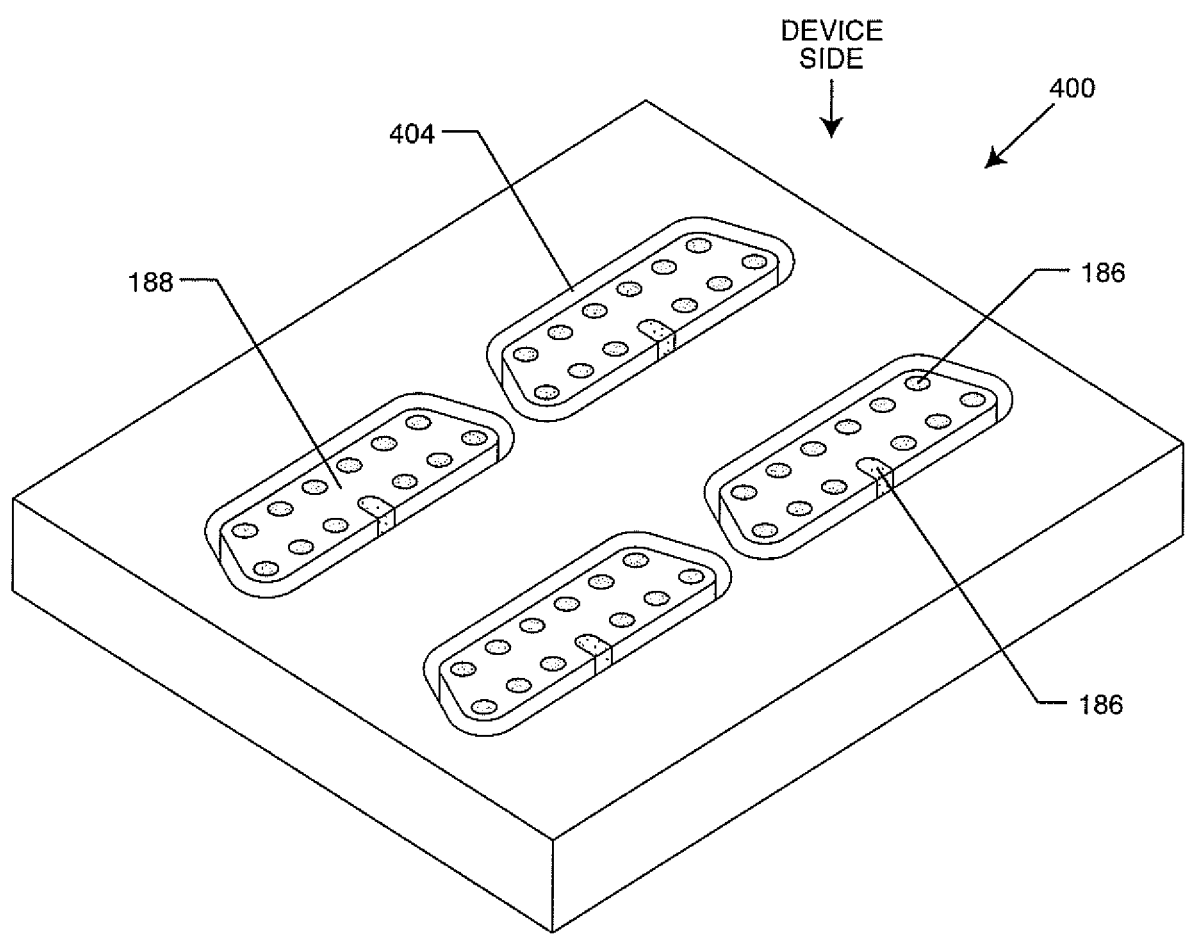
Figure 109:
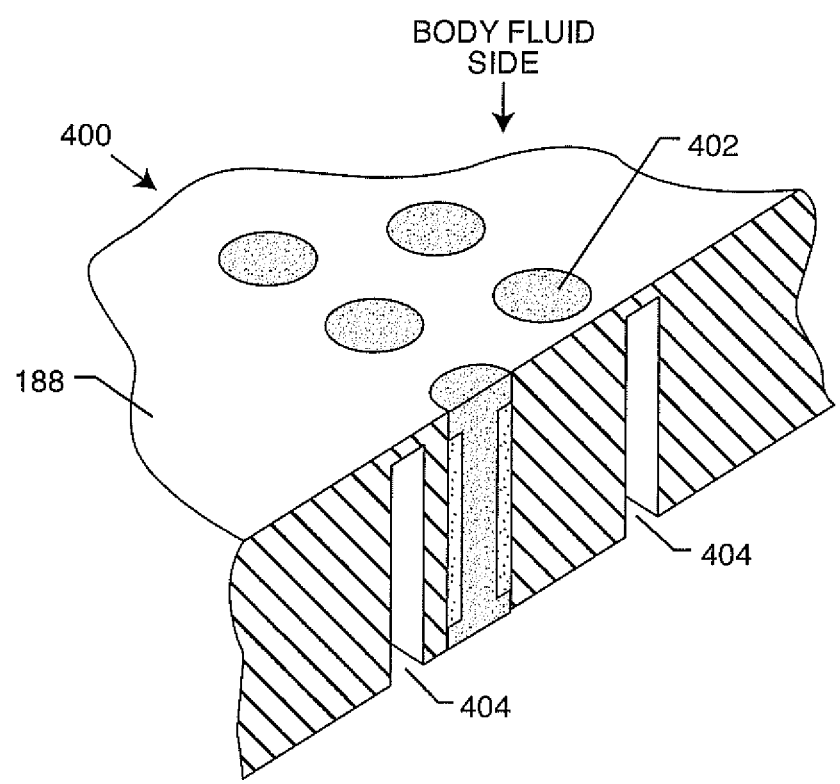

FIG. 107 shows that prior to sintering, the individual insulators 188 are removed from the bar 400. Accordingly, a slot 404 is formed by machining, by cutting, by punching or the like. In some embodiments, they can be punched or cut all the way out of the bar in one operation. However, FIG. 109 illustrates that the slot 404 can be formed almost all the way through the thickness of the bar 188, 400, such that it only takes a small pushing operation to literally break away the individual insulators 188 from the bar 400.

Figure 108:
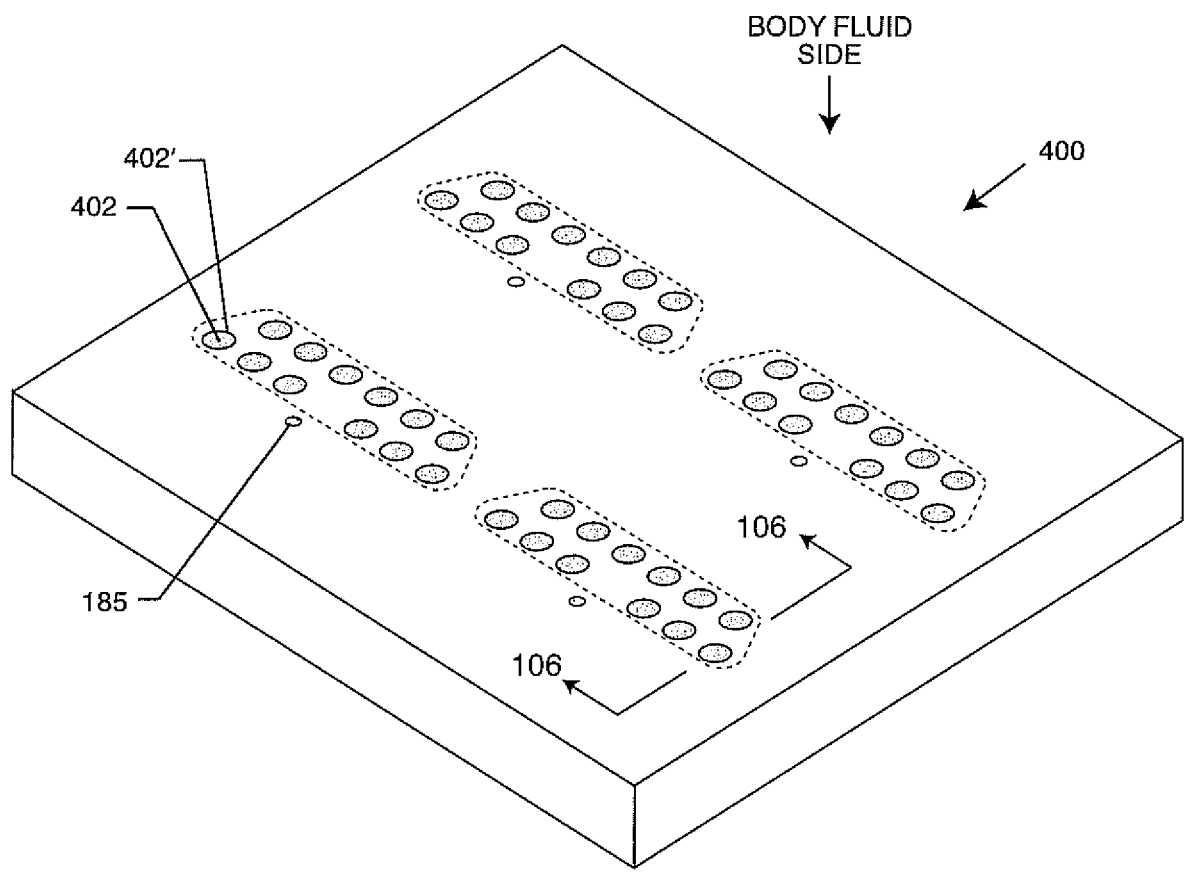

FIG. 108 illustrates the body fluid side of the device side image of FIG. 107. In this case, the slot 404 has not gone all the way through to the body fluid side, therefore, it is not visible in FIG. 108. In this case, the individual insulators 188 are ready to be broken out of the bar 400 by a simple pushing operation say, with a finger or with a robot. After the insulators are removed from the bar, they are sintered at a high temperature forming a solid monolithic structure.

FIG. 110 illustrates the insulator 188 after it's sintered with sputter layers 150 and 152 applied. FIG. 110 illustrates the body fluid side of the insulator and FIG. 111 illustrates the device side. As previously described, there is a grounding slot 185, 403. In this case, the material is CRMC 185. The adhesion layers are also applied to the CRMC material guaranteeing a low resistivity electrical connection. Again, this adhesion layer 152 and wetting layer 150 can be done in a single sputtering operation or even plating operations or the like. Importantly, gold braze will not wet directly to a sintered alumina 188 without an intermediate metallic layer to which the gold can wet.

FIGS. 112 and 113 illustrate an alternative embodiment. In this case, the slot 403 incorporates an aligned hole 405'. FIG. 112 illustrates the sintered insulator structure 188 prior to application of sputter layers 150, 152. The sputter layers are eliminated in this case, for simplicity. Referring once again to FIG. 112, one can see on the device side, the via holes, including a counterbore with pure platinum 186, in accordance with Option 4 of the present invention.

FIG. 113 is a cross-sectional view taken from section 113-113 from FIG. 112 illustrating that the slot 403 is filled with platinum 186. This would be accomplished by filling the entire slot and its aligned through-hole 405' with platinum 186. It will be understood that instead of filling with platinum, any number of CRMC materials or Cermet materials could be used. Then from the body fluid side, a counterbore is shown in the area illustrated as 405'. At this point, the insulator 188 is co-fired with the fill 186 (or Cermet). In a subsequent operation, a platinum leadwire or pin 186W is brazed 138 to the insulator body 188 forming a hermetic seal. There would be sputter layers 150, 152, not shown for clarity.

Referring to FIG. 113, it is not yet shown how the slot 403, 186 would be grounded to facilitate the attachment of an internally grounded feedthrough capacitor 124'.

Referring to FIG. 114, a novel milled or micro-blasted slot 406 exposes the side of the slot 403, which may be filled with platinum 186 as shown, or a Cermet or CRMC material, not shown. The novel slot 406 would be machined, abrasively grit micro-blasted or milled, as shown, to expose the side of the post sintered platinum fill 186.

FIG. 115 illustrates the sputter layers 150 and 152 can be applied to the side of the insulator, as shown, but also importantly, the sputter layer would also be applied to the exposed part of the platinum fill 186 of slot 403.

FIG. 116 illustrates the insulator of FIG. 115 gold brazed 140 into an AIMD ferrule 122. It will be noted that the gold braze 140 also contacts the metallization 150, 152, which makes a very low resistance and low impedance electrical connection to the slot fill material 186. Again, the slot fill material 186 could be pure platinum, or any combination of the options of the present invention. Referring back to FIG. 113 and comparing it to FIG. 116, one would see that the through-hole 405' would be optional. In other words, in one embodiment as illustrated in FIG. 116, there would be no through-hole from the ground slot 403 going all the way to the body fluid side. Referring once again to FIG. 116, one can see that the insulator structure on the device side is proud of the surface of the ferrule 122. As previously described, it could be flush or even sub-flush. For simplicity in FIG. 116, the sputter layers 150, 152 are shown as a single layer. Again, there are also single layer sputtering techniques or even plating or other metallization application techniques that could be used.

FIG. 117 illustrates that the grounding slot 140s may be replaced by a slot 403 filled with a Platinum-Alumina Cermet CRMC 185 or platinum 186 of the present invention. This provides a significant alternative to a gold braze moat 140s as previously. It is contemplated that slot 403 may alternately be filled with a metal paste such as a platinum paste, or combinations of different metal pastes, different CRMCs, or a combination of at least one metal paste and at least one CRMC.

FIG. 117A is taken from partial section 117A-117A from FIG. 117. FIG. 117A illustrates a different embodiment, in that, sputter layers 152, 150 have been eliminated and the gold braze 140 is shown wetting between the ferrule 122 and the CRMC material 185. Accordingly, gold braze 140 makes a mechanical connection and a hermetic seal between the ferrule 122, the Cermet 185 and the alumina ceramic insulator 188. It will be appreciated that solder bump 202 is easily attached to the surface of the Cermet material, which facilitates a ground connection to an internally grounded feedthrough capacitor 124' (not shown).

FIG. 118 is very similar to FIG. 74 illustrating that the Platinum-Alumina Cermet CRMC 185 filled slot 403 may also include a layer of pure platinum 186. The thin layer of pure platinum 186 facilitates ready wetting by solder of the ball grid array 202. Throughout this invention, it will be appreciated that the ball grid array 202 may encompass a solder, a solder paste, a thermal-setting conductive adhesive or the like. Furthermore, to join sub-components, ball grid array solder bumps 202 may be applied to at least one component of a subassembly, more than one component of a subassembly or all components of a full assembly. For example, solder bumps 202 may be applied to at least one surface of an insulator via hole of a hermetic feedthrough embodying any of the options previously described, or at least one metallized feedthrough hole of a feedthrough capacitor, or to both. (See FIG. 117)

FIG. 119 is best understood by first studying prior art drawings 11A, 11B and 11C herein. Referring once again to FIG. 119, the ferrule 122 has been machined thereby providing a peninsula structure 139. There has been a small circular machined indentation or slot or groove 139g that has been filled with gold braze 140d. This allows the ball grid array dot 202 to make contact to a non-oxidized very low impedance connection. This facilitates the attachment of an internally grounded feedthrough capacitor 124', as illustrated in FIG. 120 herein.

FIG. 120 illustrates a feedthrough capacitor 124' which includes one solid-filled capacitor feedthrough holes 119" and one hollow-filled capacitor feedthrough hole 119'. Referring to FIG. 119, note that the gold braze 140 is formed on the device side, whereas in FIG. 120, the gold braze 140 is formed on the body fluid side.

FIG. 121 illustrates one possible electrical schematic of the internally grounded filtered hermetic feedthrough assembly 116 of FIG. 120. The telemetry pin conductor T is optional. It will be appreciated that telemetry via conductors can be constructed of any of the Options 1 through 6 as described herein, but they would not be connected to any type of filter capacitor. It will be appreciated that body fluid side leadwires 118 and device side leadwires 118' may be connected in accordance with Options 1 through 6 as shown in any of the schematics herein.

FIG. 122 is very similar to FIG. 117, except that slot 403, CRMCs 185 includes a counterbore, including pure platinum 186 of the present invention, thereby providing a high conductivity connection 202 to a feedthrough capacitor or a circuit board (not shown). On the right-hand side of the structure of FIG. 122 is illustrated Options 2, 2A of the present invention previously illustrated in FIGS. 31 and 32.

FIG. 123 illustrates a hermetic insulator 116 of the present invention with MLCC chip capacitors 194 electrically attached between the active vias and to the ferrule 122 and ferrule gold 140. The electrical connection material 143 can be a thermal-setting conductive adhesive or a solder or the like. A connection on the device side to AIMD electronics is required, but not shown.

FIG. 124 is one possible electrical schematic of the filtered capacitor structure with MLCC chips illustrated in FIG. 123. In this case, there would be four chip capacitors 194, 194', 194" and 194'''.

FIG. 125 illustrates a circuit board 147 and MLCC capacitors 194 that are attached through a metal addition 159 to the ferrule 122. Oxide resistant or oxide-free metal additions are further described in U.S. Pat. Nos. 9,108,066 and 9,427,596, the contents of which are fully incorporated herein by reference.

FIG. 126 illustrates circuit board 147 with circuit trace 157 routed from the active via hole 402, 185, 186 to the device electronics. An MLCC capacitor 194 is shown connected to the ferrule through a metal addition 159.

FIG. 127 illustrates a direct electrical connection on the left-hand side on the MLCC capacitor 194. This electrical connection 143 is from the left-hand termination 132 of the MLCC capacitor to the gold braze 140 of the ferrule 122. This makes for a very low impedance low resistance electrical connection. It is well known that titanium can form oxides, which make for very poor electrical connections. Accordingly, contact to gold 140 is required.

FIG. 128 is very similar to FIG. 127, except that in this case, the active circuit traces 157 and 157' are embedded within circuit board 147. As illustrated, circuit trace 157 is conductively coupled to the via hole 185, 186 with electrical connection material 143, as shown. There could be any number of additional circuit traces, such as 157'. Circuit trace 157' is shown not connected to the illustrated via hole, but would instead be connected to other via holes (not shown) further into the circuit board.

FIG. 129 illustrates a circuit board 147 mounted to the ferrule 122 of a hermetic terminal subassembly 116 for an AIMD.

FIG. 130 is a sectional view taken from section 130-130 from FIG. 131 of the ground plane GND, 161 of the circuit board 147 of FIG. 129. The ground plane GND, 161 is connected at its left side and its right side to the ferrule 122 as will be shown in FIG. 131.

FIG. 131 is a sectional view taken from section 131-131 from FIG. 129. This illustrates the internal ground trace 161. It also illustrates that there is a pin 118'gnd on the left side disposed through the entire thickness of the ferrule and terminates at the body fluid side. The pin 118'gnd at the body fluid side may be flush, sub-flush or proud of the ferrule 122 surface on the body fluid side. The pin 118'gnd is co-brazed 140p into the hermetic seal ferrule 122. As illustrated, the right-hand ground pin 118'gnd is electrically connected with a solder, a thermal-setting conductive material 143 to circuit board via hole, which is in contact with circuit board ground trace 161. It will also be noted that the electrical connection material 143 also contacts a gold braze dot or platform 140d, which has been previously gold brazed to the ferrule 122. As previously discussed, this provides a low impedance and low resistance electrical connection between the ground pin 118'gnd and the ferrule 122. Referring once again to FIG. 131, it will be appreciated that a multiplicity of ground layers 161 may be employed to reduce the inductance and impedance across the circuit board ground plane (also sometimes called ground plates). In one embodiment, there could be several internal ground plates 161 and even an external ground plate 161 disposed between the circuit board and the device side of the insulator and/or ferrule. In one embodiment, for example, there could be two internal or embedded ground plates 161, in addition to one external ground plate disposed between the bottom of the circuit board and the device side of the insulator and/or ferrule 122. It is noted that the gold braze 140p to the pin 118'gnd is formed at the same time as the gold braze 140. Forming both gold brazes at the same time facilitates gold flow and enhances bond integrity in addition to reducing assembly costs. Otherwise, forming two gold brazes on opposite sides increases labor, complicates assembly and may require two separate brazing steps, likely with two different braze material formulations or brazes having different melting temperatures. Additionally, to prevent reflow of a first perimeter braze, multi-stage or active brazing methods may need to be employed. FIG. 131 also shows that on the right side there is a ground pin 118'*gnd* that is attached by electrical connection material 143 to a gold braze dot or a gold braze filled recess into ferrule 122. It will be appreciated that in accordance with the present invention, this could be gold braze dots with BGA connections 202. Note that each via shows one distinct inventive Option embodiment as disclosed herein. Beginning with the left end of FIG. 131, Options 1 or 1A are shown in the first pin to the right of ground pin 118'*gnd*. This via illustrates a Platinum/Alumina Cermet CRMC in the mid-portion of the via fill with substantially pure platinum 186 at both device and body fluid sides for mechanical attach. Option 2, 2A is shown in the second pin to the right of ground pin 118'*gnd*. This via fill shows a central pure platinum 186 with a Platinum-Alumina Cermet CRMC 185 to the right and the left of the cross-section. In the finished assembly, a layer of Platinum-Alumina Cermet CRMC 185 surrounds the pure platinum 186. Option 3, 3A is shown in the third pin to the right of ground pin 118'*gnd*. Option 3, 3A is similar to Option 2, 2A except that the substantially pure platinum paste 186 has been replaced by a substantially pure platinum solid wire 186W. Option 4, 4A is shown in the fourth pin to the right of ground pin 118'*gnd*. Option 4, 4A illustrates larger end caps created by counterbores disposed on the top and bottom of the via previously filled with Platinum/Alumina Cermet CRMC. The counterbores are then filled with pure platinum 186 to form a larger end cap on both the body fluid side and the device side leaving a Platinum/Alumina Cermet CRMC 185 disposed throughout the center of the via between the larger end cap extensions. Option 5, 5A is shown in the fifth pin to the right of ground pin 118'*gnd*. In Option 5, 5A, the pure platinum wire 186W is surrounded by two layers of material having different compositions. On the sixth pin to the right of the ground pin Option 6, 6A embodying end caps 186c as shown. It will be appreciated that the alumina insulator 188 can be counterbored to accommodate end caps 186c to provide a larger diameter contact area to attach electrical wires or ribbon cables (not shown). It will also be appreciated that the via end counterbores or countersinks filled with platinum may be added to Option 1 or 1A; or Option 4 or 4A, on the body fluid side, the device side or both, to increase the contact area as previously illustrated. It will be appreciated that these countersinks may have other configurations other than the ones show. It will also be understood to one skilled in the art that the final assembly of FIG. 131 may be configured to have all the same via fill options or may be configured to contain any combination of via fill Options previously described herein.

FIG. 131 currently shows a ground pin 118'*gnd* on the left that is gold brazed 140*p* to the ferrule 122. However, in another embodiment (not shown), the ground pin 118'*gnd* may be replaced with filled vias that directly connect with electrical connection material 143 to the gold braze 140 on a device side as previously shown in FIG. 107. Referring to the right side of FIG. 131, an alternative ground pin 118'*gnd* is illustrated which is electrically connected 143 to a gold braze dot or moat 140*d* that is gold brazed to the ferrule 122. It will be appreciated that the pins 118' of FIG. 131 would be routed to AIMD electronic circuits or to a circuit board(s) (not shown).

FIG. 132 illustrates section 132-132 from FIG. 129 showing how the MLCC capacitors are connected to the ground trace 161 and are grounded through via holes 163B and 163E. Referring back to FIG. 131, it will be appreciated that the leadwires, as shown, could be replaced by any of the Options 1 through 6 of the present invention. This is illustrated on the left side of FIG. 131 wherein the via hole is filled with a Platinum/Alumina Cermet CRMC 185 with platinum end caps 186C. Referring once again to FIG. 131, one can appreciate that a leadwire routed to the device side electronics may be provided and co-joined, as shown, to the platinum cap 186C at the same time it is connected to leadwire 118'*f*.

FIG. 133 is an enlarged view generally taken from section 133-133 from FIG. 131 illustrating how the leadwire 118'*a* is co-joined with electrical connection material 143 to the platinum end 186 of the via hole, including the Cermet CRMC. Again, it will be appreciated that any of Options 1 through 6 of the present invention are applicable to any of the previously described FIGS. herein. FIG. 133 on the left side shows a new embodiment wherein the ground pin 118'*gnd* can be a two-part pin consisting of a short platinum leadwire 117*gnd* wherein a low cost leadwire 118'*gnd* is co-joined with electrical connection material 143 to a short platinum pin 117*gnd* which is gold brazed 140*p* into ferrule 122. It will be appreciated that a single ground pin 118'*gnd* can be used in place of the two-part pin as illustrated. Two-part pins are further described by U.S. application Ser. No. 15/603,521 which is incorporated fully within herein by reference. It also will be appreciated that gold braze 140 may be formed on the device side such that the gold braze 140*p* is formed at the same time in a single gold braze furnace operation. Referring once again to FIG. 110, it will be appreciated that gold brazes 140, 140*p* may also be disposed on the device side, or, alternatively, both be disposed on the body fluid side.

FIGS. 134, 135 and 136 illustrate Options 1 and 1A of the present invention with a composite platinum-alumina via fill CRMC with platinum conductor end fills 186 co-fired into a feedthrough with a device side solder coat 197 made by dipping the sintered via and alumina substrate 188 into a solder bath of Sn63Pb37 composition typically at ~200 C (other solder alloys and temperatures may be used). The solder coating 197 may be applied to any of the Options 1, 2, 3, 4, 5, 6 described herein. An acid etch (or active flux) is generally required to remove any oxides to facilitate solder wetting. For optimal coverage, a feedthrough 188 may be repeatedly solder dipped 197 until a desired coverage/coating cover is achieved. A coverage of at least 95% is desirable. This solder dipping manufacturing operation would most likely be performed after the insulator 188 is brazed 140 to ferrule 122.

Pending material selection and processing parameters, prior to solder dipping, acid etching is a preferred method to remove oxides from the surface of the feedthrough filled via (such as oxides of platinum). In addition, before solder dipping, an acid etch may also be used to remove a thin layer of ceramic or a thin layer of diffused glass that may form at the ends of a feedthrough via fill during sintering as discussed by Karbasi[3]. Oxides of platinum, and/or thin layers of glass such as $SiO_2$, $MgO$ or $CaO$, or even a thin layer of alumina ceramic ($Al_2O_3$), are very resistive and undesirably reduce the conductivity through the via hole. $SiO_2$, $MgO$ or $CaO$ are common trace elements in Alumina ceramics and may diffuse and form at surfaces of metal-ceramic paste filled via holes 186. Lapping, grinding or other mechanical processes may also be used in lieu of fluxes (or in combination with fluxes) to remove these coatings to facilitate pin hole free minimum 95% solder coverage 197. As discussed by Karbasi[3] these glasses also diffuse into the via hole fill material such as Platinum-Alumina Cermet CRMC and form a concentration gradient (this concentration gradient discussed by Kingery forms during sintering, and has been well known as early as 1938 as evidenced by Becker's use of bond counting technology to establish composition concentration gradients at metal/oxide interfaces) and is a natural result of sintering a metal paste filled via in an alumina insulator 188. In the case of $Pt/Al_2O_3$ filled vias (CRMC 185), the onset of platinum particle coalescence and fusion enables mobility of alumina particles through the platinum fill. Given processing time and temperature, and that platinum in and of itself facilitates alumina growth, the potential for alumina migration through the platinum increases the possibility of the entire surface of each via end to be covered with an alumina layer, thereby unfavorably affecting electrical conductivity at these via end surfaces.

An embodiment as illustrated in FIG. 134 includes a first assembly having a solder pad 197 that is attachable to a second assembly (such as a leadwire, a ribbon cable, a feedthrough capacitor, an MLCC capacitor, an X2Y capacitor, or a circuit board), wherein a solder flux would not be required (or only a mildly active flux or no-clean flux) for attachability and wherein the resultant component may comprise a clean board with, but not limited to, an electroless nickel/electroless nickel gold plated pad on, for example, a PCB board. No-clean or washable acid fluxes that leave low or no post process residues are desired for long term reliability and chemical stability of the solder connection inside the AIMD. The resultant assembly may comprise two components having a solder reflow temperature wherein the solder does not require flux to create a solder pad or dome 197. The inventors (Greatbatch Cardiac & Neurology) have confirmed that with enough time and temperature, device side solder can be conformed to various intermetallics, in particular, with compositions for this kind of phase diagram; common intermetallics that conform to soldered microelectronic components are desired.

It will be appreciated that any of the previously illustrated embodiments and options may be solder coated 197 to facilitate connectability of a BGA bump 202, a feedthrough filter capacitor 124, an adjacent filter circuit board, an MLCC capacitor 194, a leadwire 118,119, a ribbon or round cable/wire or the like. The solder coating 197 greatly facilitates connection to an AIMD electronics circuit.

Referring once again to FIGS. 134 through 137, the solder coat 197 need not be done by dipping, but could be done by localized application of an acid or flux and application of a localized solder dot. In other words, one need not need to dip the entire ferrule and insulator assembly into molten solder.

Referring to FIG. 138, one can see solder coat 197 facilitating an oxide resistant attachment of solder bump 202 that enables attachment of feedthrough capacitor 124 and device side leadwires 118', 119 that would be attached to AIMD electronic circuits such as a circuit board 147.

FIG. 139 is very similar to FIG. 29 (Option 1). The insulator structure of FIG. 139 is no longer symmetrical in that it has a body fluid side and a device side. The device side is identical to that previously described in FIG. 29 comprising a pure platinum 186 and a platinum alumina CERMET or ceramic reinforced composite 185. Now referring to the body fluid side, a body fluid side leadwire 118 is shown, which would be biocompatible. This means, not only must leadwire 118 be biocompatible, but must also be biostable and non-toxic. Biostable means that in the presence of body fluids and electrical pulses, such as therapeutic pacing pulses, that the lead 118 and its hermetic seal 138 to the insulator 120,188 not degrade over time. Accordingly, the list of materials that are generally acceptable for body fluid side leadwire 118 is a relatively short list. Included are all of the noble metals, including platinum, palladium, gold and the like. However, leadwires of titanium, niobium or tantalum are also acceptable in that, they meet the biocompatible, non-toxic and biostable criteria. In general, these leadwires are hermetically sealed to the insulator 120,188 by first applying sputter layers 152 and 150 as shown. First sputter layer 152 is applied as an adhesion layer, which adheres to the high purity alumina ceramic 120,188. This adhesion layer, which is sputtered on, can include niobium, molybdenum or other suitable materials. Over the adhesion layer, there is a wetting layer 150, which is sputtered, which is generally comprised of titanium. It is also known in the art that one could sputter on a single layer which would have both high adhesion and wetting properties. The wetting property is important for gold braze 138, which is generally applied in a high temperature gold reflow furnace. In this case, the gold braze forms an electrical and hermetic seal to the leadwire 118 and also the wetting layer 150. This forms a mechanically strong and robust hermetic seal 138. In general, hermetic seals form by gold brazing 138 achieve a minimum helium leak rate of $1 \times 10^{-7}$ standard CCs helium per second. It will also be appreciated that instead of sputtering on adhesion layers 152 and 150 and gold braze 138 that this hermetic seal could also comprise a glass seal. Importantly, the gold braze 138 flows underneath the pin 118 thereby, providing a very low resistivity (high conductivity) electrical connection between body fluid side leadwire 118 and the platinum alumina ceramic 185.

Referring once again to FIG. 139, it will be appreciated that the alumina insulator body 120,188 is generally first co-fired with the platinum alumina ceramic 185 and platinum end cap 186. This changes the alumina ceramic 120,188 from a flexible green state into a post sintered solid state. After this co-firing or sintering operation, then sputter layers 152 and 150 are applied and then the lead is gold brazed in a separate operation 138 as indicated. It is important to understand the manufacturing steps of the hermetic insulator 120,188 in FIG. 139. First, a via hole would be drilled all the way through the structure and then the via hole would be filled with the platinum alumina ceramic or ceramic reinforced metal composite paste 185. Then there are two counter-bores. First counter-bore area 186 is formed and then filled with pure platinum 186 as shown. Then a second counter-bore would be formed on the body fluid side. At this point, the alumina insulator 120,188 is co-fired along with PAC or CRMC 185 and platinum fill 186. It is after this that the sputtering layers 152 and 150 are applied and then the leadwire 118 is gold brazed as shown. During the co-firing or co-sintering of the alumina insulator 120,188 along with the via hole fills 185 and 186, it has been discovered that a glass layer or a thin layer of alumina itself may disperse over the top. In general, the alumina ceramic insulator 120,188 is of high purity; however, all alumina ceramics particularly have a certain amount of glass, such as silicon dioxide, magnesium oxide and calcium oxide. It is well known to experts in the co-sintering of alumina ceramics and CERMETS that a concentration gradient occurs wherein, either glass additives or impurities of glass can disperse over the surfaces 526 and 528, as described. Also a thin layer of alumina itself can occur during certain sintering conditions over these areas. The concern is that these glasses or thin layer of alumina are insulative. In other words, undesirably a layer of glass or a layer of alumina or both could reside between the top of the PAC or CRMC layer 185 and sputter layer 152. This could create a high resistivity connection, which would be particularly undesirable for pacing pulses and very undesirable for an ICD defibrillation pulse, which involves very high currents. This is the reason for the co-fired platinum cap 186 on the device side, such that it forms a very low resistivity connection to PAC or CRMC material 185 and such that one has a pure platinum cap 186 exposed on the device side.

In the present invention, after the alumina ceramic insulator 120,188 is co-sintered with CRMC/PAC via fill 185 and 186, it is desirable to have a mechanical or abrasive grit blasting operation on both the device side and on the bottom of the counter-bore on the body fluid side, such that any formation of glass or ceramic across the tops of the CRMC or PAC 185 is removed. Referring once again to FIG. 139, one can see the grit blasted area 526 on the device side of the composite fill, which is also defined as the first side of the composite fill. Grit blaster location 528 is shown disposed on the body fluid side of the composite fill. Again, this is an area that is grit blasted prior to application of sputter layers 152 and 150. Location 528 is herein defined as the second composite fill in. Various embodiments of the co-sintered ferrules or composite ferrules will be shown, but one thing that does not change is that the first side 526 is always disposed toward the device side and the second side 528 is always disposed towards the body fluid side and recessed to the exact location where the sputter layer 152 is applied. At this point, the sputtering is applied, such that a very low resistance and high conductivity and electrical connection is formed between leadwire 118 and the CRMC/PAC via hole 185 is achieved. One could also use selective etching to make sure that any layer of alumina or glass was removed prior to sputtering 152.

Throughout this invention, it will be appreciated that the platinum or alumina ceramic or ceramic reinforced metal composite 185 can embody any CERMET material.

Referring once again to FIG. 139, one would appreciate that there would also be sputter layers on the diameter or perimeter of the insulator 120,188 (not shown). This would be to accommodate the gold brazing (generally at the same time) between the insulator and a ferrule structure 122. Gold brazing to a ferrule structure has been previously described in FIG. 35. The ferrule structures have been eliminated from FIGS. 139 and on for simplicity, but it will be understood that the gold brazing of leadwire 118 would be done at the same time that a hermetic seal gold braze was formed between the insulator 120,188 and the ferrule 122.

FIG. 140 is very similar to FIG. 139, except that FIG. 139 is a multilayer green ceramic 120,188 and in FIG. 140, it is a solid monolithic ceramic, such as a pressed or machined ceramic from a solid block.

FIG. 141 is very similar to FIG. 31 in that, the via hole is first filled with CRMC paste 185 and then it is drilled out and filled with pure platinum 186. FIG. 141 is very similar to FIG. 31, except that it has been modified to have a gold brazed body fluid side leadwire 118 as previously described in FIG. 139.

FIG. 142 is the same as FIG. 141, except instead of being a multilayer alumina insulator 188, it is a monolithic insulator 188.

FIG. 143 is very similar to FIG. 33, except that it has been modified to add the body fluid side gold braze leadwire 118 as previously described in FIG. 139.

FIG. 143A illustrates the hermetic seal insulator of FIG. 143, except that it's been gold brazed 140 into a ferrule 122 for an active implantable medical device. Referring back to FIG. 143A, one can see that the ferrule 122 comprises a body fluid side surface 520. Also shown is surface 522, which is also known as a ferrule device side surface. Surface 524 defines a ferrule opening or inside surface into which the insulator 188 is either fully or partially disposed. Referring once again to FIG. 143A, it will be appreciated that the insulator 188 can stand proud above the body fluid side 520 of the ferrule 122 or be recessed relative to the ferrule surface 520. The same is true on the device side. The ferrule 188 can stand proud of ferrule surface 522, be even with it, as illustrated or be recessed below it (not shown).

FIG. 144 is very similar to FIG. 34 (Option 2C), except that it's been modified to have a body fluid side leadwire 118, as previously described in FIG. 139.

FIG. 144A is very similar to FIG. 144 except that the body fluid side leadwire 118 has been replaced with a body fluid side metallic insert 118,NH. NH stands for nail head, but it will be appreciated that it could also be a short pin or even a wire bond cap. The nail head NH could be proud, as illustrated or flush or even sub-flush depending upon the geometry of the counter-bore and the overall height of the nail head.

FIG. 145 is very similar to FIG. 139, except that the CERMET 185 has been replaced on the outside diameter or perimeter of the alumina insulator 188 with sputter layers 152 and 150. These sputter layers are to accommodate subsequent gold brazing into a ferrule structure 122 (not shown). FIG. 145 illustrates a multilayer alumina structure 188.

FIG. 146 is the same as FIG. 145, except that the alumina structure 188 is monolithic.

FIG. 147 is very similar to FIG. 43, except that body fluid side leadwire 118 has been added, which is gold brazed as shown. This is as previously described in FIG. 139.

FIG. 148 is the same as FIG. 147, except that the insulator structure 188 is monolithic instead of multilayer.

FIG. 149 is very similar to FIG. 45, except that a body fluid side leadwire 118 has been gold brazed 138 into a multilayer insulator structure 188.

FIG. 150 is the same as FIG. 149, except in this case, the insulator structure is monolithic.

FIG. 151 is very similar to FIG. 53, except that a body fluid side leadwire 118 has been gold brazed 138 into the multilayer insulator 188.

FIG. 152 is the same as FIG. 151, except that the insulator structure 188 is monolithic. Referring once again to FIG. 152, one can see that on the device side, an optional counter-sink is shown 186'. One will appreciate that this can also be a counter-bore. This is to increase the area for bonding to a device side filter capacitor leadwire to a circuit board and the like.

FIG. 153 is very similar to FIG. 55, except that a body fluid side leadwire 118 has been gold brazed 138 into the multilayer insulator structure 188, as shown.

FIG. 154 is the same as FIG. 153, except that the insulator structure 188 is monolithic.

FIG. 155 is very similar to FIG. 57, except that a body fluid side leadwire 118 is shown gold brazed 138 into the multilayer insulator 188.

FIG. 156 is the same as FIG. 155, except that the insulator structure 188 is monolithic.

FIG. 157 is very similar to FIG. 59, except that a body fluid side leadwire 118 is shown gold brazed 138 into the multilayer insulator 188, as previously described in FIG. 139.

FIG. 158 is the same as FIG. 157, except that the alumina insulator 188 is monolithic.

FIG. 159 is very similar to FIG. 126, except that on the body fluid side leadwire 118 is shown gold brazed 138 into the insulator structure 188. A second gold braze 14 is generally formed at the same time as gold braze 138 which provides a hermetic seal between the insulator 188 and the ferrule 122. It will be appreciated that the hermetic seal, between the insulator 188 and the ferrule 122, could also be accomplished by a glass, a glass-ceramic or a ceramic bonded to a glass, each being biocompatible and biostable. Suitable glasses include but are not limited to aluminaborate, boroaluminasilicate, boroaluminate, borosilicate, aluminasilicate, lanthanoborate, alum inophosphate, calcium alum inoborate, magnesium alum inoborate, calcium magnesium auminoborate, calcium phosphate, barium silicate, barium aluminosilicate, silicate, phosphate, borate, doped calcium phosphate, calcium phosphate with transition metal oxide additions and combinations thereof. Suitable glass-ceramics include but are not limited to lithium disilicate, alumina lanthanoborate, titania lanthanoborate, ceramic oxide silicates, ceramic oxide borates, ceramic oxide aluminates, ceramic oxide phosphates, and combinations thereof. It is anticipated that the ceramic oxide formulations may be alumina, titania, zirconia and/or various stabilized or partially stabilized zirconia including ZTA and ATZ, fused silica, silicon nitride, alumina toughened zirconia, zirconia toughened alumina, zirconium dioxide, yttrium-toughened zirconium oxide, aluminum nitride, magnesium oxide, piezoceramic materials, barium (Zr, Ti) oxide, barium (CE, Ti) oxide, sodium-potassium-niobate, calcium oxide, cerium oxide, titanium oxide, apatite-wollastonite (A-W) glass ceramic, boron nitride, alumina silicate, and combinations thereof FIG. 160 is very similar to FIG. 131 showing the various options in the invention all with a body fluid side leadwire 118a through 118f. The leadwires 118a-f have been gold brazed into the insulator structures, as previously described in FIG. 139. Each leadwire 118a-f is respectively in electrical communication with its composite fill. Electrical communication means they are conductively coupled such that electricity is able to flow from and between the structures, whether the connection is made with one metallization layer, two metallization layers or a plurality of conductive connections. As shown in FIG. 160, the composite fill 185, 186 can take on many different embodiments. The composite fill 185, 186 is co-fired with the feedthrough body 188 to form a hermetically sealed structure and then the metallization layers and gold braze electrically couple the composite fill to the leadwires 118a-f.

FIG. 161 illustrates an alumina ceramic insulator 188 gold brazed 140 into ferrule structure 122. Also shown are body fluid side leadwires 118 that are gold brazed 138 into the insulator 188, as previously described in FIG. 139. A feedthrough capacitor assembly 124 is illustrated where the capacitor has been attached to the insulator and the ferrule 122. One will see that there are electrical connections between the capacitor via holes and the insulator conductive pathways thereby, connecting a feedthrough capacitor for the purpose of acting as a broadband low pass filter to protect sensitive AIMD electronic circuits from electromagnetic interference. This is a conventional capacitor in that, it's outside diameter or perimeter metallization 132, which contacts ground electrodes are electrically contacted 148 either with a solder, a thermal-setting conductive adhesive or the like to both the ferrule structure 122 and importantly, to gold braze area 140. Contact to gold braze 140 is necessary to have a very low impedance and oxide-free connection. Device side leadwires 118' are optionally shown and can be co-soldered 202 at the same time the electrical connection to the capacitor via holes are made.

Referring once again to FIG. 161, one can see that the solder bump 202, also known as a BGA bump or even a thermal-setting conductive adhesive, makes a three-way connection. That is, a connection to the insulator via hole sintered fill materials CRMC 185 and platinum core 186, at the same time that it makes a connection to the feedthrough capacitor inside diameter metallization 130 and the device side low cost leadwire 118'.

FIGS. 161A through 161E are very similar to FIG. 161 except the ferrule was either replaced or re-shaped using various structures. These structures are only examples of possible embodiments and are not intended to be limiting. FIG. 161A does not require a ferrule. (In other words, the gold braze 140 directly contacts the conductive housing 102 of the AIMD.) FIG. 161B is essentially the same as FIG. 161A except that the stamping of the AIMD housing 102 is oriented upward instead of downward. FIG. 161C illustrates that instead of a ferrule 122, one could use a piece of stamped titanium 122, which is then subsequently laser welded 128 to the AIMD housing 102. FIG. 161D is very similar to FIG. 161C except illustrated is a stress absorbing U-type shape for ferrule 122. FIG. 161E is very similar to FIGS. 161C and 161D except in this case, the stamped ferrule 122 comprises an S-shape.

FIG. 162 is very similar to FIG. 161, except that in this case, the capacitor is internally grounded. Internally grounded feedthrough capacitors are taught in prior art drawings 11A through 11C herein. In this case, a gold braze moat 138,140,408 creates a peninsula ground very similar to that illustrated in FIG. 11B as element 139. As previously illustrated, it will be appreciated that the peninsula structure could be machined from the ferrule, as illustrated in FIG. 11b, comprised of a metal clip 410 as seen in FIG. 163 or even a PAC or CRMC material 185. As previously described in FIG. 141, a body fluid side leadwire 118 has been gold brazed 138 into the alumina insulator 188. Referring once again to FIG. 162, in this case, the height of the insulator is such that it only partially resides within the ferrule structure 122. It will also be appreciated that the insulator structure 188 could sit on top of the ferrule 122 (not shown). In other words, it is not necessary that the insulator 188 be disposed partially or entirely inside of the ferrule opening, but could reside entirely on its body fluid side or its device side surface.

FIG. 163 shows the use of the novel metallic clip 410. The metallic clip 410 is disposed within the gold braze and helps the gold braze moat 138, 140, 408 form in a consistent and even manner. This is accomplished through capillary action of the gold braze interacting between the metallization 150,152 and the metallic clip 410. A thinning of the gold braze is thereby prevented and a good and reliable electrical connection is maintained.

FIG. 163A is an isometric view of the novel clip 410 that is shown in cross-section in FIG. 163. This clip 410 could be of any suitable conductive material or metal, including titanium. It will also be appreciated that this clip could be of any solderable material, such as gold, palladium, platinum and the like. It will also be appreciated that the clip 410 could first be laser welded or attached to ferrule 122 prior or after the gold brazing 138, 140, 408. The laser weld is not shown for simplicity. FIG. 163B is the clip of FIG. 163A with a hole 410h. The hole 410h facilitates the flow of gold braze 138, 140, 408 around and up into it thereby, facilitating a low impedance oxide-free electrical connection 202 as previously described. FIG. 163C is generally taken from section 163C-163C from FIG. 163. This shows the clip 410, as previously illustrated in FIG. 163A (without a hole 410h).

In this case, due to capillary action, the gold braze 138, 140, 408 wets between sputter layers 150 and 152 of the alumina insulator 188 and also to both sides of the titanium clip 410. The word titanium is used in this context, but as previously described, any suitable metal or conductive material could be used for the clip. Referring once again to FIG. 163C, one can see that the BGA, ball grid array or thermal-setting conductive adhesive dot 202 desirably contact a thickness of gold braze 138, 140, 408. In the case where the clip, for example, would be of titanium 410, it could be of heavily oxidized material. Accordingly, the gold braze forms a metallurgical bond penetrating through any oxide layer and consequently, the electrical connection material 202 makes a very low impedance and oxide free connection to the clip 410 and in turn, to the ferrule 122. As previously described, providing a low impedance and oxide-free connection is very important, such that the filter capacitor 124' provide proper filtering at high frequencies. FIG. 163D shows an alternative form of the clip 410 (shown inverted with respect to FIG. 163) and that in this case, a device side leadwire 118'$gnd$ is either co-brazed or is laser welded to the clip. This is an important alternative, referring back to prior art FIG. 11B. The unfiltered hermetic feedthrough terminal assembly 189 of prior art FIG. 11B, illustrates traditional leadwires penetrating through the insulator of the feedthrough. Also shown, is an internal ground lead 118'$gnd$. The peninsula structure 138 of the ferrule 122 is very expensive to manufacture. This is because one must start with a solid block of titanium and then cut out the opening for the insulator 120. This results in a great amount of labor and titanium scrap. The novel clip 410 and terminal pin of FIG. 163D, replaces the peninsula structure 139 in a very low cost manner. These clips can be formed by punching or stamping (or even by machining). A punched or stamped clip is far less expensive and as one will appreciate, it would also be much less expensive to machine the ferrule and simply add the clip 410 as described in FIG. 163. The novel clip 410 was first disclosed in FIG. 29 of U.S. patent application Ser. No. 15/603,521, filed on May 24, 2017, the contents of which are fully incorporated herein by reference.

As used throughout this specification, a multi-layer body structure 120,188 are all of the same construction. For example, see the multi-layer structure, as illustrated in FIGS. 29, 31, 37, 39, 41, 43, 45, 47, 49, 51, 53, 53A, 55, 57, 59, 61, 62 and the like are formed from stacking discrete layers of the green, generally alumina ceramic, and then pressing it either through hydro-static or equivalent processes to form a solid green body. After pressing, it is very difficult to distinguish the green body from solid bodies, as illustrated in FIG. 30 and the like. After sintering, it is literally impossible to distinguish (unless there is some knit line or delamination present) the multi-layer body 120, 188 of FIG. 29 from the solid body 120, 188 of FIG. 30. Solid bodies are generally formed from either cutting or pressing green layers of thick alumina or by a preferred method, a green powder slurry is pressed into molds and then sintered forming the shape as shown in FIG. 30. Referring back to FIGS. 29 and 30 and their equivalents throughout the specification, the passage way or via hole through the capacitor is generally formed in the green state either by drilling, pressing, molding or equivalent processes. Referring back to FIG. 29, after the body has been pressed 120, 188, a hole is drilled or formed all the way through the structure and then the entire structure is filled with the CRMC paste 185. This is identical to the process of FIG. 30 wherein, the solid body 120,188 has a passageway formed by drilling or equivalent process from the body fluid side to the device side of the structure.

In the green state, the CRMC paste 185 was vacuumed or pressure pressed or mechanically forced into the through passageway. This is followed by a drying step wherein, certain solvents or volatiles that are contained within the CRMC paste 185 are allowed to dry. This makes the CRMC paste 185 mechanically strong enough to hold its shape (but it is not yet sintered). Then, as shown in FIG. 29, using a counter-bore tool or equivalent mechanical process, counter-bores 186 are formed and then filled as shown with pure platinum 186. The process for the multi-layer structure FIG. 29 and that of FIG. 30 are identical. After placing the pure platinum paste 186, then the entire structure is co-sintered, meaning that the alumina ceramic body 120,188 is co-sintered at the same time as the CRMC paste 185 and the platinum end caps 186. The CRMC material 185 drying process can be done by just leaving the parts at room temperature or may be accelerated by heat, vacuumed or any combination of all of those. The exact drying technique and the amount of drying time varies with the thickness and the diameter of the CRMC paste and the platinum filled caps. One may even perform an elevated binder bake-out process, which will remove almost all of the solvents and binders prior to sintering. Referring now to FIG. 31 and FIG. 32, one can see that after pressing both of the ceramic bodies 188 are generally solid in the green state. A through-hole is first formed either during original formation of the alumina structure 188 or by subsequent drilling in the green state. The drilled hole is first filled all the way from the body fluid side to the device side with CRMC paste 185. Then as previously described, the CRMC paste is either allowed to dry or deliberately dried in one of the various processes described. At this point, the CRMC paste will be mechanically strong enough to hold its shape, while a second drilling operation is formed. A second hole is drilled right down through the center so that it can be later filled with a substantially pure platinum paste 186. Referring back to FIG. 31, prior to placement of the CRMC or the platinum fill, the empty hole or passageway extending through the green ceramic 188 from the body fluid side to the device side, may be formed by an automated printed circuit board drilling machine. There may be a backing plate or a suspension plate that has a larger diameter so that the green ceramic body 188 is held firmly in place as the drill is drilled all the way through. Alternatively, a backing plate of a disposable short green ceramic, such as an alumina may be used, and then the part subsequently separated. It will also be appreciated that water-cutting or punching processes could also be used to form the hole or passageway. After this passageway is formed, as described, then the CRMC paste 185 is inserted into the passageway to completely fill it from top to bottom. After that paste is suitably dried, then a second hole or second drilling operation is performed, such that the center of the hole can be filled with the substantially pure platinum 186.

After the entire structure of FIG. 31 or 32 are co-sintered and become a hard-monolithic body, there may be one or more mechanical or lapping operations performed on the top or bottom of the device. This is to remove a thin layer material from the entire top and the entire bottom, such that, the top and bottom of the pure platinum fill 186 is cleanly exposed and is free of the possibility of any glasses or alumina ceramic contamination 188 that could occur. These lapping processes could also be performed by a mechanical or grinding processes, by water-cutting or jetting processes, or by grit-blasting or the like.

During sintering or co-sintering of the structure, such as shown in FIGS. 31 and 32, it is common that at sintering temperatures, that materials will diffuse or even form a concentration gradient. In other words, it would be common for the pure platinum 186 to diffuse at least somewhat into the surrounding CRMC paste 185 and that the metals and glasses of the CRMC paste 185 would also diffuse into the alumina body 188. It is also common that alumina ceramics have as a contamination product various glasses, including $SiO_2$, MgO and CaO. The diffusion of these materials can occur over the two ends of the pure platinum fill 186 and inhibit conductivity. This is why subsequent lapping or cleaning of the top and bottom of the platinum filled via can become important. Referring once again to FIG. 31, one will appreciate that there are manufacturing tolerances involved in any manufacturing process. Having the CRMC fill 185 precisely and perfectly aligned with the pure platinum fill 186 is ideal, but generally not completely possible. Recent advances in printed circuit board and automated drilling machines have led to great precision recently; however, it will be appreciated that the diameter of the CRMC material 185 is sufficiently large to accommodate any off-centering of the drilling of the pure platinum fill area 186, such that, at least a thin layer of the CRMC 185 is always present.

Referring once again to FIGS. 31 and 32, it will be appreciated that the CRMC material may be of any CERMET or metal containing ceramic paste. Also the substantially pure platinum fill 186 could also comprise any number of other substantially pure metals. A complete listing of these appears later in the specification.

As mentioned, ideally, the platinum fill or substantially pure metal fill would be highly concentric with the CRMC material 185. The wall thickness between the ceramic 186 of the CRMC 185 is important and depends upon the thermal coefficient of expansion of the insulator material 188, the CRMC 185 and the metal fill 186. Where there is a great difference in thermal coefficient of expansion, it becomes necessary that the CRMC buffer layer be thicker. When the thermal coefficient of expansion of the surrounding materials are greatly mismatched, then the concentricity of the platinum fill 186 with the CRMC becomes even more important. When there is very little mismatch between surrounding materials, then a higher degree of mismatch and concentricity can be tolerated.

Referring now to FIGS. 39 and 40, one can see that the same manufacturing methods are employed, in that, a passageway through the insulator structure 188 is first built with a CERMET 185. After drying, the CERMET is drilled (in this case, we would call this double-drilled) and then the passage from the body fluid side to the device side, would be filled with a substantially pure platinum fill 186. Then, in the green state, the green materials would be counter-bored to form a counter-bored hole for post-sintered sputtering 150, 152 and gold brazing 138. In other words, after the alumina insulator 188 is co-fired along with CRMC 185 and substantially pure platinum paste 186, then the post-sintered monolithic and rigid body is sputtered 150,152 so that a gold braze 138 may be accepted and formed between the alumina ceramic base 188 and leadwire 186*w*,118.

FIG. 164 is very similar to FIGS. 39 and 40, except in this case, it is not double drilled, but multiple drilled. The word "drill" is a short-hand way of saying holes are formed either by a drilling, punching or water-jet, laser cut, CNC machining or equivalent process. Referring once again to FIG. 164, one can see that a first large passageway is formed and that entire passageway is filled with a CRMC 185*c*. In this case, the CRMC would have a relatively lower metal content, such as on the order of 20% by weight. It should be understood that this is not intended to be limiting. It could be 5%, 10%, 25% and the like. It is just an example. Then after that CRMC layer 185*c* is dried, it is then drilled out and filled with a second CRMC material 185*b*. In general, this 185*b* CRMC material would have a higher metal content than 186*c*, for example, on the order of 40%. After drying, then a third drilling (or equivalent) operation is formed to open up a passageway for CRMC material 185*a*. For example, CRMC material 185*a* could have a 70% metal fill. After drying, then the center of the 185*a* CRMC material is drilled out and then filled with a substantially pure platinum 186 fill, as shown. At this time, the entire structure, including the alumina insulator 188 can all be co-fired. The advantage of having CRMC layers with varying metal content is that stresses induced by thermal coefficient of expansion (CTE mismatches) may be graded across the structure, such that the insulator 188 is not cracked and that a mechanically strong and robust hermetic seal is formed. FIG. 164 is illustrative only. It will be appreciated that there may be one CRMC layer, two, three or . . . "n" layers.

Referring once again to FIG. 164, one will appreciate that the diameter of the substantially pure metallic or platinum fill 186 varies with the application. For example, for a retinal stimulator, the currents that must be passed through such a feedthrough are extraordinarily small (on the order of just a microamp). Accordingly, the robust and high conductivity conductor formed by the 186 fill, can be relatively small in diameter. On the other extreme, if the application is for an implantable cardioverter defibrillator, where a high voltage shock pulse consisting of many amps must pass, then the diameter and the conductivity of the pure platinum via center 186 must be particularly large and robust. It will be appreciated that whatever the core 186 conductor material is, which will be of post-sintered substantially pure metal, its conductivity will vary with its material property and also its length and cross-sectional area. All of these properties are application specific and must be carefully designed for each specific application depending upon the current density required.

FIG. 165 illustrates the basic manufacturing process steps of the present invention. As will be seen, one can form, as described, a solid block of the green alumina insulator or one can form it from sheets that are collated and then laminated. Then, the outer hole of the passageway through the insulator is drilled and completely filled with CRMC paste in accordance with the present invention. As previously described, this could also embody multiple drills with multiple metal fill densities of CRMC layers. After suitable drying, then the inner hole is drilled through CRMC material, which is then filled with platinum paste. The bar, which can contain many insulators (for example, 200 insulators), is then singulated. Singulating means that they are separated from each other so they can be placed on setters and sintered, also known as fired.

FIG. 166 illustrates a variation of the present invention, in that, it is possible to form individual sheets or layers of the ceramic 120,188 and individually fill each one of these layers with CRMC material 185. Then, one would collate these layers, otherwise known as stacking them up and then laminating them together. The handling of these individual layers is generally not preferred as it provides a stacking registration error shown by the staggered pattern of the CRMC layers 185 in FIG. 166. After the individual layers (up to "n" layers) are collated, stacked and laminated, then a hole is drilled 186, which is filled with the pure platinum paste of the present invention. Then, this entire structure is ready for co-sintering. Then, after singulation, this entire structure is ready for co-sintering. It is important to realize that unipolar structures have been illustrated in many cases in the present invention. It will be appreciated that these could be multipolar. For example, one is referred to FIGS. 97 and 98, which illustrate a bar having four different insulator structures. As mentioned, in a real bar, these could be many more, such as even hundreds. FIG. 107 illustrates the bar in the process of singulation. In other words, each one of the individual four insulators is about to be removed from the base bar. FIGS. 110 and 111 illustrate one example of an insulator after it's been singulated and is ready for sintering or firing.

FIG. 167 illustrates the manufacturing process steps of the multilayer structure previously described in FIG. 166. First alumina sheets are formed and the individual thin alumina sheets are punched with one to a multiplicity of holes. Once these outer holes are punched, they are completely filled with a metal composite or CRMC paste 185. The individual sheets are then collated and laminated or pressed together. Then what is formed at this point, is called a green bar. The green bar is then drilled such that a new hole is formed all the way through each one of the CRMC layers 185. This hole is filled with a substantially pure paste, in this case, a platinum paste 186. The individual insulators are then singulated from the bar and are then fired, otherwise known as sintering.

FIG. 168 illustrates a prior art device, which is very common in the art and employs catch pads 180cp. This illustrates either a CERMET or a substantially pure metal fill, such as a platinum fill 188 along with catch pads 180cp. The catch pads make up for misalignment, but are very volumetrically inefficient. An extreme example of catch pads, which are actually little circuit traces, are illustrated in FIG. 4 of U.S. Pat. No. 6,414,835 and FIGS. 16 and 17 of U.S. Pat. No. 8,841,558, the contents of which are incorporated herein by reference. The present invention completely avoids the use of catch pads by the final drilling of the substantially pure metal hole, as a last drilling step.

FIG. 169 illustrates a typical prior art process, which differs very significantly from the present invention. For a typical prior art process, one is referred again to U.S. Pat. No. 8,841,558, the contents of which are incorporated herein fully by reference (including its entire family). As taught in the prior art, alumina sheets are punched to form a hole that is filled with a metal composite paste, which is also known in the art as a CERMET. Then, screen print catch pads on each layer to accommodate stacking misalignments, then they are collated and laminated. This forms a structure similar to that shown in FIG. 168 herein. The individual insulators are singulated and then fired in accordance with the prior art. For example, refer to FIG. 16 of U.S. Pat. No. 9,418,778, the contents of which are incorporated herein fully by reference. Importantly, none of these prior art patents involve drilling a second hole and filling it with substantially pure metal, such as a pure metal paste. In fact, the only invention of which the inventors are aware that even begins to incorporate a CRMC layer that relieves thermal stresses to a substantially pure platinum center hole is Troetzschel U.S. Pat. No. 8,886,320, the contents of which are incorporated herein fully by reference (including its entire family). Referring now to Troetzschel FIG. 2, one can see that there is a sintered CERMET fringe body 40 that is co-sintered along with a CERMET layer 50. This structure incorporates what they call a base body, which can be of substantially pure alumina ceramic. Now here is where the substantial difference occurs. In all of Troetzschel family, they teach that a bushing body 20 is formed outside of the base body 10 and is embedded in one or more layers of a transitional layer 30, which is defined as the CERMET having a 20-70% metal content. Troetzschel consistently teaches that this bushing body and transitional layer are formed outside of the base body and then somehow (with no real description or enablement) inserts it into the base body. One is referred to the Troetzschel '320 patent column 3 starting on line 19 and ending on line 39, which describes the Troetzschel process. The following is quoted from the '320 patent: "forming the base body green blank from a ceramic slurry or a ceramic powder such as to have at least one bushing opening that extends through the base body green blank; forming the at least one bushing body green blank from a cermet slurry, a cermet powder, a metal powder and/or a slurry made of a metal powder, whereby a shape of the at least one bushing body green blank and a shape of the at least one bushing body opening are complementary to each other at least in sections thereof and prevent slippage of the bushing body green blank through the bushing opening; inserting the at least one bushing body green blank into the at least one bushing opening of the base body green blank to form the composite green blank; applying at least one force to the bushing body green blank and/or the base body green blank and sintering the composite green blank while applying the at least one force, whereby the at least one force is directed in the direction of a bracketing of the at least one bushing body green blank in the at least one bushing opening of the base body green blank." (Underline added for emphasis) In summary, Troetzschel teaches away from forming a passageway, filling it completely with a CERMET or CRMC, drying it and then drilling it out and then filling it with a substantially pure metallic material, such as pure platinum.

FIG. 170 is very similar to FIG. 41, except in this case, the gold braze body fluid side leadwire 186W, 118 has been removed for simplicity. Referring once again to FIG. 41, it will be appreciated that leadwire 186W, 118 could have also been co-brazed on the device side forming a device side leadwire 118'. However, for the body fluid side, it is desirable to gold braze 138 because on the body fluid side, the leadwire 186W, 118 must be biocompatible, non-toxic and biostable. There are a very short list of materials and attachments that meet all of these requirements. This short list includes platinum leadwires, palladium leadwires, niobium leadwires, tantalum leadwires and titanium leadwires and various alloys thereof. The problem with this list of materials is that they are either extremely expensive (such as gold, platinum or palladium) or they are heavily oxidized (such as niobium, tantalum and the like). This makes them undesirable for use on the device side where a connection to a circuit AIMD electronics or an AIMD circuit board 126 (not shown) can be accomplished in a cheaper and more efficient manner. Referring to FIG. 170, one can see that there is a ribbing cable 118' which is electrically connected primarily to the platinum sinter-fill 186 of the alumina insulator via hole. It will be appreciated that multipolar hermetic insulators are very common in the art, but unipolars are shown herein for simplicity. An electrical connection 600 is formed between the ribbon cable 118', which is better illustrated in FIG. 170A. In one embodiment, this could be a thin gold ribbon, but in a lower cost alternative, it could consist of many other materials, including copper. An electrical attachment 600 is made by ultrasonic or thermal sonic bonding. This is a very common process for attachment of ribbon cables, which can be adapted for the present purpose. During thermal sonic or ultrasonic bonding or equivalent bonding processes, a probe head comes down and localized melting 118' occurs as this is in the area depicted by numeral 600, in other words no new material has been added. It will appreciated that the ribbon cable 118' can be attached to the platinum fill 186 and/or the CRMC 185 with any of the following processes, including at least one of laser welding, arc welding, gas welding, resistance welding, projection welding, butt welding, slash welding, upset welding, solid state welding, friction welding, ultrasonic welding, fusion welding, induction welding, percussion welding or electron beam welding. It will be appreciated that equivalent processes could be used. All of these processes, as described in FIG. 170, the ribbon cable has a general rectangular cross-section as better illustrated in FIG. 170A. It will be understood that any of the wire bonding techniques described herein on the device side could be applied to the body fluid side as long as the materials used are biocompatible and non-toxic.

Referring now to FIG. 171, one can see an alternative ribbon cable, which is better illustrated in FIG. 171A. In this case, the ribbon cable includes a hole 604 that is punched or formed through it. This accommodates electrical attachment 202, 602 by soldering, by ball grid array, by solder bump, by thermal-setting conductive adhesives or the like. The weld can also be used with any of the welding or attachment processes previously described for FIG. 170.

FIG. 172 illustrates a rectangular wire bond cable 118' before being attached to the platinum fill 186 and/or CRMC 185. In this case, a bump or ball grid 202,606 of either a solder, a solder paste or a thermal-setting conductive adhesive is first dispensed. Then, the ribbon wire 118', as illustrated in FIG. 172A, is positioned over it and held in place while the entire assembly is raised to an elevated temperature. (It will be appreciated that the bump 202,606 could be applied to the ribbon cable 118' or to both the ribbon cable and the CRMC sintered paste.) The temperature elevation is either to reflow the solder or cure a conductive thermal-setting adhesive, such as a conductive epoxy or a conductive polyimide.

FIG. 173 illustrates the assembly of FIG. 172 after it's been raised to an elevated temperature and the electrical connection 202, 606 has been formed. FIG. 173A illustrates that in this case, a wire is a rectangular ribbon wire in cross-section.

FIG. 174 is exactly the same as FIG. 173 and FIG. 173A, except in this case, the wire 118' is round in cross-section as illustrated in FIG. 174A. In this case, all of the attachment methods previously described for FIG. 174, still apply, such as resistance welding, projection welding, ultra-sonic welding and the like. Referring to attachment material 608 in FIG. 174, one will appreciate that it could also be a solder or a thermal-setting conductive adhesive.

Referring now back to FIG. 170 and comparing it to FIG. 131, one will see that this is described as Options 2 and 2A of the present invention. This embodies double drilling as previously described.

FIG. 175 illustrates Option 1 and 1A when referring back to FIG. 131. In this case, the hole is formed entirely through the insulator and is filled entirely with CRMC material 185. In the present invention, this is always the first step, but in this case, a hole is drilled all the way through the center of the CRMC material 185. Then, each end of the CRMC material is counter-bored forming the dumbbell shape illustrated in Options 1 and 1A of FIG. 131 and in FIG. 175. This dumbbell shape is then completely filled with substantially pure platinum paste (or equivalent metal paste) in accordance with the present invention. Post-sintering, this forms a hard-monolithic structure. A ribbon cable 118', which is illustrated in cross-section FIG. 175A, is then attached 600 by any of the attachment processes previously described in FIG. 170. Referring back to FIG. 175, one will appreciate the attachment processes on the device side in order to provide a low-cost connection to AIMD electronic circuits, can be applied to any of the options shown in FIG. 131, including Options 1, 1A, 2, 2A, 3, 3A, 4, 4A, 5, 5A, 6 and 6A. It will be appreciated that wire 118' could be a round wire, oval wire, rectangular wire or any other shape and that all of the techniques taught herein could be applied to the body fluid side as long as the materials are biocompatible and non-toxic. One will also appreciate that the wire 118' could be disposed perpendicular to the feedthrough surface such that it is aligned with the CRMC paste 185 and metal paste 186. This structure could then be used with a nail head wire on the body fluid side as previously illustrated in FIG. 41.

FIG. 176 is a sectional view of a feedthrough dielectric body 188 resting upon a backing plate 610. A drill chuck 616 can then capture an appropriate sized drill bit 614 that will be used to drill through the feedthrough dielectric body 188. As can be seen, a hole 612 can be aligned with the hole to be drilled through the feedthrough dielectric body 188. The hole 612 can be larger in diameter in comparison to the drill bit 614. As an alternative, the backing plate 610 can be made without the hole 612 and be made as a sacrificial alumina body in the green state.

Platinum and platinum/iridium materials are generally chosen for AIMD feedthroughs, however, after sintering, they are not necessarily readily solderable, resulting in it being more difficult for attachment of critical elements within the device. The present invention resolves this issue by providing a device side solder coat 197 that simplifies attachment of critical device elements, is cost effective, and enhances manufacturability.

It should be noted that, although insulators of alumina ($Al_2O_3$) are described throughout, other biocompatible insulator materials, including but not limited to glass, insulating metal oxide, glass ceramic and other ceramic materials, formulations or combinations thereof may be used instead of alumina or in conjunction with alumina. For example, zirconia ($ZrO_2$) and/or various stabilized or partially stabilized zirconia including ZTA and ATZ may be used. Other material options include fused silica, silicon nitride, alumina toughened zirconia, zirconia toughened alumina, zirconium dioxide, yttrium-toughened zirconium oxide (Y-TZP), aluminum nitride (AlN), magnesium oxide (MgO), piezoceramic materials, barium (Zr, Ti) oxide, barium (CE, Ti) oxide, sodium-potassium-niobate, calcium oxide, cerium oxide, titanium oxide, apatite-wollastonite (A-W) glass ceramic, boron nitride, alumina silicate, and combinations thereof.

Additionally, it is also contemplated insulators comprising at least one Cermet or CRMC layer on at least one surface of an insulator body may also be used to provide for a robust insulator/conductor interface via ceramic to metal joining methods. Also contemplated is the use of laminates, single pressed preforms, solid pellets, pre-sintered laminates, pressed preforms and combinations thereof. It is also contemplated that multilayer insulators may be of the same composition, differing compositions, the same or varying resistivity, the same or varying thermal expansion coefficient, combinations thereof and may have various layering structures. Layering structures may be across a width, along a length, about a perimeter, sandwich like, wavelike and combinations thereof.

Conductive via fill materials of alumina/platinum or pure platinum are described, but other materials including Cermets may be used. For example, it will be known to those skilled in the art from this teaching that other nonlimiting ceramics, glass ceramics, and/or glass oxides may be added to the metal-containing inks/pastes to customize CTE matching/transition pending core material and/or insulator material selections. Palladium may be used instead of platinum. Other nonlimiting biocompatible metals and alloys that may be used in place of platinum include niobium, platinum/palladium, stainless steels, and titanium. Furthermore any of the following list of materials may be used alone or combination with any of the materials already discussed or within this list.

Gold (Au), silver (Ag), iridium (Ir), rhenium (Re), rhodium (Rh), titanium (Ti), tantalum (Ta), tungsten (W), zirconium (Zr), and vanadium (V)
Cobalt Chromium Molybdenum Alloy
Cobalt Chromium Nickel Iron Molybdenum Manganese Alloy
Cobalt Chromium Tungsten Nickel Iron Manganese Foil
Cobalt Nickel Chromium Iron Molybdenum Titanium Alloy
Cobalt Nickel Chromium Iron Molybdenum Tungsten Titanium Alloy
Cobalt Nickel Chromium Molybdenum Alloy
Copper Aluminum Nickel Alloy
Copper Zinc Alloy
Copper Zinc Aluminum Nickel Alloy
Copper Zinc Silver Alloy
Gold Platinum Palladium Silver Indium Alloy
Iron Chromium Alloy
Iron Chromium Nickel Alloy
Iron Chromium Nickel Aluminum Alloy
Iron Chromium Nickel Copper Alloy
Iron Chromium Nickel Copper Molybdenum Niobium Alloy
Iron Chromium Nickel Copper Niobium Alloy
Iron Chromium Nickel Copper Titanium Niobium Alloy
Iron Chromium Nickel Manganese Molybdenum Alloy
Iron Chromium Nickel Molybdenum Alloy
Iron Chromium Nickel Molybdenum Aluminum Alloy
Iron Chromium Nickel Titanium Molybdenum Alloy
Iron Manganese Chromium Molybdenum Nitrogen Alloy
Nickel Platinum Alloy
Nitinol
Nickel Titanium Alloy
Nickel Titanium Aluminum Alloy
Niobium-Titanium Alloy
Platinum Iridium Alloy
Platinum Palladium Gold Alloy
Titanium Aluminum Vanadium Alloy
Titanium Based Aluminum Iron Alloy
Titanium Based Aluminum Molybdenum Zirconium Alloy
Titanium Based Molybdenum Niobium Alloy
Titanium Based Molybdenum Zirconium Iron Alloy
Titanium based Niobium Zirconium Alloy
Titanium based Niobium Zirconium Tantalum Alloy
Titanium Molybdenum Alloy
Titanium Niobium Alloy
Titanium Platinum Alloy
Titanium-based Molybdenum Zirconium Tin Alloy Examples of some PAC, Cermet, CRMC ceramic/metal pairings include, but are not limited to:
a. Alumina ($Al_2O_3$) or zirconia ($ZrO_2$) including various stabilized or partially stabilized zirconia like zirconia toughened alumina (ZTA) and alumina toughened zirconia (ATZ) with platinum (Pt) or palladium (Pd)
b. Alumina ($Al_2O_3$) or zirconia ($ZrO_2$) with iridium, rhenium, rhodium, various Pt alloys (e.g., Pt—Ir, Pt—Pd, Pt—Rh, Pt—Re, Pt—Au, Pt—Ag etc.), Pd alloys (e.g., Pd—Ir, Pd—Re, Pd—Rh, Pd—Ag, Pd—Au, Pd—Pt, Pd—Nb, etc.), Au alloys (e.g., Au—Nb, Au—Ti, etc.), Au alloys (e.g., Au—Nb, Au—Ti, etc.), and Ti alloys (e.g., Ti—Al—V, Ti—Pt, Ti—Nb, etc.)

Any combination of the ceramics and metals is theoretically suitable for a Cermet used as disclosed herein.

It will be understood to one skilled in the art that more than one metal/ceramic, metal/glass oxide, or metal/ceramic/glass oxide formulation may be used to surround the core conductive material of ink/paste, wire, or combinations of both, to create a layering effect about the core material(s) along the longitudinal axis of the via to achieve optimal transition for CTE matching at the respective mating material interface(s).

It should also be noted that the structures disclosed herein may be provided through other methods in addition to those described herein. For example, use of laminates, single pressed preforms, solid pellets, pre-sintered assemblies/subassemblies or other such components and/or related methods of manufacture using and or leveraging developmental or commercially available processes to augment component or assembly form and function. Furthermore, methods other than already disclosed herein may also be used. Various methods that may be used to provide component structures, subassemblies and assemblies may include, but are not limited to, multi-stage brazing, reactive brazing, solder or BGA attachment, diffusion bonding, transient liquid phase bonding, transient liquid phase diffusion bonding, partial transient liquid phase bonding, sputtering, joining, pre-sintering, multi-stage sintering or sintering.

Additionally, flexible ceramics may be used in any of the structures disclosed herein. The term "flexible ceramics" is used herein to include ultrathin flexible ceramics, such as those disclosed in the article "Ultrathin Flexible Ceramics for Electronic Applications" by John A. Olenick, nanoceramics, which is more than 85% air and is very light, strong, flexible and durable, and synthetic ceramics such as Eurekite's "flexiramics", which is formed to retain the positive properties of ceramics while being flexible rather than brittle. Ultrathin ceramic or ceramic-based materials provide very thin, flexible layers which are crimpable, rollable, bendable, and foldable. Moreover flexible ceramics may be made into a number of circuitous shapes, sizes and multilayer structures commensurate with component, subassembly or assembly design. As these materials are highly flexible, they can even be rolled into cylindrical shapes, conform to rectangular, square, triangular, oval or some other shape, wrapped about an object such as a wire, lead, ribbon, braid, mandrel or other elongate object. There are a number of flexible ceramic products commercially available, such as, but not limited to, alumina (or aluminum oxide), barium titanate, zirconia-based ceramics such as YSZ (yttria-stabilized zirconia), alumina based composites, glass ceramics such as alumina-silica, and the like. Additionally, these flexible ceramic materials may be used in conjunction with flexible polymer materials to create any of the ceramic circuits and circuit boards described herein. Polymeric material examples include polydimethylsoloxanes (PDMS), polyethyleneterephthalate (PET), teflons, teflons doped with dielectrics or other, polytetrafluoroethylene (PTFE), ethylenetetrafluoroethylene (ETFE), parylenes, polyether block amide (PEBAX), polyetheretherketone (PEEK), polystyrenes, polysulfones, polypropylenes, polycarbonates, polyvinyl chloride (PVC), polyxylylene polymers, polyamides, polyimides, nylon, epoxies, and other such suitable polymers, elastomers and gels, including combinations thereof.

It should be noted that U.S. Pat. Nos. 4,424,551, 5,333,095, 5,650,759, 5,751,539, 5,896,267, 5,905,627, 5,959,829, 5,973,906, 5,978,204, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995, 7,310,216, 7,327,553, 7,489,495, 7,535,693, 7,551,963, 7,623,335, 7,797,048, 7,957,806, 8,095,224, 8,179,658 8,841,558, 8,855,768, 9,108,066, 9,427,596 and 9,492,659, U.S. Publication 2015/0314131 and U.S. Provisional Applications 62/418,834, 62/443,011, 62/450,187, and 62/461,872 are incorporated in full herein by reference.

Additionally, incorporated in full herein by reference are the following referenced literature:

Textbook "Introduction to Ceramics" in 1960 by Kingery et al. (Chapters 5 and 6)

Becker: Ann. Phys., 1938, vol. 32, pp. 128-40

Dissertation "Developing a High Density Pt/Alumina Hermetic Feedthrough" submitted to Florida International University on Jun. 15, 2012 in partial fulfillment of the requirements for the degree of Doctor of Philosophy in Materials Science and Engineering by Ali Karbasi "Ultrathin Flexible Ceramics for Electronic Applications," John A. Olenick, Ceramic Industry, October 2016 pgs. 30-31.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

What is claimed is:

1. A method for manufacturing a feedthrough that is configured for incorporation into an active implantable medical device (AIMD), the method comprising the steps of:
   a) forming a first sintered ceramic reinforced metal composite (CRMC) paste, comprising the steps of:
      i) mixing platinum with a first ceramic material to form a first CRMC material;
      ii) subjecting the first CRMC material to a first sintering step to thereby form a first sintered CRMC material;
      iii) ball-milling or grinding the first sintered CRMC material to form a first powdered sintered CRMC material; and
      iv) mixing the first powdered sintered CRMC material with a solvent to form the first sintered CRMC paste;
   b) forming a green-state ceramic body, comprising the steps of:
      i) forming a ceramic body in a green state, the green-state ceramic body having a ceramic body body fluid side opposite a ceramic body device side, wherein, when the feedthrough is attached to a housing for the AIMD, the ceramic body fluid side resides outside the AIMD and the ceramic body device side resides inside the AIMD;
      ii) forming at least one first via hole comprising a first via hole inner surface extending along a longitudinal axis through the green-state ceramic body to the body fluid and device sides;
      iii) filling the at least one first via hole in the green-state ceramic body with the first sintered CRMC paste extending to a first sintered CRMC paste first end residing at or adjacent to the ceramic body fluid side and a first sintered CRMC paste second end residing at or adjacent to the ceramic body device side;
      iv) drying the green-state ceramic body including the first sintered CRMC paste to thereby form a second CRMC material filling the at least one first via hole in the ceramic body;
      v) forming a second via hole extending through the second CRMC material to the ceramic body fluid and device sides so that an inner surface of the second CRMC material is spaced closer to the longitudinal axis than the first via hole inner surface;
      vi) providing a substantially pure metal core in the second via hole; and vii) subjecting the green-state ceramic body including the second CRMC material and the substantially pure metal core to a second sintering step to thereby form a sintered ceramic body comprising the second CRMC material surrounding the substantially pure metal core; and c) providing an electrically conductive ferrule comprising a ferrule opening; and d) hermetically sealing the sintered ceramic body to the ferrule in the ferrule opening.

2. The method of claim 1, further including forming the green-state ceramic body comprising the steps of:
a) sintering a second ceramic material;
b) ball-milling or grinding the sintered second ceramic material to form a second powdered sintered ceramic material; and
c) mixing the second powdered sintered ceramic material with a solvent to form the ceramic body in the green state.

3. The method of claim 1, including mixing the first powdered sintered CRMC material with the solvent and a binder to form the first sintered CRMC paste.

4. The method of claim 1, including providing the first sintered CRMC paste comprising platinum and, by weight or by volume, about 15% to about 80% first ceramic material.

5. The method of claim 1, including brazing a leadwire to the substantially pure metal core after the second sintering step b), vii).

6. The method of claim 1, including providing the first sintered CRMC paste containing about 20% to about 80% ceramic by weight or by volume.

7. The method of claim 1, including providing the substantially pure metal core as a substantially pure metal paste containing at least 90% metal by weight or by volume, wherein after the second sintering step, the substantially pure metal core is a sintered substantially pure metal core.

8. The method of claim 1, wherein the step of forming the ceramic body in the green state comprises stacking discrete layers of ceramic in a green state one upon another and pressing them together.

9. The method of claim 8, wherein the pressing step is by one of the group consisting of hydro-static pressing, hot pressing, cold pressing, die pressing, and mechanical pressing.

10. The method of claim 1, wherein between steps b), vi) and b), vii), including the step of forming at least one counterbore or countersink in the substantially pure metal core from at least one of the ceramic body fluid side and the ceramic body device side.

11. The method of claim 10, wherein after the second sintering step b), vii), including a step of inserting a solid leadwire at least partially into the at least one counterbore or countersink followed by brazing the solid leadwire to at least one of the second CRMC material and the substantially pure metal core in the counterbore or countersink so that the solid leadwire is electrically connected to the substantially pure metal core.

12. The method of claim 1, wherein between steps b), vi) and b), vii), including the further steps of:
a) forming at least one counterbore or countersink in the green-state ceramic body to thereby expose an inner surface of the ceramic body in the counterbore or the countersink; and
b) following the second sintering step b), vii), sputtering an adhesion metallization onto the inner surface of the sintered ceramic body in the at least one counterbore or countersink, followed by sputtering a wetting metallization onto the adhesion metallization; and
c) inserting a solid leadwire at least partially into the at least one counterbore or countersink, followed by brazing the solid leadwire to the wetting metallization in the counterbore or countersink so that the solid leadwire is electrically connected to the substantially pure metal core.

13. The method of claim 1, including the further steps of:
a) forming at least one counterbore or countersink in the second CRMC material and in the substantially pure metal core to thereby expose an inner surface of the green-state ceramic body in the counterbore or the countersink; and
b) following the second sintering step b), vii), sputtering an adhesion metallization onto the inner surface of the sintered ceramic body in the at least one counterbore or countersink, followed by sputtering a wetting metallization onto the adhesion metallization; and
c) inserting a solid leadwire at least partially into the at least one counterbore or countersink, followed by brazing the solid leadwire to the wetting metallization in the counterbore or countersink so that the solid leadwire is electrically connected to the substantially pure metal core.

14. The method of claim 11, including providing the solid leadwire residing on the body fluid side of the sintered ceramic body and comprising a nail head.

15. The method of claim 1, wherein in steps b), ii) and b), v), the respective forming step is by at least one of the group consisting of drilling, punching, machining, and waterjet cutting.

16. The method of claim 1, wherein, after drying the green-state ceramic body including the first sintered CRMC paste in step b), iv), the resulting second CRMC material is in the shape of a sleeve that surrounds the substantially pure metal core in step b), vi).

17. The method of claim 1, wherein the substantially pure metal core is a substantially pure platinum core.

18. The method of claim 1, including positioning a backing plate adjacent to the green-state ceramic body during the forming steps b), ii) and b), v).

19. The method of claim 18, including providing the backing plate comprising a backing plate hole, and aligning the backing plate hole with the at least one first via hole, and wherein the backing plate hole is larger in diameter than the at least one first via hole.

20. The method of claim 19, including providing the backing plate as a sacrificial alumina body in a green state.

21. The method of claim 1, including the additional steps of:
a) forming a second ceramic reinforced metal composite (CRMC) paste, comprising the steps of:
i) mixing platinum with a third ceramic material to form a third CRMC material;
ii) subjecting the third CRMC material to a third sintering step to thereby form a second sintered CRMC material;
iii) ball-milling or grinding the second sintered CRMC material to form a second powdered sintered CRMC material; and
iv) mixing the second powdered sintered CRMC material with a solvent to form a third sintered CRMC paste, wherein the third sintered CRMC paste has a higher percentage of metal based on weight or by volume in comparison to the first sintered CRMC paste;

b) before second sintering step b), vii), filling the second via hole with the third CRMC paste;

c) drying the green-state ceramic body including the second CRMC material and the third sintered CRMC paste to thereby form second and third CRMC materials filling the at least one via hole in the ceramic body; and d) forming a third via hole through the third CRMC material, e) wherein in step b), vi), the substantially pure metal core is provided in the third via hole.

22. The method of claim 21, including the additional steps of:

a) forming a third ceramic reinforced metal composite (CRMC) paste, comprising the steps of:

i) mixing platinum with a fourth ceramic material to form a fourth CRMC material;

ii) subjecting the fourth CRMC material to a fourth sintering step to thereby form a third sintered CRMC material;

iii) ball-milling or grinding the third sintered CRMC material to form a third powdered sintered CRMC material; and iv) mixing the third powdered sintered CRMC material with a solvent to form a fourth sintered CRMC paste, wherein the fourth sintered CRMC paste has a higher percentage of metal based on weight or by volume in comparison to the third sintered CRMC paste;

b) before second sintering step b), vii), filling the third via hole with the fourth sintered CRMC paste;

c) drying the green-state ceramic body including the second and third CRMC materials and the fourth sintered CRMC paste to thereby form second, third and fourth CRMC materials filling the at least one via hole in the ceramic body; and d) forming a fourth via hole through the fourth CRMC material, e) wherein in step b), vi), the substantially pure metal core is provided in the fourth via hole.

23. The method of claim 1, including hermetically sealing the sintered ceramic body to the ferrule using a gold braze.

24. The method of claim 1, wherein after step b), vii), but before hermetically sealing the sintered ceramic body to the ferrule, including the step of removing a thin layer of material from at least one of the ceramic body fluid side and the ceramic body device side by a technique selected from the group consisting of lapping, grinding, water-cutting, jetting processes, and by grit-blasting.

25. The method of claim 1, wherein in step b), iv), drying the green-state ceramic body comprising the first sintered CRMC paste is by at least one of the group consisting of waiting for a period of time, heating the ceramic body at an elevated temperature, and placing the ceramic body in a vacuum.

26. The method of claim 1, including after the second sintering step b), vii) of the green-state ceramic body including the second CRMC material and the substantially pure metal core to thereby form the sintered ceramic body, attaching a conductive leadwire to the substantially pure metal core adjacent to at least one of the ceramic body fluid side and the ceramic body device side.

27. The method of claim 26, including attaching the conductive leadwire to the substantially pure metal core by a technique selected from the group consisting of ultrasonic welding, thermal sonic bonding, laser welding, arc welding, gas welding, resistance welding, projection welding, butt welding, slash welding, upset welding, solid state welding, friction welding, fusion welding, inductive welding, percussion welding, and electron beam welding.

28. The method of claim 1, including providing the ferrule being configured to be attachable to an opening in a housing of an AIMD.

29. The method of claim 1, including providing the ferrule as part of a housing of the AIMD.

30. The method of claim 1, including providing the green-state ceramic body comprising at least 96% percent alumina by weight or by volume.

31. A method for manufacturing a feedthrough, the method comprising the steps of:

a) forming a green-state ceramic body, comprising the steps of:

i) forming an alumina ceramic body in a green state, the green-state alumina ceramic body having a ceramic body first side opposite a ceramic body second side; and ii) forming at least one via hole extending through the green-state alumina ceramic body to the ceramic body first and second sides;

b) providing a thermally-stable CRMC paste, comprising the steps of:

i) mixing platinum with a ceramic material to form a first CRMC material;

ii) heat-treating the first CRMC material to a temperature that is sufficient to form a thermally-stable CRMC material;

iii) ball-milling or grinding the thermally-stable CRMC material to form a powdered thermally-stable CRMC material; and iv) mixing the powdered thermally-stable CRMC material with a solvent to form the thermally-stable CRMC paste;

c) filling the at least one via hole in the green-state alumina ceramic body with the thermally-stable CRMC paste extending to a thermally-stable CRMC paste first end residing at or adjacent to the ceramic body first side and to a thermally-stable CRMC paste second end residing at or adjacent to the ceramic body second side;

d) drying the green-state alumina ceramic body including the thermally-stable CRMC paste to thereby form a second CRMC material filling the at least one via hole in the alumina ceramic body;

e) forming a second via hole extending through the second CRMC material to the ceramic body first and second sides, the second via hole being smaller in diameter than the at least one via hole so that a portion of the second CRMC material remains in the at least one via hole;

f) forming at least one counterbore or countersink in the green-state alumina ceramic body from either the ceramic body first side or the ceramic body second side;

g) filling the second via hole and the counterbore or countersink with a substantially pure metal paste; and h) sintering the green-state alumina ceramic body including the second CRMC material and the substantially pure metal paste to thereby form a sintered ceramic body comprising the second CRMC material surrounding the substantially pure metal core; and i) providing an electrically conductive ferrule comprising a ferrule opening; and j) hermetically sealing the sintered ceramic body to the ferrule in the ferrule opening.

32. A method for manufacturing a feedthrough, the method comprising the steps of:

a) forming a green-state ceramic body, comprising the steps of:
  i) forming an alumina ceramic body in a green state, the green-state alumina ceramic body having a ceramic body first side opposite a ceramic body second side; and
  ii) forming at least one via hole comprising a first via hole inner surface extending along a longitudinal axis through the green-state alumina ceramic body to the ceramic body first and second sides;
b) providing a thermally-stable CRMC paste, comprising the steps of:
  i) mixing platinum with, by weight or volume, about 15% to about 80% of a ceramic material to form a first CRMC material;
  ii) heat-treating the first CRMC material to form a thermally-stable CRMC material;
  iii) ball-milling or grinding the thermally-stable CRMC material to form a powdered thermally-stable CRMC material; and
  iv) mixing the powdered thermally-stable CRMC material with a solvent to form a thermally-stable CRMC paste;
c) filling the at least one via hole in the green-state alumina ceramic body with the thermally-stable CRMC paste extending to a thermally-stable CRMC paste first end residing at or adjacent to the ceramic body first side and to a thermally-stable CRMC paste second end residing at or adjacent to the ceramic body second side;
d) drying the green-state alumina ceramic body including the thermally-stable CRMC paste to thereby provide a second CRMC material filling the at least one via hole in the alumina ceramic body;
e) forming at least one counterbore or countersink in the second CRMC material from either the ceramic body first side or the ceramic body second side;
f) filling the counterbore or countersink with a substantially pure metal paste;
g) sintering the green-state alumina ceramic body including the second CRMC material and the substantially pure metal paste to thereby form a sintered ceramic body comprising the second CRMC material surrounding the substantially pure metal core;
h) providing an electrically conductive ferrule comprising a ferrule opening; and
i) hermetically sealing the sintered ceramic body to the ferrule in the ferrule opening.

33. A method for manufacturing a feedthrough, the method comprising the steps of:
a) forming a green-state ceramic body, comprising the steps of:
  i) forming a ceramic body in a green state, the green-state ceramic body having a ceramic body first side opposite a ceramic body second side; and
  ii) forming at least one first via hole comprising a first via hole inner surface extending along a longitudinal axis through the green-state ceramic body to the ceramic body first and second sides;
b) providing a thermally-stable CRMC paste, comprising the steps of:
  i) mixing platinum with, by weight or volume, about 15% to about 80% of a ceramic material to form a first CRMC material;
  ii) heat-treating the first CRMC material to form a thermally-stable CRMC material;
  iii) ball-milling or grinding the thermally-stable CRMC material to form a powdered thermally-stable CRMC material; and
  iv) mixing the powdered thermally-stable CRMC material with a solvent to form a thermally-stable CRMC paste;
c) filling the at least one first via in the green-state ceramic body hole with the thermally-stable CRMC paste extending to a thermally-stable CRMC paste first end residing at or adjacent to the ceramic body first side and to a thermally-stable CRMC paste second end residing at or adjacent to the ceramic body second side;
d) drying the green-state ceramic body including the thermally-stable CRMC paste to thereby form a second CRMC material filling the at least one first via hole in the ceramic body;
e) forming a second via hole extending through the second CRMC material to the ceramic body first and second sides so that an inner surface of the second CRMC material is spaced toward the longitudinal axis with respect to the first via hole inner surface;
f) providing a platinum core in the second via hole;
g) sintering the green-state ceramic body including the second CRMC material and the platinum core to thereby form a sintered ceramic body comprising the second CRMC material surrounding the substantially pure metal core;
h) providing an electrically conductive ferrule comprising a ferrule opening; and
i) hermetically sealing the sintered ceramic body to the ferrule in the ferrule opening.

34. The method of claim 31, including heat-treating the first CRMC material to a temperature greater than 1,000° C. to thereby form the thermally-stable CRMC material.

35. The method of claim 32, including heat-treating the first CRMC material to a temperature greater than 1,000° C. to thereby form the thermally-stable CRMC material.

* * * * *